(12) United States Patent
Ueno et al.

(10) Patent No.: US 9,822,110 B2
(45) Date of Patent: Nov. 21, 2017

(54) SULFONAMIDE DERIVATIVE AND PHARMACEUTICAL USE THEREOF

(71) Applicant: EA Pharma Co., Ltd., Tokyo (JP)

(72) Inventors: Hirokazu Ueno, Kawasaki (JP); Takashi Yamamoto, Kawasaki (JP); Tomoko Miyazawa, Kawasaki (JP); Kenji Shinkai, Kawasaki (JP); Harumi Arisaka, Kawasaki (JP); Toshiyuki Takanohashi, Kawasaki (JP)

(73) Assignee: EA Pharma Co., Ltd., Tokyo (JP)

( * ) Notice: Subject to any disclaimer, the term of this patent is extended or adjusted under 35 U.S.C. 154(b) by 0 days.

(21) Appl. No.: 15/142,858

(22) Filed: Apr. 29, 2016

(65) Prior Publication Data

US 2016/0244451 A1   Aug. 25, 2016

Related U.S. Application Data

(63) Continuation of application No. PCT/JP2014/078644, filed on Oct. 28, 2014.

(30) Foreign Application Priority Data

Oct. 29, 2013  (JP) ................ 2013-224694

(51) Int. Cl.
  *C07D 471/04* (2006.01)
  *C07D 239/54* (2006.01)
  *C07D 487/04* (2006.01)
  *C07D 401/14* (2006.01)
  *C07D 403/12* (2006.01)
  *C07D 403/14* (2006.01)
  *C07D 405/12* (2006.01)
  *C07D 405/14* (2006.01)

(52) U.S. Cl.
  CPC ......... *C07D 471/04* (2013.01); *C07D 239/54* (2013.01); *C07D 401/14* (2013.01); *C07D 403/12* (2013.01); *C07D 403/14* (2013.01); *C07D 405/12* (2013.01); *C07D 405/14* (2013.01); *C07D 487/04* (2013.01)

(58) Field of Classification Search
  CPC .. C07D 239/54; C07D 471/04; C07D 487/04; C07D 405/14; C07D 403/12; C07D 403/14; C07D 405/12; C07D 401/14
  See application file for complete search history.

(56) References Cited

U.S. PATENT DOCUMENTS

| | | | |
|---|---|---|---|
| 6,380,387 B1 | 4/2002 | Sidduri et al. | |
| 6,521,666 B1 | 2/2003 | Sircar et al. | |
| 7,153,963 B2 * | 12/2006 | Makino | C07D 239/22 544/284 |
| 7,250,516 B2 * | 7/2007 | Okuzumi | A61K 31/403 546/153 |
| 7,345,049 B2 * | 3/2008 | Sagi | A61K 31/517 514/266.2 |
| 7,452,905 B2 * | 11/2008 | Suzuki | A61K 31/395 514/311 |
| 7,605,165 B2 * | 10/2009 | Sagi | C07D 239/54 514/266.21 |
| 7,759,388 B2 * | 7/2010 | Suzuki | A61K 31/395 514/417 |
| 7,872,125 B2 * | 1/2011 | Makino | C07D 239/22 544/284 |
| 7,884,204 B2 * | 2/2011 | Okuzumi | A61K 31/403 544/224 |
| 8,222,405 B2 * | 7/2012 | Makino | C07D 239/22 544/11 |
| 8,309,561 B2 * | 11/2012 | Sagi | A61K 31/517 514/266.2 |
| 8,426,588 B2 * | 4/2013 | Makino | C07D 239/22 544/183 |
| 9,533,985 B2 * | 1/2017 | Ueno | C07D 403/12 |
| 2003/0191118 A1 | 10/2003 | Sircar et al. | |
| 2003/0220268 A1 * | 11/2003 | Makino | C07D 239/22 544/284 |
| 2003/0220318 A1 * | 11/2003 | Suzuki | A61K 31/395 514/211.03 |
| 2004/0235848 A1 * | 11/2004 | Okuzumi | A61K 31/403 514/248 |
| 2005/0101779 A1 * | 5/2005 | Sagi | C07D 239/54 544/285 |
| 2005/0222141 A1 * | 10/2005 | Sagi | A61K 31/517 514/227.8 |

(Continued)

FOREIGN PATENT DOCUMENTS

| CN | 1288457 A | 3/2001 |
|---|---|---|
| CN | 1407972 A | 4/2003 |

(Continued)

OTHER PUBLICATIONS

D. D'Ambrosio et al., 273 Journal of Immunological Methods 3-13 (2003).*
P.J. Koelink et al., 133 Pharmacology & Therapeutics, 1-18 (2012).*
E. R. Sutherland et al., 350 The New England Journal of Medicine, 2689-2697 (2004).*
S. Judge et al., 111 Pharmacology & Therapeutics, 224-259 (2006).*
V. Brinkmann et al., 9 Nature Reviews | Drug Discovery, 883-897 (2010).*
S Hariharan et al., 18 Annals of Oncology, 1400-1407 (2006).*
C. Kummer et al., 72 Biochemical Pharmacology, 1460-1468 (2006).*
D Picarella et al., 158 The Journal of Immunology, 2099-2106 (1997).*
W-J Pan et al., 78 British Journal of Clinical Pharmacology, 1315-1333 (2014).*
J. Rivera-Nieves et al., 174 The Journal of Immunology, 2343-2352 (2005).*
H.S. Souza et al., 45 Gut, 856-863 (1999); Fischer et al., Gut, 1-24 (2015).*

(Continued)

*Primary Examiner* — Alexander R Pagano
(74) *Attorney, Agent, or Firm* — Oblon, McClelland, Maier & Neustadt, L.L.P.

(57) ABSTRACT

Provided is a sulfonamide derivative represented by the following general formula (1) and having an α4 integrin inhibitory effect with high selectivity with a low effect on α4β1 and a high effect on α4β7, or a pharmaceutically acceptable salt thereof (in the general formula (1), A, B, D, E, $R_{41}$, and a to h are as described in the description).

27 Claims, No Drawings

(56) References Cited

U.S. PATENT DOCUMENTS

| | | | |
|---|---|---|---|
| 2005/0276803 A1 | 12/2005 | Chan et al. | |
| 2006/0223836 A1* | 10/2006 | Makino | C07D 239/22 514/266.31 |
| 2008/0075719 A1 | 3/2008 | Chan et al. | |
| 2008/0108634 A1* | 5/2008 | Sagi | A61K 31/517 514/258.1 |
| 2008/0280909 A1* | 11/2008 | Okuzumi | A61K 31/403 514/248 |
| 2009/0048236 A1* | 2/2009 | Suzuki | A61K 31/395 514/217 |
| 2011/0065918 A1* | 3/2011 | Makino | C07D 239/22 544/12 |
| 2012/0253041 A1* | 10/2012 | Makino | C07D 239/22 544/183 |
| 2015/0051395 A1 | 2/2015 | Ueno et al. | |

FOREIGN PATENT DOCUMENTS

| | | |
|---|---|---|
| CN | 1469867 A | 1/2004 |
| JP | 2012-098562 | 4/2012 |
| JP | 2013-054270 | 3/2013 |
| WO | 99/36393 A1 | 7/1999 |
| WO | 01/42225 A2 | 6/2001 |
| WO | 02/16329 A1 | 2/2002 |
| WO | 03/070709 A1 | 8/2003 |
| WO | 03/089410 A1 | 10/2003 |
| WO | 2005/061466 A1 | 7/2005 |
| WO | 2005/113003 A2 | 12/2005 |
| WO | 2013/161904 A1 | 10/2013 |

OTHER PUBLICATIONS

K. Zhi et al., Cellular Physiology and Biochemistry, 1876-1887 (2014).*

H. Yusuf-Makagiansar et al., 22 Medicinal Research Reviews, 146-167 (2002).*

International Search Report mailed Dec. 9, 2014 issued in PCT/JP2014/078644 (with English translation).

Office Action mailed Jan. 11, 2016 issued in corresponding Taiwanese patent application No. 103137436.

* cited by examiner

SULFONAMIDE DERIVATIVE AND PHARMACEUTICAL USE THEREOF

CROSS REFERENCE TO RELATED APPLICATIONS

The present application is a continuation application of International patent application PCT/JP2014/078644, filed on Oct. 28, 2014, published as WO/2015/064580 on May 7, 2015, the text of which is incorporated by reference, and claims the benefit of the filing date of Japanese application no. 2013-224694, filed on Oct. 29, 2013, the text of which is also incorporated by reference.

TECHNICAL FIELD

The present invention relates to a sulfonamide derivative or a pharmaceutically acceptable salt thereof, and a pharmaceutical composition containing such a compound as an active ingredient. In particular, the present invention relates to a compound that is useful as a therapeutic medicine or a preventive medicine for inflammatory disease in which an α4 integrin-dependent adhesion process is involved in pathological conditions.

BACKGROUND ART

Orally available compounds having an α4 integrin inhibitory effect that are useful as a therapeutic medicine or a preventive medicine for inflammatory disease in which an α4 integrin-dependent adhesion process is involved in pathological conditions have already been known. For example, Patent Literature 1 discloses a phenylalanine derivative represented by the general formula (1) or a pharmaceutically acceptable salt thereof, and a typical compound thereof has the following chemical structure.

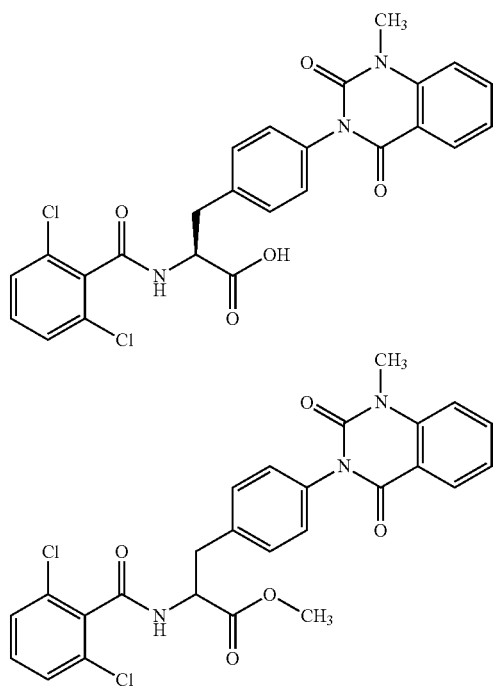

Further, Patent Literature 1 shows the results of VCAM inhibitory activity (VCAM-1/α4β1 binding assay) and (VCAM-1/α4β7 binding assay).

Further, Patent Literature 2 also discloses a phenylalanine derivative represented by the general formula (1) below and having $R_{12}$ ($R_{13}$) N—X1-group at an end or a pharmaceutically acceptable salt thereof.

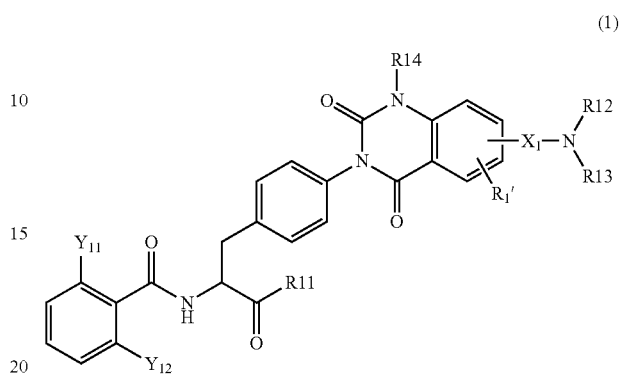

It is shown that this compound has high VCAM-1/α4β1 integrin inhibitory activity in the presence of serum as compared with the compound of Example 1 of Patent Literature 1. Further, Patent Literatures 3 and 4 also disclose compounds having an α4 integrin inhibitory effect.

CITATION LIST

Patent Literature

Patent Literature 1: WO 02/016329 A1
Patent Literature 2: WO 05/061466 A1
Patent Literature 3: WO 03/070709 A1
Patent Literature 4: WO 01/042225 A1

SUMMARY OF INVENTION

The present invention aims to provide a new compound having a chemical structural formula that is unknown so far and having excellent α4 integrin inhibitory effect.

In particular, the present invention aims to provide a new compound having an α4 integrin inhibitory effect with high selectivity with a low effect on α4β1 and a high effect on α4β7.

The present invention also aims to provide an orally available compound having excellent α4 integrin inhibitory effect.

The present invention also aims to provide a pharmaceutical composition containing such a new compound as described above and a pharmaceutically acceptable carrier.

The present invention also aims to provide a medicine containing such a new compound as described above.

The present invention also aims to provide a therapeutic agent or a preventive agent for inflammatory disease in which an α4β7 integrin-dependent adhesion process is involved in pathological conditions.

The present invention also aims to provide an α4 integrin inhibitor.

The present invention has been accomplished based on the finding that a sulfonamide derivative having a specific chemical structure and containing, at an end, a sulfonamide group having, as a substituent, a hetero ring group containing a heteroatom as a constituent element or a phenyl group, or a pharmaceutically acceptable salt thereof has excellent α4 integrin inhibitory activity, and use of such a compound can solve the above-described problems.

That is, the present invention includes the following aspects [1] to [17].

[1] A sulfonamide derivative represented by the general formula (1) below or a pharmaceutically acceptable salt thereof:

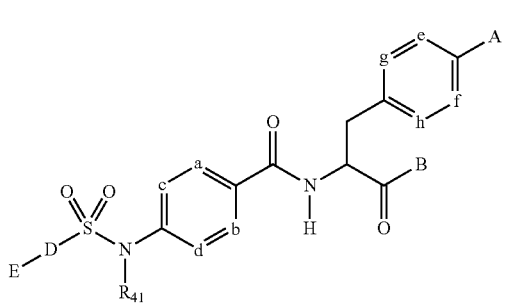

wherein

A represents a group represented by the general formula (2-1), (2-2), or (2-3) below:

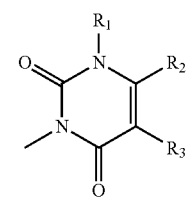

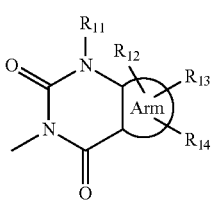

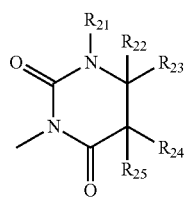

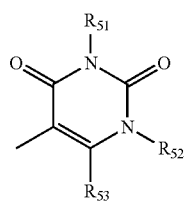

wherein

Arm is a cyclic alkyl group or an aromatic ring containing 0, 1, 2, 3, or 4 heteroatoms selected from oxygen atoms, sulfur atoms, and nitrogen atoms, R1, R11, R21, R51, and R52 each independently represent any one of a hydrogen atom, a halogen atom, a hydroxyl group, a lower alkyl group, a lower alkenyl group, a lower alkynyl group, a lower alkoxy group, a lower alkylthio group, a hydroxy-lower alkyl group, a hydroxy-lower alkenyl group, a hydroxy-lower alkoxy group, a halogeno-lower alkyl group, a halogeno-lower alkoxy group, a halogeno-lower alkylthio group, a halogeno-lower alkenyl group, a nitro group, a cyano group, an amino group, a lower alkylamino group, a lower alkylamino-lower alkyl group, a carboxyl group, a lower alkyloxycarbonyl group, a carbamoyl group, a lower alkanoyl group, an aroyl group, a lower alkylsulfonyl group, a sulfamoyl group, and an ammonium group, R12, R13, and R14 each independently represent any one of a hydrogen atom, a halogen atom, a hydroxyl group, a lower alkyl group, a lower alkenyl group, a lower alkynyl group, a lower alkoxy group, a lower alkylthio group, a hydroxy-lower alkyl group, a hydroxy-lower alkenyl group, a hydroxy-lower alkoxy group, a halogeno-lower alkyl group, a halogeno-lower alkoxy group, a halogeno-lower alkylthio group, a halogeno-lower alkenyl group, a nitro group, a cyano group, an amino group, a lower alkylamino group, a lower alkoxy-lower alkylene group, a lower alkylthio-lower alkylene group, a lower alkylamino-lower alkylene group, a lower alkylamino-lower alkyl group, a carboxyl group, a lower alkyloxycarbonyl group, a carbamoyl group, a lower alkanoyl group, an aroyl group, a lower alkylsulfonyl group, a sulfamoyl group, and an ammonium group, and R2, R3, R22, R23, R24, R25, and R53 each independently represent any one of a hydrogen atom, a halogen atom, a hydroxyl group, a lower alkyl group, a lower alkenyl group, a lower alkynyl group, a lower alkoxy group, a lower alkylthio group, a hydroxy-lower alkyl group, a hydroxy-lower alkenyl group, a hydroxy-lower alkoxy group, a halogeno-lower alkyl group, a halogeno-lower alkoxy group, a halogeno-lower alkylthio group, a halogeno-lower alkenyl group, a nitro group, a cyano group, an amino group, a lower alkylamino group, a lower alkylamino-lower alkyl group, a carboxyl group, a lower alkyloxycarbonyl group, a carbamoyl group, a lower alkanoyl group, an aroyl group, a lower alkylsulfonyl group, a sulfamoyl group, and an ammonium group, B represents any one of an alkoxy group having 1 to 10 carbon atoms, a hydroxyl group, or a hydroxyamino group, these groups being optionally substituted with a substituent selected from the group consisting of an aryl group, a hydroxyl group, an alkyl group having 1 to 10 carbon atoms, a lower alkoxy group, a lower alkylamino group, a halogen atom, and a heterocyclic group, R41 represents a hydrogen atom or a lower alkyl group, a, b, c, and d independently represent C—R31, C—R32, C—R33, or C—R34, respectively, wherein one or two of a, b, c, and d may represent a nitrogen atom, R31, R32, R33, and R34 each independently represent any one of a hydrogen atom, a halogen atom, a lower alkyl group, a lower alkoxy group, and a nitro group, wherein any one of R31, R32, R33, and R34 is a halogen atom or a lower alkyl group, e, f, g, and h independently represent C—R35, C—R36, C—R37, or C—R38, respectively, wherein one or two of e, f, g, and h may represent a nitrogen atom, R35, R36, R37, and R38 each independently represent any one of a hydrogen atom, a halogen atom, a lower alkyl group, a lower alkoxy group, and a nitro group, D represents a phenyl group or a heterocyclic group, optionally having a substituent selected from the group consisting of a halogen atom, a hydroxyl group, a lower alkyl group, a lower alkenyl group, a lower alkynyl group, a lower alkoxy group, a lower alkylthio group, a hydroxy-lower alkyl group, a hydroxy-lower alkenyl group, a hydroxy-lower alkoxy group, a halogeno-lower alkyl group, a halogeno-lower alkoxy group, a halogeno-lower alkylthio group, a halogeno-lower alkenyl group, a nitro group, a cyano group, an amino group, a carboxyl group, a lower alkyloxycarbonyl group, a carbamoyl group, a lower alkanoyl group, an aroyl group, a lower alkylsulfonyl group, a sulfamoyl group, a lower alkoxy-lower alkylene group, a lower alkylthio-lower alkylene group, a lower alkylamino-lower alkylene group, and an ammonium group, when A represents a group represented by the general formula (2-1), (2-2), or (2-3), E represents: a 5- or 6-membered heterocyclic group substituted with a substituent selected from the group consisting of a 3- to 8-membered saturated ring group containing a nitrogen atom connected by a carbon atom, a 3- to 8-membered saturated or unsaturated ring group containing a heteroatom selected from an oxygen atom and a sulfur atom, a lower alkoxy-lower alkylene group, a lower alkylthio-lower alkylene group, a lower alkylamino-lower alkylene group, a lower alkylamino group, and a lower alkenylamino group; or a 5- or 6-membered cyclic ketone group containing 1 to 4 nitrogen atoms as atoms constituting the ring, the cyclic ketone group being substituted with a lower alkyl group or a lower alkenyl group, and when A represents a group represented by the general formula (2-4), E represents: a phenyl group or a 5- or 6-membered heterocyclic group optionally having a substituent selected from the group consisting of a halogen atom, a hydroxyl group, a lower alkyl group, a lower alkenyl group, a lower alkynyl group, a lower alkoxy group, a lower alkylthio group, a hydroxy-lower alkyl group, a hydroxy-lower alkenyl group, a hydroxy-lower alkoxy group, a halogeno-lower alkyl group, a halogeno-lower alkoxy group, a halogeno-lower alkylthio group, a halogeno-lower alkenyl group, a nitro group, a cyano group, an amino group, a 4- to 6-membered cyclic amino group, a carboxyl group, a lower alkyloxycarbonyl group, a carbamoyl group, a lower alkanoyl group, an aroyl group, a lower alkylsulfonyl group, a sulfamoyl group, and an ammonium group; an aminocarbonyl group optionally having a substituent selected from the group consisting of a hydroxyl group, a lower alkyl group, a lower alkenyl group, a lower alkynyl group, a lower alkoxy group, a hydroxy-lower alkyl group, a hydroxy-lower alkenyl group, a hydroxy-lower alkoxy group, a halogeno-lower alkyl group, a halogeno-lower alkoxy group, a halogeno-lower alkenyl group, an amino group, a lower alkylamino group, an aryl group, a heterocyclic group, a heterocyclic lower alkyl group, a lower alkylsulfonyl group, and a sulfamoyl group; a hydrogen atom; a halogen atom; a hydroxyl group; a lower alkyl group; a lower alkenyl group; a lower alkynyl group; a lower alkoxy group; a lower alkylthio group; a hydroxy-lower alkyl group; a hydroxy-lower alkenyl group; a hydroxy-lower alkoxy group; a halogeno-lower alkyl group; a halogeno-lower alkoxy group; a halogeno-lower alkylthio group; a halogeno-lower alkenyl group; a nitro group; a cyano group; an amino group; a carboxyl group; a dihydroxyboryl group; a lower alkylcarbonyl group; a lower alkyloxycarbonyl group; a carbamoyl group; a lower alkanoyl group; an aroyl group; a lower alkylsulfonyl group; a sulfamoyl group; an ammonium group; a lower alkylaminoalkylene group; a 5- or 6-membered heterocyclic group substituted with a substituent selected from the group consisting of a 3- to 8-membered saturated ring group containing a nitrogen atom connected by a carbon atom, a 3- to 8-membered saturated or unsaturated ring group containing a heteroatom selected from an oxygen atom and a sulfur atom, a lower alkoxy-lower alkylene group, a lower alkylthio-lower alkylene group, a lower alkylamino-lower alkylene group, a lower alkylamino group, and a lower alkenylamino group; or a 5- or 6-membered cyclic ketone group containing 1 to 4 nitrogen atoms as atoms constituting the ring, the cyclic ketone group being substituted with a lower alkyl group or a lower alkenyl group, wherein the lower alkylcarbonyl group and the lower alkyloxycarbonyl group may form a fused ring by being bonded to the phenyl group of D, provided that the sulfonamide derivative excludes sulfonamide derivatives selected from the group consisting of (a) to (h) below:

(a) (2S)-2-[[2,5-difluoro-4-[[4-(2-tetrahydropyran-4-ylpyrimidin-5-yl)phenyl]sulfonylamino]benzoyl]amino]-3-[4-(1-methyl-2,4-dioxo-pyrido[3,4-d]pyrimidin-3-yl)phenyl]propanoic acid

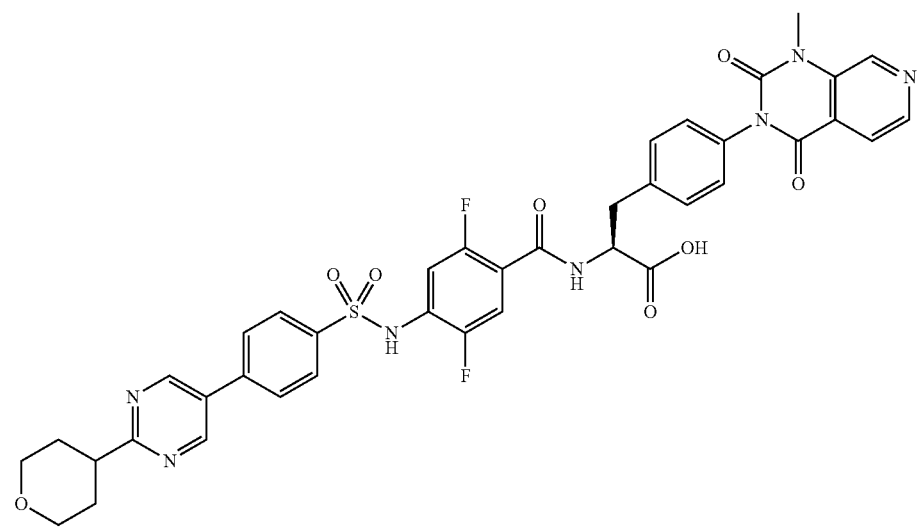

(b) cyclohexyl (2S)-2-[[2,5-difluoro-4-[[4-(2-tetra-hydropyran-4-ylpyrimidin-5-yl)phenyl]sulfonylamino]benzoyl]amino]-3-[4-(1-methyl-2,4-dioxo-pyrido[3,4-d]pyrimidin-3-yl)phenyl]propionate
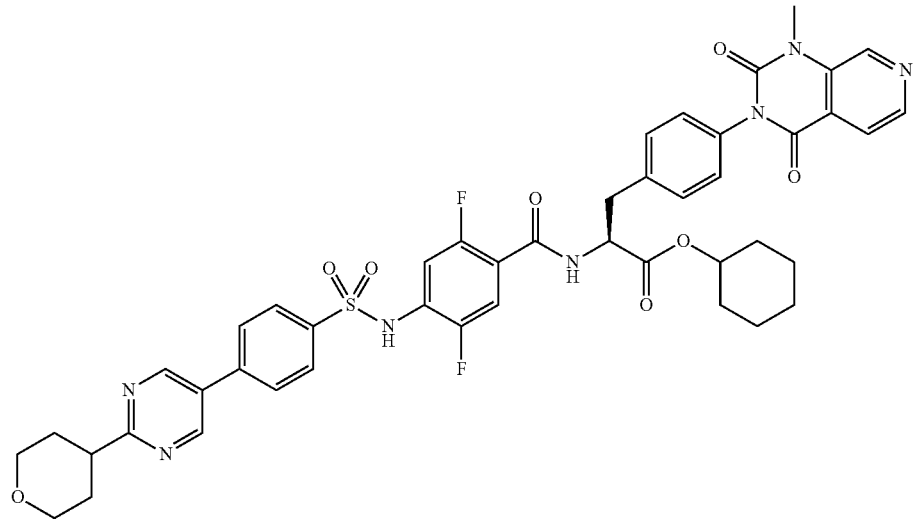 [SMILES: Cn1c(=O)n(-c2ccc(C[C@H](NC(=O)c3cc(F)c(NS(=O)(=O)c4ccc(-c5cnc(C6CCOCC6)nc5)cc4)cc3F)C(=O)OC3CCCCC3)cc2)c(=O)c2ccncc21]
(c) (2S)-2-[[2,5-difluoro-4-[[4-(2-tetrahydropyran-4-ylpyrimidin-5-yl)phenyl]sulfonylamino]benzoyl]amino]-3-[6-(1-methyl-2,4-dioxo-pyrido[3,4-d]pyrimidin-3-yl)-3-pyridyl]propanoic acid
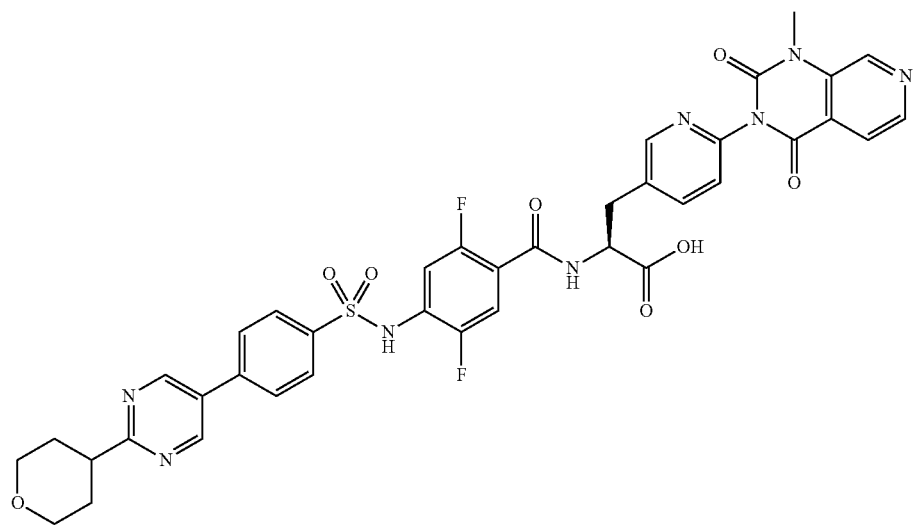 [SMILES: Cn1c(=O)n(-c2ccc(C[C@H](NC(=O)c3cc(F)c(NS(=O)(=O)c4ccc(-c5cnc(C6CCOCC6)nc5)cc4)cc3F)C(=O)O)cn2)c(=O)c2ccncc21]

(d) cyclohexyl (2S)-2-[[2,5-difluoro-4-[[4-(2-tetrahydropyran-4-ylpyrimidin-5-yl)phenyl]sulfonylamino]benzoyl]amino]-3-[6-(1-methyl-2,4-dioxopyrido[3,4-d]pyrimidin-3-yl)-3-pyridyl]propanoate
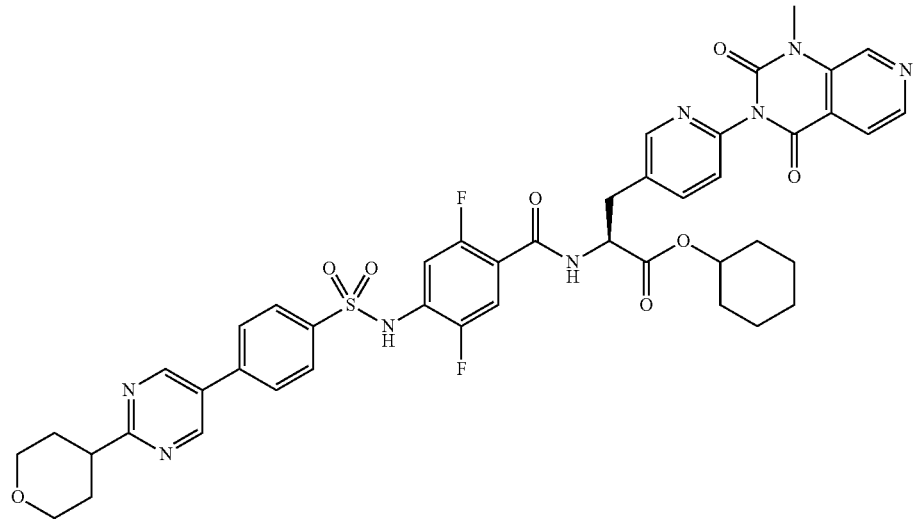 [SMILES: Cn1c(=O)n(-c2ccc(C[C@H](NC(=O)c3cc(F)c(NS(=O)(=O)c4ccc(-c5cnc(C6CCOCC6)nc5)cc4)cc3F)C(=O)OC3CCCCC3)cn2)c(=O)c2ccncc21]
(e) (2S)-2-[[2,5-difluoro-4-[[4-[2-(methoxymethyl)pyrimidin-5-yl]phenyl]sulfonyl amino]benzoyl]amino]-3-[4-(1-methyl-2,4-dioxo-pyrido[3,4-d]pyrimidin-3-yl)phenyl]propanoic acid
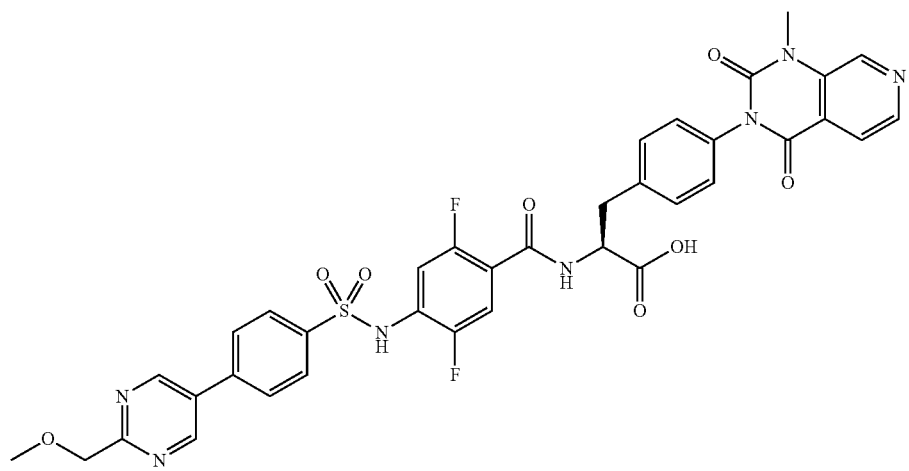 [SMILES: COCc1ncc(-c2ccc(S(=O)(=O)Nc3cc(F)c(C(=O)N[C@@H](Cc4ccc(-n5c(=O)c6ccncc6n(C)c5=O)cc4)C(=O)O)cc3F)cc2)cn1]

(f) cyclohexyl (2S)-2-[[2,5-difluoro-4-[[4-[2-(methoxymethyl)pyrimidin-5-yl]phenyl]sulfonyl amino]benzoyl]amino]-3-[4-(1-methyl-2,4-dioxo-pyrido[3,4-d]pyrimidin-3-yl)phenyl]propanoate
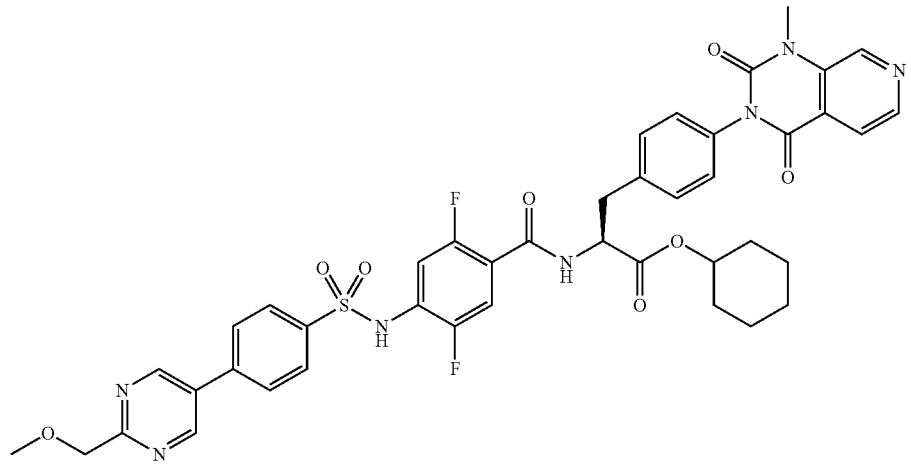 [SMILES: COCc1ncc(-c2ccc(S(=O)(=O)Nc3cc(F)c(C(=O)N[C@@H](Cc4ccc(-n5c(=O)c6ccncc6n(C)c5=O)cc4)C(=O)OC4CCCCC4)cc3F)cc2)cn1]
(g) (2S)-2-[[2,5-difluoro-4-[[4-[2-(methoxymethyl) pyrimidin-5-yl]phenyl]sulfonyl amino]benzoyl]amino]-3-[6-(1-methyl-2,4-dioxo-pyrido[3,4-d]pyrimidin-3-yl)-3-pyridyl]propanoic acid
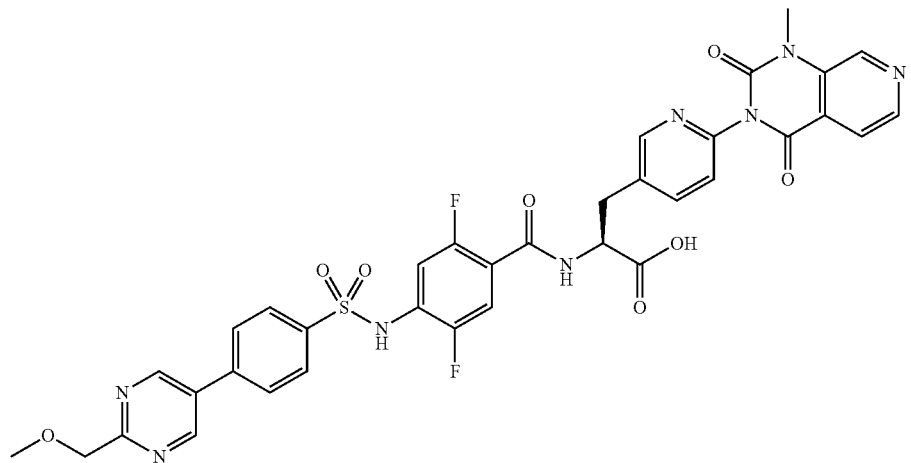 [SMILES: COCc1ncc(-c2ccc(S(=O)(=O)Nc3cc(F)c(C(=O)N[C@@H](Cc4ccc(-n5c(=O)c6ccncc6n(C)c5=O)nc4)C(=O)O)cc3F)cc2)cn1]
and (h) cyclohexyl (2S)-2-[[2,5-difluoro-4-[[4-[2-(methoxymethyl)pyrimidin-5-yl]phenyl]sulfonylamino]benzoyl]amino]-3-[6-(1-methyl-2,4-dioxo-pyrido[3,4-d]pyrimidin-3-yl)-3-pyridyl]propanoate

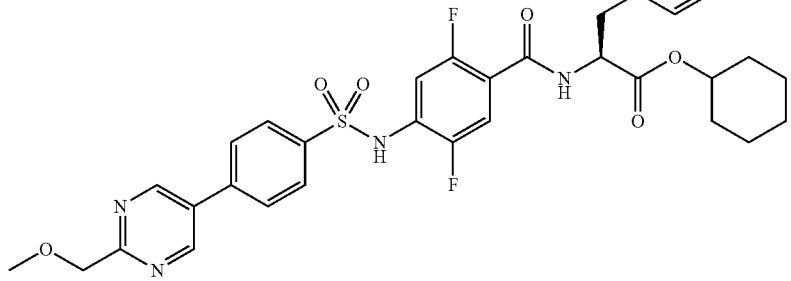

[2] The sulfonamide derivative or a pharmaceutically acceptable salt thereof according to [1], wherein D is a phenyl group optionally having a substituent selected from the group consisting of a lower alkyl group, a halogen atom, a hydroxyl group, and a lower alkoxy group.

[3] The sulfonamide derivative or a pharmaceutically acceptable salt thereof according to [1], wherein D is a 6-membered aromatic heterocyclic group optionally having a substituent selected from the group consisting of a lower alkyl group, a halogen atom, and a lower alkoxy group, and having a nitrogen atom as an atom constituting the ring.

[4] The sulfonamide derivative or a pharmaceutically acceptable salt thereof according to [4], wherein the heterocyclic group of D is a pyridyl group or a pyrrole group optionally having a substituent selected from the group consisting of a lower alkyl group, a halogen atom, and a lower alkoxy group.

[5] The sulfonamide derivative or a pharmaceutically acceptable salt thereof according to any one of [1] to [4], wherein the 5- or 6-membered heterocyclic group of E is selected from the group consisting of a pyridyl group, a pyridazyl group, a pyrimidyl group, a pyrazinyl group, a pyrrolyl group, a triazolyl group, and a tetrazole group, and the cyclic ketone group of E is a 5- or 6-membered cyclic ketone group containing 2 or 3 nitrogen atoms as atoms constituting the ring.

[6] The sulfonamide derivative or a pharmaceutically acceptable salt thereof according to any one of [1] to [4], wherein A represents a group represented by the general formula (2-4), and E is a 5- or 6-membered aromatic heterocyclic group containing 1, 2, 3, or 4 heteroatoms selected from oxygen atoms, sulfur atoms, or nitrogen atoms and optionally having a substituent selected from the group consisting of a lower alkyl group, a lower alkoxy group, a lower alkoxy-lower alkylene group, and a halogen atom.

[7] The phenylalanine derivative or a pharmaceutically acceptable salt thereof according to [6], wherein the aromatic heterocyclic group is selected from the group consisting of a pyridyl group, a pyridazyl group, a pyrimidyl group, a pyrazinyl group, a pyrrolyl group, a furanyl group, a thiophenyl group, a thiazolyl group, an oxazolyl group, a triazolyl group, and a tetrazole group.

[8] The sulfonamide derivative or a pharmaceutically acceptable salt thereof according to any one of [1] to [4], wherein A represents a group represented by the general formula (2-4), and E is an aminocarbonyl group optionally substituted with a lower alkyl group, a heterocyclic group, or a heterocyclic lower alkyl group, or a lower alkylaminoalkylene group.

[9] The sulfonamide derivative or a pharmaceutically acceptable salt thereof according to any one of [1] to [4], and [5], wherein the heterocyclic group of E is a pyridyl group, a pyrimidyl group, a triazolyl group, and a tetrazole group optionally having a substituent selected from the group consisting of a 3- to 8-membered saturated or unsaturated ring group containing a heteroatom selected from an oxygen atom and a sulfur atom, a lower alkoxy-lower alkylene group, or a lower alkylamino-lower alkylene group.

[10] The sulfonamide derivative or a pharmaceutically acceptable salt thereof according to any one of [1] to [5] and [9], wherein A represents a group represented by the general formula (2-2), and R11, R12, and R13 are selected from the group consisting of a lower alkyl group, a lower alkoxy group, a lower alkoxy-lower alkylene group, a lower alkylamino-lower alkylene group, and a halogen atom.

[11] The sulfonamide derivative or a pharmaceutically acceptable salt thereof according to any one of [1] to [10], wherein B is a lower alkoxy group optionally substituted with a substituent selected from the group consisting of a lower alkyl group, a lower alkoxy group, a lower alkylamino group, a halogen atom, and a heterocyclic group; or a hydroxyl group.

[12] The sulfonamide derivative or a pharmaceutically acceptable salt thereof according to any one of [1] to [6],

[8], [9], [10], and [11], wherein the lower alkyl group is a straight-chain, branched-chain, or cyclic alkyl group.

[13] The sulfonamide derivative or a pharmaceutically acceptable salt thereof according to any one of [1] to [12], wherein R1, R11, R21, R51, and R52 are lower alkyl groups.

[14] The sulfonamide derivative or a pharmaceutically acceptable salt thereof according to any one of [1] to [13], wherein Arm is selected from the group consisting of a phenyl group, a pyridyl group, a pyrimidyl group, and an imidazolyl group.

[15] The sulfonamide derivative or a pharmaceutically acceptable salt thereof according to any one of [1] to [4], wherein
A represents a group represented by the general formula (2-2), and
E represents a 5- or 6-membered heterocyclic group containing 1 to 4 nitrogen atoms, the 5- or 6-membered heterocyclic group being substituted with a substituent selected from the group consisting of a lower alkyl group, a lower alkoxy-lower alkylene group, and a 5- or 6-membered heterocyclic group containing an oxygen atom; or a cyclic ketone group containing 1 to 4 nitrogen atoms, the cyclic ketone group being substituted with a lower alkyl group or a lower alkenyl group.

[16] The sulfonamide derivative or a pharmaceutically acceptable salt thereof according to [15], wherein
B is optionally substituted with a substituent selected from the group consisting of an alkyl group having 1 to 10 carbon atoms, a lower alkoxy group, and a heterocyclic group containing 1 to 4 heteroatoms selected from oxygen atoms and nitrogen atoms, and
Arm is a pyridyl group.

[17] The sulfonamide derivative or a pharmaceutically acceptable salt thereof according to any one of [1] to [4], wherein
A represents a group represented by the general formula (2-4),
E is a 5- or 6-membered heterocyclic group containing an oxygen atom, or a 5- or 6-membered heterocyclic group containing 1 to 4 nitrogen atoms, and
E optionally has a substituent selected from a lower alkyl group, a lower alkoxy-lower alkylene group, and a 5- or 6-membered heterocyclic group containing an oxygen atom.

[18] A pharmaceutical composition comprising the sulfonamide derivative or a pharmaceutically acceptable salt thereof according to any one of [1] to [17].

[19] A therapeutic agent or a preventive agent for inflammatory disease in which an α4β7 integrin-dependent adhesion process is involved in pathological conditions, the agent comprising: the sulfonamide derivative or a pharmaceutically acceptable salt thereof according to any one of [1] to [17] as an active ingredient.

[20] An α4β7 integrin inhibitor comprising: the sulfonamide derivative or a pharmaceutically acceptable salt thereof according to any one of [1] to [17] as an active ingredient.

DESCRIPTION OF EMBODIMENTS

The term "lower" of the lower alkyl group or the like in this description means a group having 1 to 6 carbon atoms, preferably a group having 1 to 4 carbon atoms. An alkyl group, an alkenyl group, and an alkynyl group serving as a component of an alkyl group, an alkenyl group, an alkynyl group, an alkoxy group, an alkylthio group, an alkanoyl group, an alkylamino group, or the like can be straight chain or branched. Alternatively, they may be cyclic. Examples of the alkyl group include a methyl group, an ethyl group, a propyl group, an isopropyl group, a butyl group, a secondary butyl group, a tertiary butyl group, a pentyl group, a 2-pentyl group, a 3-pentyl group, a hexyl group, a cyclopropyl group, a cyclobutyl group, a cyclopentyl group, a cyclohexyl group, a cyclopropylmethyl group, and a cyclopropylethyl group, preferably having 1 to 6 carbon atoms, more preferably having 1 to 4 carbon atoms. Examples of the alkenyl group include a vinyl group, a propenyl group, a butenyl group, and a pentenyl group, preferably having 2 to 6 carbon atoms, more preferably having 2 to 4 carbon atoms. Examples of the alkynyl group include an ethynyl group, a propynyl group, and a butynyl group, preferably having 2 to 6 carbon atoms, more preferably having 2 to 4 carbon atoms.

Examples of the alkoxy group include a methoxy group, an ethoxy group, a propyloxy group, and an isopropyloxy group, preferably having 1 to 6 carbon atoms, more preferably having 1 to 4 carbon atoms. Examples of the heteroatom include nitrogen, oxygen, and sulfur. Examples of the halogen atom include fluorine, chlorine, bromine, and iodine. Examples of the halogeno-alkyl group include a chloromethyl group, a trichloromethyl group, a trifluoromethyl group, a trifluoroethyl group, and a pentafluoromethyl group. Examples of the halogeno-alkoxy group include a trichloromethoxy group, and a trifluoromethoxy group. Examples of the hydroxyalkyl group include a hydroxymethyl group, and a hydroxyethyl group.

In this description, the aryl group means a substituted or unsubstituted aryl group, and examples thereof include a phenyl group, a 1-naphthyl group, and a 2-naphthyl group, in which a phenyl group and a substituted phenyl group are preferable, where a halogen atom, an alkoxy group, an alkyl group, a hydroxyl group, a halogeno-alkyl group, and a halogeno-alkoxy group are particularly preferable as a substituent. The heterocyclic group means a 4- to 7-membered hetero ring group that consists of one to three rings and that is composed of carbon and nitrogen, oxygen, sulfur, or the like, and specific examples thereof include a pyridyl group, a dihydropyranyl group, a tetrahydropyranyl group, a pyridazyl group, a pyrimidyl group, a pyrazyl group, a pyrrolyl group, a furyl group, a thienyl group, a thienyl group, a thiazolyl group, a triazolyl group, an isoxazolyl group, an isothiazolyl group, an oxazolyl group, an indolyl group, a quinolyl group, an isoquinolyl group, a benzoimidazolyl group, a pyrazolyl group, an imidazolyl group, a thiadiazolyl group, a pyrrolidyl group, a piperidyl group, a piperazyl group, a morpholyl group, an oxetanyl ring, an isoindolyl group, a benzofuryl group, an isobenzofuryl group, a benzothienyl group, a benzopyrazolyl group, a benzoimidazolyl group, a benzoxazolyl group, and a benzothiazolyl group, in which a pyridyl group, a pyrazyl group, a pyrimidyl group, a furyl group, and a thienyl group are preferable.

In the general formula (1) of the present invention, it is preferable that (i) D be a phenyl group optionally having a substituent selected from the group consisting of a lower alkyl group, a halogen atom, a hydroxy group, and a lower alkoxy group, or (ii) D be a 6-membered aromatic heterocyclic group optionally having a substituent selected from the group consisting of a lower alkyl group, a halogen atom, and a lower alkoxy group and having a nitrogen atom as an atom constituting the ring. It is particularly preferable that the heterocyclic group of D be a pyridyl group.

Further, in the general formula (1) of the present invention, B represents any one of an alkoxy group having 1 to 10 carbon atoms, a hydroxyl group, or a hydroxyamino group, and these groups are optionally substituted with a substituent selected from the group consisting of an aryl group, a hydroxyl group, an alkyl group having 1 to 10 carbon atoms, a lower alkoxy group, a lower alkylamino group, a halogen atom, and a heterocyclic group, in which a lower alkoxy group optionally substituted with a substituent selected from the group consisting of a lower alkyl group, a lower alkoxy group, a lower alkylamino group, a halogen atom, and a heterocyclic group, or a hydroxyl group is preferable. The heterocyclic group when B is any one of an alkoxy group substituted with a heterocyclic group and having 1 to 10 carbon atoms, a hydroxyl group, or a hydroxyamino group is preferably a saturated ring group containing a heteroatom selected from a nitrogen atom, an oxygen atom, and a sulfur atom, and specific examples thereof include a morpholyl group, a piperazyl group, a tetrahydropyranyl group, and an oxetanyl group, in which a tetrahydropyranyl group is preferable.

Further, in the general formula (1) of the present invention, when A represents a group represented by the general formula (2-1), (2-2), or (2-3), E preferably represents a 5- or 6-membered heterocyclic group substituted with a substituent selected from the group consisting of a 3- to 8-membered saturated ring group containing a nitrogen atom connected by a carbon atom, a 3- to 8-membered saturated or unsaturated ring group containing a heteroatom selected from an oxygen atom and a sulfur atom, a lower alkoxyalkylene group, a lower alkylthioalkylene group, a lower alkylaminoalkylene group, a lower alkylamino group, and a lower alkenylamino group (preferably, a 5- or 6-membered cyclic amino group containing 1 to 4 nitrogen atoms having the above-described substituent); or a 5- or 6-membered cyclic ketone group containing 1 to 4 nitrogen atoms as atoms constituting the ring, the cyclic ketone group being substituted with a lower alkyl group or a lower alkenyl group, in combination with the above-described (i) or (ii).

It is preferable that the 5- or 6-membered heterocyclic group of E be selected from the group consisting of a pyridyl group, a pyridazyl group, a pyrimidyl group, a pyrazyl group, a pyrrolyl group, a triazolyl group, and a tetrazole group, and the cyclic ketone group be a 5- or 6-membered cyclic ketone group containing 2 or 3 nitrogen atoms as atoms constituting the ring.

Further, the lower alkylene group of the lower alkoxy-lower alkylene group, the lower alkylthio-lower alkylene group, or the lower alkylamino-lower alkylene group preferably has 1 to 6 carbon atoms, more preferably has 1 to 3 carbon atoms, and the lower alkyl group preferably has 1 to 3 carbon atoms.

Further, the 3- to 8-membered saturated or unsaturated ring group containing a heteroatom selected from an oxygen atom and a sulfur atom is preferably a 5- or 6-membered saturated or unsaturated ring group containing one heteroatom selected from an oxygen atom and a sulfur atom, and specifically, tetrahydropyran, tetrahydrofuran, oxetane, furan, thiophene, or the like is preferable.

The 3- to 8-membered saturated ring group containing a nitrogen atom is preferably a 5- or 6-membered saturated ring group containing one nitrogen atom, and specifically, pyrrolidine, piperidine, or the like is preferable.

Further, the cyclic ketone group is specifically preferably a pyrimidinone group, and the lower alkyl group or the lower alkenyl group is preferably bonded to the nitrogen atoms constituting the cyclic ketone group.

When A represents a group represented by the general formula (2-4), E preferably represents a phenyl group or a 5- or 6-membered heterocyclic group optionally having a substituent selected from the group consisting of a halogen atom, a hydroxyl group, a lower alkyl group, a lower alkenyl group, a lower alkynyl group, a lower alkoxy group, a lower alkylthio group, a hydroxy-lower alkyl group, a hydroxy-lower alkenyl group, a hydroxy-lower alkoxy group, a halogeno-lower alkyl group, a halogeno-lower alkoxy group, a halogeno-lower alkylthio group, a halogeno-lower alkenyl group, a nitro group, a cyano group, an amino group, a carboxyl group, a lower alkyloxycarbonyl group, a carbamoyl group, a lower alkanoyl group, an aroyl group, a lower alkylsulfonyl group, a sulfamoyl group, and an ammonium group; an aminocarbonyl group optionally having a substituent selected from the group consisting of a hydroxyl group, a lower alkyl group, a lower alkenyl group, a lower alkynyl group, a lower alkoxy group, a hydroxy-lower alkyl group, a hydroxy-lower alkenyl group, a hydroxy-lower alkoxy group, a halogeno-lower alkyl group, a halogeno-lower alkoxy group, a halogeno-lower alkenyl group, an amino group, a lower alkylamino group, an aryl group, a heterocyclic group, a lower alkylsulfonyl group, and a sulfamoyl group; a hydrogen atom; a halogen atom; a hydroxyl group; a lower alkyl group; a lower alkenyl group; a lower alkynyl group; a lower alkoxy group; a lower alkylthio group; a hydroxy-lower alkyl group; a hydroxy-lower alkenyl group; a hydroxy-lower alkoxy group; a halogeno-lower alkyl group; a halogeno-lower alkoxy group; a halogeno-lower alkylthio group; a halogeno-lower alkenyl group; a nitro group; a cyano group; an amino group; a carboxyl group; a dihydroxyboryl group; a lower alkyloxycarbonyl group; a carbamoyl group; a lower alkanoyl group; an aroyl group; a lower alkylsulfonyl group; a sulfamoyl group; an ammonium group; a lower alkylaminoalkylene group; or a 5- or 6-membered heterocyclic group substituted with a substituent selected from the group consisting of a 3- to 8-membered saturated ring group containing a nitrogen atom connected by a carbon atom, a 3- to 8-membered saturated or unsaturated ring group containing a heteroatom selected from an oxygen atom and a sulfur atom, a lower alkoxyalkylene group, a lower alkylthioalkylene group, a lower alkylaminoalkylene group, a lower alkylamino group, and a lower alkenylamino group (preferably, a 5- or 6-membered cyclic amino group containing 1 to 4 nitrogen atoms having the above-described substituent); or a 5- or 6-membered cyclic ketone group containing 1 to 4 nitrogen atoms as atoms constituting the ring, the cyclic ketone group being substituted with a lower alkyl group or a lower alkenyl group.

Note that, preferable examples of E are the same as described for the case where A represents a group represented by the general formula (2-1), (2-2), or (2-3).

Further, when A represents a group represented by the general formula (2-4), E is preferably a 5- or 6-membered aromatic heterocyclic group containing 1, 2, 3, or 4 heteroatoms selected from oxygen atoms, sulfur atoms, or nitrogen atoms and optionally having a substituent selected from the group consisting of a lower alkyl group, a lower alkoxy group, and a halogen atom, in combination with the above-described (i) or (ii). It is preferable that the aromatic heterocyclic group be selected from the group consisting of a pyridyl group, a pyridazyl group, a pyrimidyl group, a pyrazinyl group, a pyrrolyl group, a furanyl group, a thiophenyl group, a thiazolyl group, an oxazolyl group, a triazolyl group, and a tetrazole group.

When A represents a group represented by the general formula (2-4), E is preferably an aminocarbonyl group optionally substituted with a lower alkyl or a heterocyclic or heterocyclic lower alkyl group; or a lower alkylaminoalkylene group, in combination with the above-described (i) or (ii). Further, E is also preferably a pyridyl group, a pyrimidyl group, a triazolyl group, or a pyrrolyl group optionally having a lower alkyl group or a 4 to 6-membered cyclic amino group; or an aminocarbonyl group optionally substituted with a lower alkyl or heterocyclic lower alkyl group. Examples of the 4 to 6-membered cyclic amino group include an azetidinyl group, and examples of the heterocyclic lower alkyl group include a tetrapyran lower alkyl group.

Further, when E represents a lower alkylcarbonyl group or a lower alkyloxycarbonyl group, examples of a fused ring formed by such a group bonding to the phenyl group of D include a 1-oxoindanyl group and a 3-oxo-1H-isobenzofuranyl group.

Further, in the general formula (1) of the present invention, or in any one of the above-described preferable aspects, R1, R11, R21, R51, and R52 are preferably lower alkyl groups.

Further, in the general formula (1) of the present invention, or in any one of the above-described preferable aspects, Arm is preferably selected from the group consisting of a phenyl group, a pyridyl group, a pyrimidyl group, and an imidazolyl group.

Further, in the general formula (1) of the present invention, or in any one of the above-described preferable aspects, it is preferable that one of R31, R32, R33, and R34 be a halogen atom with the others being hydrogen atoms, two of them be halogen atoms with the others being hydrogen atoms, or four of them be halogen atoms.

Further, in the general formula (1) of the present invention, or in any one of the above-described preferable aspects, it is preferable that g be a carbon or nitrogen atom, and e be a carbon or nitrogen atom.

In the present invention, compounds represented by the following formulae or pharmaceutically acceptable salts thereof are particularly preferable. Further, prodrugs of these compounds or pharmaceutically acceptable salts thereof are also preferable.

(2S)-2-[[2,5-Difluoro-4-[[4-(2-tetrahydropyran-4-ylpyrimidin-5-yl)phenyl]sulfonylamino]benzoyl]amino]-3-[5-(1-methyl-2,4-dioxo-pyrido[3,4-d]pyrimidin-3-yl-2-pyridyl]propionic acid

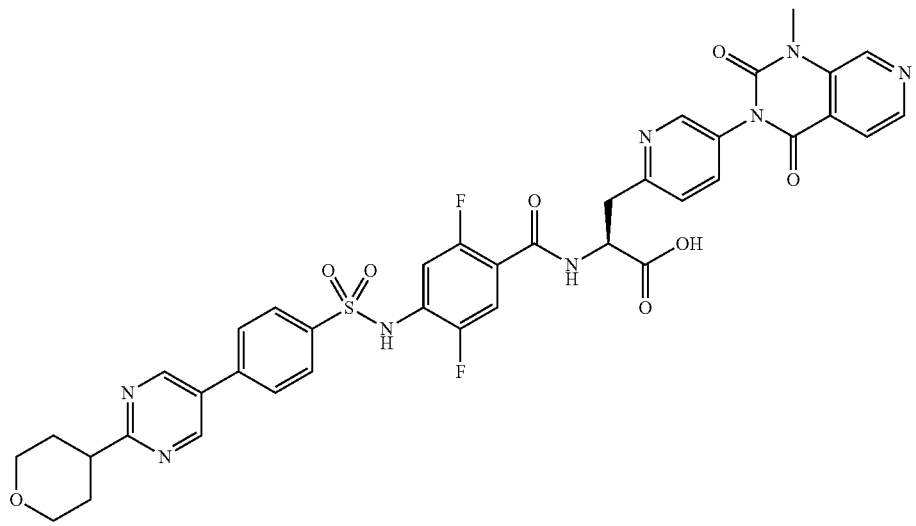 [SMILES: Cn1c(=O)n(-c2ccc(C[C@H](NC(=O)c3cc(F)c(NS(=O)(=O)c4ccc(-c5cnc(C6CCOCC6)nc5)cc4)cc3F)C(=O)O)nc2)c(=O)c2ccncc21]

Cyclohexyl (2S)-2-[[2,5-difluoro-4-[[4-(2-tetrahydropyran-4-ylpyrimidin-5-yl)phenyl]sulfonylamino]benzoyl]amino]-3-[5-(1-methyl-2,4-dioxo-pyrido[3,4-d]pyrimidin-3-yl)-2-pyridyl]propanoate
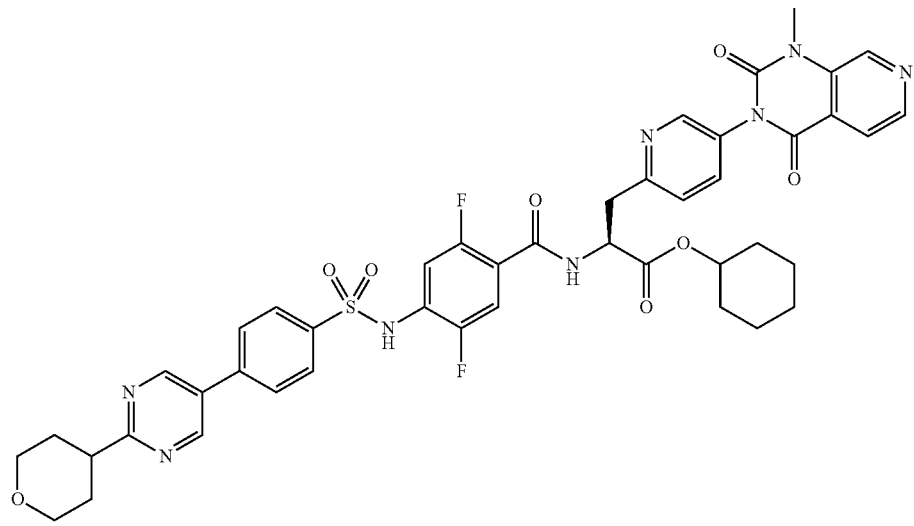 [SMILES: Cn1c(=O)n(-c2ccc(C[C@H](NC(=O)c3cc(F)c(NS(=O)(=O)c4ccc(-c5cnc(C6CCOCC6)nc5)cc4)cc3F)C(=O)OC3CCCCC3)nc2)c(=O)c2ccncc21]
Isopropyl (2S)-2-[[2,5-difluoro-4-[[4-[2-(methoxymethyl)pyrimidin-5-yl]phenyl]sulfonyl amino]benzoyl]amino]-3-[6-(1-methyl-2,4-dioxo-pyrido[3,4-d]pyrimidin-3-yl)-3-pyridyl]propanoate
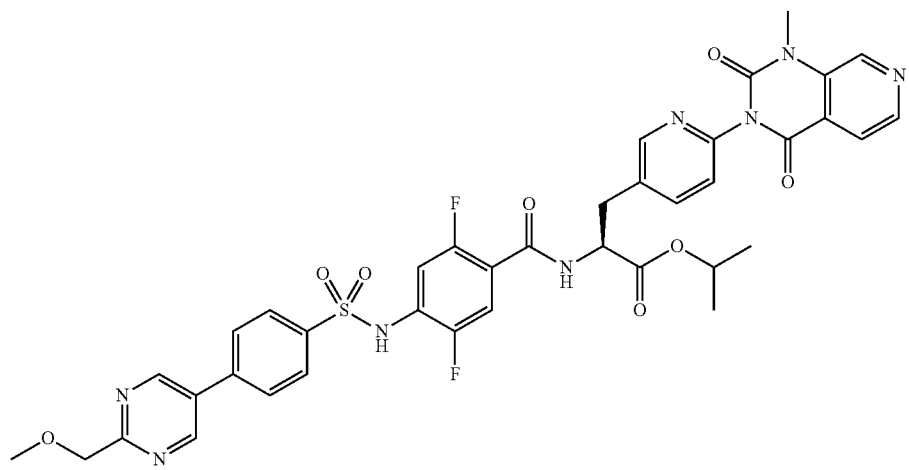 [SMILES: COCc1ncc(-c2ccc(S(=O)(=O)Nc3cc(F)c(C(=O)N[C@@H](Cc4ccc(-n5c(=O)c6ccncc6n(C)c5=O)nc4)C(=O)OC(C)C)cc3F)cc2)cn1]

1-Ethylpropyl (2S)-2-[[2,5-difluoro-4-[[4-[2-(methoxymethyl)pyrimidin-5-yl]phenyl]sulfonyl amino]benzoyl]amino]-3-[6-(1-methyl-2,4-dioxo-pyrido[3,4-d]pyrimidin-3-yl)-3-pyridyl]propanoate
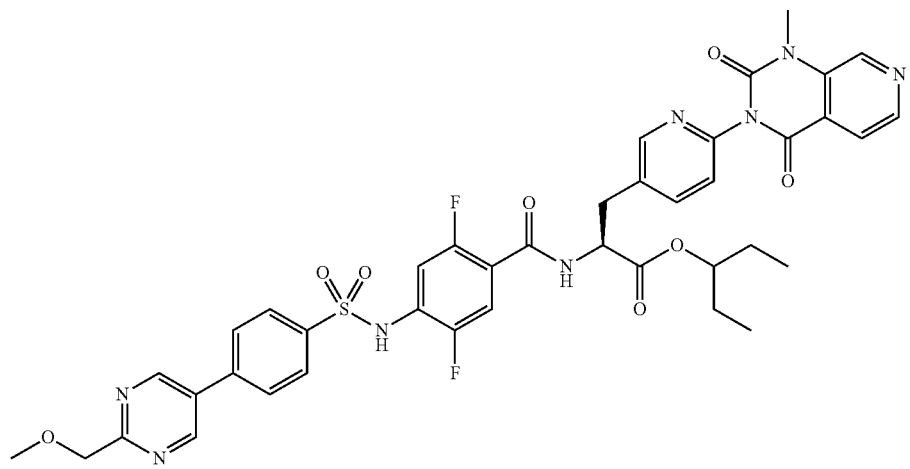 [SMILES: CCC(CC)OC(=O)[C@H](Cc1ccc(-n2c(=O)c3ccncc3n(C)c2=O)nc1)NC(=O)c1cc(F)c(NS(=O)(=O)c2ccc(-c3cnc(COC)nc3)cc2)cc1F]
4,4-Dimethylcyclohexyl (2S)-2-[[2,5-difluoro-4-[[4-[2-(methoxymethyl)pyrimidin-5-yl]phenyl]sulfonyl amino]benzoyl]amino]-3-[6-(1-methyl-2,4-dioxo-pyrido[3,4-d]pyrimidin-3-yl)-3-pyridyl]propanoate
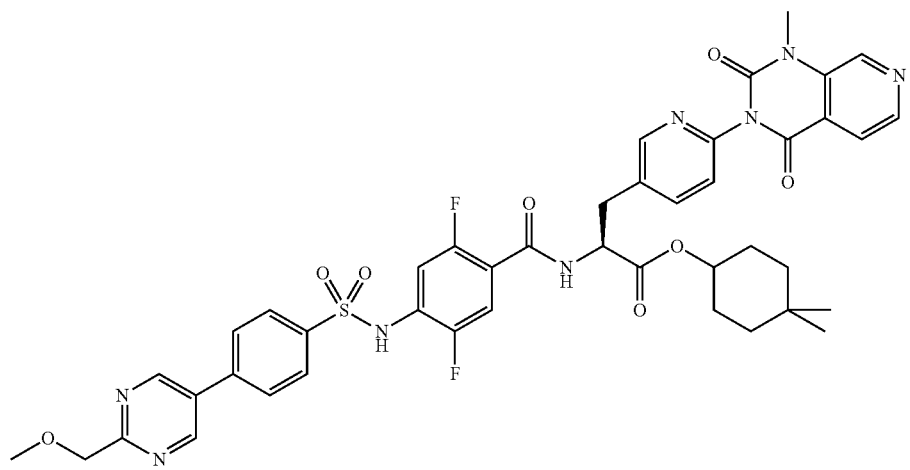 [SMILES: COCc1ncc(-c2ccc(S(=O)(=O)Nc3cc(F)c(C(=O)N[C@@H](Cc4ccc(-n5c(=O)c6ccncc6n(C)c5=O)nc4)C(=O)OC4CCC(C)(C)CC4)cc3F)cc2)cn1]

Cyclopentyl (2S)-2-[[2,5-difluoro-4-[[4-[2-(methoxymethyl)pyrimidin-5-yl]phenyl]sulfonyl amino]benzoyl]amino]-3-[6-(1-methyl-2,4-dioxo-pyrido[3,4-d]pyrimidin-3-yl)-3-pyridyl]propanoate
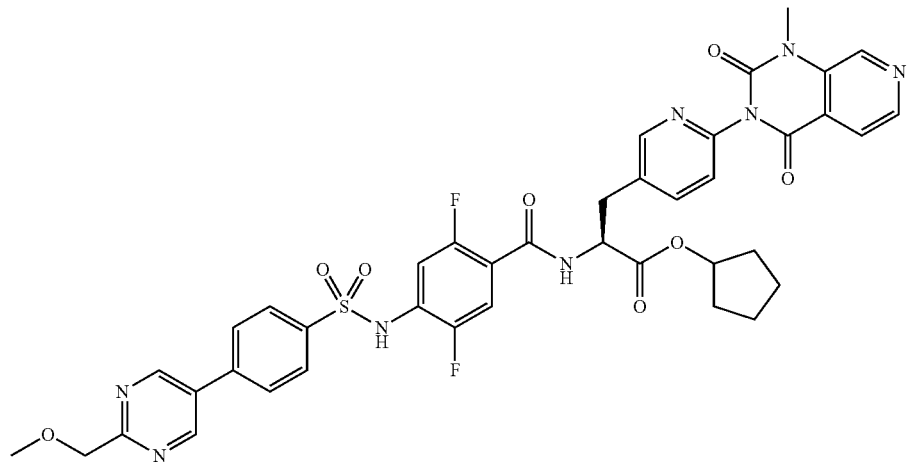 [SMILES: COCc1ncc(-c2ccc(S(=O)(=O)Nc3cc(F)c(C(=O)N[C@@H](Cc4ccc(-n5c(=O)c6ccncc6n(C)c5=O)nc4)C(=O)OC4CCCC4)cc3F)cc2)cn1]
Cycloheptyl (2S)-2-[[2,5-difluoro-4-[[4-[2-(methoxymethyl)pyrimidin-5-yl]phenyl]sulfonyl amino]benzoyl]amino]-3-[6-(1-methyl-2,4-dioxo-pyrido[3,4-d]pyrimidin-3-yl)-3-pyridyl]propanoate
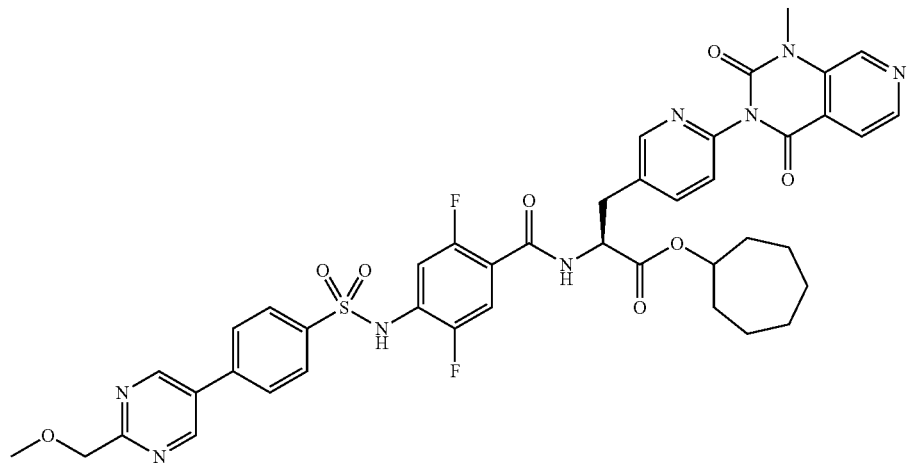 [SMILES: COCc1ncc(-c2ccc(S(=O)(=O)Nc3cc(F)c(C(=O)N[C@@H](Cc4ccc(-n5c(=O)c6ccncc6n(C)c5=O)nc4)C(=O)OC4CCCCCC4)cc3F)cc2)cn1]

2,2-Dimethylpropyl (2S)-2-[[2,5-difluoro-4-[[4-[2-(methoxymethyl)pyrimidin-5-yl]phenyl]sulfonylamino]benzoyl]amino]-3-[6-(1-methyl-2,4-dioxo-pyrido[3,4-d]pyrimidin-3-yl)-3-pyridyl]propanoate
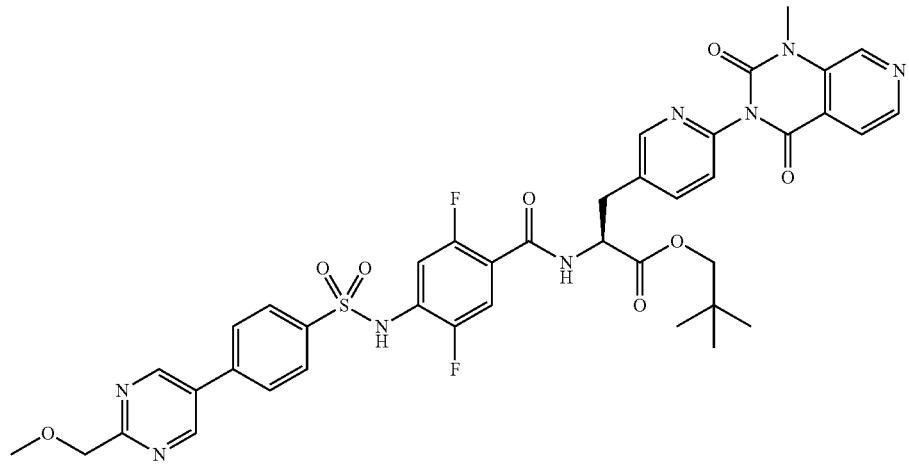 [SMILES: COCc1ncc(-c2ccc(S(=O)(=O)Nc3cc(F)c(C(=O)N[C@@H](Cc4ccc(-n5c(=O)c6ccncc6n(C)c5=O)nc4)C(=O)OCC(C)(C)C)cc3F)cc2)cn1]
Cyclobutylmethyl (2S)-2-[[2,5-difluoro-4-[[4-[2-(methoxymethyl)pyrimidin-5-yl]phenyl]sulfonylamino]benzoyl]amino]-3-[6-(1-methyl-2,4-dioxo-pyrido[3,4-d]pyrimidin-3-yl)-3-pyridyl]propanoate
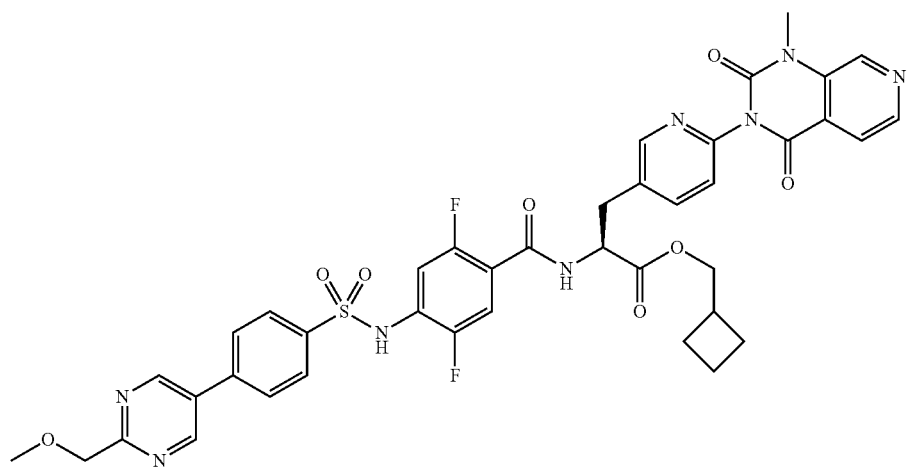 [SMILES: COCc1ncc(-c2ccc(S(=O)(=O)Nc3cc(F)c(C(=O)N[C@@H](Cc4ccc(-n5c(=O)c6ccncc6n(C)c5=O)nc4)C(=O)OCC4CCC4)cc3F)cc2)cn1]

(2S)-2-[[2,5-Difluoro-4-(2-furylsulfonylamino)ben-zoyl]amino]-3-[4-(1,3,4-trimethyl-2,6-dioxo-pyrimi-din-5-yl)phenyl]propanoic acid

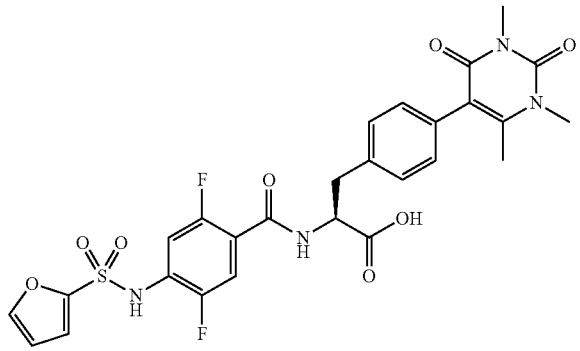 [SMILES: Cc1c(-c2ccc(C[C@H](NC(=O)c3cc(F)c(NS(=O)(=O)c4ccco4)cc3F)C(=O)O)cc2)c(=O)n(C)c(=O)n1C]

(2S)-2-[[2,5-Difluoro-4-[[4-[2-(isopropoxymethyl) pyrimidin-5-yl]phenyl]sulfonylamino]benzoyl] amino]-3-[4-(1,3,4-trimethyl-2,6-dioxo-pyrimidin-5-yl)phenyl]propanoic acid tetrahydropyranyl group; or a pyrimidinone group substituted with a lower alkenyl group.

Further, B preferably represents an alkoxy group having 1 to 10 carbon atoms, a hydroxyl group, or a hydroxyamino group, wherein B is optionally substituted with a substituent selected from the group consisting of an alkyl group having 1 to 10 carbon atoms, a lower alkoxy group, and a heterocyclic group containing 1 to 4 heteroatoms selected from oxygen atoms and nitrogen atoms.

Further, Arm is preferably a pyridyl group.

Further, when A represents a group represented by the general formula (2-4), E is preferably a 5- or 6-membered heterocyclic group containing an oxygen atom, or a 5- or 6-membered heterocyclic group containing 1 to 4 nitrogen atoms, wherein E optionally has a substituent selected from the group consisting of a lower alkyl group, a lower alkoxy-lower alkylene group, and a 5- or 6-membered heterocyclic group containing an oxygen atom.

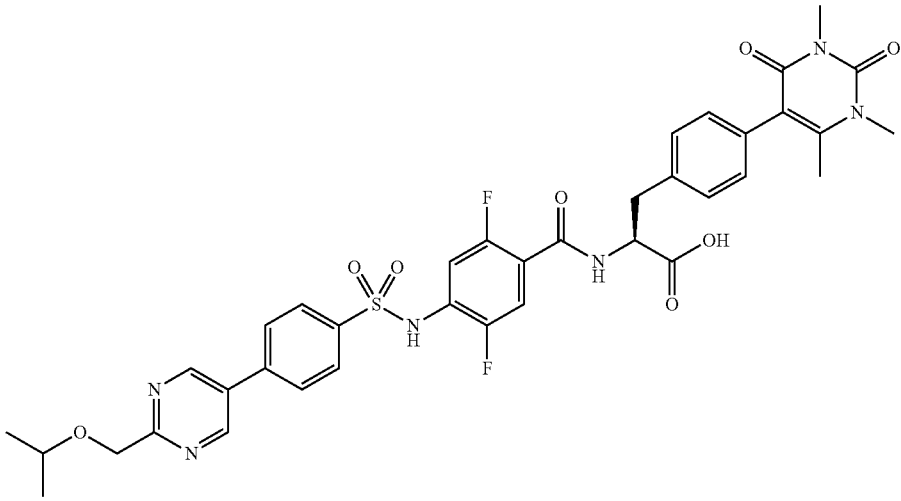 [SMILES: Cc1c(-c2ccc(C[C@H](NC(=O)c3cc(F)c(NS(=O)(=O)c4ccc(-c5cnc(COC(C)C)nc5)cc4)cc3F)C(=O)O)cc2)c(=O)n(C)c(=O)n1C]

Further, when A represents a group represented by the general formula (2-2), E preferably represents a 5- or 6-membered heterocyclic group containing 1 to 4 nitrogen atoms, the 5- or 6-membered heterocyclic group being substituted with a substituent selected from a lower alkyl group, a lower alkoxy-lower alkylene group, and a 5- or 6-membered heterocyclic group containing an oxygen atom; or a cyclic ketone group containing 1 to 4 nitrogen atoms, the cyclic ketone group being substituted with a lower alkyl group or a lower alkenyl group.

Further, E preferably represents a pyridyl group substituted with a lower alkoxy-lower alkylene group or a Further, E is preferably a tetrahydropyranyl group or a pyrimidyl group, wherein E optionally has a substituent selected from the group consisting of a lower alkyl group and a tetrahydropyranyl group.

Further, B is preferably a lower alkoxy group or a hydroxyl group.

Further, $R_{51}$, $R_{52}$, and $R_{53}$ are each preferably a lower alkyl group.

Further, in the present invention, compounds represented by the following formulae or pharmaceutically acceptable salts thereof are particularly preferable. Further, prodrugs of these compounds or pharmaceutically acceptable salts thereof are also preferable.

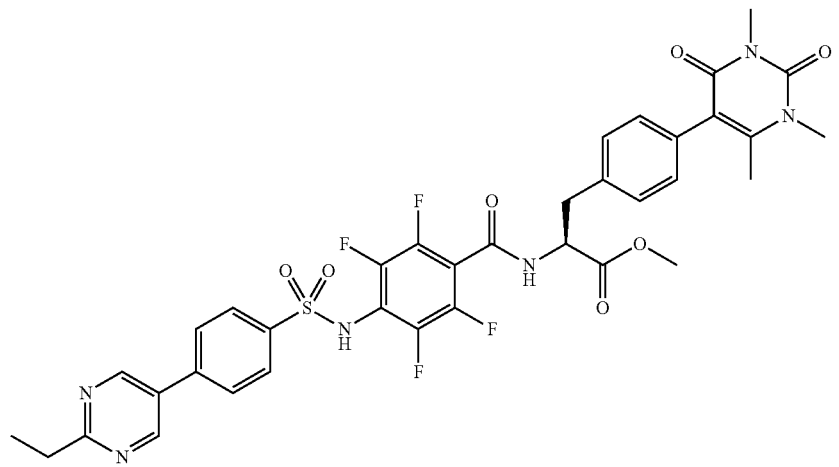
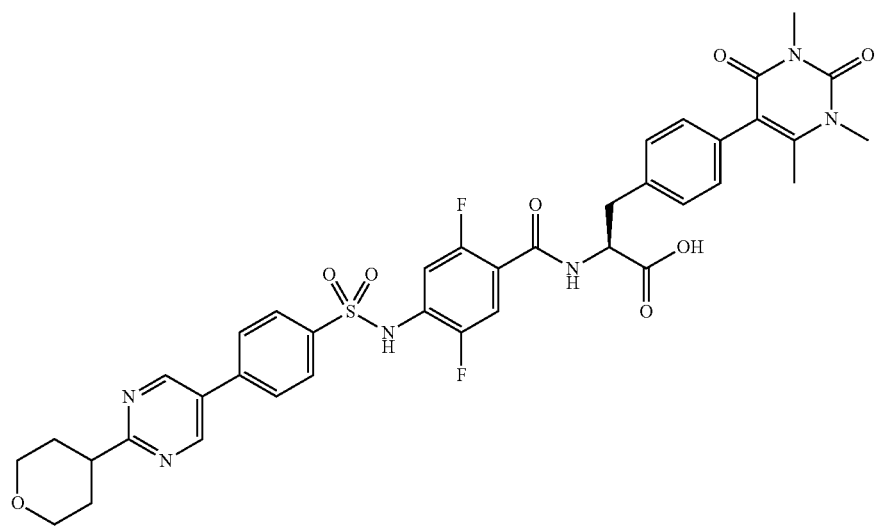
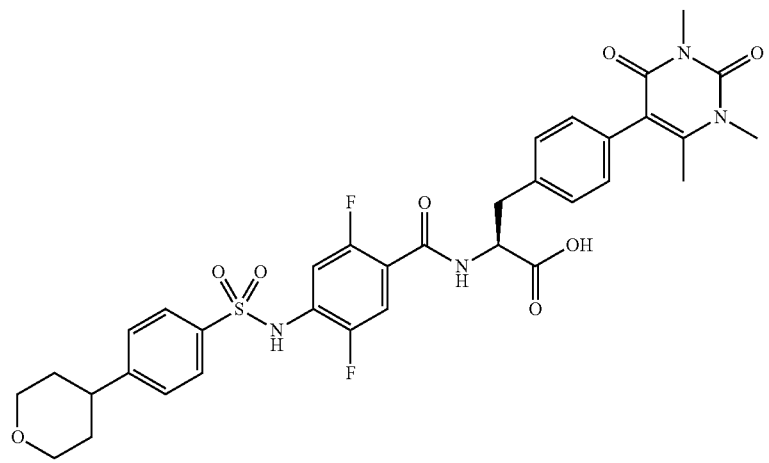

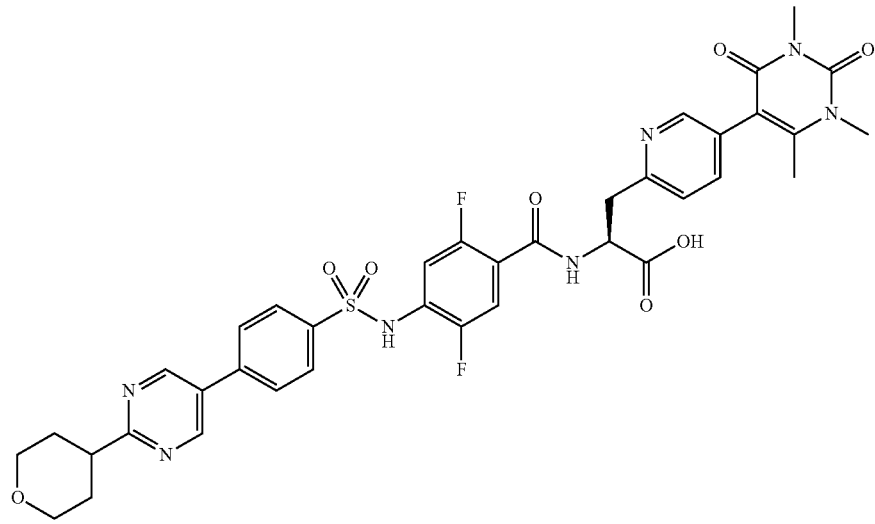
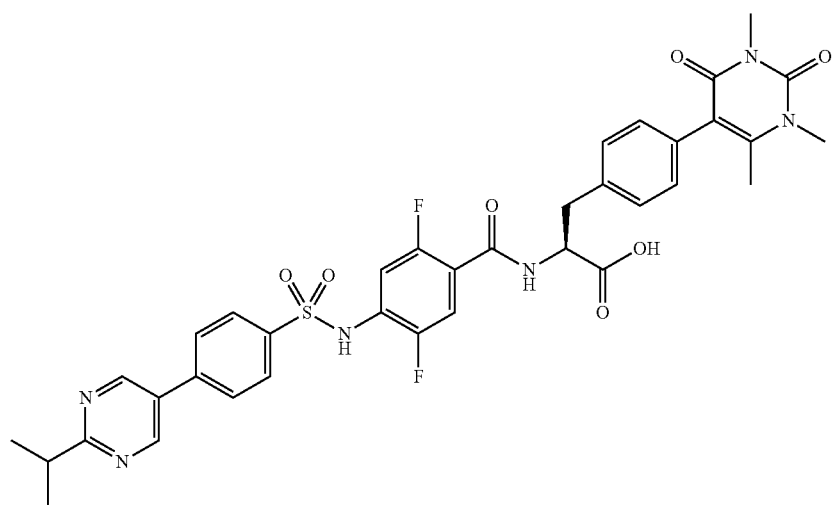
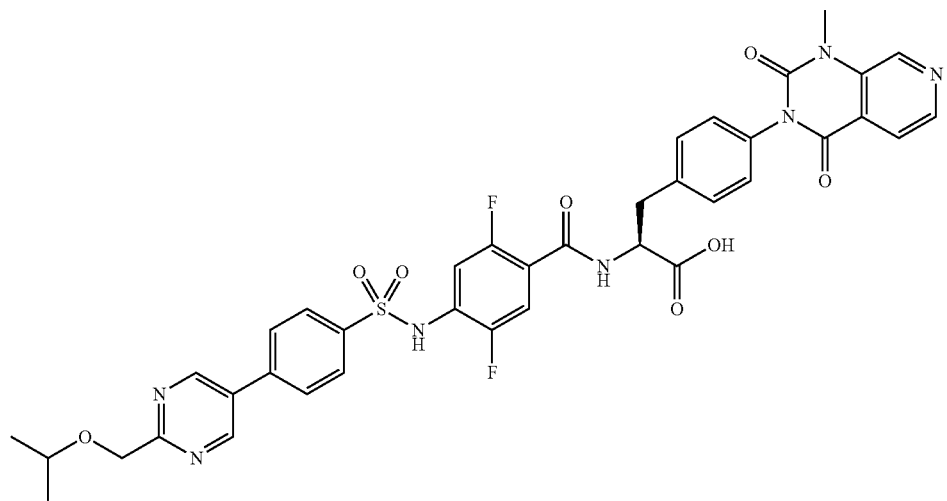

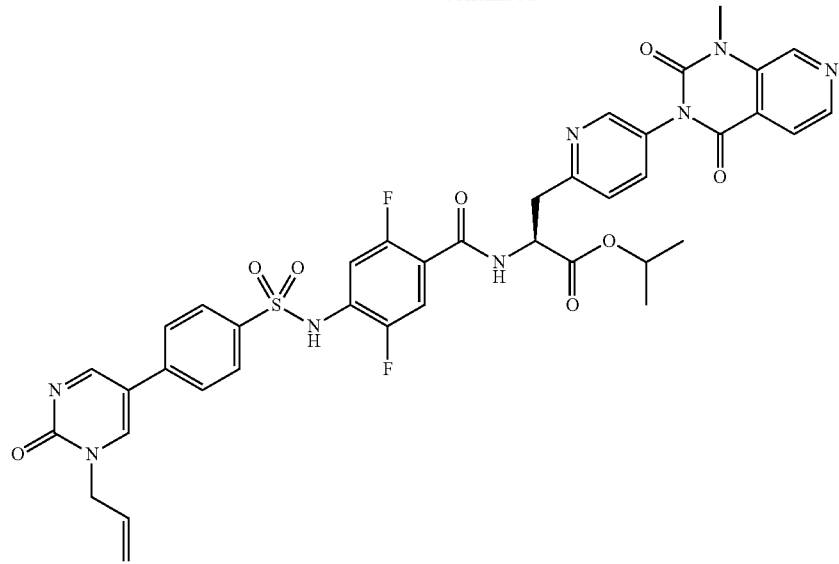
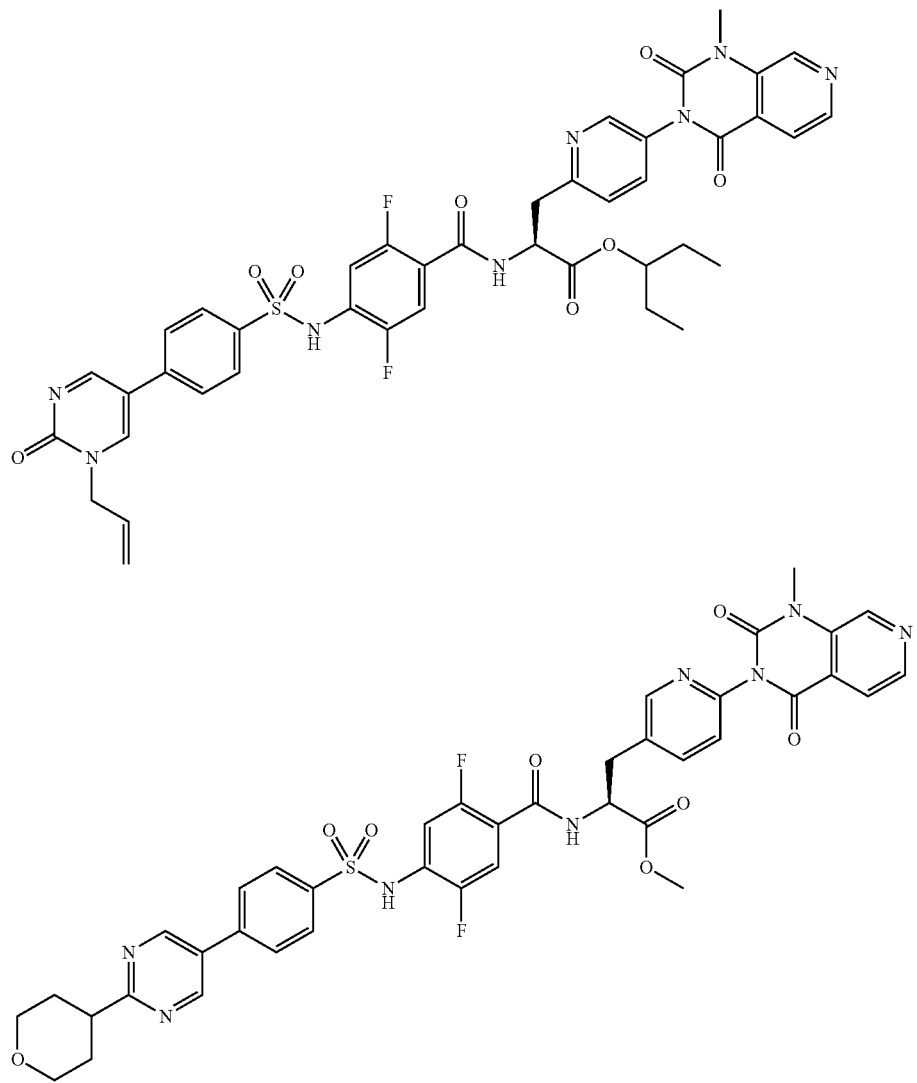

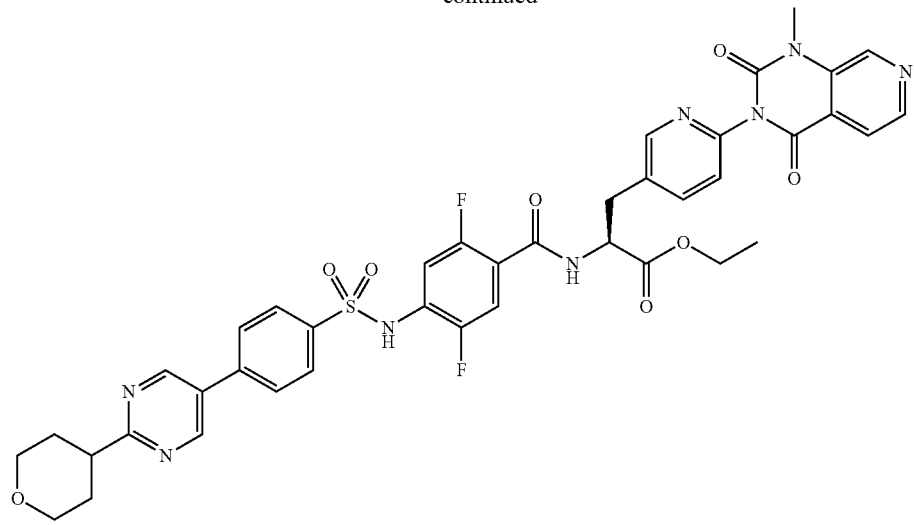
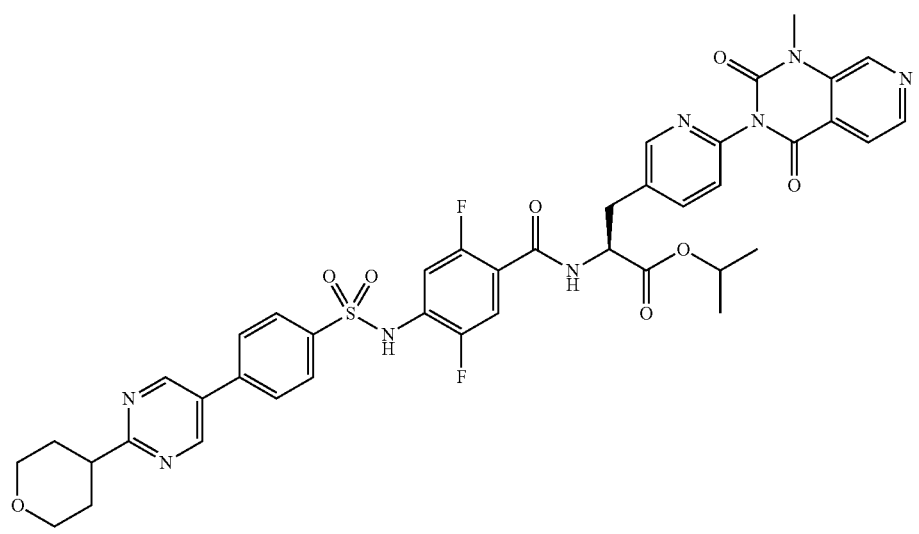
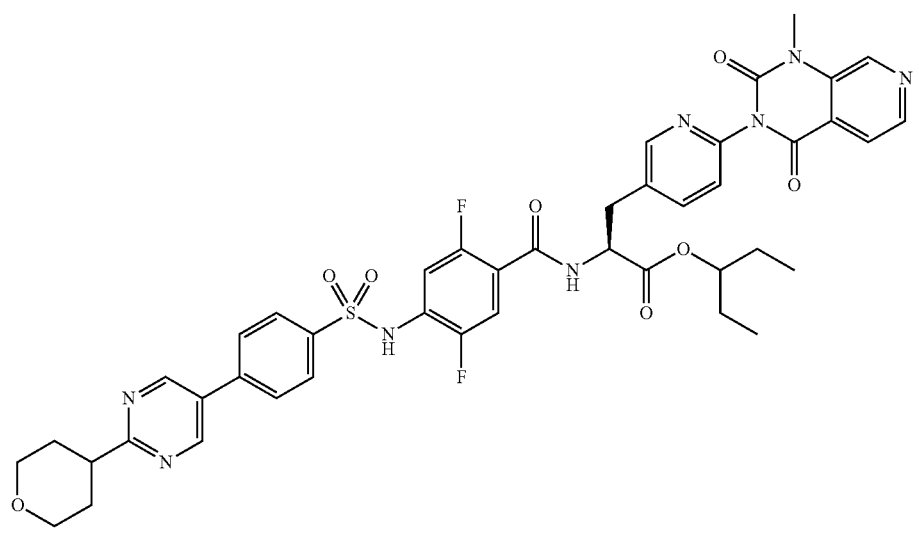

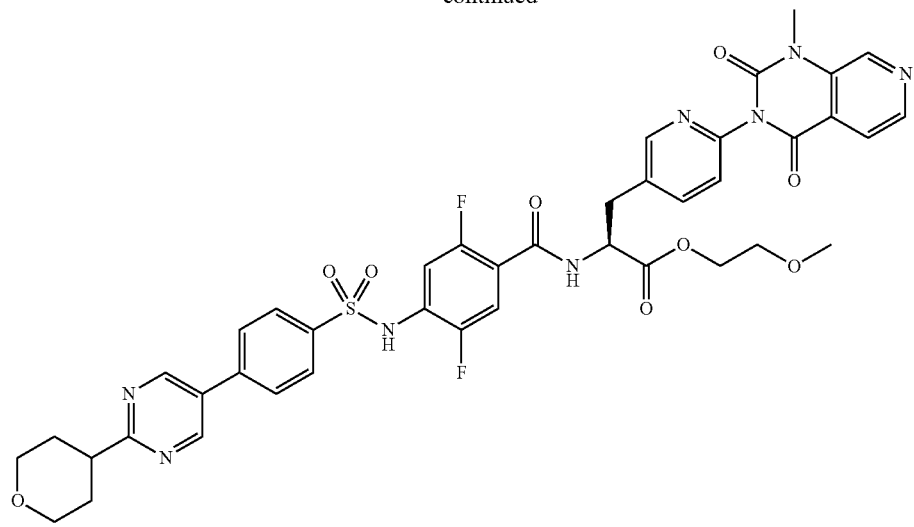
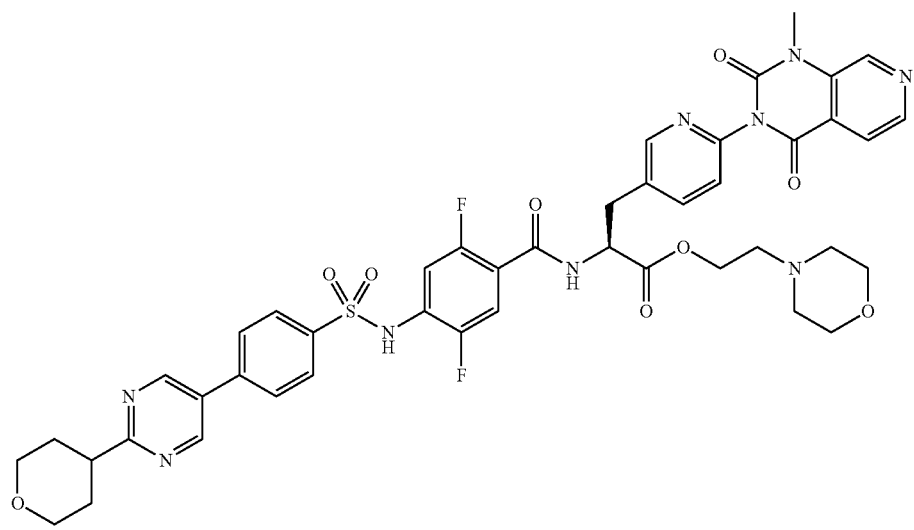
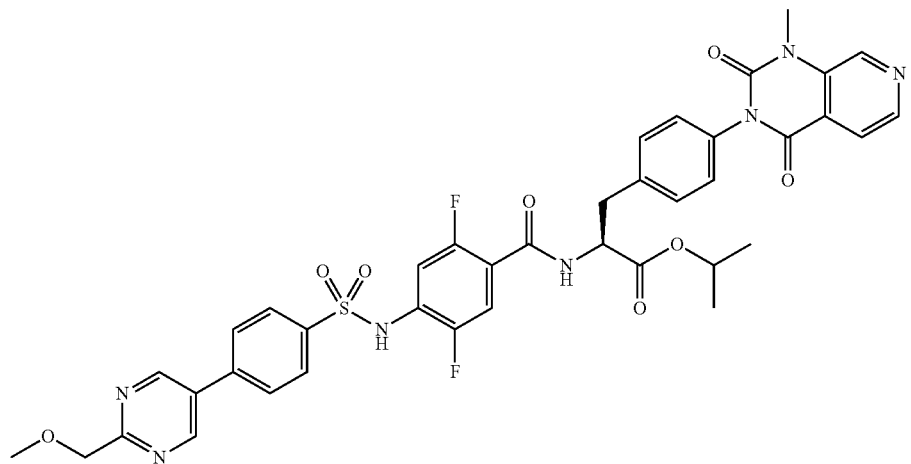

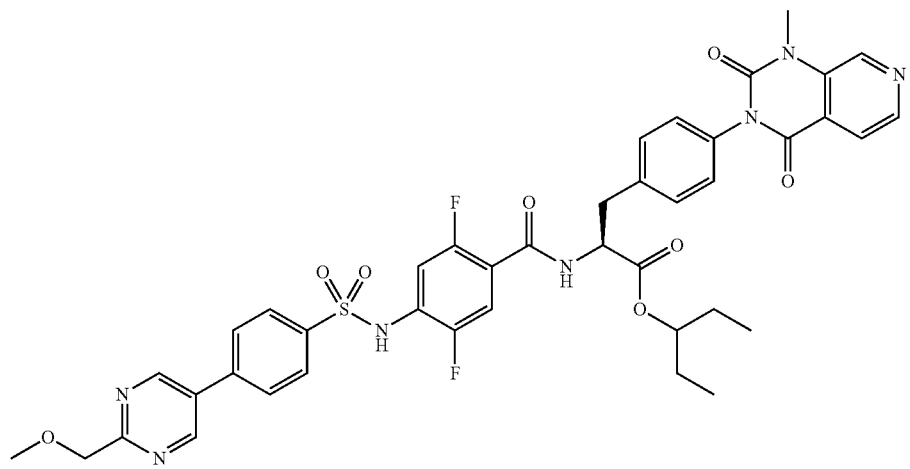
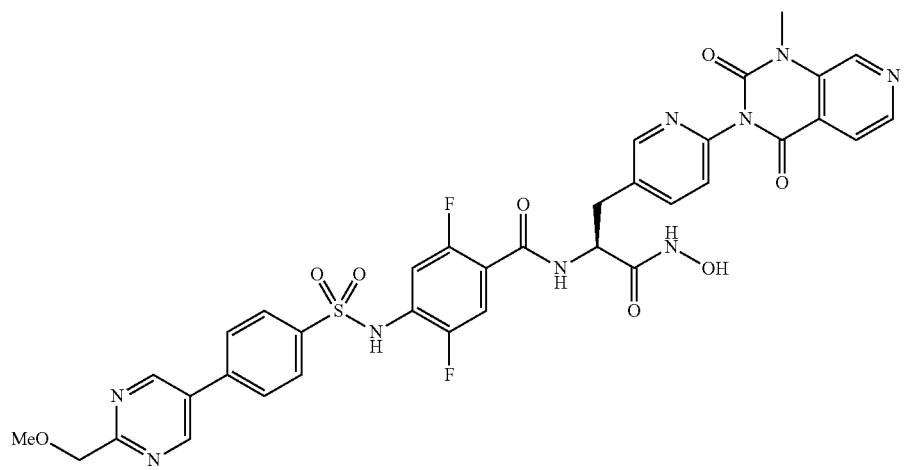
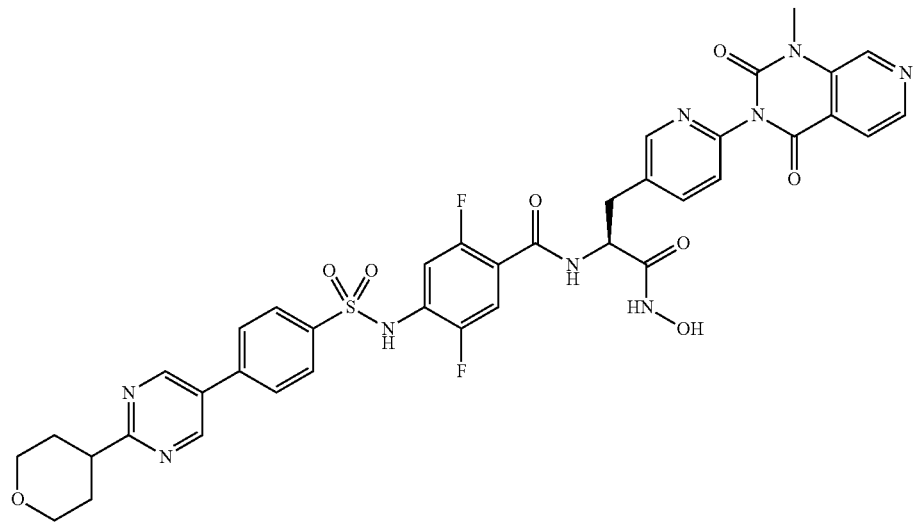

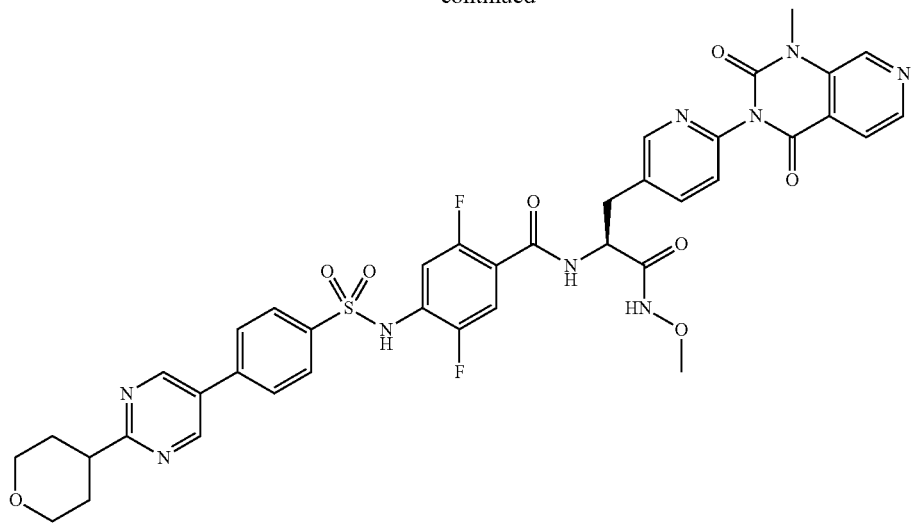

When the compound represented by the general formula (1) of the present invention can take the form of a salt, the salt thereof may be pharmaceutically acceptable, and examples thereof for the acidic group such as the carboxyl group in the formula can include ammonium salts, salts with alkali metals such as sodium and potassium, salts with alkaline earth metals such as calcium and magnesium, aluminum salts, zinc salts, salts with organic amines such as triethylamine, ethanolamine, morpholine, piperidine, and dicyclohexylamine, and salts with basic amino acids such as arginine and lysine. Examples thereof for the basic group when the basic group is present in the formula can include salts with inorganic acids such as hydrochloric acid, sulfuric acid, and phosphoric acid, salts with organic carboxylic acids such as acetic acid, citric acid, benzoic acid, maleic acid, fumaric acid, tartaric acid, and succinic acid, and salts with organic sulfonic acids such as methanesulfonic acid and p-toluenesulfonic acid. As a method for forming salts, salts can be obtained by mixing the compound of the general formula (1) with a necessary acid or base at a suitable quantitative ratio in a solvent or dispersant, or performing cation exchange or anion exchange from other forms of salts.

The compound of the present invention may contain a solvate of the compound represented by the general formula (1), such as hydrates and alcohol adducts.

The compound of the present invention includes embodiments of prodrugs of the compound represented by the general formula (1). A prodrug of the compound of the present invention means a compound converted into the compound represented by the general formula (1) by reaction with enzyme, gastric acid, or the like under physiological conditions in vivo, that is, a compound transformed into the compound represented by the general formula (1) by undergoing enzymatic oxidation, reduction, hydrolysis, or the like, or a compound transformed into the compound represented by the general formula (1) by undergoing hydrolysis by gastric acid or the like. The prodrug of the compound represented by the general formula (1) is exemplified by the compounds of Examples, but is not limited thereto, and examples thereof to be used include, when the compound represented by the general formula (1) has amino, compounds obtained by acylation, alkylation, or phosphorylation of the amino (e.g., compounds obtained by eicosanoylation, alanylation, pentylaminocarbonylation, (5-methyl-2-oxo-1,3-dioxolen-4-yl)methoxycarbonylation, tetrahydrofuranylation, pyrrolidylmethylation pivaloyloxymethylation, or tert-butylation of the amino of the compound represented by the general formula (1)); when the compound represented by the general formula (1) has hydroxy, compounds obtained by acylation, alkylation, phosphorylation, or boration of the hydroxy (e.g., compounds obtained by acetylation, palmitoylation, propanoylation, pivaloylation, succinylation, fumarylation, alanylation, or dimethylaminomethylcarbonylation of the hydroxy of the compound represented by the general formula (1)); and when the compound represented by the general formula (1) has carboxyl, compounds obtained by esterification or amidation of the carboxyl (e.g., compounds obtained by ethyl esterification, phenyl esterification, isopropyl esterification, isobutyl esterification, cyclopentyl esterification, cyclohexyl esterification, cycloheptyl esterification, cyclobutylmethyl esterification, cyclohexylmethyl esterification, n-hexyl esterification, sec-butyl esterification, tert-butyl esterification, (4-tetrahydropyranyl)methyl esterification, (4-tetrahydropyranyl) esterification, carboxymethyl esterification, dimethylaminomethyl esterification, pivaloyloxymethyl esterification, ethoxycarbonyloxyethyl esterification, phthalidyl esterification, (5-methyl-2-oxo-1,3-dioxolen-4-yl)methyl esterification, cyclohexyloxycarbonylethyl esterification, or methylamidation of the carboxyl of the compound represented by the general formula (1)). These compounds can be produced from the compound represented by the general formula (1) by known methods.

Further, the prodrug of the compound (1) may be a compound transformed into the compound (1) under physiological conditions as described in "IYAKUHIN no KAIHATSU (Development of Pharmaceuticals)", Vol. 7, Design of Molecules, p. 163 to 198, published by HIROKAWA SHOTEN in 1990.

The present invention includes all isotopes of the compound represented by formula (1). An isotope of the compound of the present invention has at least one atom substituted with an atom having the same atomic number (the number of protons) and a different mass number (the sum of the number of protons and neutrons). Examples of the isotope contained in the compound of the present invention include a hydrogen atom, a carbon atom, a nitrogen atom, an oxygen atom, a phosphorus atom, a sulfur atom, a fluorine atom, and a chlorine atom, which respectively contain $^2H$, $^3H$, $^{13}C$, $^{14}C$, $^{15}N$, $^{17}O$, $^{18}O$, $^{31}P$, $^{32}P$, $^{35}S$, $^{18}F$, $^{36}Cl$, or the like. In particular, unstable radioactive isotopes that emit radiation to emit neutrons, such as $^3H$ and $^{14}C$, are useful for distribution examination of pharmaceutical products or compounds in body tissues. Stable isotopes can be used with safety, since they do not disintegrate, their abundance is less likely to change, and they are not radioactive. The isotope of the compound of the present invention can be converted according to conventional methods by replacing a reagent used for synthesis with a reagent containing a corresponding isotope.

The compound represented by the general formula (1) of the present invention can be produced, for example, by subjecting an intermediate represented by the general formula (M-I) and having an amino group at an end and an intermediate represented by the general formula (M-II) and having a carboxyl group at an end to dehydration reaction.

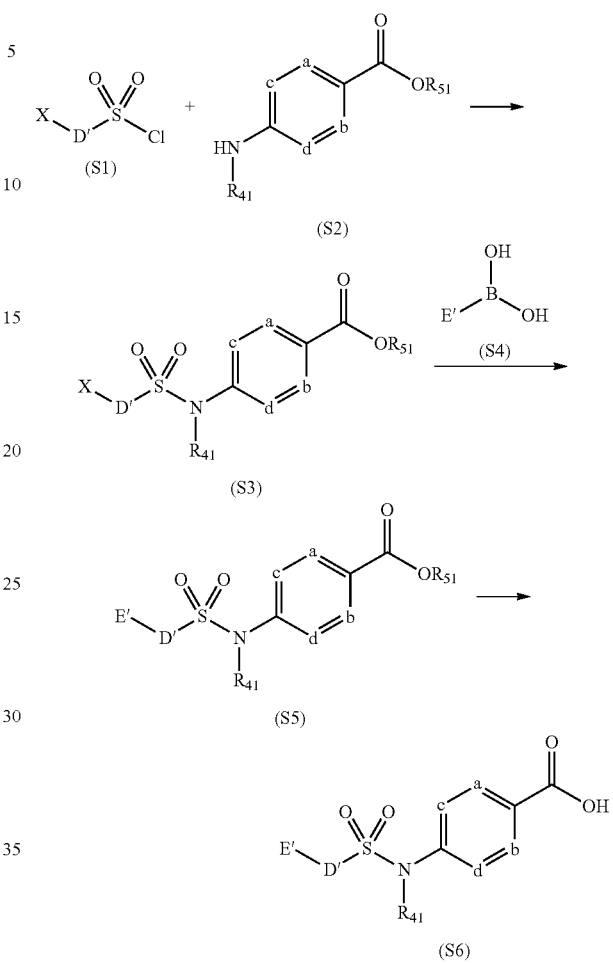

Of these intermediates, the intermediate represented by the general formula (M-II) and having a carboxyl group at an end can be produced, for example, by the following method.

A typical method for producing a compound of the intermediate represented by the general formula (M-II) and having a carboxyl group at an end, which is the compound of the present invention, is shown below. In the following description, the symbols in the formulae are the same as defined in the formula (I), unless otherwise specified.

(1) In the general formula (M-II), an intermediate (S6) having a carboxyl group at an end in which D is a phenyl group or a pyridyl group optionally having a substituent selected from the group consisting of a lower alkyl group and a halogen atom, and E is a 5- or 6-membered aromatic heterocyclic group containing 1, 2, 3, or 4 heteroatoms selected from oxygen atoms, sulfur atoms, or nitrogen atoms and optionally having a substituent can be synthesized, for example, using methods described below (production methods A, B, C, and D).

<Production Method A>

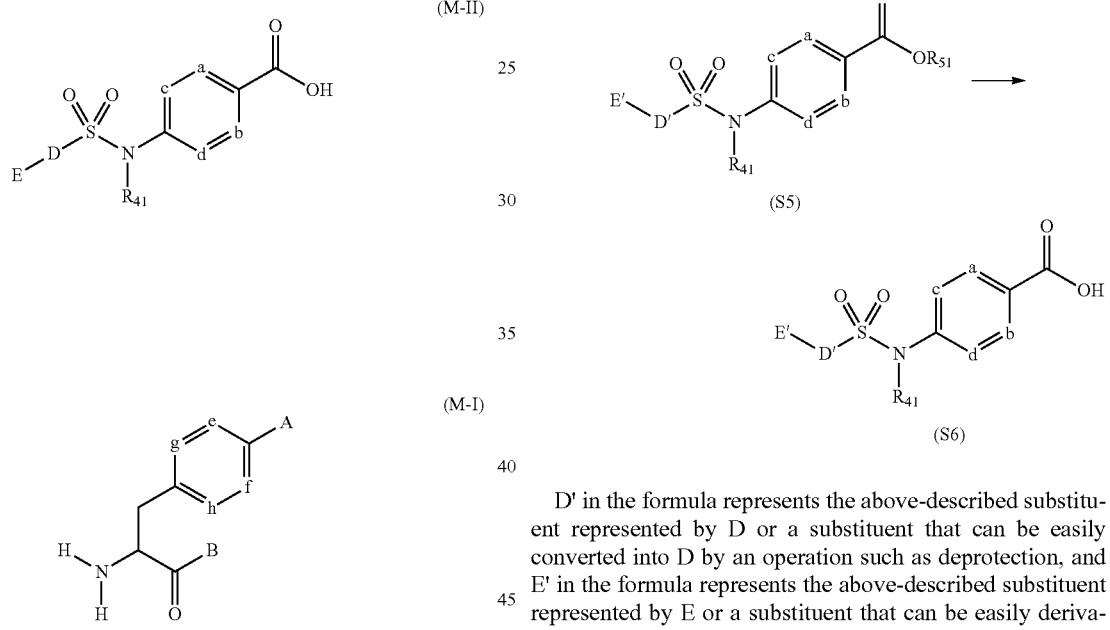

D' in the formula represents the above-described substituent represented by D or a substituent that can be easily converted into D by an operation such as deprotection, and E' in the formula represents the above-described substituent represented by E or a substituent that can be easily derivatized to E by an operation such as deprotection. Further, R51 represents a common substituent of ester such as a lower alkyl group.

A sulfonamide derivative (S3) can be synthesized by allowing a sulfonyl chloride derivative (S1) (X in the formula represents a halogen atom such as chlorine, bromine, and iodine, or a leaving group such as a trifluoromethanesulfonyloxy group) to react with an amine derivative (S2) in a solvent having no adverse effect on the present reaction such as methylene chloride in the presence of a base such as pyridine. The resulting sulfonamide derivative (S3) can be derivatized to a corresponding sulfonamide derivative (S5) by Suzuki coupling reaction with a boronic acid derivative (S4). Subsequently, the target intermediate (S6) having a carboxyl group at an end can be produced by subjecting the resulting sulfonamide derivative (S5) to alkaline hydrolysis using a base such as sodium hydroxide or deprotection such as acid hydrolysis, for example, using hydrochloric acid or trifluoroacetic acid, in a solvent having no adverse effect on the present reaction such as tetrahydrofuran, methanol, and ethanol.

Suzuki coupling reaction is known, and is performed by allowing a boronic acid derivative or a boronic acid ester derivative to react with a halogen derivative, trifluoromethanesulfonate, or methanesulfonate in a solvent having no adverse effect on the present reaction such as 1,4-dioxane, tetrahydrofuran, toluene, dimethylsulfoxide, and 1,2-dimethoxyethane in the presence or absence of a cosolvent such as water using a transition metal catalyst such as tetrakis(triphenylphosphine)palladium(0), [1,1'-bis(diphenylphosphino)ferrocene] and tris(dibenzylideneacetone)dipalladium (0), or using a transition metal catalyst such as palladium(II) acetate and a ligand such as triphenylphosphine in the presence of a base such as potassium carbonate, sodium carbonate, potassium phosphate, sodium methoxide, and sodium hydroxide.

<Production Method B>

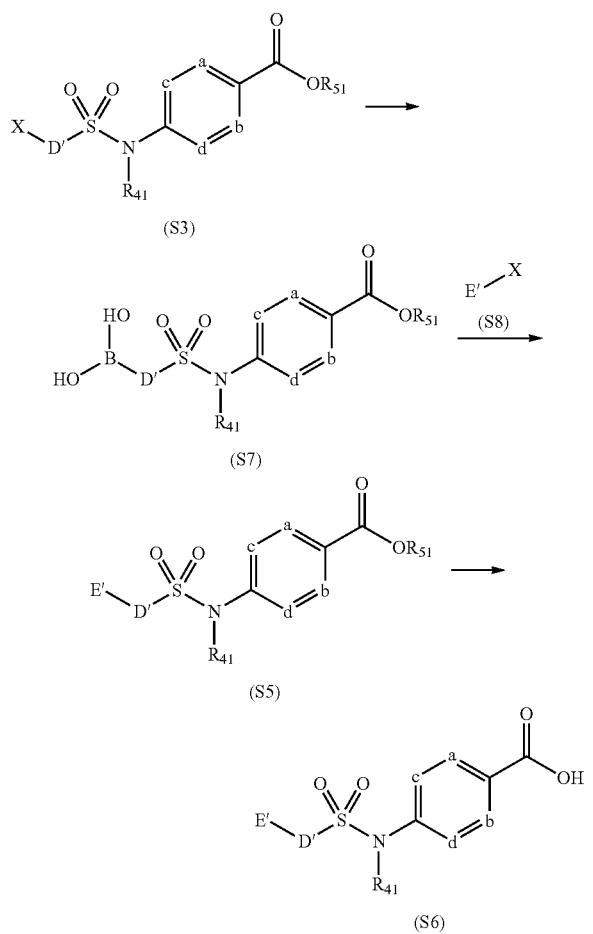

D' in the formula represents the above-described substituent represented by D, or a substituent that can be easily converted into D by an operation such as deprotection, and E' in the formula represents the above-described substituent represented by E or a substituent that can be easily derivatized to E by an operation such as deprotection. Further, R51 represents a common substituent of ester such as a lower alkyl group.

A corresponding boronic acid derivative (S7) can be synthesized by coupling reaction of the sulfonamide derivative (S3) that is the intermediate described in <Production method A> with a borane derivative such as bis(pinacolato) diborane in a solvent having no adverse effect on the present reaction such as N,N-dimethylformamide in the presence of a base such as potassium acetate using a metal catalyst such as [1,1'-bis(diphenylphosphino)ferrocene]dichloropalladium(II) to lead it to a corresponding boronic acid ester derivative, and subsequently subjecting the resulting boronic acid ester derivative to treatment, for example, by adding sodium periodate, ammonium acetate, and water in a solvent having no adverse effect on the present reaction such as acetone to remove boronic acid ester. The resulting boronic acid derivative (S7) can be derivatized to the corresponding sulfonamide derivative (S5) by Suzuki coupling reaction (described above) with a halogen derivative (S8) (X in the formula represents a halogen atom such as chlorine, bromine, and iodine, or a leaving group such as a trifluoromethanesulfonyloxy group). The target intermediate (S6) having a carboxyl group at an end can be produced by subjecting the sulfonamide derivative (S5) to deprotection by hydrolysis or the like using the method described in <Production method A>.

<Production Method C>

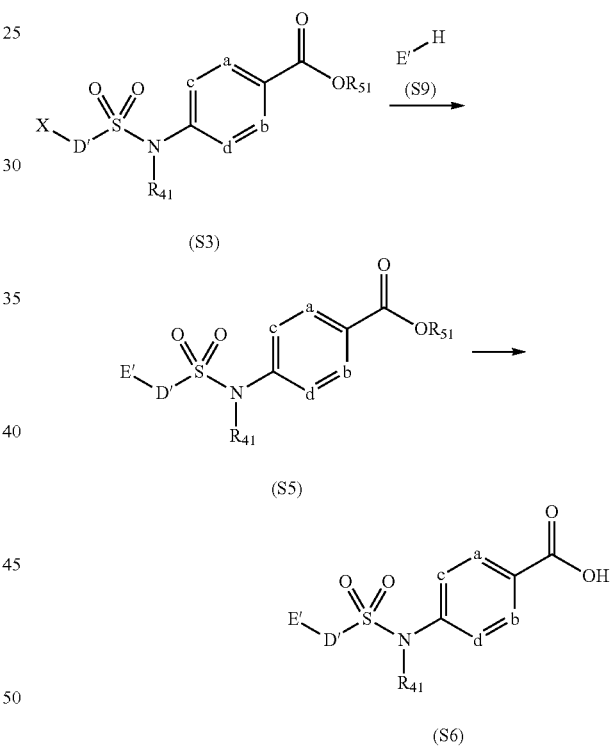

D' in the formula represents the above-described substituent represented by D or a substituent that can be easily converted into D by an operation such as deprotection, and E' in the formula represents the above-described substituent represented by E or a substituent that can be easily derivatized to E by an operation such as deprotection. Further, R51 represents a common substituent of ester such as a lower alkyl group.

The sulfonamide derivative (S3) that is the intermediate described in <Production method A> (X in the formula represents a halogen atom such as chlorine, bromine, and iodine, or a leaving group such as a trifluoromethanesulfonyloxy group) can be derivatized to the corresponding sulfonamide derivative (S5) by coupling reaction with an aromatic heterocycle (S9) in a solvent having no adverse effect on the present reaction such as N-methylpyrrolidone in the presence of a ligand that is commonly used for organic synthesis such as trans-N,N'-dimethylcyclohexane-1,2-diamine and a base such as potassium phosphate using a metal catalyst such as copper(I) iodide. Subsequently, the target intermediate (S6) having a carboxyl group at an end can be produced by subjecting the resulting sulfonamide derivative (S5) to deprotection by hydrolysis or the like using the method described in <Production method A>.

<Production Method D>

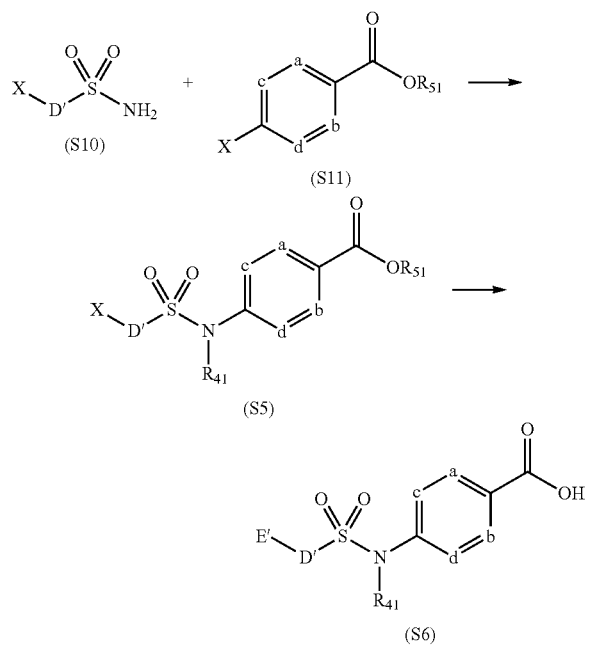

D' in the formula represents the above-described substituent represented by D or a substituent that can be easily converted into D by an operation such as deprotection, and E' in the formula represents the above-described substituent represented by E or a substituent that can be easily derivatized to E by an operation such as deprotection. Further, R51 represents a common substituent of ester such as a lower alkyl group.

A sulfonamide derivative (S10) (X in the formula represents a halogen atom such as chlorine, bromine, and iodine, or a leaving group such as a trifluoromethanesulfonyloxy group) can be derivatized to the corresponding sulfonamide derivative (S5) by coupling reaction with a halogen derivative (S11) in a solvent having no adverse effect on the present reaction such as 1,4-dioxane in the presence of a metal catalyst such as tris(dibenzylideneacetone)dipalladium(0), a ligand commonly used for organic synthesis such as XantPHOS, and a base such as cesium carbonate. Subsequently, the target intermediate (S6) having a carboxyl group at an end can be produced by subjecting the resulting sulfonamide derivative (S5) to deprotection such as hydrolysis, for example, by the method described in <Production method A>.

An intermediate having a carboxyl group at an end in which D is a phenyl group or a pyridyl group optionally having a substituent selected from the group consisting of a lower alkyl group and a halogen atom, and E is an aminocarbonyl group optionally substituted with a lower alkyl, a heterocycle, or a lower alkyl substituted with a heterocycle, in the general formula (M-II) can be synthesized using the method described below (production method E).

<Production Method E>

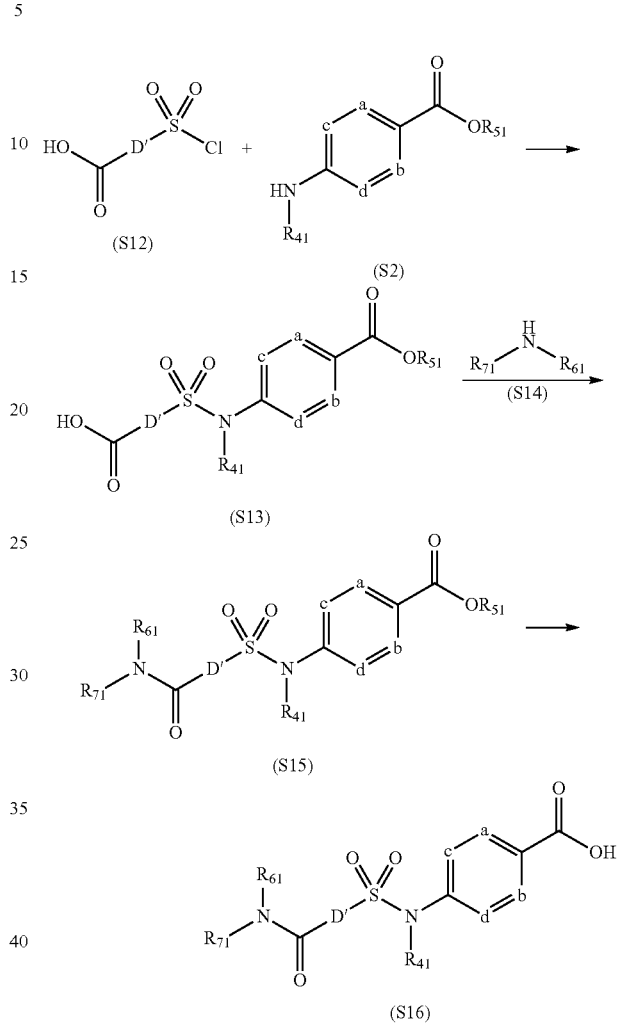

D' in the formula represents the above-described substituent represented by D or a substituent that can be easily converted into D by an operation such as deprotection. Further, R51 represents a common substituent of ester such as a lower alkyl group. Further, R61 and R71 represent common substituents on the amine such as a lower alkyl group, a heterocyclic group, or a lower alkyl group substituted with a heterocycle.

A corresponding carboxylic acid derivative (S13) can be synthesized by allowing a sulfonyl chloride derivative (S12) having carboxylic acid or a substituent that can be easily converted into carboxylic acid to react with the amine derivative (S2) in a solvent having no adverse effect on the present reaction such as methylene chloride in the presence of a base such as pyridine. A corresponding amide derivative (S15) can be synthesized by amidation of the resulting carboxylic acid derivative (S13) with an amine derivative (S14).

Subsequently, an intermediate (S16) having a carboxyl group at an end can be produced by subjecting the resulting amide derivative (S15) to deprotection such as hydrolysis using the method described in <Production method A>.

The amidation reaction is known, and examples thereof include (1) a method using a condensing agent and (2) a method using an acid halide.

(1) The method using a condensing agent is performed by allowing carboxylic acid to react with amine or a salt thereof in a solvent having no adverse effect on the present reaction such as dichloromethane, tetrahydrofuran, 1,4-dioxane, N,N-dimethylformamide, or acetonitrile in the presence or absence of a base such as pyridine, triethylamine, or N-ethykliisopropylamine in the presence or absence of a condensation aid such as 1-hydroxybenzotriazole (HOBt), 1-hydroxy-7-azabenzotriazole (HOAt), or N-hydroxysuccinimide (HOSu) using a condensing agent such as 1-ethyl-3-(3'-dimethylaminopropyl)carbodiimide (WSC), 1,3-dicyclohexylcarbodiimide (DCC), or (benzotriazol-1-yl)-N,N,N',N'-tetramethyluronium hexafluorophosphate (HATU).

(2) The method using an acid halide is performed by allowing carboxylic acid to react with thionyl chloride, oxalyl chloride, thionyl bromide, or the like, in a solvent having no adverse effect on the present reaction such as dichloromethane or in the absence of the solvent, in the presence or absence of a catalyst such as N,N-dimethylformamide to obtain an acid halide, and allowing the acid halide to react with amine or a salt thereof in a solvent having no adverse effect on the present reaction such as dichloromethane or tetrahydrofuran in the presence of a base such as pyridine, triethylamine, or N-ethyldiisopropylamine.

In each step, the synthesis can be performed using generally replacable reaction conditions, which should be appropriately selected depending on the types or the like of raw material compounds. The compound of the present invention obtained by the above-described methods can be purified by techniques that are generally used for organic synthesis, such as extraction, distillation, crystallization, and column chromatography.

The intermediate represented by the general formula (M-I) and having an amino group at an end, which is the compound of the present invention, can be synthesized, for example, using the method disclosed in Patent Literature 1 or the production methods (production methods F and G) described below. In the following description, the symbols in the formulae are the same as defined in the formula (I), unless otherwise specified.

<Production Method F>

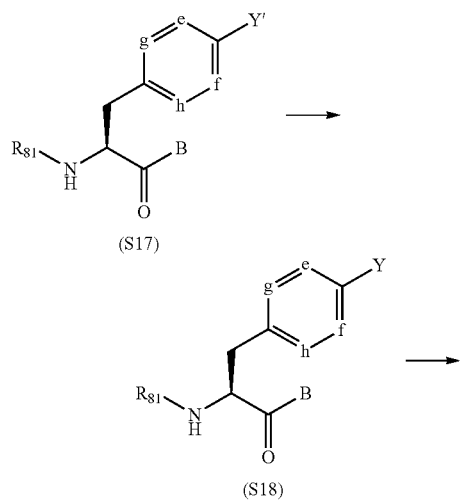

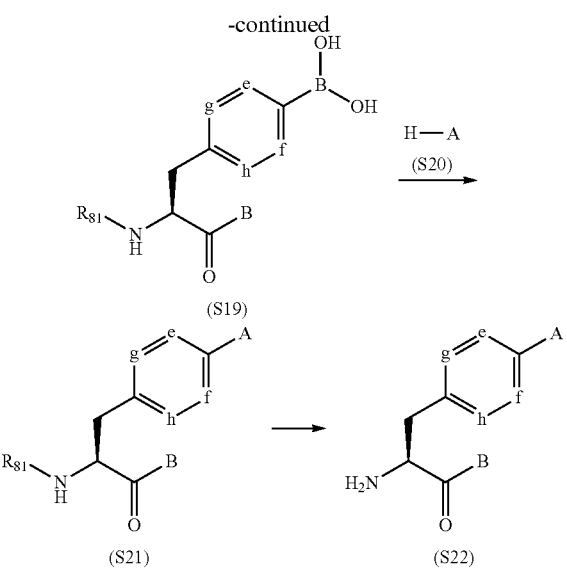

In the formula, R81 represents a common substituent of amine that can be removed by an operation such as deprotection, such as a tert-butoxycarbonyl group and a benzyloxycarbonyl group, and Y in the formula represents a halogen atom such as chlorine, bromine, and iodine, or a leaving group such as a trifluoromethanesulfonyloxy group. Y' in the formula represents a substituent that can be easily derivatized to Y by an operation such as trifluoromethanesulfonylation.

A corresponding amino acid derivative (S18) can be synthesized by allowing an amino acid derivative (S17) to react, for example, with N-phenyl bis(trifluoromethanesulfonamide) in a solvent having no adverse effect on the present reaction such as tetrahydrofuran in the presence of a base such as diisopropylethylamine. A corresponding boronic acid derivative (S19) can be synthesized by subjecting the resulting amino acid derivative (S18) to coupling reaction with a boronic acid derivative such as bis(2,2,3,3-tetramethyl-2,3-butanedionate)diboron in a solvent having no adverse effect on the present reaction such as 1,4-dioxane in the presence of a base such as potassium acetate using a metal catalyst such as [1,1'-bis(diphenylphosphino)ferrocene]dichloropalladium(II) to lead it to a corresponding boronic acid ester derivative, and subsequently subjecting the resulting boronic acid ester derivative to treatment, for example, by adding sodium periodate, ammonium acetate, and water in a solvent having no adverse effect on the present reaction such as acetone to hydrolyze the boronic acid ester. An amino acid derivative (S21) can be produced by coupling reaction of the resulting boronic acid derivative (S19) with a compound (S20) in a solvent having no adverse effect on the present reaction such as methylene chloride in the presence of a base such as triethylamine using a metal catalyst such as copper acetate (II), or coupling reaction thereof in a solvent having no adverse effect on the present reaction such as 1,4-dioxane in the presence of a base such as sodium carbonate using a metal catalyst such as [1,1'-bis(diphenylphosphino)ferrocene]dichloropalladium(II). A target intermediate (S22) having an amino group at an end can be produced by subjecting the resulting amino acid derivative (S21) to acid hydrolysis, for example, using hydrochloric acid or trifluoroacetic acid, or deprotection by hydrogenation reaction or the like in the presence of hydrogen using a catalyst such as palladium carbon.

<Production Method G>

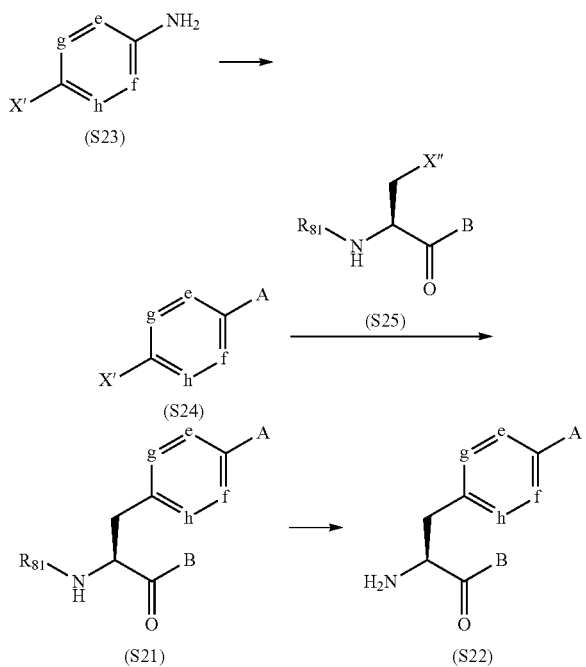

In the formula, R81 represents a common substituent of amine that can be removed by an operation such as deprotection, such as a tert-butoxycarbonyl group and a benzyloxycarbonyl group, and X' and X" in the formula each independently represent a halogen atom such as chlorine, bromine, and iodine, or a leaving group such as a trifluoromethanesulfonyloxy group.

A corresponding halogen derivative (S24) can be synthesized by subjecting an amine derivative (S23) to the method disclosed, for example, in Patent Literature 1, or by subjecting the same substrate as disclosed in Patent Literature 1 to ureation with triphosgene or the like in a solvent having no adverse effect on the present reaction such as methylene chloride, subsequently to cyclization with potassium carbonate and p-toluenesulfonic acid methyl, methyl iodide, or the like in a solvent having no adverse effect on the present reaction such as N,N-dimethylformamide, and subsequently to N-methylation. An amino acid derivative (S25) can be derivatized to the corresponding amino acid derivative (S21) by coupling reaction with the halogen derivative (S24) in a solvent having no adverse effect on the present reaction such as N,N-dimethylformamide in the presence of metal such as zinc using a metal catalyst such as bis(triphenylphosphine)palladium(II) dichloride. A target intermediate (S22) having an amino group at an end can be produced by subjecting the resulting amino acid derivative (S21) to acid hydrolysis, for example, using hydrochloric acid or trifluoroacetic acid, or deprotection by hydrogenation or the like in the presence of hydrogen using a catalyst such as palladium carbon.

A compound in which A has a group represented by the general formula (2-4) also can be produced according to the above-described method or the method disclosed in Patent Literature 4.

The compound represented by the general formula (1) or a salt thereof is administered as it is or as various pharmaceutical compositions. Examples of the dosage forms of the pharmaceutical compositions include tablets, powders, pills, granules, capsules, suppositories, solutions, dragees, depot preparations, or syrups, and the pharmaceutical compositions can be produced according to conventional methods using common formulation aids.

For example, a tablet can be obtained by mixing the phenylalanine derivative that is the active ingredient of the present invention with known auxiliary substances, e.g., inert diluents such as lactose, calcium carbonate, or calcium phosphate, binders such as gum arabic, corn starch, or gelatin, swelling agents such as alginic acid, corn starch, or pregelatinized starch, sweeteners such as sucrose, lactose, or saccharin, flavoring agents such as peppermint, *Gaultheria adenothrix* (Akamono) oil, or cherry, wetting agents such as magnesium stearate, talc, or carboxymethylcellulose, excipients for soft gelatin capsules and suppositories such as fats, waxes, semi-solid and liquid polyols, natural oils, or hardened oils, or excipients for solutions such as water, alcohol, glycerol, polyol, sucrose, invert sugar, glucose, or vegetable oils.

An inhibitor containing the compound represented by the general formula (1) or a salt thereof as an active ingredient can be used as a therapeutic agent or a preventive agent for any one of inflammatory disease in which an α4 integrin-dependent adhesion process is involved in pathological conditions, rheumatoid arthritis, inflammatory bowel disease, systemic lupus erythematosus, multiple sclerosis, Sjogren's syndrome, asthma, psoriasis, allergy, diabetes, cardiovascular disease, arteriosclerosis, restenosis, tumor growth, tumor metastasis, and transplantation rejection.

The dose used for the above-described object is determined depending on the target therapeutic effect, the administration method, the treatment period, the age, the body weight, or the like, but the adult dose per day by a route of oral or parenteral administration may be generally 1 μg to 5 g in the case of oral administration, and 0.01 μg to 1 g in the case of parenteral administration.

EXAMPLES

The present invention will be described in detail below with reference to the following Examples. The Examples are preferred embodiments of the present invention, and the present invention will not be limited to the Examples.

Example 1

Synthesis of M-1

(Step 1) Methyl 3-[(5-bromo-2-pyridyl)carbamoylamino]pyridine-4-carboxylate

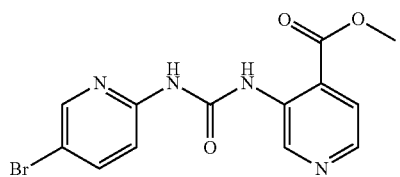 [SMILES: COC(=O)c1ccncc1NC(=O)Nc1ccc(Br)cn1]

Methyl 3-aminopyridine-4-carboxylate (31.8 g, 209 mmol) was dissolved in methylene chloride (1.1 L), a solution (50 ml) of triphosgene (20.7 g, 69.8 mmol) in methylene chloride was added thereto, and the resulting mixture was stirred at 0° C. for 3 hours. A solution (50 ml) of 5-bromopyridin-2-amine (30.0 g, 174 mmol) in methylene chloride was added to the reaction solution, and the resulting mixture was stirred at room temperature for 12 hours. The precipitated solid was filtered, washed with methylene chloride, and then dried under reduced pressure to obtain the title compound (30 g, 49%).

$^1$H NMR (400 MHz, DMSO-$d_6$): δ 11.02 (s, 1H), 10.36 (s, 1H), 9.44 (s, 1H), 8.39 (s, 2H), 7.98 (d, J=8.0 Hz, 1H), 7.74-7.73 (m, 1H), 7.48 (d, J=8.0 Hz, 1H), 3.92 (s, 3H).

(Step 2) 3-(5-Bromo-2-pyridyl)-1-methyl-pyrido[3,4-d]pyrimidine-2,4-dione

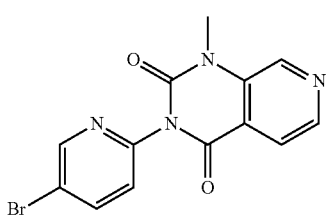 [SMILES: Cn1c(=O)n(-c2ccc(Br)cn2)c(=O)c2ccncc21]

Methyl 3-[(5-bromo-2-pyridyl)carbamoylamino]pyridine-4-carboxylate <see (step 1)> (30 g, 85.7 mmol) was dissolved in N,N-dimethylformamide (600 ml), an aqueous solution (80 ml) of potassium carbonate (23.7 g, 171 mmol) was added thereto, and the resulting mixture was stirred at room temperature for 3 hours. To the resulting solution, potassium carbonate (23.7 g, 171 mmol) and p-toluenesulfonic acid methyl ester (31.9 g, 171 mmol) were further added, and the resulting mixture was stirred at room temperature for 90 minutes. The reaction liquid was cooled to 0° C., and then diluted with water and extracted with ethyl acetate (100 ml×4). The extracts were combined, washed with a saturated saline solution, dried over anhydrous sodium sulfate, and then the solvent was removed under reduced pressure. The obtained residue was stirred in petroleum ether for 20 minutes, and the obtained solid was filtered and dried under reduced pressure to obtain the title compound (9.8 g, 34%).

$^1$H NMR (400 MHz, DMSO-$d_6$): δ 9.00 (s, 1H), 8.77 (m, 1H), 8.58 (d, J=4.8 Hz, 1H), 8.32-8.29 (m, 1H), 7.91 (d, J=4.8 Hz, 1H), 7.52 (d, J=8.4 Hz, 1H), 3.61 (s, 3H).

(Step 3) Cyclohexyl (2S)-3-benzyloxy-2-(tert-butoxycarbonylamino)propanoate

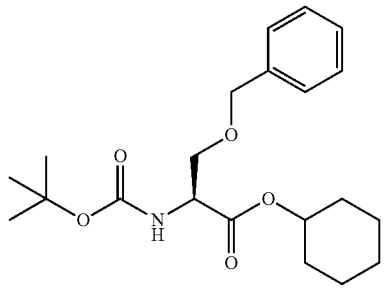 [SMILES: CC(C)(C)OC(=O)N[C@@H](COCc1ccccc1)C(=O)OC1CCCCC1]

(2S)-3-Benzyloxy-2-(tert-butoxycarbonylamino)propionic acid (300 g, 1.02 mol) was dissolved in N,N-dimethylformamide (2.0 L), EDCL (189 g, 1.22 mmol), cyclohexanol (210 g, 2.10 mol), and N,N-dimethyl-4-aminopyridine (12.4 g, 102 mmol) were added thereto, and the resulting mixture was stirred in the presence of nitrogen gas at room temperature for 90 minutes. The reaction solution was diluted with water (5.0 L) and then extracted with ethyl acetate (1.0 L×2). The extracts were combined and washed with water (1.0 L), 1 N hydrochloric acid (900 ml), a saturated aqueous solution of sodium hydrogen carbonate (1.0 L), and a saturated saline solution (900 ml), dried over anhydrous sodium sulfate, and then the solvent was removed under reduced pressure to obtain the title compound (360 g, 94%).

$^1$H NMR (400 MHz, DMSO-$d_6$): δ 7.35-7.25 (m, 5H), 7.06 (d, J=8.4 Hz, 1H), 4.73-4.69 (m, 1H), 4.51-4.39 (m, 2H), 4.26-4.21 (m, 1H), 3.73-3.64 (m, 2H), 1.47-1.10 (m, 19H).

(Step 4) Cyclohexyl (2S)-2-(tert-butoxycarbonylamino)-3-hydroxy-propanoate

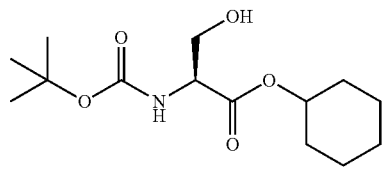 [SMILES: CC(C)(C)OC(=O)N[C@@H](CO)C(=O)OC1CCCCC1]

Cyclohexyl (2S)-2-(tert-butoxycarbonylamino)-3-hydroxy-propanoate (360 g, 954 mmol) <see (step 3)> was dissolved in ethanol (1.6 L), palladium hydroxide 20% on carbon (40 g) was added thereto, and the resulting mixture was stirred in the presence of hydrogen gas (50 psi) at 70° C. for 3 days. The reaction solution was filtered, and the obtained filtrate was concentrated and then dried under reduced pressure to obtain the title compound (250 g, 91%).

$^1$H NMR (400 MHz, DMSO-$d_6$): δ 6.80 (d, J=8.0 Hz, 1H), 4.82 (s, 1H), 4.72-4.67 (m, 1H), 4.37 (s, 1H), 4.01-3.99 (m, 1H), 3.46-3.38 (m, 1H), 1.48-1.35 (m, 19H).

(Step 5) Cyclohexyl (2R)-2-(tert-butoxycarbonylamino)-3-iodine-propanoate

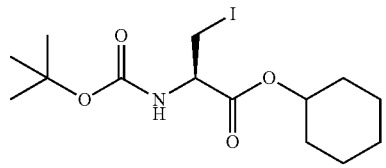 [SMILES: CC(C)(C)OC(=O)N[C@@H](CI)C(=O)OC1CCCCC1]

Triphenylphosphine (275 g, 1.05 mol) and imidazole (75.0 g, 1.05 mol) were dissolved in methylene chloride (3.0 L), the resulting solution was cooled to 0° C., then iodine (270 g, 1.05 mol) was added thereto, and the resulting mixture was stirred in the presence of nitrogen gas at room temperature for 30 minutes. The reaction solution was cooled to 0° C., then a solution (500 ml) of cyclohexyl (2S)-2-(tert-butoxycarbonylamino)-3-hydroxy-propanoate <see (step 4)> (250 g, 871 mmol) in methylene chloride was slowly added dropwise over 1 hour, and the reaction liquid was stirred at room temperature for 2 hours. The reaction liquid was filtered, the obtained residue was washed with hexane/diethyl ether (1:1), and the obtained filtrate was purified by silica gel column chromatography (petroleum ether:ethyl acetate=1:1 to 1:2) to obtain the title compound (200 g, 58%).

$^1$H NMR (400 MHz, DMSO-d$_6$): δ 7.24 (d, J=8.0 Hz, 1H), 4.75-4.69 (m, 1H), 4.21-4.16 (m, 1H), 3.51-3.47 (m, 1H), 3.36-3.33 (m, 1H), 1.75-1.10 (m, 19H).

(Step 6) Cyclohexyl (2S)-2-(tert-butoxycarbonylamino)-3-[6-(1-methyl-2,4-dioxo-pyrido[3,4-d]pyrimidin-3-yl)-3-pyridyl]propanoate

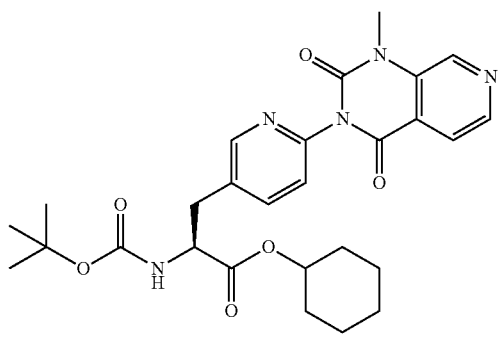 [SMILES: Cn1c(=O)n(-c2ccc(C[C@H](NC(=O)OC(C)(C)C)C(=O)OC3CCCCC3)cn2)c(=O)c2ccncc21]

Zinc (9.50 g, 146 mmol) was heated at 210° C. for 10 minutes, cooled to 70° C., then heated to 210° C. again, and stirred for 10 minutes. The resultant was cooled to room temperature, then N,N-dimethylformamide (20 ml) and a solution (5.0 ml) of dibromoethane (2.10 g, 11.2 mmol) in N,N-dimethylformamide were added thereto, and the resulting mixture was stirred at 90° C. for 30 minutes. The reaction mixture was cooled to room temperature, then trimethylsilyl chloride (243 mg, 2.25 mmol) was added thereto, and the resulting mixture was stirred at room temperature for 10 minutes. A solution (15 ml) of cyclohexyl (2R)-2-(tert-butoxycarbonylamino)-3-iodine-propanoate <see (step 5)> (8.90 g, 22.5 mmol) in N,N-dimethylformamide was added to the reaction liquid, and the resulting mixture was stirred at 35° C. for 90 minutes. This zinc derivative was added to a suspension of 3-(5-bromo-2-pyridyl)-1-methyl-pyrido[3,4-d]pyrimidine-2,4-dione <see (step 2)> (2.50 g, 7.49 mmol) and Pd(PPh$_3$)$_2$Cl$_2$ (788 mg, 1.12 mmol) in N,N-dimethylformamide (20 ml), and the resulting mixture was stirred in the presence of nitrogen gas at 80° C. for 2 hours. The reaction mixture was cooled to room temperature, then the reaction solution was filtered, the obtained filtrate was diluted with water (150 ml) and extracted with ethyl acetate (100 ml×3). The extracts were combined, washed with a saturated saline solution, dried over anhydrous sodium sulfate, and then the solvent was removed under reduced pressure. The obtained residue was purified by silica gel column chromatography (petroleum ether:ethyl acetate=1:1 to 1:2) to obtain the title compound (1.88 g, 48%).

$^1$H NMR (400 MHz, DMSO-d$_6$)=δ 8.99 (s, 1H), 8.56 (d, J=4.8 Hz, 1H), 8.46-8.45 (m, 1H), 7.92-7.89 (m, 2H), 7.43-7.40 (m, 2H), 4.69-4.67 (m, 1H), 4.26-4.21 (m, 1H), 3.60 (s, 3H), 3.13-2.96 (m, 2H), 1.76-1.20 (m, 19H).

(Step 7) Cyclohexyl 3-[6-(1-methyl-2,4-dioxo-1,4-dihydropyrido[3,4-d]pyrimidin-3(2H)-yl)pyridin-3-yl]-L-alaninate (M-1)

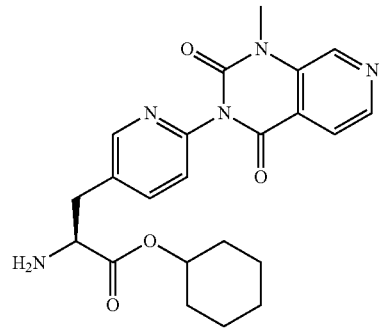 [SMILES: Cn1c(=O)n(-c2ccc(C[C@H](N)C(=O)OC3CCCCC3)cn2)c(=O)c2ccncc21]

Cyclohexyl (2S)-2-(tert-butoxycarbonylamino)-3-[6-(1-methyl-2,4-dioxo-pyrido[3,4-d]pyrimidin-3-yl)-3-pyridyl]propanoate <see (step 6)> (7.50 g, 14.3 mmol) was dissolved in ethyl acetate (20 ml), 4 N hydrochloric acid/ethyl acetate (25 ml) was added thereto, and the resulting mixture was stirred at room temperature for 1 hour. The solvent was removed under reduced pressure, then ethyl acetate (30 ml) was added thereto, and the resulting mixture was stirred for 5 minutes. The obtained white solid was filtered and dried under reduced pressure to obtain the title compound (5.77 g, 87%) as a hydrochloride.

$^1$H NMR (400 MHz, CD$_3$OD); δ 9.29 (s, 1H), 8.75 (d, J=6.0 Hz, 1H), 8.61 (d, J=2.0 Hz, 1H), 8.58 (d, J=5.6 Hz, 1H), 8.11 (dd, J=8.0, 2.4 Hz, 1H), 7.61 (d, J=8.0 Hz, 1H), 4.87-4.83 (m, 1H), 4.47 (t, J=7.6 Hz, 1H), 3.73 (s, 3H), 3.40-3.38 (m, 2H), 1.87-1.29 (m, 10H); MS (ESI) m/z 424 (M+H)$^+$

Example 2

Synthesis of M-2

(Step 1) 5-Iodine-6-methyl-1H-pyrimidine-2,4-dione

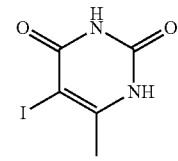

Iodobenzene diacetate (38.0 g, 119 mmol) was dissolved in dichloromethane (100 ml), iodine (5.00 g, 19.8 mmol) was added thereto, and the resulting mixture was stirred for 30 minutes. 6-Methyl-1H-pyrimidine-2,4-dione (5.01 g, 39.7 mmol) was added to the reaction solution, and the resulting mixture was stirred. The reaction solution was concentrated under reduced pressure and then purified by silica gel column chromatography (petroleum ether:ethyl acetate=1:1 to 1:3) to obtain the title compound (3.50 g, 35%).

$^1$H NMR (DMSO-d$_6$, 300 MHz): δ 11.3 (s, 2H), 2.27 (s, 3H).

(Step 2)
5-Iodine-1,3,6-trimethyl-1H-pyrimidine-2,4-dione

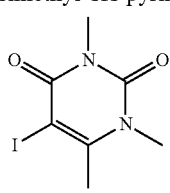

5-Iodine-6-methyl-1H-pyrimidine-2,4-dione (3.50 g, 13.9 mmol) <see (step 1)> and potassium carbonate (5.70 g, 41.7 mmol) were dissolved in N,N-dimethylformamide (50 ml), iodomethane (5.02 g, 34.7 mmol) was added thereto, and the resulting mixture was stirred at room temperature for 12 hours. The reaction liquid was diluted with water and then extracted with ethyl acetate (50 ml×3). The organic layers were combined, then washed with a saturated saline solution and dried over magnesium sulfate. The solvent was removed under reduced pressure to obtain the title compound (3.15 g, 81%).

$^1$H NMR (DMSO-$d_6$, 300 MHz): δ 3.41 (s, 3H), 3.22 (s, 3H), 2.61 (s, 3H)

(Step 3) Methyl N-(tert-butoxycarbonyl)-O-[(trifluoromethyl)sulfonyl]-L-tyrosinate

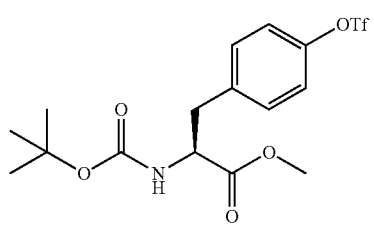 [SMILES: COC(=O)[C@H](Cc1ccc(OS(=O)(=O)C(F)(F)F)cc1)NC(=O)OC(C)(C)C]

Methyl N-(tert-butoxycarbonyl)-L-tyrosinate (60.0 g, 203 mmol) was dissolved in tetrahydrofuran, N-phenylbis(trifluoromethanesulfonamide) (79.8 g, 224 mmol) and diisopropylethylamine (90.0 g, 714 mmol) were added thereto, and the resulting mixture was stirred at room temperature for 12 hours. The reaction solution was concentrated under reduced pressure, then the obtained residue was purified by silica gel column chromatography (petroleum ether:ethyl acetate=3:1) to obtain the title compound (74.0 g, 85%).

1H NMR (CDCl3, 400 MHz): δ 7.25-7.19 (m, 4H), 5.08-5.06 (m, 1H), 4.61-4.59 (m, 1H), 3.71 (3H, s), 3.19-3.15 (m, 1H), 3.06-3.01 (m, 1H), 1.41 (s, 9H); MS (ESI) m/z 328 (M+H)$^+$ (Step 4) Methyl N-(tert-butoxycarbonyl)-4-(4,4,5,5-tetramethyl-1,3,2-dioxaborolan-2-yl)-L-phenylalaninate

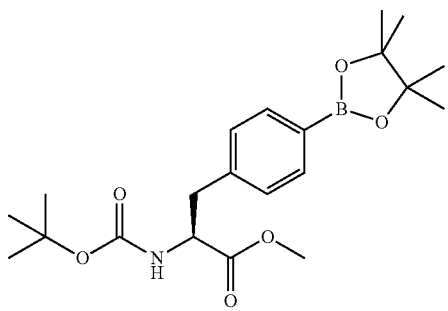 [SMILES: COC(=O)[C@H](Cc1ccc(B2OC(C)(C)C(C)(C)O2)cc1)NC(=O)OC(C)(C)C]

Methyl N-(tert-butoxycarbonyl)-O-[trifluoromethyl)sulfonyl]-L-tyrosinate <see (step 3)> (74.0 g, 173 mmol) and bis (pinacolato)diborane (66.0 g, 260 mmol) were dissolved in N,N-dimethylformamide (1.0 L). [1,1'-bis(Diphenylphosphino)ferrocene]dichloropalladium (II) (13.6 g, 18.6 mmol) and potassium acetate (60.0 g, 612 mmol) were added to the solution, and the resulting mixture was stirred at 95° C. for 12 hours. The reaction mixture was cooled to room temperature, then the reaction solution was filtered through Celite, and the filtrate was concentrated under reduced pressure. The obtained residue was purified by silica gel column chromatography (petroleum ether:ethyl acetate=4:1) to obtain the title compound (45.0 g, 65%).

1H NMR (CDCl3, 400 MHz): δ 7.73 (d, J=8 Hz, 2H), 7.12 (d, J=8 Hz, 2H), 4.59-4.57 (m, 1H), 3.70 (3H, s), 3.11-3.06 (m, 2H), 1.41 (s, 9H), 1.13 (s, 12H); MS (ESI) m/z 306 (M+H)$^+$ (Step 5) [4-[(2S)-2-(tert-Butoxycarbonylamino)-3-methoxy-3-oxo-propyl]phenyl]boronic acid

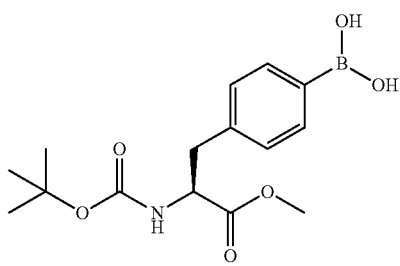 [SMILES: COC(=O)[C@H](Cc1ccc(B(O)O)cc1)NC(=O)OC(C)(C)C]

Methyl N-(tert-butoxycarbonyl)-4-(4,4,5,5-tetramethyl-1,3,2-dioxaborolan-2-yl)-L-phenylalaninate <see (step 4)> (67.0 g, 165 mmol) was dissolved in acetone (700 ml), sodium periodate (71.0 g, 330 mmol), ammonium acetate (25.0 g, 330 mmol), and water (300 ml) were added thereto, and the resulting mixture was stirred at room temperature for 55 hours. The reaction solution was filtered through Celite, then the filtrate was concentrated under reduced pressure, ethyl acetate was added, washed with water and a saturated saline solution, and dried over anhydrous sodium sulfate. The solvent was removed under reduced pressure, and the precipitated solid was washed with a mixed solvent of petroleum ether:ethyl acetate (1:10) and then dried to obtain the title compound (29.0 g, 55%).

1H NMR (CDCl3, 400 MHz): δ: 7.71-7.56 (m, 2H), 7.25-7.16 (m, 2H), 4.39-4.37 (m, 1H), 3.71 (s, 3H), 3.14-3.10 (m, 1H), 2.96-2.90 (m, 1H), 1.40 (s, 9H); MS (ESI) m/z 224 (M+H)$^+$ (Step 6) Methyl (2S)-2-(tert-butoxycarbonylamino)-3-[4-(1,3,4-trimethyl-2,6-dioxo-pyrimidin-5-yl)phenyl]propanoate

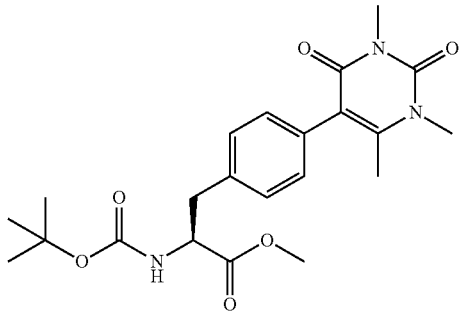 [SMILES: COC(=O)[C@H](Cc1ccc(-c2c(C)n(C)c(=O)n(C)c2=O)cc1)NC(=O)OC(C)(C)C]

5-Iodine-1,3,6-trimethyl-1H-pyrimidine-2,4-dione <see (step 2)> (0.52 g, 1.8 mmol), [4-[(2S)-2-(tert-butoxycarbonylamino)-3-methoxy-3-oxo-propyl]phenyl]boronic acid <see (step 5)> (0.50 g, 1.5 mmol), sodium carbonate (0.49 g, 4.65 mmol), and Pd(dppf)Cl$_2$ (57 mg, 0.078 mmol) were dissolved in dioxane (100 ml) and water (3.0 ml), and the resulting mixture was stirred in the presence of nitrogen gas at 100° C. for 3 hours. The reaction solution was concentrated under reduced pressure, and then the obtained residue was purified by silica gel column chromatography (petroleum ether:ethyl acetate=3:1 to 1:1) to obtain the title compound (0.35 g, 51%).

$^1$H NMR (CDCl$_3$, 300 MHz): δ 7.20-7.13 (m, 4H), 5.04-5.02 (m, 1H), 4.63-4.60 (m, 1H), 3.74 (s, 3H), 3.51 (s, 3H), 3.41 (s, 3H), 3.14-3.07 (m, 2H), 2.05 (s, 3H), 1.35 (s, 9H); MS (ESI) m/z 432 (M+H)$^+$ (Step 7) Methyl (2S)-2-amino-3-[4-(1,3,4-trimethyl-2,6-dioxo-pyrimidin-5-yl)phenyl]propanoate (M-2)

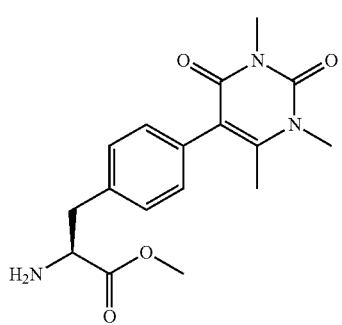

Methyl (2S)-2-(tert-butoxycarbonylamino)-3-[4-(1,3,4-trimethyl-2,6-dioxo-pyrimidin 5-yl)phenyl]propanoate <see step 6> (1.30 g, 2.80 mmol) was dissolved in dichloromethane (10 ml), the reaction solution was cooled to 0° C., then 3 N hydrochloric acid/dichloromethane (10.0 ml, 30.0 mmol) was added thereto, and the resulting mixture was stirred at room temperature for 1 hour. The reaction solution was concentrated under reduced pressure, then dichloromethane (10.0 ml) was added thereto, and the resulting mixture was stirred at room temperature for 30 minutes. The precipitated solid was filtered and dried to obtain the title compound (0.84 g, 82%) as a white solid.

$^1$H NMR (CD$_3$OD, 400 MHz): δ 7.35 (d, J=10.0 Hz, 2H), 7.24 (t, J=11.2 Hz, 2H), 4.39 (dd, J=11.2, 7.6 Hz, 1H), 3.88 (s, 3H), 3.53 (s, 3H), 3.36 (s, 3H), 3.34-3.15 (m, 2H), 2.21 (s, 3H); MS (ESI) m/z 332 (M+H)$^+$

Example 3

Synthesis of M-3

(Step 1) 5-(Methylaminomethyl)-2-nitro-benzoic acid

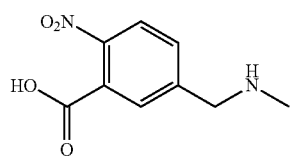

5-Methyl-2-nitro-benzoic acid (50.0 g, 276 mmol) and 5-dimethylhydantoin (36.6 g, 128 mmol) were suspended in chlorobenzene (100 ml), and the suspension was heated at 40° C. in the presence of argon gas. Azobis(2-methylpropionitrile) (1.26 g, 7.69 mmol) was added thereto, and the resulting mixture was stirred at 80° C. for 1 hour. The reaction liquid was cooled to 40° C. once, then 5-dimethylhydantoin (18.3 g, 64.1 mmol) and azobis(2-methylpropionitrile) (1.26 g, 7.69 mmol) were added again, and the resulting mixture was stirred at 80° C. for 2 hours. The reaction liquid was cooled to 10° C., and then the resulting mixture was stirred for 12 hours. The crystallized solid was filtered off, the obtained filtrate was added dropwise to a 40% methylamine/methanol solution (260 ml, 2.56 mol) that had been cooled to 10° C. over 80 minutes, and the resulting mixture was stirred at 25° C. The reaction liquid was concentrated under reduced pressure, then 2-propanol (100 ml) was added thereto, the resulting mixture was stirred at 50° C. for 1 hour and then cooled to 9° C., and the precipitated solid was filtered off, washed with 2-propanol (100 ml) and dried to obtain the title compound (42.2 g, 52%) as a white solid.

1H NMR (400 MHz, D$_2$O): δ8.03 (d, J=8.44 Hz, 1H), 7.55 (dd, J=8.44 Hz, 1.92 Hz, 1H), 7.49 (t, 1H), 4.25 (s, 2H), 2.70 (s, 3H); MS (ESI) m/z 210.8 (M+H)$^+$ (Step 2) 5-[[Formyl(methyl)amino]methyl]-2-nitro-benzoic acid

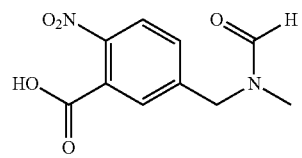

5-(Methylaminomethyl)-2-nitro-benzoic acid <see (step 1)> (5.58 g) and sodium formate (0.65 g, 9.52 mmol) were dissolved in formic acid (4.00 ml) and acetic anhydride (2.70 mml, 14.3 mmol), and the resulting mixture was stirred at room temperature for 1 hour. The reaction liquid was diluted with water (32 ml), a crystal was precipitated, and a slurry was obtained. The slurry was stirred at 9° C. for 12 hours, and the precipitated solid was filtered off and dried under reduced pressure to obtain the title compound (3.95 g, 87%) as a white solid.

1H-NMR (400 MHz, DMSO-d$_6$): δ8.32 (s, 1H), 8.19 (s, 1H), 8.01 (d, J=8.24 Hz, 1H), 7.98 (d, J=8.24 Hz, 1H), 7.73 (d, 1H, J=1.88 Hz), 7.66 (d, J=1.92 Hz, 1H), 7.65 (dd, J=8.24 Hz, 1.72 Hz, 1H), 7.58 (dd, J=8.24 Hz, 1.92 Hz, 1H), 4.62 (s, 2H), 4.57 (s, 2H), 2.89 (s, 3H), 2.65 (s, 3H); MS (ESI) m/z 239 (M+H)$^+$ (Step 3) 2-Amino-5-[[formyl(methyl)amino]methyl]benzoic acid

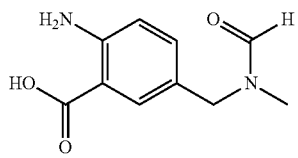

5-[[Formyl(methyl)amino]methyl]-2-nitro-benzoic acid <see (step 2)> (6.96 g, 25.19 mmol) was suspended in methanol (48.0 ml), and a 6 N aqueous solution of sodium hydroxide (3.5 ml) was added thereto and dissolved. 5% Pd/C (1.03 g, 0.250 mmol) was added, and the resulting mixture was stirred in the presence of hydrogen gas at 40° C. for 5 hours. The reaction liquid was cooled to room temperature and filtered, and the solvent was removed under reduced pressure. Water (48 ml) and a 2 N aqueous solution of hydrochloric acid (11.0 ml) were added to the obtained residue, the precipitated solid was filtered off, washed with water (24.0 ml), and dried under reduced pressure to obtain the title compound (4.84 g, 92.3%) as a white solid.

1H NMR (400 MHz, DMSO-d$_6$): δ8.49 (bs, 2H), 8.25 (s, PhCCH$_2$NMeCH$_a$O), 8.08 (s, PhCCH2NMeCH$_b$O), 7.60 and 7.59 (s, 1H), 7.12 (m, 1H), 6.74 (m, 1H), 4.27 (s, 2H), 2.77 and 2.58 (s, 3H); MS (ESI) m/z 231 (M+H)$^+$ (Step 4) Methyl (2S)-2-[tert-butoxycarbonylamino]-3-[4-[6-[[formyl(methyl)amino]methyl]-1-methyl-2,4-dioxo-quinazolin-3-yl]phenyl]propanoate

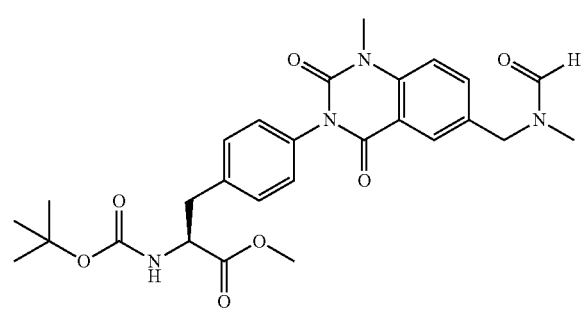 [SMILES: COC(=O)[C@H](Cc1ccc(-n2c(=O)c3cc(CN(C)C=O)ccc3n(C)c2=O)cc1)NC(=O)OC(C)(C)C]

Carbodiimidazole (16.4 g, 101 mmol) was dissolved in N,N-dimethylformamide (50 methyl (2S)-3-(4-aminophenyl)-2-(tert-butoxycarbonylamino)propanoate (25.0 g, 84.9 mmol) and 2-amino-5-[[formyl(methyl)amino]methyl]benzoic acid <see (step 3)> (17.6 g, 84.5 mmol) were added thereto, and the resulting mixture was stirred at 65° C. The reaction liquid was cooled to room temperature, then car-bodiimidazole (16.4 g, 101 mmol) was added again, and the resulting mixture was stirred at 65° C. After the reaction was completed, the reaction liquid was diluted with water (2,000 ml) and extracted with methylene chloride (500 ml, 100 ml). The extracts were combined, washed with a saturated saline solution, and dried. The obtained compound was used in (step 5).

(Step 5) Methyl (2S)-2-amino-3-[4-[6-[[formyl(methyl)amino]methyl]-1-methyl-2,4-quinazolin-3-yl]phenyl]propanoate (M-3)

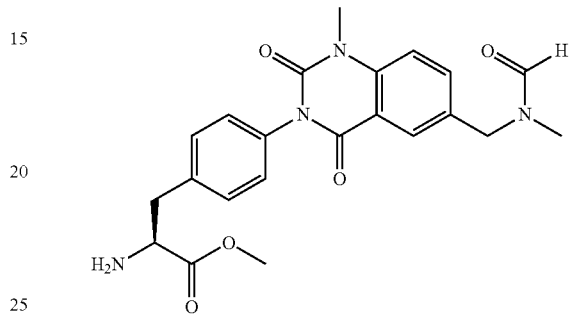

The compound obtained in (step 4) was dissolved in N,N-dimethylformamide (150 ml), potassium carbonate (21.7 g) and methyl p-toluenesulfonate (17.8 ml) was added thereto, and the resulting mixture was stirred at 40° C. for 4 hours. Acetic acid (9.0 ml) was added, then the reaction liquid was diluted with water (1,500 ml) and extracted with methylene chloride (1,000 ml), and the solvent was removed under reduced pressure. The obtained residue was purified by silica gel column chromatography (methylene chloride: methanol=9:1). The obtained compound was dissolved in isopropyl alcohol (150 ml), 4 N hydrochloric acid/dioxane (150 ml) was added thereto, and the resulting mixture was stirred at room temperature for 1 hour. The precipitated solid was filtered, washed with isopropyl alcohol (100 ml) and dried to obtain a hydrochloride of the title compound (28.0 g).

$^1$H NMR (400 MHz, DMSO-d$_6$) δ 8.70 (s, 3H), 8.35 (s, PhCCH$_2$NMeCH$_a$O), 8.16 (s, PhCCH2NMeCH$_b$O), 7.93 (dd, J=15.8, 2.1 Hz, 1H), 7.77-7.66 (m, 1H), 7.53 (dd, J=11.7, 8.6 Hz, 1H), 7.38-7.33 (m, 2H), 7.30-7.25 (m, 2H), 4.55 and 4.53 (s, 2H), 4.36 (dd, J=7.3, 6.0 Hz, 1H), 3.70 (s, 3H), 3.54 and 3.53 (s, 3H), 3.33 (s, 3H), 3.25 (dd, J=14.1, 5.9 Hz, 1H), 3.16 (dd, J=14.1, 7.3 Hz, 1H); MS (ESI) m/z 425.48 (M+H)$^+$ Example 4

Synthesis of M-4

(Step 1) 2-Chloro-5-nitro-pyridine-4-carboxylic acid

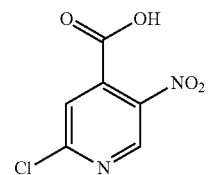 [SMILES: O=C(O)c1cc(Cl)ncc1[N+](=O)[O-]]

2-Chloro-4-methyl-5-nitro-pyridine (20.5 g, 119 mmol) was dissolved in concentrated sulfuric acid (200 ml), the resulting solution was cooled to 0° C., then chromium(VI) oxide (40.0 g, 400 mmol) was added thereto, and the resulting mixture was stirred at 0° C. for 1 hour and then at room temperature for 12 hours. The reaction liquid was diluted with water (2,000 ml), and the precipitated solid was filtered and dried to obtain the title compound (18.0 g, 75%).

$^1$H NMR (400 MHz, CD$_3$OD): δ 10.8 (br, s, 1H), 9.13 (s, 1H), 7.70 (s, 1H).

(Step 2) Methyl 2-chloro-5-nitro-pyridine-4-carboxylate

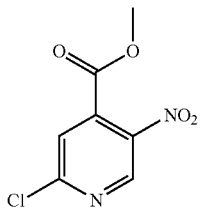

2-Chloro-5-nitro-pyridine-4-carboxylic acid <see (step 1)> (20.2 g, 100 mmol) was dissolved in ethyl acetate (100 ml), the resulting solution was cooled to 0° C., then a diazomethane/diethyl ether solution was added thereto, and the resulting mixture was stirred at 0° C. for 1 hour. The reaction liquid was concentrated, then the obtained residue was purified by silica gel column chromatography (petroleum ether:ethyl acetate=6:1 to 2:1) to obtain the title compound (20.0 g, 92%).

(Step 3) Methyl 2-methoxy-5-nitro-pyridine-4-carboxylate

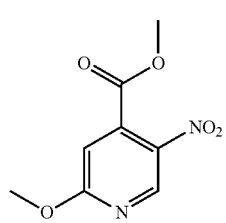

Methyl 2-chloro-5-nitro-pyridine-4-carboxylate <see (step 2)> (10.8 g, 50.0 mmol) was dissolved in methanol (100 ml), sodium methoxide (8.10 g, 150 mmol) was added thereto, and the resulting mixture stirred at 65° C. for 4 hours. The reaction liquid was concentrated under reduced pressure, and then the obtained residue was purified by silica gel column chromatography (petroleum ether:ethyl acetate=8:1 to 4:1) to obtain the title compound (8.0 g, 75%).

(Step 4) Methyl 5-amino-2-methoxy-pyridine-4-carboxylate

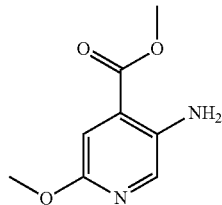

Methyl 2-methoxy-5-nitro-pyridine-4-carboxylate <see (step 3)> (8.0 g, 37 mmol) was dissolved in methanol (100 ml), a saturated aqueous solution of ammonium chloride (50 ml) and iron (10.6 g, 175 mmol) were added thereto, and the resulting mixture was stirred at 65° C. for 2 hours. The reaction liquid was cooled to room temperature, then the pH was adjusted to >7.0 with an aqueous solution of sodium hydrogen carbonate, and the reaction solution was filtered and extracted with ethyl acetate (100 ml×3). The extracts were combined, washed with a saturated saline solution, dried over anhydrous sodium sulfate, and then the solvent was removed under reduced pressure. The obtained residue was purified by silica gel column chromatography (petroleum ether:ethyl acetate=4:1 to 1:1) to obtain the title compound (5.80 g, 84%).

1H NMR (400 MHz, CDCl$_3$): δ 7.80 (s, 1H), 7.15 (s, 1H), 5.10 (s, 2H), 3.90 (s, 3H), 3.84 (s, 3H).

(Step 5) 3-(6-Bromo-3-pyridyl)-6-methoxy-1-methyl-pyrido[3,4-d]pyrimidine-2,4-dione

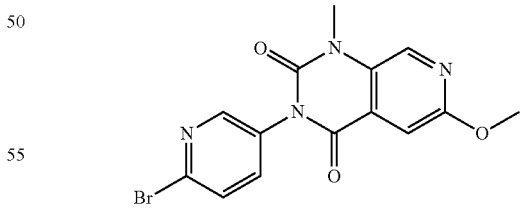

Two steps similar to Example 1 (step 1), (step 2) were performed to methyl 5-amino-2-methoxy-pyridine-4-carboxylate <see (step 4)> (21.0 g, 115 mmol) and 6-bromopyridin-3-amine (19.9 g, 115 mmol) to obtain the title compound (12.9 g, 31%).

1H NMR (400 MHz, DMSO-d$_6$): δ 8.58 (s, 1H), 8.40 (s, 1H), 7.87-7.78 (m, 2H), 7.30 (s, 1H), 3.93 (s, 3H), 3.57 (s, 3H).

(Step 6) Methyl (2S)-2-(tert-butoxycarbonylamino)-3-[5-(6-methoxy-1-methyl-2,4-dioxo-pyrido[3,4-d]pyrimidin-3-yl)-2-pyridyl]propanoate

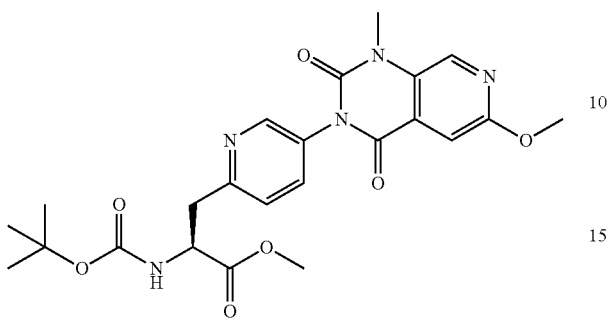

A method similar to Example 1 (step 6) was performed to 3-(6-bromo-3-pyridyl)-6-methoxy-1-methyl-pyrido[3,4-d]pyrimidine-2,4-dione <see (step 5)> (12.5 g, 34.6 mmol) to obtain the title compound (10.0 g, 60%).

1H NMR (400 MHz, DMSO-$d_6$): δ 8.57 (s, 1H), 8.45 (s, 1H), 7.43 (d, J=17.2 Hz, 1H), 7.34 (d, J=8 Hz, 1H), 7.29 (s, 1H), 4.55-4.49 (m, 1H), 3.93 (s, 3H), 3.62 (s, 3H), 3.56 (s, 3H), 3.33-3.07 (m, 2H), 1.37 (s, 9H).

(Step 7) Methyl (2S)-2-amino-3-[5-(6-methoxy-1-methyl-2,4-dioxo-pyrido[3,4-d]pyrimidin-3-yl)-2-pyridyl]propanoate (M-4)

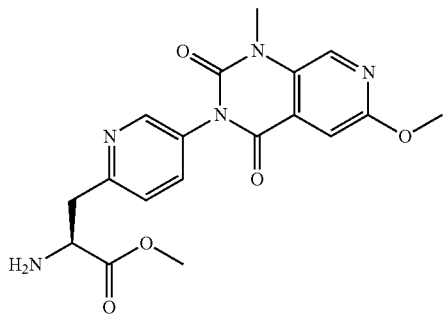 [SMILES: COC(=O)[C@@H](N)Cc1ccc(-n2c(=O)c3cc(OC)ncc3n(C)c2=O)cn1]

A method similar to Example 1 (step 7) was performed to methyl (2S)-2-(tert-butoxycarbonylamino)-3-[5-(6-methoxy-1-methyl-2,4-dioxo-pyrido[3,4-d]pyrimidin-3-yl)-2-pyridyl]propanoate <see (step 6)> (10.0 g, 20.0 mmol) to obtain a hydrochloride of the title compound. A saturated aqueous solution of sodium hydrogen carbonate (100 ml) was added to the obtained hydrochloride, then the resulting mixture was extracted with ethyl acetate (100 ml×2), the extracts were combined, the resulting mixture was washed with a saturated saline solution, dried over anhydrous sodium sulfate, and then the solvent was removed under reduced pressure to obtain the title compound (4.20 g, 53%).

$^1$H NMR (400 MHz, CD$_3$OD): δ 8.49 (s, 1H), 8.46 (d, J=2.0 Hz, 1H), 7.75 (dd, J=8.4, 2.4 Hz, 1H), 7.49 (d, J=8.4 Hz, 1H), 7.41 (s, 1H), 4.02-3.98 (m, 4H), 3.73 (s, 3H), 3.67 (s, 3H), 3.33-3.30 (m, 1H), 3.22-3.16 (m, 1H); MS (ESI) m/z 386 (M+H)$^+$

Example 5

Synthesis of M-5

(Step 1) Methyl N-(tert-butoxycarbonyl)-4-(3-methyl-2,6-dioxo-3,6-dihydropyrimidine-1(2H)-yl)-L-phenylalaninate

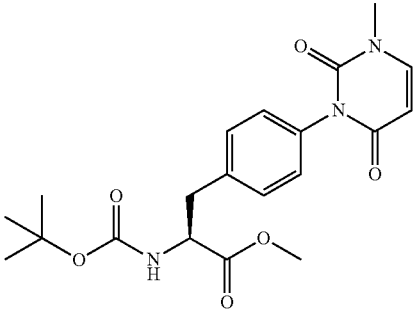 [SMILES: COC(=O)[C@H](Cc1ccc(-n2c(=O)ccn(C)c2=O)cc1)NC(=O)OC(C)(C)C]

Pyrimidine-2,4(1H,3H)-dione (30.0 g, 268 mmol), 1,1,1,3,3,3-hexamethyldisilazane (550 ml), and trimethylchlorosilane (55 ml) were stirred at 130° C. for 5 hours. The reaction solution was cooled to 60° C., then methyl iodide (200 ml) was added thereto, and the resulting mixture was stirred at 60° C. for 30 hours. The reaction solution was cooled to 0° C., acetic acid (500 ml) was slowly added thereto, and the solvent was removed under reduced pressure. 2-Propanol (1,600 ml) was added to the residue, the resulting mixture was intensely stirred, and then the obtained solid was filtered and washed with water (500 ml) to obtain a white solid (22 g, 67%). [4-[(2S)-2-(tert-Butoxycarbonylamino)-3-methoxy-3-oxo-propyl]phenyl]boron is acid <see Example 2 (step 5)> (49.0 g, 152 mmol) was dissolved in methylene chloride (500 ml), then the obtained white solid (22.0 g, 175 mmol), copper(II) acetate (18.0 g, 98.9 mmol), and triethylamine (40 ml) were added thereto, and the resulting mixture was stirred at room temperature for 60 hours. The reaction solution was concentrated under reduced pressure, and then the obtained residue was purified by silica gel column chromatography (petroleum ether:ethyl acetate=1:1) to obtain the title compound (6.0 g, 10%) as a white crystal.

1H NMR (CDCl3, 400 MHz): δ 7.20-7.15 (m, 3H), 7.08 (d, J=8.0 Hz, 2H), 5.76 (d, J=8.0 Hz, 1H), 4.55-4.51 (m, 1H), 3.60 (s, 3H), 3.35 (s, 3H), 3.06 (d, J=4.0 Hz, 1H), 1.36 (s, 9H); MS (ESI) m/z 421 (M+H)$^+$ (Step 2) Methyl 4-(3-methyl-2,6-dioxo-3,6-dihydropyrimidine-1(2H)-yl)-L-phenylalaninate (M-5)

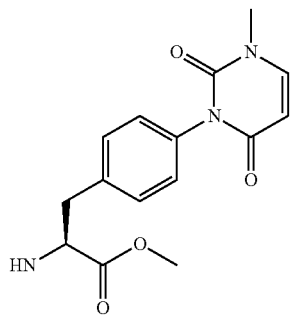

·HCl

Methyl N-(tert-butoxycarbonyl)-4-(3-methyl-2,6-dioxo-3,6-dihydropyrimidine-1(2H)-yl)-L-phenylalaninate <see (step 1)> (6.00 g, 15.0 mmol) was dissolved in a 3 N hydrochloric acid/ethyl acetate solution (100 ml), and the resulting mixture was stirred at room temperature for 1 hour. The solvent was removed under reduced pressure, then ethyl acetate (50 ml) was added, and the resulting mixture was further stirred at room temperature for 0.5 hours. The suspension was filtered, and the obtained solid was dried to obtain the title compound (4.0 g, 80%) as a white solid.

1H NMR (CD3OD, 500 MHz): δ 7.72 (d, J=8 Hz, 1H), 7.45 (d, J=8 Hz, 2H), 7.29 (d, J=8 Hz, 2H), 5.85 (d, J=8 Hz, 1H), 4.44-4.41 (m, 1H), 3.91 (s, 3H), 3.49-3.45 (m, 4H), 3.23-3.17 (m, 1H); MS (ESI) m/z 304 (M+H)$^+$

Example 6

Synthesis of M-6

(Step 1) Methyl 4-aminopyrimidine-5-carboxylate

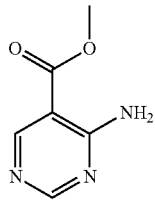

4-Aminopyrimidine-5-carboxylic acid (10.0 g, 71.9 mmol) was dissolved in methanol (100 ml), the reaction solution was cooled to 0° C., then concentrated sulfuric acid (25 ml) was slowly added dropwise, and the resulting mixture was stirred at 85° C. for 12 hours. The reaction liquid was concentrated under reduced pressure, then the resulting solution was diluted with water, and sodium hydrogen carbonate (10.0 g) was added. The resulting mixture was extracted with ethyl acetate (80 ml×4), the extracts were combined, washed with a saturated saline solution, and dried over anhydrous sodium sulfate. The solvent was removed under reduced pressure, the obtained residue was stirred in a mixed solvent (petroleum ether:ethyl acetate=8:1), and the precipitated solid was filtered and dried to obtain the title compound (9.90 g, 90%).

$^1$H-NMR (400 MHz, DMSO-d$_6$): δ 8.72 (s, 1H), 8.53 (s, 1H), 8.04 (s, 1H), 7.62 (s, 1H), 3.83 (s, 3H); MS (ESI) m/z 154 (M+H)$^+$ (Step 2) 3-(6-Bromo-3-pyridyl)-1-methyl-pyrimido[4,5-d]pyrimidine-2,4-dione

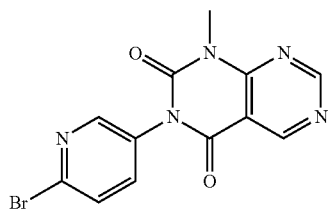 [SMILES: Cn1c(=O)n(-c2ccc(Br)nc2)c(=O)c2cncnc21]

Two steps similar to Example 1 (step 1), (step 2) were performed (methyl iodide was used instead of p-toluenesulfonic acid methyl ester) to methyl 4-aminopyrimidine-5-carboxylate <see (step 1)> (4.50 g, 29.4 mmol) and 6-bromopyridin-3-amine (4.20 g, 24.7 mmol) to obtain the title compound (3.10 g, 38%).

$^1$H NMR (400 MHz, DMSO-d$_6$): δ 9.30 (s, 1H), 9.23 (s, 1H), 8.40 (s, 1H), 7.89 (d, J=11.2 Hz, 1H), 7.81-7.77 (m, 1H), 3.57 (s, 3H).

(Step 3) Methyl (2S)-2-(tert-butoxycarbonylamino)-3-[5-(1-methyl-2,4-dioxo-pyrimido[4,5-d]pyrimidin-3-yl)-2-pyridyl]propanoate

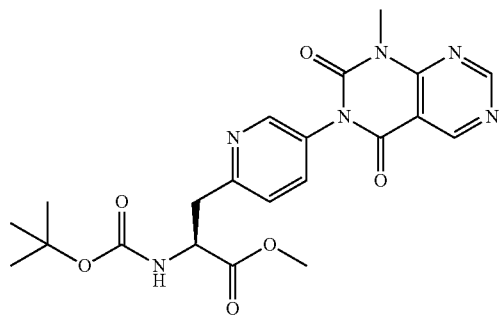 [SMILES: COC(=O)[C@H](Cc1ccc(-n2c(=O)c3cncnc3n(C)c2=O)cn1)NC(=O)OC(C)(C)C]

A method similar to Example 1 (step 6) was performed to 3-(6-bromo-3-pyridyl)-1-methyl-pyrimido[4,5-d]pyrimidine-2,4-dione <see (step 2)> (1.50 g, 4.50 mmol) to obtain the title compound (1.33 g, 65%).

$^1$H NMR (400 MHz, DMSO-d$_6$): δ 9.29 (s, 1H), 9.20 (s, 1H), 8.44 (s, 1H), 7.73-7.70 (m, 1H), 7.44 (d, J=8.0 Hz, 1H), 7.38 (d, J=7.6 Hz, 1H), 4.55-4.50 (m, 1H), 3.62 (s, 3H), 3.56 (s, 3H), 3.22-3.06 (m, 2H), 1.36 (s, 9H); MS (ESI) m/z 457 (M+H)$^+$ (Step 4) Methyl (2S)-2-amino-3-[5-(1-methyl-2,4-dioxo-pyrimido[4,5-d]pyrimidin-3-yl)-2-pyridyl]propanoate (M-6)

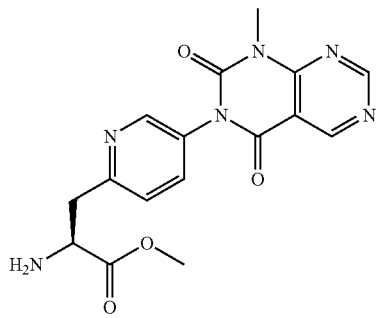 [SMILES: COC(=O)[C@@H](N)Cc1ccc(-n2c(=O)c3cncnc3n(C)c2=O)cn1]

A method similar to Example 1 (step 7) was performed to methyl (2S)-2-(tert-butoxycarbonylamino)-3-[5-(1-methyl-2,4-dioxo-pyrimido[4,5-d]pyrimidin-3-yl)-2-pyridyl]propanoate <see (step 3)> (1.30 g, 2.85 mmol) to obtain a hydrochloride of the title compound (1.10 g, 98%).

$^1$H NMR (400 MHz, DMSO-d$_6$): δ 9.36 (s, 1H), 9.33 (s, 1H), 8.70 (d, J=2.4 Hz, 1H), 8.09 (dd, J=8.4, 2.4 Hz, 1H), 7.78 (d, J=8.4 Hz, 1H), 4.70 (t, J=6.4 Hz, 1H), 3.86 (s, 3H), 3.76 (s, 3H), 3.68-3.65 (m, 2H); MS (ESI) m/z 357 (M+H)$^+$

Example 7

Synthesis of M-7

(Step 1) Methyl (2S)-2-(tert-butoxycarbonylamino)-3-[4-[2,4-dioxo-6-(trifluoromethyl)-1H-pyrimidin-3-yl]phenyl]propanoate

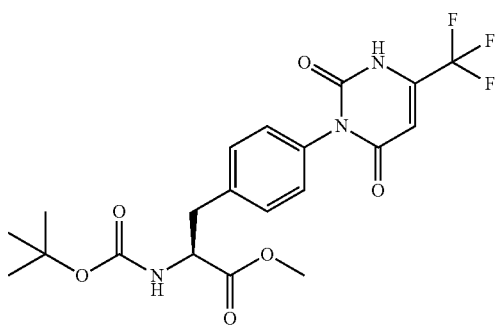 [SMILES: COC(=O)[C@H](Cc1ccc(-n2c(=O)cc(C(F)(F)F)[nH]c2=O)cc1)NC(=O)OC(C)(C)C]

6-(Trifluoromethyl)-1H-pyrimidine-2,4-dione (1.00 g, 5.60 mmol) and [4-[(2S)-2-(tert-butoxycarbonylamino)-3-methoxy-3-oxo-propyl]phenyl]boronic acid <see Example 2 (step 5)> (2.00 g, 6.20 mmol) were dissolved in methylene chloride (10 ml), copper(II) acetate (3.01 g, 15.1 mmol) and triethylamine (2.40 g, 2.40 mmol) were added thereto, and the resulting mixture was stirred at room temperature for 12 hours. The reaction liquid was filtered and the filtrate was concentrated under reduced pressure. The obtained residue was purified by silica gel column chromatography (petroleum ether:ethyl acetate=5:1 to 1:1) to obtain the title compound (750 mg, 29%) as a yellow crystal.

$^1$H NMR (CD$_3$OD, 400 MHz): δ 7.26 (d, J=8.0 Hz, 2H), 7.22 (d, J=8.0 Hz, 2H), 6.27 (s, 1H), 4.45-4.41 (m, 1H), 3.73 (s, 3H), 3.21-3.16 (m, 1H), 3.07-3.02 (m, 1H), 1.43 (s, 9H)

(Step 2) Methyl (2S)-2-(tert-butoxycarbonylamino)-3-[4-[3-methyl-2,6-dioxo-4-(trifluoromethyl)pyrimidin-1-yl]phenyl]propanoate

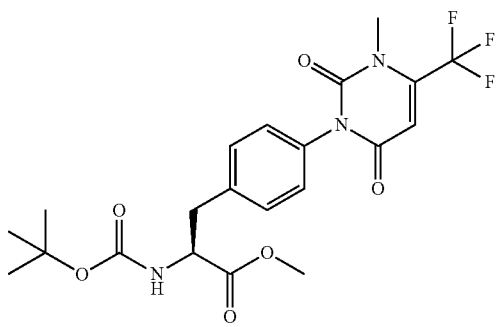 [SMILES: COC(=O)[C@H](Cc1ccc(-n2c(=O)cc(C(F)(F)F)n(C)c2=O)cc1)NC(=O)OC(C)(C)C]

Methyl (2S)-2-(tert-butoxycarbonylamino)-3-[4-[2,4-dioxo-6-(trifluoromethyl)-1H-pyrimidin-3-yl]phenyl]propanoate <see (step 1)> (700 mg, 1.53 mmol) was dissolved in N,N-dimethylformamide (15 ml), potassium carbonate (400 mg, 2.90 mmol) and methyl iodide (6.60 g, 46.0 mmol) were added thereto, and the resulting mixture was stirred at room temperature for 90 minutes. The reaction liquid was concentrated under reduced pressure, diluted with water (20 ml), and then extracted with ethyl acetate. The extracts were combined, washed with a saturated saline solution, dried over anhydrous sodium sulfate, and the solvent was removed under reduced pressure to obtain the title compound (700 mg, 97%) as a yellow solid.

$^1$H NMR (CD$_3$OD, 400 MHz): δ 7.37 (d, J=8.4 Hz, 2H), 7.21 (d, J=8.0 Hz, 2H), 6.42 (s, 1H), 4.45-4.42 (m, 1H), 3.73 (s, 3H), 3.34 (s, 3H), 3.21-3.16 (m, 1H), 3.07-3.02 (m, 1H), 1.43 (s, 9H)

(Step 3) Methyl (2S)-2-amino-3-[4-[3-methyl-2,6-dioxo-4-(trifluoromethyl)pyrimidin-1-yl]phenyl]propanoate (M-7)

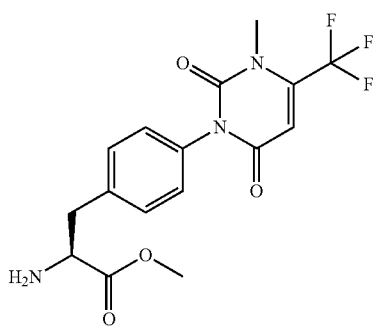 [SMILES: COC(=O)[C@@H](N)Cc1ccc(-n2c(=O)cc(C(F)(F)F)n(C)c2=O)cc1]

Methyl (2S)-2-(tert-butoxycarbonylamino)-3-[4-[3-methyl-2,6-dioxo-4-(trifluoromethyl)pyrimidin-1-yl]phenyl]propanoate <see (step 2)> (604 mg, 1.28 mmol) was dissolved in 6 N hydrochloric acid/ethyl acetate (10.0 ml), and the resulting solution was stirred at room temperature for 1 hour. The reaction liquid was concentrated under reduced pressure, ethyl acetate (30.0 ml) was added to the obtained residue, and the resulting mixture was stirred at room temperature for 30 minutes. The precipitated solid was filtered and dried to obtain a hydrochloride of the title compound (470 mg, 90%) as a white solid.

$^1$H NMR (CD$_3$OD, 400 MHz): δ 7.34 (d, J=8.4 Hz, 2H), 7.20 (d, J=8.4 Hz, 2H), 6.34 (s, 1H), 4.33-4.29 (m, 1H), 3.78 (s, 3H), 3.43 (s, 3H), 3.36-3.31 (m, 1H), 3.13-3.07 (m, 1H); MS (ESI) m/z 372 (M+H)$^+$

Example 8

Synthesis of M-8

(Step 1) Methyl N-(tert-butoxycarbonyl)-4-(2,4-dioxo-1,4-dihydropyrido[3,4-d]pyrimidin-3(2H)-yl)-L-phenylalaninate

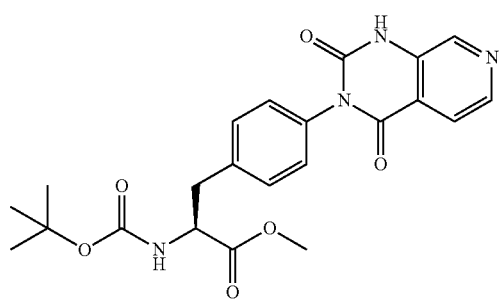 [SMILES: COC(=O)[C@H](Cc1ccc(-n2c(=O)[nH]c3cnccc3c2=O)cc1)NC(=O)OC(C)(C)C]

Methyl 3-aminoisonicotinate (10.0 g, 65.0 mmol) was dissolved in methylene chloride (100 ml), diisopropylethylamine (17.0 g, 130 mmol) and triphosgene (6.40 g, 22.0 mmol) were added thereto, and the resulting mixture was stirred at 0° C. for 3 hours. Methyl 4-amino-N-(tert-butoxycarbonyl)-L-phenylalaninate (19.0 g, 65.0 mmol) was added to the solution, and then the resulting mixture was stirred for 12 hours while the temperature was slowly raised from 0° C. to room temperature. The reaction solution was concentrated under reduced pressure, then ethyl acetate was added, and the resulting solution was washed with water and a saturated saline solution and dried over anhydrous sodium sulfate. The solvent was removed under reduced pressure, and the resulting product was purified by silica gel column chromatography (petroleum ether/ethyl acetate=1:1). The obtained compound was dissolved in N,N-dimethylformamide (200 ml), an aqueous solution of potassium carbonate (1.20 g, 8.70 mmol) was added thereto, and the resulting mixture was stirred at room temperature for 3 hours. The reaction solution was concentrated under reduced pressure, then ethyl acetate was added, and the resulting solution was washed with water and a saturated saline solution and dried over anhydrous sodium sulfate. The solvent was removed under reduced pressure, and then the obtained residue was purified by silica gel column chromatography (petroleum ether:ethyl acetate=1:1) to obtain the title compound (12.0 g, 43% for two steps).

1H NMR (CD3Cl3, 400 MHz): δ 10.07 (1H, s), 8.54 (d, J=5.2 Hz, 1H), 8.14 (s, 1H), 7.92 (d, J=8.8 Hz, 1H), 7.35 (d, J=7.6 Hz, 2H), 7.23 (d, J=8.0 Hz, 2H), 6.12-6.10 (m, 1H), 4.73-4.69 (m, 1H), 3.71 (s, 3H), 3.22-3.21 (m 2H), 1.44 (s, 9H)

(Step 2) Methyl N-(tert-butoxycarbonyl)-4-(1-methyl-2,4-dioxo-1,4-dihydropyrido[3,4-d]pyrimidin-3(2H)-yl)-L-phenylalaninate

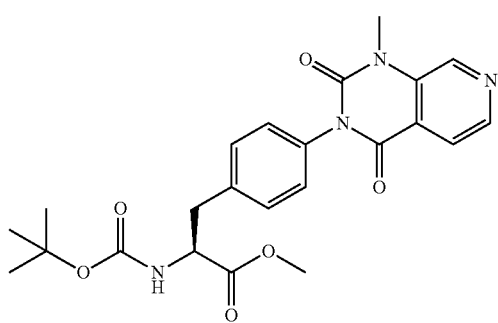 [SMILES: COC(=O)[C@H](Cc1ccc(-n2c(=O)c3ccncc3n(C)c2=O)cc1)NC(=O)OC(C)(C)C]

Methyl N-(tert-butoxycarbonyl)-4-(2,4-dioxo-1,4-dihydropyrido[3,4-d]pyrimidin-3 (2H)-yl)-L-phenylalaninate <see (step 1)> (8.00 g, 18.5 mmol) was dissolved in N,N-dimethylformamide (100 ml), potassium carbonate (5.10 g, 37.0 mmol) and methyl iodide (1.9 ml, 37 mmol) were added thereto, and the resulting mixture was stirred at room temperature for 3 hours. The suspension was filtered, and the filtrate was concentrated under reduced pressure and then purified by silica gel column chromatography (petroleum ether:ethyl acetate=1:1) to obtain the title compound (3.5 g, 43%).

1H NMR (CD3Cl3, 400 MHz): δ 8.81 (1H, s), 8.60 (d, J=4.8 Hz, 1H), 8.03 (d, J=5.6 Hz, 1H), 7.30 (d, J=8.0 Hz, 2H), 7.19 (d, J=8.4 Hz, 2H), 5.05-5.03 (m, 1H), 4.65-4.63 (m, 1H), 3.73 (s, 3H), 3.71 (s, 3H), 3.18-3.16 (m 2H), 1.44 (s, 9H); MS (ESI) m/z 355 (M+H-Boc)+

(Step 3) Methyl 4-(1-methyl-2,4-dioxo-1,4-dihydropyrido[3,4-d]pyrimidin-3(2H)-yl)-L-phenylalaninate (M-8)

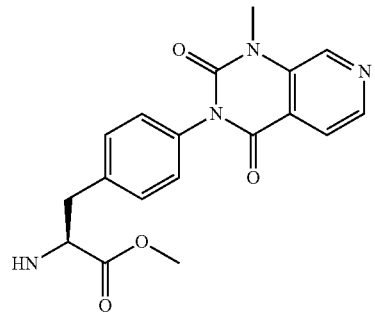

Methyl N-(tert-butoxycarbonyl)-4-(1-methyl-2,4-dioxo-1,4-dihydropyrido[3,4-d]pyrimidin-3(2H)-yl)-L-phenylalaninate (3.5 g, 7.7 mmol) was dissolved in a 4 N hydrochloric acid/ethyl acetate solution (40 ml), and the resulting mixture was stirred at room temperature for 1 hour. The reaction liquid was filtered, then the obtained solid was dried under reduced pressure to obtain the title compound (3.0 g, 94%).

1H NMR (CD3OD, 400 MHz): δ 9.28 (s, 1H), 8.76 (d, J=0.8 Hz, 1H), 8.56 (d, J=1.6 Hz, 1H), 7.51 (d, J=8.4 Hz, 2H), 7.41 (d, J=8.4 Hz, 2H), 4.48-4.44 (m, 1H), 3.90 (s, 3H), 3.76 (s, 3H), 3.49-3.44 (m 1H), 3.30-3.24 (m, 1H); MS (ESI) m/z 355 (M+H)+

Example 9

Synthesis of M-9

(Step 1) 6-Bromopyridin-3-amine

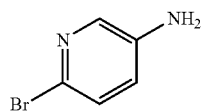

2-Bromo-5-nitro-pyridine (202 g, 1.0 mol) was dissolved in methanol (2.0 L), a saturated aqueous solution of ammonium chloride (2.0 L) was added thereto, the resulting mixture was stirred at 50° C., then iron (224 g, 4.0 mol) was slowly added thereto, and the resulting mixture was stirred at 50° C. for 6 hours. The reaction solution was cooled to room temperature and then filtered and washed with ethyl acetate. The filtrate was diluted with water and then extracted with ethyl acetate (1.0 L×6). The extracts were combined, washed with a saturated aqueous solution of sodium hydrogen carbonate (2.0 L) and a saturated saline solution, dried over anhydrous sodium sulfate, and then the solvent was removed under reduced pressure. The obtained residue was purified by silica gel column chromatography (petroleum ether:ethyl acetate=1:1) to obtain the title compound (126 g, 73%).

1H NMR (400 MHz, DMSO-d$_6$): δ 7.69 (d, J=2.8 Hz, 1H), 7.19 (d, J=8.4 Hz, 1H), 6.90 (dd, J=8.4 Hz, 2.8 Hz, 1H), 5.50 (s, 2H)

(Step 2) 3-(6-Bromo-3-pyridyl)-1-methyl-pyrido[3,4-d]pyrimidine-2,4-dione

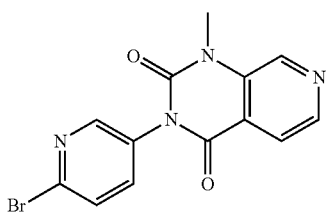 [SMILES: Cn1c(=O)n(-c2ccc(Br)nc2)c(=O)c2ccncc21]

A method similar to Example 1 (step 1), (step 2) was performed to 6-bromopyridin-3-amine <see (step 1)> (67.7 g, 394 mmol) to obtain the title compound (32.5 g, 24.8% for two steps).

1H NMR (400 MHz, DMSO-d$_6$): δ 9.00 (s, 1H), 8.59 (d, J=8.8 Hz, 1H), 8.41 (d, J=4.8 Hz, 1H), 7.92 (d, J=4.8 Hz, 1H), 7.86 (d, J=8.0 Hz, 1H), 7.80 (dd, J=8.4 Hz, 2.0 Hz, 1H), 3.62 (s, 3H)

(Step 3) Cyclohexyl (2S)-2-(tert-butoxycarbonylamino)-3-[5-(1-methyl-2,4-dioxo-pyrido[3,4-d]pyrimidin-3-yl)-2-pyridyl]propanoate

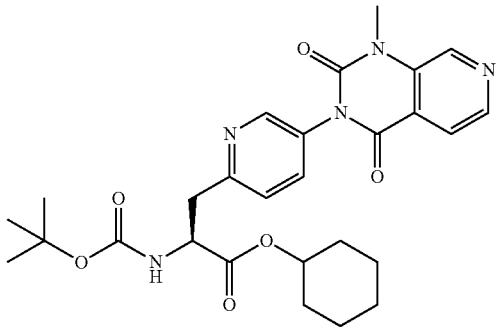 [SMILES: Cn1c(=O)n(-c2ccc(C[C@H](NC(=O)OC(C)(C)C)C(=O)OC3CCCCC3)nc2)c(=O)c2ccncc21]

A method similar to Example 1 (step 6) was performed to 3-(6-bromo-3-pyridyl)-1-methyl-pyrido[3,4-d]pyrimidine-2,4-dione <see (step 2)> (23.0 g, 69.2 mmol) to obtain the title compound (21.7 g, 60%).

1H NMR (400 MHz, DMSO-d$_6$): δ 8.99 (s, 1H), 8.56 (d, J=4.8 Hz, 1H), 8.46 (d, J=1.6 Hz, 1H), 7.91 (d, J=5.2 Hz, 1H), 7.72 (dd, J=8.0, 2.4 Hz, 1H), 7.42 (d, J=8.0 Hz, 1H), 7.31 (d, J=8.0 Hz, 1H), 4.67-4.65 (m, 1H), 4.48-4.47 (m, 1H), 3.61 (s, 3H), 3.17-3.13 (m, 2H), 1.71-1.25 (m, 19H)

(Step 4) Cyclohexyl 3-[5-(1-methyl-2,4-dioxo-1,4-dihydropyrido[3,4-d]pyrimidin-3(2H)-yl)pyridin-2-yl]-L-alaninate (M-9)

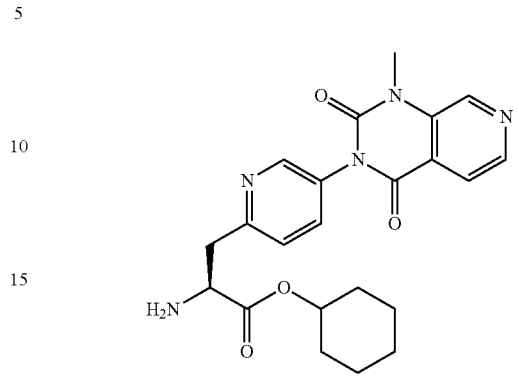

A method similar to Example 1 (step 7) was performed to cyclohexyl (2S)-2-(tert-butoxycarbonylamino)-3-[5-(1-methyl-2,4-dioxo-pyrido[3,4-d]pyrimidin-3-yl)-2-pyridyl]propanoate <see (step 3)> (35.0 g, 66.9 mmol) to obtain the title compound (27.9 g, 91%) as a hydrochloride.

$^1$H NMR (400 MHz, CD$_3$OD): δ 9.16 (s, 1H), 8.65 (d, J=5.6 Hz, 1H), 8.52 (d, J=2.0 Hz, 1H), 8.44 (d, J=5.6 Hz, 1H), 7.89 (dd, J=8.4, 2.4 Hz, 1H), 7.61 (d, J=8.4 Hz, 1H); 4.80 (m, 1H), 4.54 (t, J=6.0 Hz, 1H), 3.65 (s, 3H), 3.46-3.59 (m, 2H), 1.70-1.20 (m, 10H); MS (ESI) m/z 424 (M+H)$^+$

Example 10

Synthesis of M-10

(Step 1) tert-Butyl 4-(5-bromopyrimidin-2-yl)-3,6-dihydro-2H-pyridine-1-carboxylate

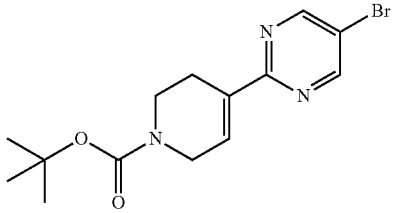 [SMILES: CC(C)(C)OC(=O)N1CC=C(c2ncc(Br)cn2)CC1]

5-Bromo-2-iodine-pyrimidine (210 mg, 0.74 mmol) and tert-butyl 4-(5-bromopyrimidin-2-yl)-3,6-dihydro-2H-pyridine-1-carboxylate (275 mg, 0.890 mmol) were dissolved in N,N-dimethylformamide (50 ml) and water (10 ml), potassium carbonate (255 mg, 1.85 mmol) and Pd(PPh$_3$)$_4$ (805 mg, 1.10 mmol) were added thereto, and the resulting mixture was stirred in the presence of nitrogen gas at 100° C. for 4 hours. The reaction liquid was concentrated under reduced pressure and the obtained residue was purified by silica gel column chromatography (petroleum ether:ethyl acetate=5:1 to 1:1) to obtain the title compound (78 mg, 31%).

1H NMR (300 MHz, CDCl3): δ 8.72 (s, 2H), 7.23-7.20 (m, 1H), 4.19-4.17 (m, 2H), 3.66-3.62 (m, 2H), 2.72-2.66 (m, 2H), 8.72 (s, 9H)

(Step 2) 4-Bromo-2,5-difluorobenzoic acid

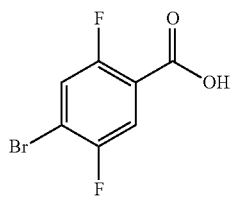 [SMILES: O=C(O)c1cc(F)c(Br)cc1F]

1,4-Dibromo-2,5-difluorobenzene (51.2 g, 188 mmol) was dissolved in 1,2-diethoxyethane (400 ml), and a 2.5 M n-butyllithium/hexane solution (76.0 ml, 190 mmol) was slowly added thereto dropwise at −78° C. in the presence of nitrogen gas. The reaction solution was stirred at −78° C. for 30 minutes, then dry ice was added, and the resulting mixture was further stirred for 30 minutes. The temperature was gradually raised to room temperature, and then water (200 ml) was added to the reaction liquid. The reaction liquid was diluted with ethyl acetate, the resulting solution was washed with a 10% aqueous solution of sodium carbonate (200 ml×2), then the obtained aqueous layers were combined, 1 N hydrochloric acid was added for adjustment to acidic pH, and the precipitated yellow solid was filtered and dried to obtain the title compound (30.0 g, 67%).

$^1$H NMR (DMSO-$d_6$, 400 MHz): δ 7.90-7.87 (m, 1H), 7.79-7.75 (m, 1H); MS (ESI) m/z 191 (M+H−44)$^+$ (Step 3) Methyl 4-bromo-2,5-difluorobenzoate

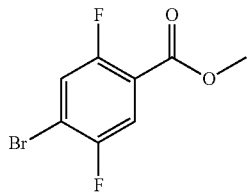

4-Bromo-2,5-difluorobenzoic acid <see (step 2)> (30.0 g, 127 mmol) was dissolved in ethyl acetate (500 ml), the reaction solution was cooled to 0° C., then a diazomethane/ether solution was added thereto. The reaction liquid was stirred at 0° C. for 1 hour, and the solvent was removed under reduced pressure. The obtained residue was purified by silica gel column chromatography (petroleum ether:ethyl acetate=6:1 to 2:1) to obtain the title compound (25.0 g, 78%).

$^1$H NMR (DMSO-$d_6$, 400 MHz): δ 7.93-7.89 (m, 1H), 7.80-7.77 (m, 1H), 3.86 (s, 3H)

(Step 4) Methyl 4-amino-2,5-difluorobenzoate

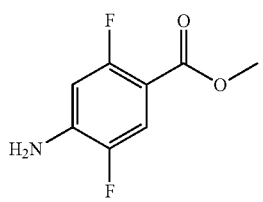

Methyl 4-bromo-2,5-difluorobenzoate <see (step 3)> (25.0 g, 99.6 mmol) and BINAP (1.86 g, 3.00 mmol) were dissolved in toluene (500 ml). Palladium(II) acetate (672 mg, 3.00 mmol), cesium carbonate (52.0 g, 160 mmol), and benzophenone imine (25.3 g, 140 mmol) were added to the solution, and the resulting mixture was stirred at 110° C. for 12 hours. The reaction mixture was cooled to room temperature, and then filtered through Celite and washed with ethyl acetate. The obtained filtrate was concentrated under reduced pressure. The obtained compound was dissolved in water (30 ml) and tetrahydrofuran (80 ml), concentrated hydrochloric acid (30 ml) was added thereto, and the resulting mixture was stirred at room temperature for 2 hours. The precipitated solid was filtered to obtain a white solid. The filtrate was also concentrated under reduced pressure until a white solid was precipitated, the obtained solid was filtered, the white solids were combined, and the resulting product was dried to obtain the title compound (9.8 g, 53% for two steps).

$^1$H NMR (CD$_3$OD, 400 MHz): δ 7.53-7.49 (m, 1H), 6.60-6.56 (m, 1H), 3.85 (s, 3H); MS (ESI) m/z 188 (M+H)$^+$ (Step 5) Methyl 4-[(4-bromophenyl)sulfonylamino]-2,5-difluoro-benzoate

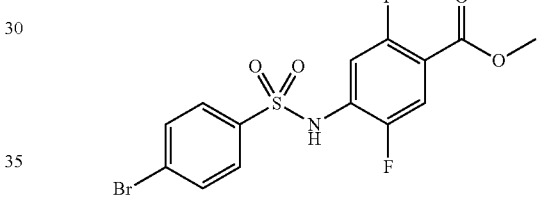

Methyl 4-amino-2,5-difluoro-benzoate <see (step 4)> (24.4 g, 130 mmol) was dissolved in methylene chloride (1.0 L), 4-bromobenzenesulfonyl chloride (50.0 g, 196 mmol) and pyridine (100 ml) were added thereto, and the resulting mixture was stirred at room temperature for 12 hours. The reaction liquid was concentrated under reduced pressure, then 6 N hydrochloric acid was added to the obtained residue for adjustment to pH=1.0. The obtained yellow solid was filtered, washed with water and methylene chloride, and dried to obtain the title compound (36.5 g, 69%) as a yellow solid.

MS (ESI) m/z 406 (M+H)$^+$ (Step 6) [4-[(2,5-Difluoro-4-methoxycarbonyl-phenyl)sulfamoyl]phenyl]boronic acid

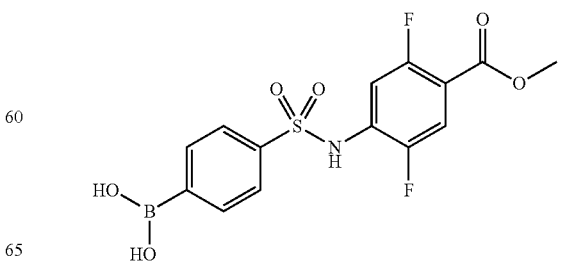

Methyl 4-[(4-bromophenyl)sulfonylamino]-2,5-difluorobenzoate <see (step 5)> (40.5 g, 100 mmol) and bis(pinacolato)diborane (35.5 g, 140 mmol) were dissolved in N,N-dimethylformamide (800 ml). [1,1'-Bis(diphenylphosphino)ferrocene]dichloropalladium(II) (2.20 g, 3.00 mmol) and potassium acetate (29.4 g, 300 mmol) were added to the solution, and the resulting mixture was stirred in the presence of nitrogen gas at 90° C. for 12 hours. The reaction liquid was cooled to room temperature, and then diluted with water and extracted with ethyl acetate (600 ml×3). The extracts were combined, washed with a saturated saline solution, dried over anhydrous sodium sulfate, and then the solvent was removed under reduced pressure. The obtained residue was purified by silica gel column chromatography (petroleum ether:ethyl acetate=4:1 to 2:1) to obtain methyl 2,5-difluoro-4-[[4-(4,4,5,5-tetramethyl-1,3,2-dioxaborolan-2-yl)phenyl]sulfonylamino]benzoate (40.0 g, 88%).

$^{1}$H NMR (CD$_3$OD, 400 MHz): δ 7.89 (s, 4H), 7.62-7.58 (m, 1H), 7.44-7.40 (m, 1H), 3.87 (s, 3H), 1.36 (s, 12H); MS (ESI) m/z 454 (M+H)$^+$

The obtained methyl 2,5-difluoro-4-[[4-(4,4,5,5-tetramethyl-1,3,2-dioxaborolan-2-yl)phenyl]sulfonylamino]benzoate (59.0 g, 130 mmol) was dissolved in acetone (450 ml), sodium periodate (83.6 g, 390 mmol), ammonium acetate (30.0 g, 390 mmol), and water (150 ml) were added thereto, and the resulting mixture was stirred at room temperature for 72 hours. The reaction liquid was concentrated under reduced pressure, and then diluted with water and extracted with ethyl acetate (500 ml×3). The extracts were combined, washed with a saturated saline solution, dried over anhydrous sodium sulfate, and then the solvent was removed under reduced pressure. The obtained residue was washed with a mixed solvent (petroleum ether:ethyl acetate=1:10) and dried under reduced pressure to obtain the title compound (43.0 g, 89%).

1H NMR: (400 MHz, DMSO-d$_6$): δ 11.05 (s, 1H), 8.37 (s, 2H), 7.94 (d, J=8.4 Hz, 2H), 7.81 (d, J=8.0 Hz, 2H), 7.65-7.61 (m, 1H), 7.27-7.23 (m, 1H), 3.80 (s, 3H): MS (ESI) m/z 372 (M+H)$^+$ (Step 7) tert-Butyl 4-[5-[4-[(2, 5-difluoro-4-methoxycarbonyl-phenyl)sulfamoyl]phenyl]pyrimidin-2-yl]-3,6-dihydro-2H-pyridine-1-carboxylate

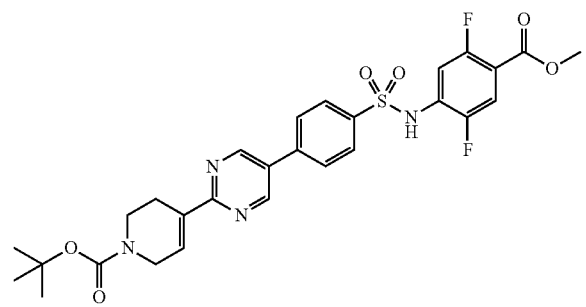 [SMILES: COC(=O)c1cc(F)c(NS(=O)(=O)c2ccc(-c3cnc(C4=CCN(C(=O)OC(C)(C)C)CC4)nc3)cc2)cc1F]

tert-Butyl 4-(5-bromopyrimidin-2-yl)-3,6-dihydro-2H-pyridine-1-carboxylate <see (step 1)> (100 mg, 0.290 mmol), [4-[(2,5-difluoro-4-methoxycarbonyl-phenyl)sulfamoyl]phenyl]boronic acid <see (step 6)> (131 mg, 0.350 mmol), sodium carbonate (93.8 mg, 0.885 mmol), and Pd(dppf)Cl$_2$ (11.0 mg, 0.030 mmol) were dissolved in dioxane (10.0 ml) and water (0.50 ml), and the resulting mixture was stirred in the presence of nitrogen gas at 100° C. for 8 hours. The reaction liquid was concentrated under reduced pressure, and then the obtained residue was purified by silica gel column chromatography (petroleum ether:ethyl acetate=3:1 to 1:1) to obtain the title compound (50.0 mg, 29%).

MS (ESI) m/z 587 (M+H)$^+$ (Step 8) tert-Butyl 4-[5-[4-[(2,5-difluoro-4-methoxycarbonyl-phenyl)sulfamoyl]phenyl]pyrimidin-2-yl]piperidine-1-carboxylate

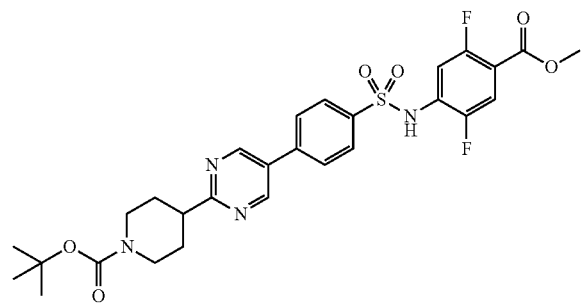 [SMILES: COC(=O)c1cc(F)c(NS(=O)(=O)c2ccc(-c3cnc(C4CCN(C(=O)OC(C)(C)C)CC4)nc3)cc2)cc1F]

tert-Butyl 4-[5-[4-[(2,5-difluoro-4-methoxycarbonyl-phenyl)sulfamoyl]phenyl]pyrimidin-2-yl]-3,6-dihydro-2H-pyridine-1-carboxylate <see (step 7)> (120 mg, 0.20 mmol) and 10% Pd/C (wet, 50 mg) were suspended in methanol (10 ml), and the resulting mixture was stirred in the presence of hydrogen gas (50 psi) at 50° C. for 24 hours. The reaction liquid was cooled to room temperature and then filtered, and the filtrate was concentrated under reduced pressure to obtain the title compound (31.0 mg, 27%).

MS (ESI) m/z 589 (M+H)$^+$

Step 9) 4-[[4-[2-(1-tert-Butoxycarbonyl-4-piperidyl)pyrimidin-5-yl]phenyl]sulfonylamino]-2,5-difluorobenzoic acid (M-10)

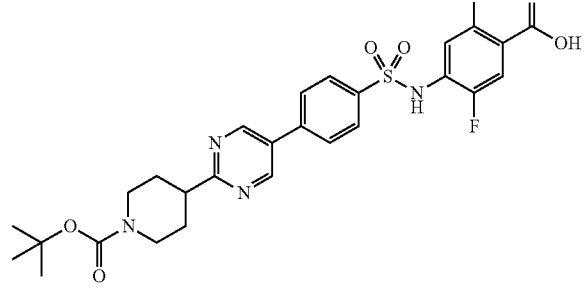

tert-Butyl 4-[5-[4-[(2,5-difluoro-4-methoxycarbonyl-phenyl)sulfamoyl]phenyl]pyrimidin-2-yl]piperidine-1-carboxylate <see (step 8)> (60 mg, 0.10 mmol) was dissolved in methanol (10 ml), a 2 N aqueous solution of lithium hydroxide (3.0 ml) was added thereto, and the resulting mixture was stirred at room temperature for 2 hours. The completion of the reaction was verified with TLC, and 4 N hydrochloric acid was added for adjustment to pH=5.0. The precipitated solid was filtered, washed with a mixed solvent of methylene chloride:methanol (10:1), and dried to obtain the title compound (45 mg, 78%) as a white solid.

¹H NMR (CD₃OD, 400 MHz): δ 8.93 (s, 2H), 7.94-7.91 (m, 2H), 7.80 (d, J=8.4 Hz, 2H), 7.50-7.45 (m, 1H), 7.36-7.32 (m, 1H), 4.10-4.07 (m, 2H), 3.05-2.99 (m, 1H), 2.90-2.81 (m, 2H), 1.91-1.89 (m, 2H), 1.76-1.69 (m, 2H), 1.43 (s, 9H); MS (ESI) m/z 573 (M-1)

Example 11

Synthesis of M-11

(Step 1) 5-Bromo-2-(3,6-dihydro-2H-pyran-4-yl)pyrimidine

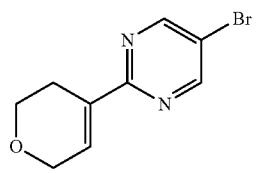 [SMILES: Brc1cnc(C2=CCOCC2)nc1]

5-Bromo-2-iodopyrimidine (5.87 g, 20.7 mmol), 2-(3,6-dihydro-2H-pyran-4,4,5,5-tetramethyl-1,3,2-dioxaborane (4.35 g, 20.7 mmol), potassium carbonate (5.70 g, 41.4 mmol), and Pd(dppf)Cl₂ (805 mg, 1.10 mmol) were suspended in N,N-dimethylformamide (50 ml) and water (10 ml), and the resulting mixture was stirred under a nitrogen gas atmosphere at 100° C. for 4 hours. The reaction liquid was concentrated under reduced pressure, and the obtained residue was purified by silica gel column chromatography (petroleum ether:ethyl acetate=5:1 to 1:1) to obtain the title compound (1.44 g, 29%).

¹H NMR (400 MHz, CDCl₃): δ 8.72 (s, 2H), 7.25 (s, 1H), 4.42-3.38 (m, 2H), 3.94-3.91 (m, 2H), 2.68-2.66 (m, 2H)

(Step 2) Methyl 4-[[4-[2-(3,6-dihydro-2H-pyran-4-yl)pyrimidin-5-yl]phenyl]sulfonylamino]-2,5-difluorobenzoate

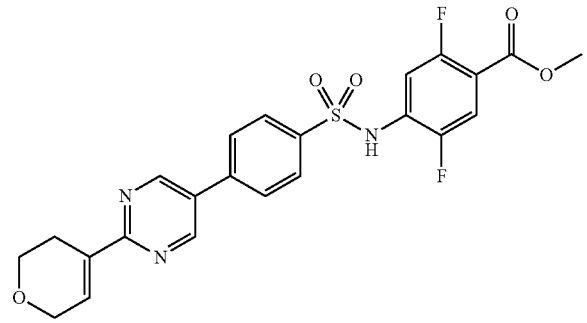 [SMILES: COC(=O)c1cc(F)c(NS(=O)(=O)c2ccc(-c3cnc(C4=CCOCC4)nc3)cc2)cc1F]

5-Bromo-2-(3,6-dihydro-2H-pyran-4-yl)pyrimidine <see (step 1)> (1.44 g, 6.00 mmol), [4-[(2,5-difluoro-4-methoxycarbonyl-phenyl)sulfamoyl]phenyl]boronic acid (see Example 10 (step 6)> (2.20 g, 6.00 mmol), sodium carbonate (1.27 g, 12.0 mmol), and Pd(dppf)Cl₂ (220 mg, 0.3 mmol) were suspended in dioxane (20 ml) and water (5.0 ml), and the resulting mixture was stirred at 100° C. for 8 hours. The reaction liquid was concentrated under reduced pressure, and the obtained residue was purified by silica gel column chromatography (petroleum ether:ethyl acetate=3:1 to 1:1) to obtain the title compound (1.20 g, 41%).

MS (ESI) m/z 488 (M+H)⁺

(Step 3) Methyl 2,5-difluoro-4-[[4-(2-tetrahydropyran-4-ylpyrimidin-5-yl)phenyl]sulfonylamino]benzoate

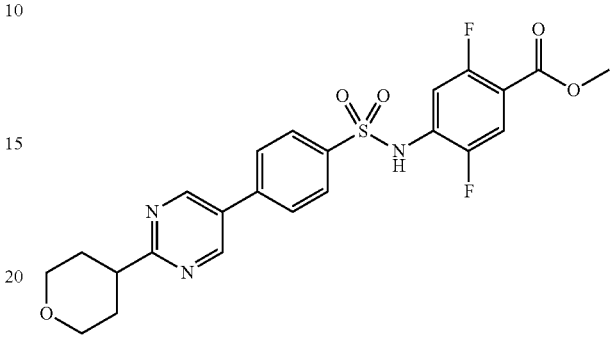

Methyl 4-[[4-[2-(3,6-dihydro-2H-pyran-4-yl)pyrimidin-5-yl]phenyl]sulfonylamino]-2, 5-difluorobenzoate <see (step 2)> (1.20 g, 2.46 mmol) was dissolved in methanol (10 ml), Pd/C (10%, 500 mg) was added thereto, and the resulting mixture was stirred under hydrogen atmosphere (50 psi) at 50° C. for 24 hours. The reaction liquid was cooled to room temperature and then filtered, and the solvent was removed under reduced pressure to obtain the title compound (843 mg, 70%).

MS (ESI) m/z 490 (M+H)⁺

Step 4) 2,5-Difluoro-4-[[4-(2-tetrahydropyran-4-ylpyrimidin-5-yl)phenyl]sulfonylamino]benzoic acid (M-11)

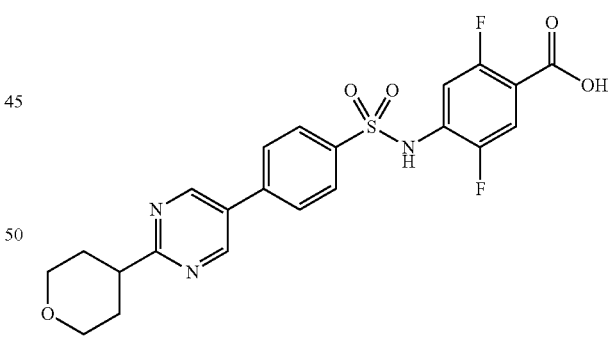

Methyl 2,5-difluoro-4-[[4-(2-tetrahydropyran-4-ylpyrimidin-5-yl)phenyl]sulfonylami no]benzoate <see (step 3)> (600 mg, 1.22 mmol) was dissolved in methanol (10 ml), a 2 N aqueous solution of lithium hydroxide (3.0 ml) was added thereto, and the resulting mixture was stirred at room temperature for 2 hours. The completion of the reaction was verified with TLC, 4 N hydrochloric acid was added for adjustment of the pH to 4 to 5, and the precipitated white solid was filtered off, dried, and washed with dichloromethane:methanol=10:1 to obtain the title compound (512 mg, 88%) as a white solid.

1H NMR (CD$_3$OD, 400 MHz): δ 9.07 (s, 2H), 8.06 (d, J=8.4 Hz, 2H), 7.93 (d, J=8.4 Hz, 2H), 7.63-7.59 (m, 1H), 7.50-7.45 (m, 1H), 4.10-4.07 (m, 2H), 3.66-3.59 (m, 2H), 3.25-3.19 (m, 1H), 2.04-1.94 (m, 4H): MS (ESI) m/z 476 (M+H)$^+$

Example 12

Synthesis of M-12

(Step 1) Chloromethyl benzoate

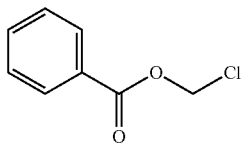 [SMILES: O=C(OCCl)c1ccccc1]

Paraformaldehyde (4.5 g) and zinc chloride (catalyst amount) were mixed at 0° C. Benzoyl chloride (20 g, 0.14 mol) was added dropwise thereto over 1 hour. The temperature of the reaction liquid was raised to room temperature, and then the reaction liquid was stirred at 55° C. for 10 hours. The reaction liquid was cooled and then purified by silica gel column chromatography (petroleum ether:ethyl acetate=30:1 to 10:1) to obtain the title compound (9.7 g, 40%).

$^1$H NMR (CDCl$_3$, 400 MHz): δ 8.09-8.07 (m, 2H), 7.63-7.60 (m, 1H), 7.49-7.44 (m, 2H), 5.96 (s, 2H)

(Step 2) Iodomethyl benzoate

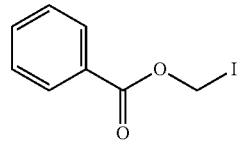 [SMILES: O=C(OCI)c1ccccc1]

Chloromethyl benzoate <see (step 1)> (10.0 g, 58.8 mmol) was dissolved in acetonitrile (70.0 ml), sodium iodide (17.6 g, 117 mmol) was added thereto, and the resulting mixture was stirred at room temperature for 24 hours. Acetonitrile was distilled off under reduced pressure, and diethyl ether was added. The precipitated solid was filtered off, washed with diethyl ether, and dried under reduced pressure, and then purified by silica gel column chromatography (petroleum ether:ethyl acetate=30:1 to 10:1) to obtain the title compound (14.5 g, 94%).

$^1$H NMR (CDCl$_3$, 400 MHz): δ 8.06-8.04 (m, 2H), 7.64-7.62 (m, 1H), 7.49-7.44 (m, 2H), 6.17 (s, 2H)

(Step 3) (5-Bromopyrimidin-2-yl)methyl benzoate

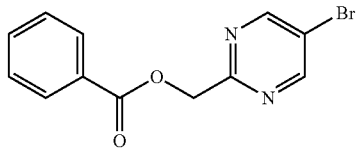 [SMILES: O=C(OCc1ncc(Br)cn1)c1ccccc1]

Zinc (21.6 g, 332 mmol) was heated at 210° C. for 10 minutes, then cooled to 70° C., heated to 210° C. again, stirred for 10 minutes, and cooled to room temperature. N,N-dimethylformamide (100 ml) and a dibromomethane (7.72 g, 41.2 mmol)/N,N-dimethylformamide (20 ml) solution was added thereto, and the resulting mixture was stirred at 90° C. for 30 minutes. The reaction solution was cooled to room temperature, chlorotrimethylsilane (900 mg, 8.30 mmol) was added, and the resulting mixture was stirred at room temperature for 10 minutes. Iodomethyl benzoate <see (step 2)> (14.5 g, 55.3 mmol)/N,N-dimethylformamide solution (60 ml) was added dropwise at 35° C., and the resulting mixture was stirred for 90 minutes. 5-Bromo-2-iodopyrimidine (7.90 g, 28.0 mmol) and Pd(PPh$_3$)$_2$Cl$_2$ (3.0 g, 4.1 mmol) were suspended in N,N-dimethylformamide (80 ml), the zinc reagent obtained in the above step was added with a syringe, and the resulting mixture was stirred under a nitrogen atmosphere at 80° C. for 2 hours. The reaction liquid was cooled to room temperature and filtered, and then the filtrate was diluted with water (600 ml) and extracted with ethyl acetate (200 ml×3). The extracts were combined, washed with a saturated saline solution, and dried over sodium sulfate. The solvent was removed under reduced pressure, and then the obtained residue was purified by silica gel column chromatography (petroleum ether:ethyl acetate=6:1 to 2:1) to obtain the title compound (7.38 g, 90%).

$^1$H NMR (CDCl$_3$, 400 MHz): δ 8.79 (s, 2H), 8.15-8.13 (m, 2H), 7.63-7.57 (m, 1H), 7.47-7.45 (m, 2H), 5.63 (s, 2H)

(Step 4) (5-Bromopyrimidin-2-yl)methanol

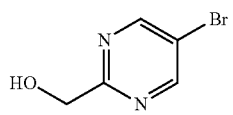

(5-Bromopyrimidin-2-yl)methyl benzoate <see (step 3)> (7.30 g, 25.0 mmol) was dissolved in methanol (15 ml), a 1 N sodium methoxide/methanol solution (50.0 ml, 0.500 mmol) was added thereto, and the resulting mixture was stirred at room temperature. The solvent was distilled off after deprotection was completed, and the obtained residue was purified by silica gel column chromatography (dichloromethane:methanol=30:1 to 15:1) to obtain the title compound (3.58 g, 76%).

$^1$H NMR (CDCl$_3$, 400 MHz): δ 8.80 (s, 2H), 4.82 (d, J=4.0 Hz, 2H), 3.39 (s, 1H)

(Step 5) 5-Bromo-2-(methoxymethyl)pyrimidine

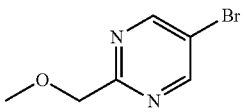

(5-Bromopyrimidin-2-yl)methanol <see (step 4)> (3.72 g, 19.8 mmol) was dissolved in tetrahydrofuran (10 ml), the resulting solution was cooled to 0° C., then sodium hydride (60% in oil, 1.19 g, 29.7 mmol) and methyl iodide (4.20 g, 29.7 mmol) were added thereto, and the resulting mixture was stirred at room temperature for 1 hour. The reaction liquid was concentrated under reduced pressure, and the obtained residue was purified by silica gel column chromatography to obtain the title compound (2.40 g, 60%).

(Step 6) Methyl 2,5-difluoro-4-[[4-[2-(methoxymethyl)pyrimidin-5-yl]phenyl]sulfonylamino]benzoate

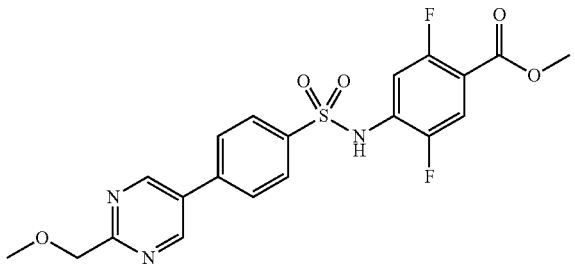

5-Bromo-2-(methoxymethyl)pyrimidine <see (step 5)> (2.30 g, 11.3 mmol), [4-[(2, 5-difluoro-4-methoxycarbonylphenyl)sulfamoyl]phenyl]boronic acid <see Example 10 (step 6)> (4.20 g, 11.3 mmol), sodium carbonate (2.40 g, 22.6 mmol), and Pd(dppf)Cl$_2$ (415 mg, 0.57 mmol) were suspended in dioxane (50 ml) and water (10 ml), and the resulting mixture was stirred at 100° C. for 8 hours. The reaction liquid was concentrated under reduced pressure, and the obtained residue was purified by silica gel column chromatography (petroleum ether:ethyl acetate=2:1 to 1:4) to obtain the title compound (2.95 g, 58%).

MS (ESI) m/z 450 (M+H)$^+$

Step 7) 2,5-Difluoro-4-[[4-[2-(methoxymethyl)pyrimidin-5-yl]phenyl]sulfonylamino]benzoic acid (M-12)

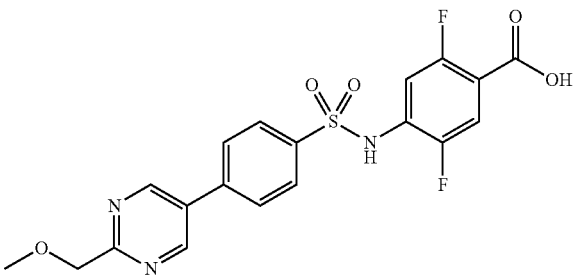 [SMILES: COCc1ncc(-c2ccc(S(=O)(=O)Nc3cc(F)c(C(=O)O)cc3F)cc2)cn1]

Methyl 2,5-difluoro-4-[[4-[2-(methoxymethyl)pyrimidin-5-yl]phenyl]sulfonylamino]benzoate <see (step 5)> (700 mg, 1.56 mmol) was dissolved in methanol (10 ml), a 2 N aqueous solution of lithium hydroxide (3.0 ml) was added thereto, and the resulting mixture was stirred at room temperature for 2 hours. The completion of the reaction was verified with TLC, and then 4 N hydrochloric acid was added for adjustment of the pH to 4 to 5. The precipitated white solid was filtered, dried, and washed with a mixed solvent (methylene chloride:methanol=10:1) to obtain the title compound (617 mg, 91%) as a white solid.

$^1$H NMR (CD$_3$OD, 400 MHz): δ 9.06 (s, 2H), 8.01 (d, J=8.4 Hz, 2H), 7.90 (d, J=8.4 Hz, 2H), 7.56-7.52 (m, 1H), 7.43-7.39 (m, 1H), 4.68 (s, 2H), 3.47 (s, 3H); MS (ESI) m/z 436 (M+H)$^+$

Example 13

Synthesis of M-13

(Step 1) 4-Methoxy-2-butynoic acid

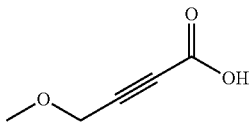

3-Methoxypropyne (1.00 g, 14.3 mmol) was dissolved in tetrahydrofuran (100 ml), the resulting solution was cooled to −78° C., and then a 2.5 M n-butyllithium/hexane solution (24.4 ml, 61.0 mmol) was added dropwise. The resulting mixture was stirred at −78° C., then dry ice was added to the reaction liquid, and the temperature of the reaction liquid was gradually raised to room temperature. The reaction liquid was diluted with water, and then 4 N hydrochloric acid was added for adjustment of the pH to 5.0. The resulting liquid was extracted with methylene chloride (50 ml×3), the organic layers were combined and dried over sodium sulfate, and the solvent was removed under reduced pressure to obtain the title compound (1.50 g, 92%) as a yellow oil.

$^1$H NMR (CDCl$_3$, 400 MHz): δ 8.97 (s, 1H), 4.27 (s, 2H), 3.44 (s, 3H)

(Step 2) Methyl 2,5-difluoro-4-[(4-iodophenyl)sulfonylamino]benzoate

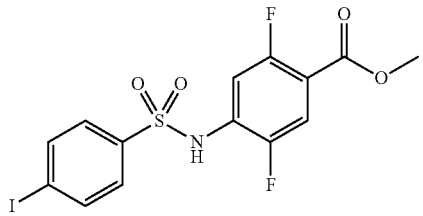 [SMILES: COC(=O)c1cc(F)c(NS(=O)(=O)c2ccc(I)cc2)cc1F]

A method similar to Example 10 (step 5) was performed to methyl 4-amino-2,5-difluoro-benzoate <see Example 10 (step 4)> (6.50 g, 34.8 mmol) and 4-iodobenzenesulfonyl chloride (21.0 g, 69.5 mmol) to obtain the title compound (14.0 g, 89%) as a yellow solid.

MS (ESI) m/z 452 (M-1)

(Step 3) Methyl 2,5-difluoro-4-[[4-[4-(methoxymethyl)triazol-1-yl]phenyl]sulfonylamino]benzoate

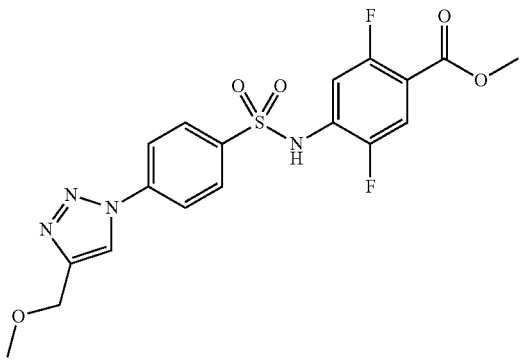

4-Methoxy-2-butynoic acid <see (step 1)> (502 mg, 4.40 mmol) and methyl 2,5-difluoro-4-[(4-iodopheny)sulfonylamino]benzoate <see (step 2)> (2.00 g, 4.40 mmol) were dissolved in dimethylsulfoxide (25.0 ml) and water (3.0 ml), L-proline (102 mg, 0.880 mmol), copper(II) sulfate pentahydrate (110 mg, 0.440 mmol), sodium ascorbate (175 mg, 0.880 mmol), sodium azide (345 mg, 5.30 mmol), and potassium carbonate (731 mg, 5.30 mmol) were sequentially added, and the resulting mixture was stirred at 65° C. for 12 hours. Ethyl acetate (50 ml), ammonium water (50 ml), and water (100 ml) were added to the reaction liquid, then the resulting mixture was extracted with ethyl acetate (60 ml×10), the organic layers were combined and washed with a saturated saline solution (300 ml), dried over sodium sulfate, and the solvent was removed under reduced pressure to obtain the title compound (510 mg, 26%).

$^1$H NMR (CD$_3$OD, 400 MHz): δ 8.48 (s, 1H), 7.98 (d, J=8.4 Hz, 2H), 7.86 (d, J=8.0 Hz, 2H), 7.30-7.26 (m, 1H), 6.94-6.88 (m, 1H), 4.50 (s, 2H), 3.68 (s, 3H), 3.31 (s, 3H)

Step 4) 2,5-Difluoro-4-[[4-[4-(methoxymethyl)triazol-1-yl]phenyl]sulfonylamino]benzoic acid (M-13)

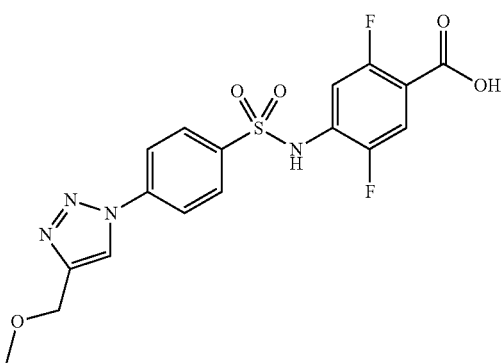 [SMILES: COCc1cn(-c2ccc(S(=O)(=O)Nc3cc(F)c(C(=O)O)cc3F)cc2)nn1]

Methyl 2,5-difluoro-4-[[4-[4-(methoxymethyl)triazol-1-yl]phenyl]sulfonylamino]benzoate <see (step 3)> (500 mg, 1.14 mmol) was dissolved in methanol (10 ml), a 2 N aqueous solution of lithium hydroxide (5.0 ml) was added thereto, and the resulting mixture was stirred at room temperature for 2 hours. The completion of the reaction was verified with TLC, and then 4 N hydrochloric acid was added for adjustment of the pH to 5.0. The precipitated solid was filtered and dried to obtain the title compound (450 mg, 93%) as a yellow solid.

$^1$H NMR (CD$_3$OD, 400 MHz): δ 8.66 (s, 1H), 8.14-8.08 (m, 4H), 7.56-7.47 (m, 2H), 4.64 (s, 2H), 3.44 (s, 3H); MS (ESI) m/z 425 (M+H)$^+$

Example 14

Synthesis of M-14

(Step 1) 2-Allyloxy-5-bromo-pyrimidine

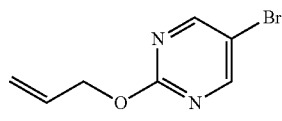

5-Bromo-2-chloro-pyrimidine (30.0 g, 0.150 mol) was dissolved in tetrahydrofuran (300 potassium-tert butoxide (20.1 g, 0.180 mol) and allyl alcohol (19.9 g, 0.170 mol) were added thereto, and the resulting mixture was stirred at 0° C. for 2 hours. The reaction liquid was diluted with water and extracted with diethyl ether (300 ml×3). The extracts were combined and washed with a saturated saline solution, dried over sodium sulfate, and the solvent was removed under reduced pressure to obtain the title compound (23.3 g, 70%).

$^1$H NMR (CDCl$_3$, 300 MHz): δ 8.53 (s, 2H), 6.11-6.02 (m, 1H), 5.45-5.39 (m, 1H), 5.30-5.26 (m, 1H), 4.89-4.87 (m, 2H)

(Step 2) Methyl 4-[[4-(1-allyl-2-oxo-pyrimidin-5-yl)phenyl]sulfonylamino]-2,5-difluoro-benzoate

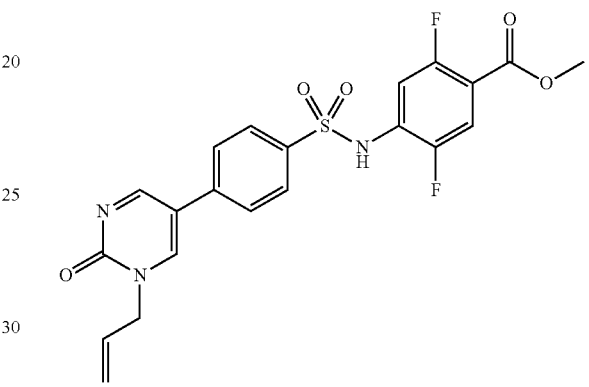

2-Allyloxy-5-bromo-pyrimidine <see (step 1)> (7.12 g, 3.30 w mmol), [4-[(2,5-difluoro-4-methoxycarbonyl-phenyl)sulfamoyl]phenyl]boronic acid <see Example 10 (step 6)> (8.19 g, 22.1 mmol), sodium carbonate (7.03 g, 66.1 mmol), and Pd(dppf)Cl$_2$ (2.40 g, 3.30 mmol) were dissolved in N,N-dimethylformamide (200 ml) and water (20 ml), and the resulting mixture was stirred in the presence of nitrogen gas at 100° C. for 2 hours. The reaction liquid was concentrated under reduced pressure, and then the obtained residue was purified by HPLC (acetonitrile in water) to obtain the title compound (3.56 g, 35%).

MS (ESI) m/z 462 (M+H)$^+$ (Step 3) 4-[[4-(1-Allyl-2-oxo-pyrimidin-5-yl)phenyl]sulfonylamino]-2,5-difluoro-benzoic acid

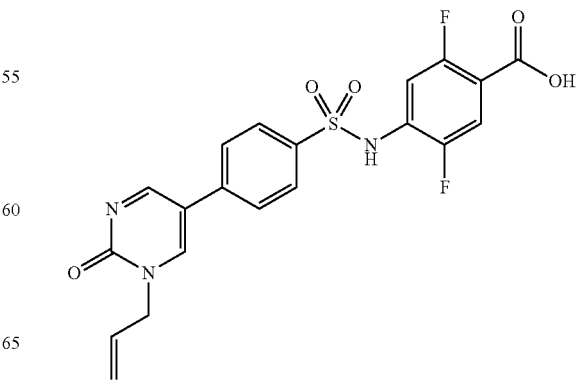

Methyl 4-[[4-(1-allyl-2-oxo-pyrimidin-5-yl)phenyl]sulfonylamino]-2,5-difluoro-benzoate <see (step 2)> (3.51 g, 7.60 mmol) was dissolved in methanol (30 ml), a 2 N aqueous solution of lithium hydroxide (10.0 ml) was added thereto, and the resulting mixture was stirred at room temperature for 2 hours. The completion of the reaction was verified with TLC, and then 4 N hydrochloric acid was added for adjustment of the pH to 5.0. The precipitated solid was filtered and dried to obtain the title compound (2.72 g, 80%) as a yellow solid.

$^1$H NMR (DMSO-$d_6$, 400 MHz): δ 13.42-13.40 (br, 1H), 11.13-11.05 (br, 1H), 9.04 (d, J=3.3 Hz, 1H), 8.72 (d, J=3.3 Hz, 1H), 7.93-7.85 (m, 4H), 7.67-7.57 (m, 1H), 6.07-5.95 (m, 1H), 5.25-5.18 (m, 2H), 4.58-4.51 (m, 2H); MS (ESI) m/z 448 (M+H)$^+$

Example 15

Synthesis of M-15

(Step 1) 5-Bromo-2-ethoxymethyl)pyrimidine

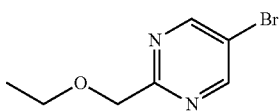

(5-Bromopyrimidin-2-yl)methanol <see Example 12 (step 4)> (3.72 g, 19.8 mmol) was dissolved in tetrahydrofuran (10.0 ml), the reaction solution was cooled to 0° C., then sodium hydride (60% wt in mineral oil, 1.19 g, 29.7 mmol) and ethane iodide (4.63 mmol, 29.7 mmol) were sequentially added, and the resulting mixture was stirred at room temperature for 1 hour. The reaction liquid was concentrated under reduced pressure, and the obtained residue was purified by silica gel column chromatography (petroleum ether) to obtain the title compound (2.58 g, 60%).

(Step 2) Methyl 4-[[4-[2-(ethoxymethyl)pyrimidin-5-yl]phenyl]sulfonylamino]-2,5-difluoro-benzoate

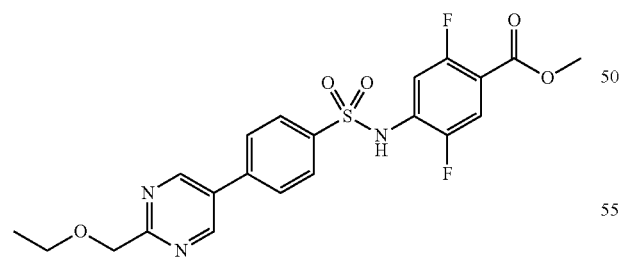

5-Bromo-2-(ethoxymethyl)pyrimidine <see (step 1)> (2.45 g, 11.3 mmol), [4-[(2,5-difluoro-4-methoxycarbonylphenyl)sulfamoyl]phenyl]boronic acid <see Example 10 (step 6)> (4.20 g, 11.3 mmol), sodium carbonate (2.40 g, 22.6 mmol), and Pd(dppf)Cl$_2$ (415 mg, 0.57 mmol) were dissolved in dioxane (50.0 ml) and water (10.0 ml), and the resulting mixture was stirred in the presence of nitrogen at 100° C. for 8 hours. The reaction liquid was concentrated under reduced pressure, and then the obtained residue was purified by silica gel column chromatography (petroleum ether:ethyl acetate=2:1 to 1:4) to obtain the title compound (2.94 g, 56%).

MS (ESI) m/z 464 (M+H)$^+$

Step 3) 4-[[4-[2-(Ethoxymethyl)pyrimidin-5-yl]phenyl]sulfonylamino]-2,5-difluoro-benzoic acid (M-15)

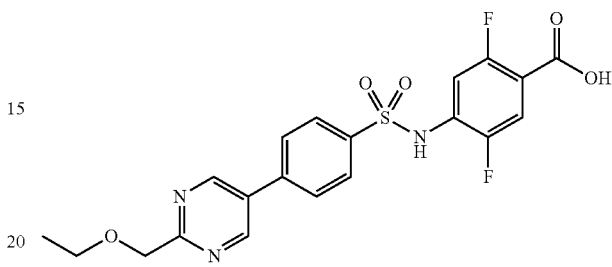

Methyl 4-[[4-[2-(ethoxymethyl)pyrimidin-5-yl]phenyl]sulfonylamino]-2,5-difluoro-benzoate <see (step 2)> (800 mg, 1.72 mmol) was dissolved in methanol (10 ml), a 2 N aqueous solution of lithium hydroxide (3.0 ml) was added thereto, and the resulting mixture was stirred at room temperature for 2 hours. The completion of the reaction was verified with TLC, and then 4 N hydrochloric acid was added for adjustment of the pH to 5.0. The precipitated solid was filtered, washed with a mixed solution of methylene chloride:methanol (10:1), and dried to obtain the title compound (698 mg, 90%) as a white solid.

$^1$H NMR (DMSO-$d_6$, 400 MHz): δ 13.35 (br, 1H), 11.19 (br, 1H), 9.25 (d, J=7.6 Hz, 2H), 8.16-7.96 (m, 4H), 7.63-7.56 (m, 1H), 7.31-7.27 (m, 1H), 4.67 (s, 2H), 3.63-3.48 (m, 2H), 1.23-1.15 (m, 3H); MS (ESI) m/z 450 (M+H)$^+$

Example 16

Synthesis of M-16

(Step 1) 4-Nitro-2-tetrahydropyran-4-yl-pyridine

Zinc (19.2 g, 293 mmol) was heated at 210° C. for 10 minutes, cooled to 70° C., then heated to 210° C. again, and the resulting mixture was stirred for 10 minutes. The reaction mixture was cooled to room temperature, then a solution of N,N-dimethylformamide (100 ml) and dibromoethane (6.87 g, 33.6 mmol) in N,N-dimethylformamide (10.0 ml) was added thereto, and the resulting mixture was stirred at 90° C. for 30 minutes. The reaction mixture was cooled to room temperature, then trimethylsilyl chloride (800 mg, 7.30 mmol) was added thereto, and the resulting mixture was stirred at room temperature for 10 minutes. A solution of 4-iodine tetrahydropyran (10.4 g, 49.2 mmol) in N,N-dimethylformamide (60.0 ml) was added to the reaction liquid, and the resulting mixture was stirred at 35° C. for 90 minutes. This zinc derivative was added to a suspension of 2-bromo-4-nitro-pyridine (5.00 g, 24.6 mmol) and Pd(PPh$_3$)$_2$Cl$_2$ (2.60 g, 3.70 mmol) in N,N-dimethylformamide (80.0 ml), and the resulting mixture was stirred in the presence of nitrogen gas at 90° C. for 2 hours. The reaction mixture was cooled to room temperature, then the reaction solution was filtered, and the obtained filtrate was diluted with water (600 ml) and extracted with ethyl acetate (200 ml×3). The extracts were combined, washed with a saturated saline solution, dried over anhydrous sodium sulfate, and then the solvent was removed under reduced pressure. The obtained residue was purified by silica gel column chromatography (petroleum ether:ethyl acetate=10:1 to 5:1) to obtain the title compound (900 mg, 17%).

$^1$H NMR (CDCl$_3$, 400 MHz): δ 8.85 (d, J=5.6 Hz, 1H), 7.90-7.86 (m, 2H), 4.15-4.11 (m, 2H), 3.61-3.54 (m, 2H), 3.16-3.10 (m, 1H), 2.00-1.91 (m, 4H)

(Step 2) 2-Tetrahydropyran-4-ylpyridin-4-amine

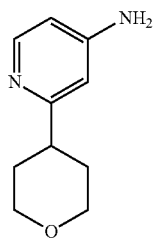 [SMILES: Nc1ccnc(C2CCOCC2)c1]

4-Nitro-2-tetrahydropyran-4-yl-pyridine <see (step 1)> (900 mg, 4.30 mmol) and 10% Pd/C (wet, 100 mg) were suspended in methanol (5.0 ml), and the resulting mixture was stirred in the presence of hydrogen at room temperature for 24 hours. The reaction liquid was filtered, and the filtrate was concentrated under reduced pressure to obtain the title compound (700 mg, 91%).

$^1$H NMR (CD$_3$OD, 300 MHz): δ 7.89 (d, J=5.7 Hz, 1H), 6.49-6.41 (m, 2H), 4.07-4.01 (m, 2H), 3.59-3.50 (m, 2H), 2.80-2.71 (m, 1H), 1.84-1.76 (m, 4H)

(Step 3) 4-Bromo-2-tetrahydropyran-4-yl-pyridine

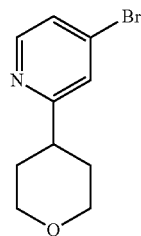

2-Tetrahydropyran-4-ylpyridin-4-amine <see (step 2)> (700 mg, 3.90 mmol) was dissolved in bromoform (30 ml), amyl nitrite (20 ml) was added thereto, and the resulting mixture was stirred in the presence of nitrogen gas at 85° C. for 4 hours. The reaction mixture was cooled to room temperature, then the reaction liquid was concentrated under reduced pressure, and the obtained residue was purified by silica gel column chromatography (petroleum ether:ethyl acetate=10:1 to 5:1) to obtain the title compound (350 mg, 37%).

$^1$H NMR (CDCl$_3$, 300 MHz): δ 8.37 (d, 1H, J=5.4 Hz), 7.36-7.27 (m, 2H), 4.13-4.07 (m, 2H), 3.59-3.50 (m, 2H), 2.97-2.92 (m, 1H), 1.92-1.84 (m, 4H)

(Step 4) 2-Benzylsulfanyl-5-bromo-pyridine

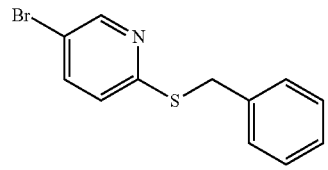 [SMILES: Brc1ccc(SCc2ccccc2)nc1]

5-Bromo-2-chloro-pyridine (80.0 g, 645 mmol) was dissolved in tetrahydrofuran (600 ml), sodium hydride (60% wt in mineral oil, 45.0 g, 1.13 mol) was added thereto over 20 minutes, and the resulting mixture was stirred at room temperature for 30 minutes. Benzyl thiol (123 g, 640 mmol) was added to the reaction liquid, and the resulting mixture was stirred at room temperature for 3 hours. The reaction liquid was diluted with water, extracted with diethyl ether, the extracts were combined, and washed with a saturated aqueous solution of sodium hydrogen carbonate, and a saturated saline solution. The obtained residue was dried over magnesium sulfate, and the solvent was removed under reduced pressure to obtain the title compound (148 g, 82%).

(Step 5) 5-Bromopyridine-2-sulfonyl chloride

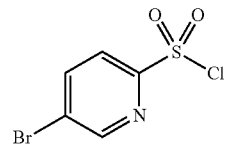 [SMILES: O=S(=O)(Cl)c1ccc(Br)cn1]

2-Benzylsulfanyl-5-bromo-pyridine <see (step 4)> (250 g, 0.89 mol) was suspended in acetic acid (2,250 ml) and water (750 ml), NCS (340 g, 2.60 mol) was added thereto, and the resulting mixture was stirred at room temperature for 2 hours. The reaction liquid was diluted with water and extracted with methylene chloride. The extracts were combined, washed with a saturated aqueous solution of sodium hydrogen carbonate and a saturated saline solution, and dried over magnesium sulfate. The obtained residue was purified by silica gel column chromatography (petroleum ether:ethyl acetate=30:1) to obtain the title compound (60.4 g, 26%).

(Step 6) Methyl 4-[(5-bromo-2-pyridyl)sulfonylamino]difluoro-benzoate

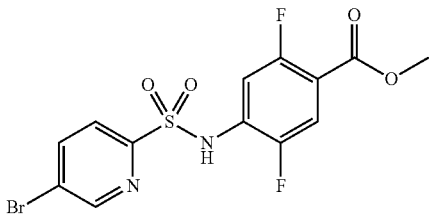 [SMILES: COC(=O)c1cc(F)c(NS(=O)(=O)c2ccc(Br)cn2)cc1F]

Methyl 4-amino-2,5-difluoro-benzoate <see Example 10 (step 4)> (14.1 g, 75.0 mmol) and 5-bromopyridine-2-sulfonyl chloride <see (step 5)> (29.0 g, 113 mmol) were dissolved in methylene chloride (250 ml), pyridine (23 ml) was added thereto, and the resulting mixture was stirred at room temperature for 12 hours. The reaction liquid was concentrated under reduced pressure, 6 N hydrochloric acid was added for adjustment of the pH to 1.0, and the precipitated yellow solid was filtered. The obtained solid was washed with water and dried to obtain the title compound (21.4 g, 70%) as a yellow solid.

$^1$H NMR (400 MHz, DMSO-$d_6$): δ 11.30 (s, 1H), 8.91 (d, J=2.0 Hz, 1H), 8.40 (dd, J=8.4, 2.4 Hz, 1H), 8.00 (d, J=8.4 Hz, 1H), 7.69-7.65 (m, 1H), 7.45-7.39 (m, 1H), 3.83 (s, 3H); MS (ESI) m/z 407, 409 (M+H)$^+$ (Step 7) [6-[(2,5-Difluoro-4-methoxycarbonyl-phenyl)sulfamoyl]-3-pyridyl]boronic acid

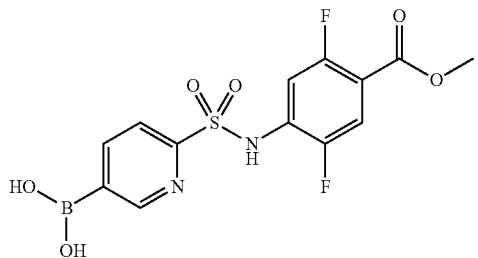 [SMILES: COC(=O)c1cc(F)c(NS(=O)(=O)c2ccc(B(O)O)cn2)cc1F]

Two steps similar to Example 10 (step 6) were performed to methyl 4-[(5-bromo-2-pyridyl)sulfonylamino]-2,5-difluoro-benzoate <see (step 6)> (41 g, 0.10 mol) to obtain the title compound (30 g, 81%) as a black oil.
MS (ESI) m/z 371 (M-1)

(Step 8) Methyl 2,5-difluoro-4-[[5-(2-tetrahydropyran-4-yl-4-pyridyl)-2-pyridyl]sulfonylamino]benzoate

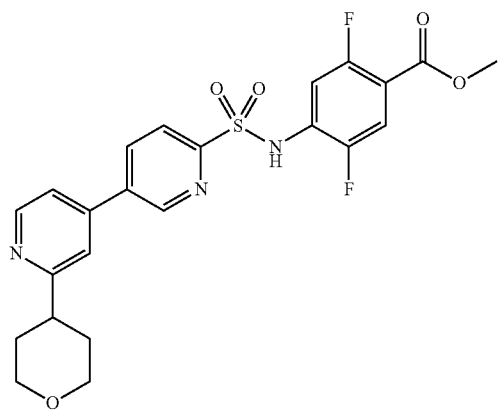 [SMILES: COC(=O)c1cc(F)c(NS(=O)(=O)c2ccc(-c3ccnc(C4CCOCC4)c3)cn2)cc1F]

4-Bromo-2-tetrahydropyran-4-yl-pyridine <see (step 3)> (350 mg, 1.45 mmol), [6-[(2,5-difluoro-4-methoxycarbonyl-phenyl)sulfamoyl]-3-pyridyl]boronic acid <see (step 7)> (647 mg, 1.74 mmol), sodium carbonate (462 mg, 4.83 mmol), and Pd(dppf)Cl$_2$ (106 mg, 0.14 mmol) were dissolved in dioxane (10.0 ml) and water (2.0 ml), and the resulting solution was stirred in the presence of nitrogen at 105° C. for 2 hours. The reaction liquid was concentrated under reduced pressure, and then the obtained residue was purified by silica gel column chromatography (petroleum ether ethyl acetate=10:1 to 1:1) to obtain the title compound (210 mg, 29%).

Step 9) 2,5-Difluoro-4-[[5-(2-tetrahydropyran-4-yl-4-pyridyl)-2-pyridyl]sulfonylamino]benzoic acid (M-16)

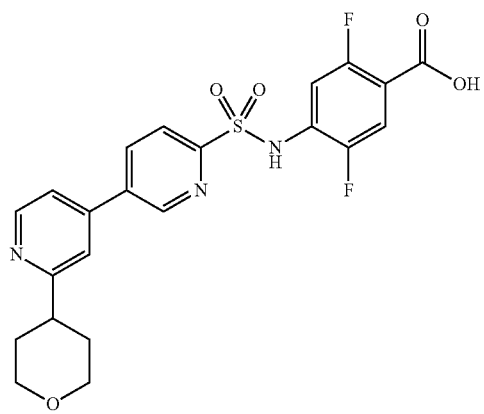 [SMILES: O=C(O)c1cc(F)c(NS(=O)(=O)c2ccc(-c3ccnc(C4CCOCC4)c3)cn2)cc1F]

Methyl 2,5-difluoro-4-[[5-(2-tetrahydropyran-4-yl-4-pyridyl)-2-pyridyl]sulfonylamino]benzoate <see (step 8)> (210 mg, 0.43 mmol) was dissolved in methanol (5.0 ml), a 2 N aqueous solution of lithium hydroxide (3.0 ml) was added thereto, and the resulting mixture was stirred at room temperature for 2 hours. The completion of the reaction was verified with TLC, and then 4 N hydrochloric acid was added for adjustment of the pH to 5.0. The precipitated solid was filtered and dried to obtain the title compound (140 mg, 69%) as a white solid.

$^1$H NMR (DMSO-$d_6$, 300 MHz): δ 13.32 (br s, 1H), 11.27 (br s, 1H), 9.18 (s, 1H), 8.65 (d, J=3.6 Hz, 1H), 8.53 (dd, J=6.0, 1.2 Hz, 1H), 8.15 (d, J=6.0 Hz, 1H), 7.77 (s, 1H), 7.69 (d, J=3.6 Hz, 1H), 7.61 (dd, J=8.1, 5.1 Hz, 1H), 7.45 (dd, J=9.3, 5.1 Hz, 1H), 3.98-3.96 (m, 2H), 3.49-3.43 (m, 2H), 3.04-2.99 (m, 1H), 1.87-1.78 (m, 4H); MS (ESI) m/z 476 (M+H)$^+$

Example 17

Synthesis of M-17

(Step 1) (5-Bromopyrimidin-2-yl)methyl methanesulfonate

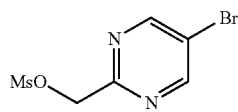

(5-Bromopyrimidin-2-yl)methanol <see Example 12 (step 4)> (3.72 g, 19.7 mmol) was dissolved in tetrahydrofuran (10 ml), triethylamine (3.0 g, 30 mmol), mesyl chloride (3.38 g, 29.6 mmol) was added at 0° C., and the resulting mixture was stirred at room temperature for 1 hour. The reaction liquid was concentrated under reduced pressure, and then the obtained residue was purified by silica gel column chromatography (petroleum ether:ethyl acetate=10:1) to obtain the title compound (4.54 g, 86%).

$^1$H NMR (CDCl$_3$, 400 MHz): δ 8.83 (s, 2H), 5.39 (s, 2H), 3.20 (s, 3H)

(Step 2)
N-[(5-Bromopyrimidin-2-yl)methyl]propan-2-amine

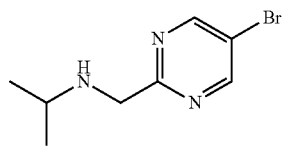

(5-Bromopyrimidin-2-yl)methyl methanesulfonate <see (step 1)> (200 mg, 0.750 mmol) was dissolved in ethanol (10 ml), isopropylamine (88.5 mg, 1.50 mmol) and triethylamine (151 mg, 1.50 mmol) were added thereto, and the resulting mixture was stirred at 80° C. for 1 hour. The reaction liquid was concentrated under reduced pressure, and then the obtained residue was purified by silica gel column chromatography (petroleum ether:ethyl acetate=3:1 to 1:1) to obtain the title compound (144 mg, 84%).

$^1$H NMR (CDCl$_3$, 400 MHz): δ 8.77 (s, 2H), 4.08 (s, 2H), 2.89-2.83 (m, 1H), 1.12 (d, J=6.4 Hz, 6H)

(Step 3) Methyl 2,5-difluoro-4-[[4-[2-[(isopropylamino)methyl]pyrimidin-5-yl]phenyl]sulfonyl amino]benzoate

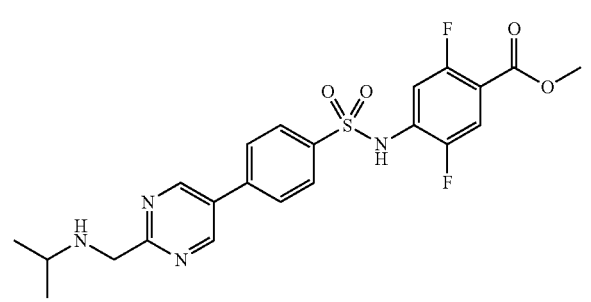 [SMILES: COC(=O)c1cc(F)c(NS(=O)(=O)c2ccc(-c3cnc(CNC(C)C)nc3)cc2)cc1F]

N-[(5-Bromopyrimidin-2-yl)methyl]propan-2-amine <see (step 2)> (0.260 g, 1.13 mmol), [4-[(2,5-difluoro-4-methoxycarbonyl-phenyl)sulfamoyl]phenyl]boronic acid <see Example 10 (step 6)> (0.420 g, 1.13 mmol), sodium carbonate (0.24 g, 2.2 mmol), and Pd(dppf)Cl$_2$ (41.5 mg, 0.057 mmol) were dissolved in dioxane (5.0 ml) and water (1.0 ml), and the resulting mixture was stirred in the presence of nitrogen gas at 100° C. for 8 hours. The reaction liquid was concentrated under reduced pressure, and then the obtained residue was purified by silica gel column chromatography (petroleum ether:ethyl acetate=2:1 to 1:4) to obtain the title compound (0.32 g, 59%).

MS (ESI) m/z 477 (M+H)$^+$

Step 4) 2,5-Difluoro-4-[[4-[2-[(isopropylamino)methyl]pyrimidin-5-yl]phenyl]sulfonyl amino]benzoic acid (M-17)

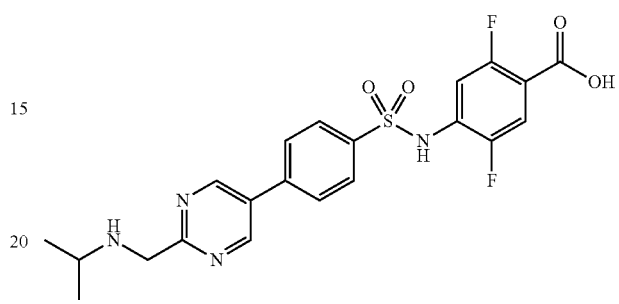

Methyl 2,5-difluoro-4-[[4-[2-[(isopropylamino)methyl]pyrimidin-5-yl]phenyl]sulfonyl amino]benzoate <see (step 3)> (476 mg, 1.00 mmol) was dissolved in methanol (10 ml), a 2 N aqueous solution of lithium hydroxide (3.0 ml) was added thereto, and the resulting mixture was stirred at room temperature for 2 hours. The completion of the reaction was verified with TLC, and then 4 N hydrochloric acid was added for adjustment of the pH to 5.0. The precipitated solid was filtered, washed with a mixed solution of methylene chloride:methanol (10:1), and dried to obtain the title compound (406 mg, 88%) as a white solid.

$^1$H NMR (CD$_3$OD, 400 MHz): δ 9.06 (s, 2H), 7.88 (d, J=8.8 Hz, 2H), 7.80 (d, J=8.4 Hz, 2H), 7.63-7.56 (m, 2H), 4.44 (s, 2H), 3.48-3.45 (m, 1H), 1.33 (d, J=6.4 Hz, 6H); MS (ESI) m/z 463 (M+H)$^+$

Example 18

Synthesis of M-18

(Step 1) 5-Bromo-2-vinyl-pyrimidine

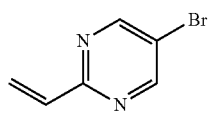

5-Bromo-2-iodine-pyrimidine (28.4 g, 0.100 mol) and Pd(PPh$_3$)$_4$ (1.73 g, 1.50 mmol) were dissolved in tetrahydrofuran (350 ml), a 1.5 M solution of vinyl magnesium bromide/tetrahydrofuran (75.0 ml, 0.110 mol) was added thereto, and the resulting mixture was stirred at room temperature for 16 hours. The reaction liquid was diluted with water (200 ml) and extracted with ethyl acetate (200 ml×3). The extracts were combined, washed with a saturated saline solution, dried over anhydrous sodium sulfate, and then the solvent was removed under reduced pressure to obtain the title compound.

MS (ESI) m/z 185, 187 (M+H)+

(Step 2) 2-(5-Bromopyrimidin-2-yl)-N,N-dimethylethanamine

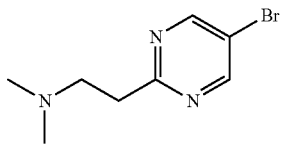

5-Bromo-2-vinyl-pyrimidine <see (step 1)> was dissolved in methanol (50 ml), dimethylamine (a 40% aqueous solution, 19.0 ml, 0.250 mol) was added thereto, and the resulting mixture was stirred at room temperature for 90 minutes. The reaction liquid was concentrated under reduced pressure, and then the obtained residue was purified by silica gel column chromatography (methylene chloride:methanol=100:1 to 10:1) to obtain the title compound (6.90 g, 30%, two steps).

$^1$H NMR (CD$_3$OD, 300 MHz): δ 8.82 (s, 2H), 3.33-3.32 (m, 2H), 2.88-2.83 (m, 2H), 2.30 (s, 6H)

(Step 3) Methyl 4-[[4-[2-(2-dimethylaminoethyl)pyrimidin-5-yl]phenyl]sulfonylamino]-2,5-difluoro-benzoate

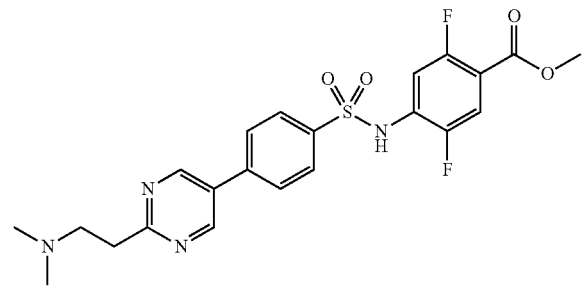

2-(5-Bromopyrimidin-2-yl)-N,N-dimethylethanamine <see (step 2)> (5.20 g, 22.6 mmol), methyl 2,5-difluoro-4-[[4-(4,4,5,5-tetramethyl-1,3,2-dioxaborolan-2-yl)phenyl]sulfonylamino]benzoate <see Example 10 (step 6)> (10.2 g, 22.6 mmol), sodium carbonate (3.60 g, 33.9 mmol), and Pd(dppf)Cl$_2$ (830 mg, 1.14 mmol) were dissolved in dioxane (60 ml) and water (20 ml), and the resulting mixture was stirred in the presence of nitrogen at 100° C. for 8 hours. The reaction liquid was concentrated under reduced pressure, and then the obtained residue was purified by silica gel column chromatography (methylene chloride:methanol=100:1 to 10:1) to obtain the title compound (5.90 g, 55%).

MS (ESI) m/z 477 (M+H)+

Step 4) 4-[[4-[2-(2-Dimethylaminoethyl)pyrimidin-5-yl]phenyl]sulfonylamino]-2,5-difluoro-benzoic acid (M-18)

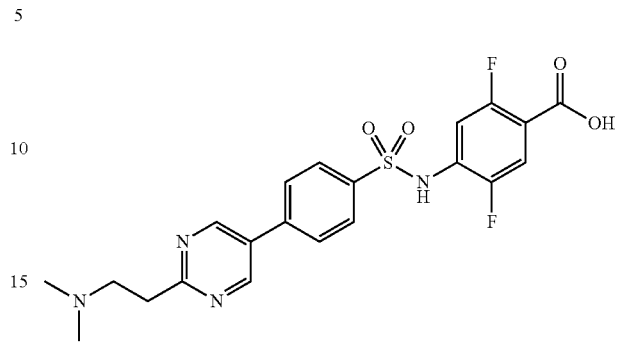

Methyl 4-[[4-[2-(2-dimethylaminoethyl)pyrimidin-5-yl]phenyl]sulfonylamino]-2,5-difluoro-benzoate <see (step 3)> (5.90 g, 12.4 mmol) was dissolved in methanol (10 ml), a 2 N aqueous solution of lithium hydroxide (30 ml) was added thereto, and the resulting mixture was stirred at room temperature for 2 hours. The completion of the reaction was verified with TLC, and then 4 N hydrochloric acid was added for adjustment of the pH to 5.0. The precipitated solid was filtered and dried to obtain the title compound (4.6 g, 81%) as a white solid.

$^1$H NMR (DMSO-d$_6$, 300 MHz): δ 9.11 (s, 2H), 7.86 (s, 4H), 7.30-7.23 (m, 1H), 6.99-6.92 (m, 1H), 3.55-3.51 (m, 2H), 3.38-3.34 (m, 2H), 2.81 (s, 6H); MS (ESI) m/z 463 (M+H)+

Example 19

Synthesis of M-19

(Step 1) 5-Bromo-2-(isopropoxymethyl)pyrimidine

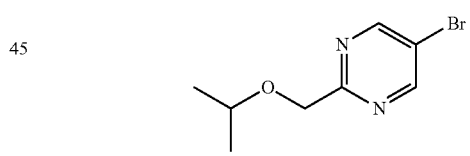

Isopropanol (10 ml) was added to sodium hydride (60% wt in mineral oil, 225 mg, 5.60 mmol), and the resulting mixture was stirred at 60° C. for 30 minutes. The reaction liquid was cooled to room temperature, then (5-bromopyrimidin-2-yl)methyl methanesulfonate <see Example 17 (step 1)> (1.0 g, 3.7 mmol) a solution of isopropanol (15 ml) was added thereto, and the resulting mixture was stirred at 0° C. for 3 hours. The reaction liquid was diluted with water (50 ml), extracted with diethyl ether (50 ml×3), the extracts were combined, washed with a saturated saline solution, dried over anhydrous sodium sulfate, then the solvent was removed under reduced pressure, and the obtained residue was purified by silica gel column chromatography (petroleum ether:ethyl acetate=10:1) to obtain the title compound (657 mg, 76%).

1H NMR (CDCl3, 400 MHz): δ 8.80 (s, 2H), 4.71 (s, 2H), 3.82-3.79 (m, 1H), 1.28-1.27 (d, J=6.0 Hz, 6H)

(Step 2) Methyl 2,5-difluoro-4-[[4-[2-(isopropoxymethyl)pyrimidin-5-yl]phenyl]sulfonylamino]benzoate

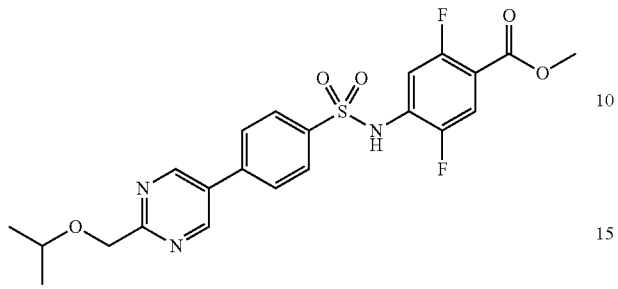

5-Bromo-2-(isopropoxymethyl)pyrimidine <see (step 1)> (508 mg, 2.20 mmol), [4-[(2,5-difluoro-4-methoxycarbonylphenyl)sulfamoyl]phenyl]boronic acid <see Example 10 (step 6)> (820 mg, 2.20 mmol), sodium carbonate (700 mg, 6.60 mmol), and Pd(dppf)Cl$_2$ (48 mg, 0.066 mmol) were dissolved in dioxane (20 ml) and water (7.0 ml), and the resulting mixture was stirred in the presence of nitrogen at 105° C. for 12 hours. The reaction liquid was concentrated under reduced pressure, then the obtained residue was washed with diethyl ether (20 ml) and dried to obtain the title compound (1.50 g).

MS (ESI) m/z 478 (M+H)$^+$

Step 3) 2,5-Difluoro[[4-[2-(isopropoxymethyl)pyrimidin-5-yl]phenyl]sulfonylamino]benzoic acid (M-19)

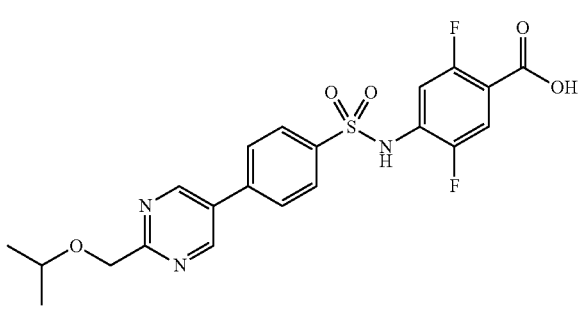 [SMILES: CC(C)OCc1ncc(-c2ccc(S(=O)(=O)Nc3cc(F)c(C(=O)O)cc3F)cc2)cn1]

Methyl 2,5-difluoro-4-[[4-[2-(isopropoxymethyl)pyrimidin-5-yl]phenyl]sulfonylamino]benzoate <see (step 2)> (1.50 g) was dissolved in methanol (10 ml), a 2 N aqueous solution of lithium hydroxide (6.0 ml) was added thereto, and the resulting mixture was stirred at room temperature for 2 hours. The completion of the reaction was verified with TLC, and then 4 N hydrochloric acid was added for adjustment of the pH to 4.0. The precipitated solid was filtered off, washed with acetonitrile, and dried to obtain the title compound (763 mg, 75% for two steps) as a yellow solid.

$^1$H NMR (DMSO-d$_6$, 400 MHz): δ 13.41 (br, 1H), 11.15 (br, 1H), 9.19 (s, 2H), 8.07-7.97 (m, 4H), 7.62 (dd, J=10.8, 6.4 Hz, 1H), 7.31 (dd, J=12.0, 6.4 Hz, 1H), 4.66 (s, 2H), 3.81-3.75 (m, 1H), 1.24 (d, J=6.0 Hz, 6H): MS (ESI) m/z 464 (M+H)$^+$

Example 20

Synthesis of M-20

(Step 1) 2-(Azetidin-1-yl)-5-bromo-pyrimidine

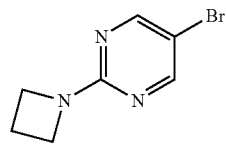 [SMILES: Brc1cnc(N2CCC2)nc1]

5-Bromo-2-chloro-pyrimidine (29.9 g, 0.150 mol) was dissolved in N,N-dimethylformamide (300 azetidine (11.4 g, 0.200 mol) and potassium carbonate (42.5 g, 0.310 mol) were added thereto, and the resulting mixture was stirred at 50° C. for 12 hours. The reaction liquid was diluted with water, extracted with diethyl ether (300 ml×3), the extracts were combined, washed with a saturated saline solution, and dried over anhydrous sodium sulfate. The solvent was removed under reduced pressure to obtain the title compound (30 g, 93%).

$^1$H NMR (CDCl$_3$, 400 MHz): δ 8.26 (s, 2H), 4.12 (t, J=7.4 Hz, 4H), 2.40-2.33 (m, 2H)

(Step 2) Methyl 4-[[4-[2-(azetidin-1-yl)pyrimidin-5-yl]phenyl]sulfonylamino]-2,5-difluoro-benzoate

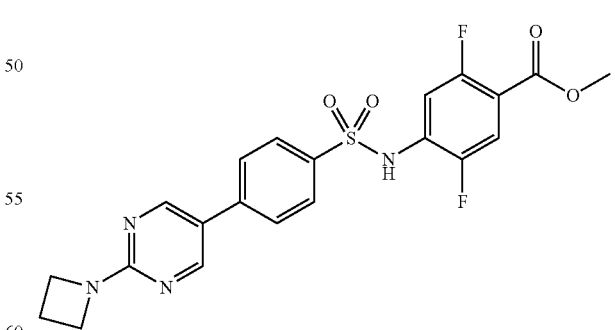

A method similar to Example 10 (step 7) was performed to 2-(Azetidin-1-yl)-5-bromo-pyrimidine <see (step 1)> (10.7 g, 50.4 mmol) to obtain the title compound (15.0 g, 64%).

MS (ESI) m/z 461 (M+H)$^+$

Step 3) 4-[[4-[2-(Azetidin-1-yl)pyrimidin-5-yl]phenyl]sulfonylamino]-2,5-difluoro-benzoic acid (M-20)

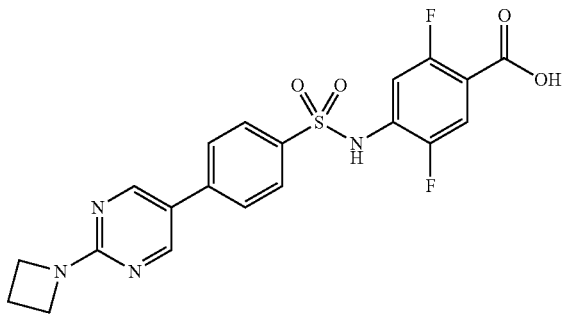 [SMILES: O=C(O)c1cc(F)c(NS(=O)(=O)c2ccc(-c3cnc(N4CCC4)nc3)cc2)cc1F]

Methyl 4-[[4-[2-(azetidin-1-yl)pyrimidin-5-yl]phenyl]sulfonylamino]-2,5-difluoro-benzoate <see (step 2)> (15.0 g, 32.6 mmol) was dissolved in methanol (180 ml), a 2 N aqueous solution of lithium hydroxide (60 ml) was added thereto, and the resulting mixture was stirred at room temperature for 2 hours. The completion of the reaction was verified with TLC, and then 4 N hydrochloric acid was added for adjustment of the pH to 4.0. The precipitated solid was filtered, washed with a mixed solvent (methylene chloride:methanol=10:1), and dried to obtain the title compound (10.0 g, 69%) as a white solid.

$^1$H NMR (DMSO-$d_6$, 400 MHz): δ 13.43-13.40 (br, 1H), 11.13-11.05 (br, 1H), 8.78 (d, J=10.0 Hz, 2H), 7.98-7.88 (m, 4H), 7.62 (dd, J=10.4, 6.8 Hz, 1H), 7.29 (dd, J=12.0, 6.4 Hz, 1H), 4.12 (t, J=7.2 Hz, 4H), 2.52-2.32 (m, 2H); MS (ESI) m/z 447 (M+H)$^+$

Example 21

Synthesis of M-21

(Step 1) Methyl 2,5-difluoro-4-[[5-(4-methyltriazol-1-yl)-2-pyridyl]sulfonylamino]benzoate

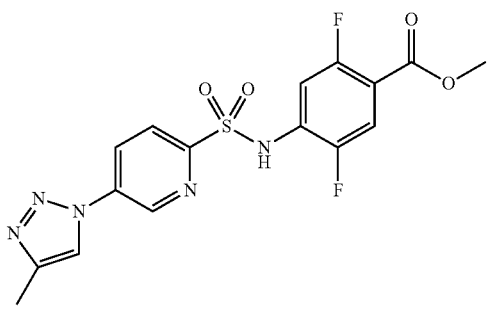 [SMILES: COC(=O)c1cc(F)c(NS(=O)(=O)c2ccc(-n3cc(C)nn3)cn2)cc1F]

2-Butynoic acid (3.70 g, 44.0 mmol) and methyl 2,5-difluoro-4-[(5-iodine-2-pyridyl)sulfonylamino]benzoate <synthesized by a method similar to Example 16 (step 6)> (20.0 g, 44.0 mmol) were dissolved in dimethylsulfoxide (250 ml) and water (30 ml), L-proline (1.00 g, 8.80 mmol), copper(II) sulfate pentahydrate (1.10 g, 4.40 mmol), sodium ascorbate (1.70 g, 8.80 mmol), sodium azide (4.29 g, 66.0 mmol), and potassium carbonate (7.30 g, 53.0 mmol) were sequentially added, and the resulting mixture was stirred at 65° C. for 12 hours. Ethyl acetate (500 ml), ammonium water (500 ml), and water (1,000 ml) were added to the reaction liquid, then the reaction liquid was extracted with ethyl acetate (600 ml×15), the organic layers were combined and washed with a saturated saline solution (3,000 ml), dried over sodium sulfate, and the solvent was removed under reduced pressure. The obtained residue was purified by HPLC separation to obtain the title compound (4.70 g, 26%).

$^1$H NMR (CD$_3$OD, 300 MHz): δ 9.11 (s, 1H), 8.43-8.42 (m, 2H), 8.22-8.19 (m, 1H), 7.43-7.30 (m, 2H), 3.83 (s, 311), 2.43 (s, 3H)

(Step 2) 2,5-Difluoro-4-[[5-(4-methyltriazol-1-yl)-2-pyridyl]sulfonylamino]benzoic acid (M-21)

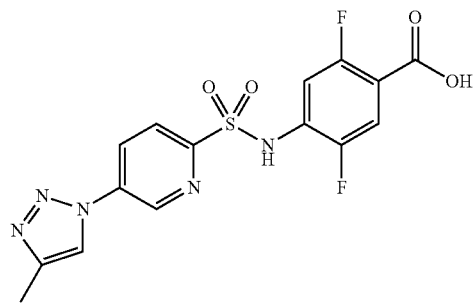 [SMILES: Cc1cn(-c2ccc(S(=O)(=O)Nc3cc(F)c(C(=O)O)cc3F)nc2)nn1]

Methyl 2,5-difluoro-4-[[5-(4-methyltriazol-1-yl)-2-pyridyl]sulfonylamino]benzoate <see (step 1)> (4.50 g, 11.0 mmol) was dissolved in methanol (60 ml), a 2 N aqueous solution of lithium hydroxide (15 ml) was added thereto, and the resulting mixture was stirred at room temperature for 30 minutes. The completion of the reaction was verified with TLC, and then 4 N hydrochloric acid was added for adjustment of the pH to 4.0. The precipitated solid was filtered off, washed with a saturated saline solution, and dried to obtain the title compound (3.90 g, 90%) as a white solid.

$^1$H NMR (CD$_3$OD, 400 MHz): δ 9.22 (d, J=2.0 Hz, 1H), 8.58-8.47 (d, J=9.2, 2.8 Hz, 1H), 8.47 (s, 1H), 8.29 (d, J=8.8 Hz, 1H), 7.66-7.58 (m, 2H), 2.44 (s, 3H); MS (ESI) m/z 396 (M+H)$^+$

Example 22

Synthesis of M-22

(Step 1) Furan-2-sulfonyl chloride

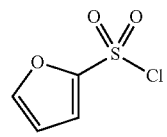

Furan (3.67 g, 53.9 mmol) was dissolved in diethyl ether (50 ml), the reaction solution was cooled to 0° C., then a solution of t-butyllithium/hexane (1.3 mold, 50 ml) was slowly added dropwise, and the resulting mixture was stirred for 15 minutes. Sulfur dioxide was added to the reaction liquid, and the resulting mixture was further stirred for 15 minutes. Then N-chlorosuccinimide (8.65 g, 64.8 mmol) was added thereto, and the resulting mixture was stirred at room temperature for 30 minutes. The reaction liquid was diluted with water and extracted with ethyl acetate (100 ml×2), then the extracts were combined, washed with a saturated saline solution, and dried over anhydrous sodium sulfate. The solvent was removed under reduced pressure, and then the residue was purified by silica gel column chromatography (petroleum ether:ethyl acetate=10:1 to 5:1) to obtain the title compound (3.2 g, 36%) as a yellow oil.

(Step 2) Methyl 2,5-difluoro-4-[(2-furylsulfonyl)amino]benzoate

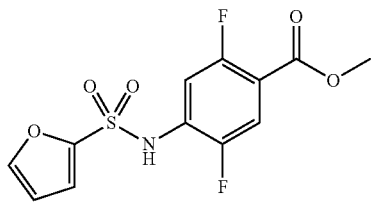 [SMILES: COC(=O)c1cc(F)c(NS(=O)(=O)c2ccco2)cc1F]

Methyl 4-amino-2,5-difluorobenzoate (1.40 g, 7.48 mmol)<see Example 10 (step 4)> was dissolved in methylene chloride (60 ml), furan-2-sulfonyl chloride <see (step 1)> (3.00 g, 18.0 mmol) and pyridine (10 ml) were added thereto, and the resulting mixture was stirred at room temperature for 12 hours. The reaction liquid was diluted with water and extracted with ethyl acetate. The extracts were combined, washed with a saturated saline solution, dried over anhydrous sodium sulfate, the solvent was removed under reduced pressure, and then the obtained residue was purified by silica gel column chromatography (petroleum ether:ethyl acetate=10:1 to 5:1) to obtain the title compound (800 mg, 34%) as a gray solid.

$^1$H NMR (DMSO-$d_6$, 400 MHz): δ 8.02 (s, 1H), 7.71-6.66 (m, 1H), 7.32-7.25 (m, 2H), 6.70-6.66 (m, 1H), 3.82 (s, 3H); MS (ESI) m/z 318 (M+H)$^+$ (Step 3) 2,5-Difluoro-4-[(2-furylsulfonyl)amino] benzoic acid (M-22)

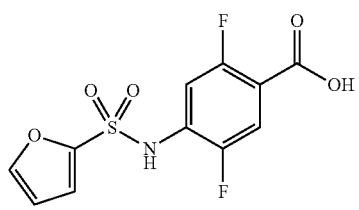 [SMILES: O=C(O)c1cc(F)c(NS(=O)(=O)c2ccco2)cc1F]

Methyl 2,5-difluoro-4-[(2-furylsulfonyl)amino]benzoate <see (step 2)> (800 mg, 2.52 mmol) was dissolved in methanol (10 ml), a 6 N aqueous solution of sodium hydroxide (10.0 ml) was added thereto, and the resulting mixture was stirred at room temperature for 30 minutes. The completion of the reaction was verified with TLC, and then 4 N hydrochloric acid was added for adjustment of the pH to 4.0. The precipitated solid was filtered and dried to obtain the title compound (600 mg, 79%).

$^1$H NMR (CD$_3$OD, 400 MHz): δ 7.74 (dd, J=2.4, 1.6 Hz, 1H), 7.61 (dd, J=14.4, 8.4 Hz, 1H), 7.38 (dd, J=15.6, 8.4 Hz, 1H), 7.18 (dd, J=4.8, 1.6 Hz, 1H), 6.58 (dd, J=4.8, 2.4 Hz, 1H); MS (ESI) m/z 304 (M+H)$^+$

Example 23

Synthesis of M-23

(Step 1) Methyl 4-amino-2,3,5,6-tetrafluoro-benzoate

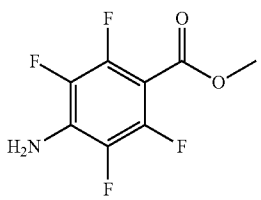

4-Amino-2,3,5,6-tetrafluoro-benzoic acid (10.0 g, 47.8 mmol) was dissolved in methanol (80 ml), the reaction solution was cooled to 0° C., then thionyl chloride (15 ml) was added dropwise, and the resulting mixture was stirred at 65° C. for 12 hours. The reaction liquid was concentrated under reduced pressure, and then the obtained residue was purified by silica gel column chromatography (petroleum ether:ethyl acetate=5:1 to 2:1) to obtain the title compound (9.28 g, 87%).

NMR (CDCl$_3$, 400 MHz): δ 4.38 (br s, 2H), 3.92 (s, 3H).

(Step 2) Methyl 4-[(4-bromophenyl)sulfonylamino]-2,3,5,6-tetrafluoro-benzoate

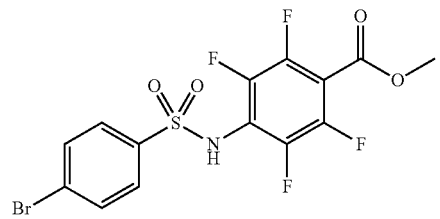 [SMILES: COC(=O)c1c(F)c(F)c(NS(=O)(=O)c2ccc(Br)cc2)c(F)c1F]

Methyl 4-amino-2,3,5,6-tetrafluoro-benzoate <see (step 1)> (4.60 g, 20.6 mmol) was dissolved in tetrahydrofuran (50 ml), sodium hydride (60% in oil, 1.64 g, 41.0 mmol) was added thereto, and the resulting mixture was stirred in the presence of nitrogen gas at room temperature for 30 minutes. 4-Bromobenzenesulfonyl chloride (5.70 g, 22.3 mmol) was added to the reaction liquid, and the resulting mixture was stirred at 60° C. for 2 hours. A saturated aqueous solution of sodium hydrogen carbonate was added to the reaction liquid and the resulting mixture was extracted with ethyl acetate (50 ml×3). The extracts were combined, washed with a saturated saline solution, and dried over anhydrous sodium sulfate. The solvent was removed under reduced pressure, and the obtained residue was purified by silica gel column chromatography (petroleum ether:ethyl acetate=5:1 to 1:1) to obtain the title compound (6.29 g, 69%).

H NMR (CDCl$_3$, 400 MHz): δ 7.75 (d, J=7.8 Hz, 2H), 7.50 (d, J=7.8 Hz, 2H), 3.90 (s, 3H)

(Step 3) Methyl 4-[[4-(2-ethylpyrimidin-5-yl)phenyl]sulfonylamino]-2,3,5,6-tetrafluoro-benzoate

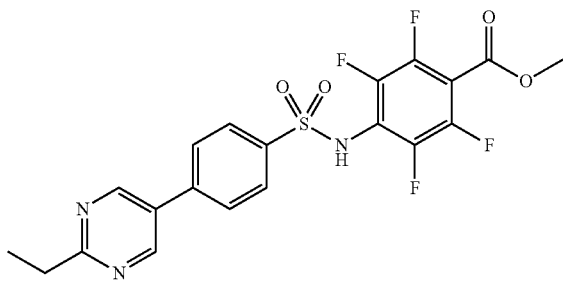 [SMILES: CCc1ncc(-c2ccc(S(=O)(=O)Nc3c(F)c(F)c(C(=O)OC)c(F)c3F)cc2)cn1]

Methyl 4-[(4-bromophenyl)sulfonylamino]-2,3,5,6-tetrafluoro-benzoate <see (step 2)> (587 mg, 1.33 mmol) and 2-ethyl-5-(4,4,5,5-tetramethyl-1,3,2-dioxaborolan-2-yl)pyrimidine (311 mg, 1.33 mmol) were dissolved in N,N-dimethylformamide (25 ml) and water (4.0 ml), sodium carbonate (421 mg, 3.98 mmol) and Pd(dppf)Cl$_2$ (194 mg, 0.266 mmol) were added thereto, and the resulting mixture was stirred in the presence of nitrogen gas at 100° C. for 4 hours. The reaction liquid was concentrated under reduced pressure, and then the obtained residue was purified by silica gel column chromatography (petroleum ether:ethyl acetate=5:1 to 1:1) to obtain the title compound (541 mg, 87%).

$^1$H NMR (CDCl$_3$, 400 MHz): δ 8.91 (s, 2H), 8.03 (d, J=7.8 Hz, 2H), 7.73 (d, J=7.8 Hz. 2H), 3.98 (s, 3H), 3.08 (q, J=8.0 Hz, 2H), 1.42 (t, J=8.0 Hz, 3H)

Step 4) 4-[[4-(2-Ethylpyrimidin-5-yl)phenyl]sulfonylamino]-2,3,5,6-tetrafluoro-benzoic acid (M-23)

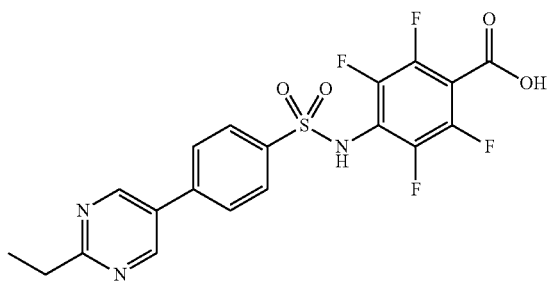 [SMILES: CCc1ncc(-c2ccc(S(=O)(=O)Nc3c(F)c(F)c(C(=O)O)c(F)c3F)cc2)cn1]

Methyl 4-[[4-(2-ethylpyrimidin-5-yl)phenyl]sulfonylamino]-2,3,5,6-tetrafluoro-benzoate <see (step 3)> (541 mg, 1.15 mmol) was dissolved in methanol (5.0 ml), a 2 N aqueous solution of lithium hydroxide (1.0 ml) was added thereto, and the resulting mixture was stirred at room temperature for 30 minutes. The completion of the reaction was verified with TLC, and then 4 N hydrochloric acid was added for adjustment of the pH to 4.0. The precipitated solid was filtered and dried to obtain the title compound (260 mg, 49%) as a white solid.

$^1$H NMR (DMSO-d$_6$, 400 MHz): 9.31 (s, 2H), 8.11 (d, J=8.0 Hz, 2H), 7.92 (d, J=8.0 Hz, 2H), 3.04 (q, J=8.0 Hz, 2H), 1.38 (t, J=8.0 Hz, 3H); MS (ESI) m/z 456 (M+H)$^+$

Example 24

Synthesis of M-24

(Step 1) Methyl 4-[(4-bromo-2-methyl-phenyl)sulfonylamino]-2-fluoro-benzoate

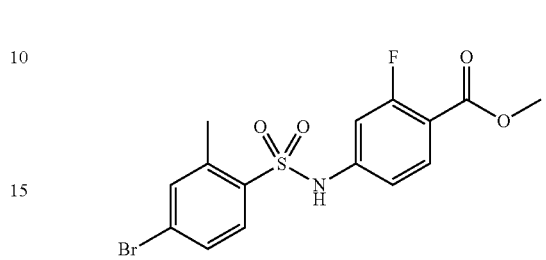

Methyl 4-amino-2-fluoro-benzoate (2.00 g, 12.0 mmol) and 4-bromo-2-methyl-benzensulphonyl chloride (4.70 g, 17.0 mmol) were dissolved in methylene chloride (50 ml), pyridine (10 ml) was added thereto, and the resulting mixture was stirred at room temperature for 12 hours. The reaction solution was concentrated under reduced pressure, then the obtained residue was purified by silica gel column chromatography (petroleum ether:ethyl acetate=4:1) to obtain the title compound (3.28 g, 69%).

MS (ESI) m/z 402, 404 (M+H)$^+$ (Step 2) Methyl 2-fluoro-4-[[2-methyl-4-(4,4,5,5-tetramethyl-1,3,2-dioxaborolan-2-yl)phenyl]sulfonylamino]benzoate

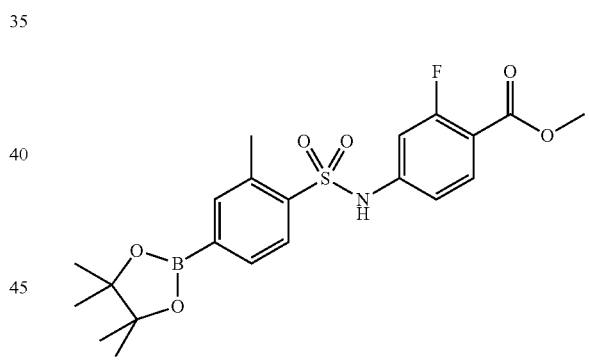

Methyl 4-[(4-bromo-2-methyl-phenypsulfonylamino]-2-fluoro-benzoate <see (step 1)> (2.30 g, 5.70 mmol) and bis(pinacolato)diborane (1.70 g, 6.90 mmol) were dissolved in N,N-dimethylformamide (30 ml), [1,1'-bis(diphenylphosphino)ferrocene]dichloropalladium(II) (22 mg, 0.030 mmol) and potassium acetate (1.70 g, 17.0 mmol) were added thereto, and the resulting mixture was stirred in the presence of nitrogen gas at 85° C. for 12 hours. The reaction liquid was cooled to room temperature and then filtered, and the filtrate was extracted with methylene chloride (30 ml×4). The extracts were combined and concentrated under reduced pressure, the obtained residue was diluted with water, the precipitated solid was filtered off, washed with a mixed solvent (petroleum ether:methylene chloride=5:2), and dried to obtain the title compound (1.90 g, 74%) as a brown solid.

$^1$H NMR (DMSO-d$_6$, 400 MHz): δ 8.00 (d, J=8.0 Hz, 1H), 7.95 (s, 1H), 7.92 (s, 1H), 7.76 (t, J=8.8 Hz, 1H), 7.68-7.68

(m, 1H), 6.97 (dd, J=8.8, 2.0 Hz, 1H), 6.90 (dd, J=8.8, 2.0 Hz, 1H), 3.79 (s, 3H), 2.60 (s, 3H), 1.28 (s, 12H)

(Step 3) [4-[(3-Fluoro-4-methoxycarbonyl-phenyl)sulfamoyl]-3-methyl-phenyl]boronic acid

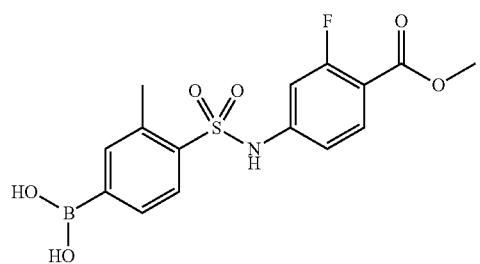 [SMILES: COC(=O)c1ccc(NS(=O)(=O)c2ccc(B(O)O)cc2C)cc1F]

Methyl 2-fluoro-4-[[2-methyl-4-(4,4,5,5-tetramethyl-1,3,2-dioxaborolan-2-yl)phenyl]sulfonylamino]benzoate <see (step 2)> (1.50 g, 3.30 mmol) was dissolved in acetone (15 ml), sodium periodate (1.40 g, 6.60 mmol), ammonium acetate (500 mg, 6.60 mmol), and water (6.0 ml) were added thereto, and the resulting mixture was stirred at room temperature for 48 hours. The reaction liquid was concentrated under reduced pressure, then diluted with water, and extracted with ethyl acetate (500 ml×3). The extracts were combined, washed with a saturated saline solution, and dried over anhydrous sodium sulfate, and then the solvent was removed under reduced pressure. The obtained residue was washed with a mixed solvent (petroleum ether:ethyl acetate=1:10) and dried under reduced pressure to obtain the title compound (1.00 g, 82%).
$^1$H NMR (DMSO-$d_6$, 400 MHz): δ 8.70 (d, J=4.4 Hz, 1H), 7.76 (t, J=8.4 Hz, 1H), 7.65-7.57 (m, 2H), 6.93-6.87 (m, 2H), 3.80 (s, 3H), 2.64 (s, 3H)

(Step 4) Methyl 2-fluoro-4-[[2-methyl-4-(2-pyridyl)phenyl]sulfonylamino]benzoate

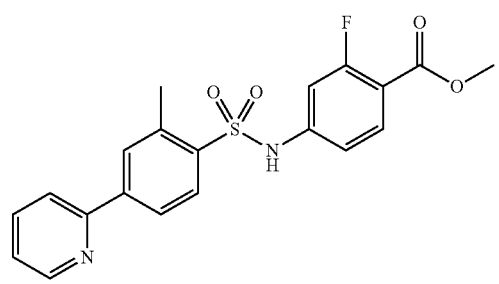 [SMILES: COC(=O)c1ccc(NS(=O)(=O)c2ccc(-c3ccccn3)cc2C)cc1F]

[4-[(3-Fluoro-4-methoxycarbonyl-phenyl)sulfamoyl]-3-methyl-phenyl]boronic acid <see (step 3)> (800 mg, 2.18 mmol) and 2-bromopyridine (680 mg, 4.35 mmol) were dissolved in dioxane (20 ml) and water (5.0 ml), sodium carbonate (530 mg, 5.00 mmol) and Pd(dppf)Cl$_2$ (162 mg, 0.200 mmol) were added thereto, and the resulting mixture was stirred in the presence of nitrogen at 110° C. for 4 hours. The reaction liquid was concentrated under reduced pressure, and then the obtained residue was purified by silica gel column chromatography (n-hexane:ethyl acetate=10:1 to 1:1) to obtain the title compound (530 mg, 61%).

$^1$H NMR (CD$_3$OD, 400 MHz): δ 8.70 (d, J=8.0 Hz, 1H), 8.12-8.03 (m, 3H), 8.00 (d, J=8.0 Hz, 1H), 7.96-7.90 (m, 2H), 7.76 (t, J=8.4 Hz, 1H), 7.44-7.41 (m, 1H), 7.02-6.91 (m, 2H), 3.76 (s, 3H), 2.69 (s, 3H)

Step 5) 2-Fluoro-4-[[2-methyl-4-(2-pyridyl)phenyl]sulfonylamino]benzoic acid (M-24)

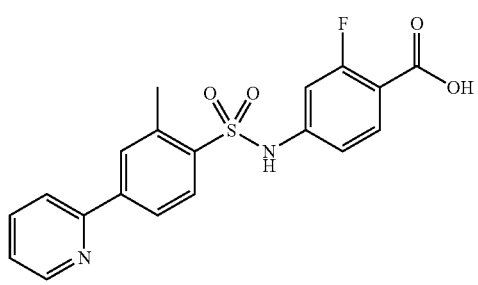 [SMILES: Cc1cc(-c2ccccn2)ccc1S(=O)(=O)Nc1ccc(C(=O)O)c(F)c1]

Methyl 2-fluoro-4-[[2-methyl-4-(2-pyridyl)phenyl]sulfonylamino]benzoate <see (step 4)> (630 mg, 1.57 mmol) was dissolved in methanol (10 ml), a 6 N aqueous solution of sodium hydroxide (5.0 ml) was added thereto, and the resulting mixture was stirred at room temperature for 30 minutes. The completion of the reaction was verified with TLC, and then 4 N hydrochloric acid was added for adjustment of the pH to 4.0. The precipitated solid was filtered and dried to obtain the title compound (560 mg, 92%) as a white solid.
$^1$H NMR (CD$_3$OD, 400 MHz): δ 8.67 (d, J=4.8 Hz, 1H), 8.18 (d, J=8.0 Hz, 1H), 7.99-7.96 (m, 4H), 7.81 (t, J=8.4 Hz, 1H), 7.47-7.45 (m, 1H), 6.99-6.94 (m, 2H), 2.77 (s, 3H); MS (ESI) m/z 385 (M-1)

Example 25

Synthesis of M-25

(Step 1) 4-({[3,5-Difluoro-4-(methoxycarbonyl)phenyl]amino}sulfonyl)benzoic acid

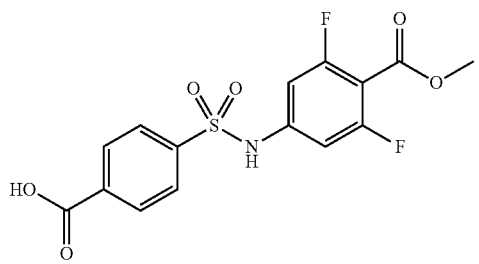 [SMILES: COC(=O)c1c(F)cc(NS(=O)(=O)c2ccc(C(=O)O)cc2)cc1F]

4-(Chlorosulfonyl)benzoic acid (25.0 g, 113 mmol) and methyl 4-amino-2,6-difluorobenzoate (19.0 g, 101 mmol) were dissolved in methylene chloride (500 ml), pyridine (25.0 ml, 285 mmol) was added thereto, and the resulting mixture was stirred at room temperature for 12 hours. The reaction solution was concentrated under reduced pressure, the obtained residue was diluted with water, a 6 N aqueous solution of hydrochloric acid was added for adjustment of the pH to 1.0, and the precipitated solid was filtered and washed with water. The obtained solid was suspended in water again, washed with a saturated aqueous solution of sodium hydrogen carbonate, and then extracted with ethyl acetate (100 ml×2). A 6 N aqueous solution of hydrochloric acid was added to the obtained aqueous layer for adjustment of the pH to 6.0, and ethyl acetate was added (100 ml×2) for extraction. The extracts were combined, washed with a saturated saline solution, dried over anhydrous sodium sulfate, and then the solvent was removed to obtain the title compound (15.0 g, 36%).

$^1$H NMR (d-DMSO, 400 MHz): δ 11.50 (s, 1H), 8.14 (d, J=8.4 Hz, H), 8.01 (d, J=8.4 Hz, 2H), 6.67 (d, J=10.4 Hz, 2H), 3.87 (s, 3H); MS (ESI) m/z 372 (M+H)$^+$

Step 2) 4-[({4-[(Cyclopropylamino)carbonyl]phenyl}sulfonyl)amino]-2,6-difluorobenzoic acid (M-25)

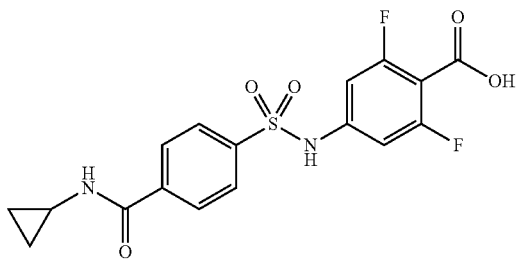 [SMILES: O=C(NC1CC1)c1ccc(S(=O)(=O)Nc2cc(F)c(C(=O)O)c(F)c2)cc1]

4-({[3,5-Difluoro-4-(methoxycarbonyl)phenyl]amino}sulfonyl)benzoic acid <see (step 1)> (1.5 g, 4.0 mmol) was dissolved in thionyl chloride (40 ml), and the resulting mixture was stirred at 75° C. for 4 hours. The reaction solution was cooled to room temperature, and then concentrated under reduced pressure. The obtained residue was dissolved in methylene chloride (30 ml), cyclopropylamine (680 mg, 12.0 mmol), and the resulting mixture was stirred at room temperature for 30 minutes. The solvent was removed under reduced pressure, and the obtained residue was purified by silica gel column chromatography (petroleum ether:ethyl acetate=2:1 to 1:1). A part of the obtained compound (740 mg, 1.8 mmol) was dissolved in methanol (15 ml), a 3 N aqueous solution of sodium hydroxide (5.0 ml) was added thereto, and the resulting mixture was stirred at room temperature for 30 minutes. A 6 N aqueous solution of hydrochloric acid was added for adjustment of the pH to 4.0, and the precipitated solid was filtered and then dried under reduced pressure to obtain the title compound (670 mg, 51% for two steps) as a white solid.

$^1$H NMR (d-DMSO, 400 MHz): δ 7.79-7.72 (m, 4H), 6.62 (d, J=10 Hz, 2H), 2.67-2.65 (m, 1H), 0.63-0.59 (m, 2H), 0.45-0.43 (m, 2H); MS (ESI) m/z 397 (M+H)$^+$

The following compounds (Examples 26 to 47) were synthesized by using methods similar to Example 28 (step 1), (step 2) performed to intermediates corresponding to M-1 to M-25 and compounds similar thereto.

Example 26

Synthesis of A-1

(Step 1) (2S)-2-[[2,5-Difluoro-4-[[4-[2-(4-piperidyl)pyrimidin-5-yl]phenyl]sulfonylamino]benzoyl]amino]-3-[5-(1-methyl-2,4-dioxo-pyrido[3,4-d]pyrimidin-3-yl)-2-pyridyl]propanoic acid (A-1)

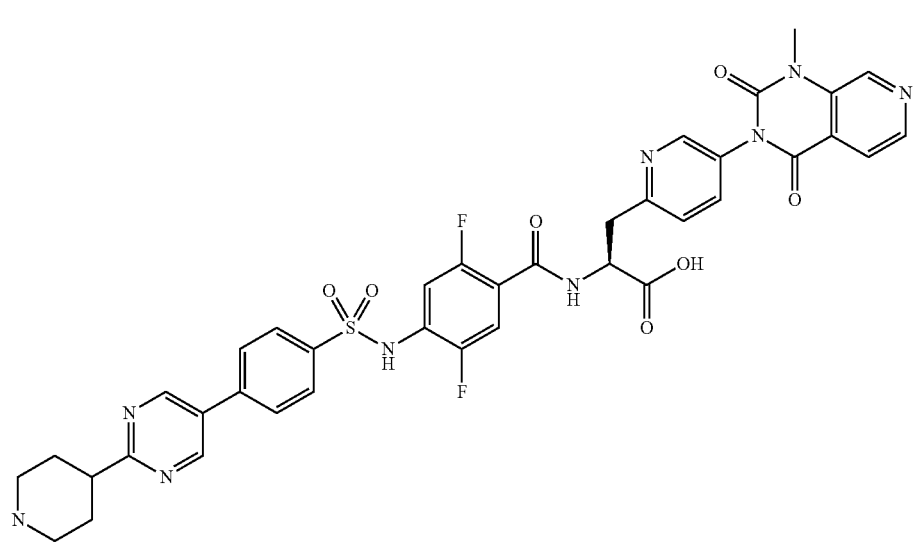

·3 TFA $^1$H NMR (400 MHz, DMSO-d$_6$) δ 10.99 (s, 1H), 9.16 (s, 2H), 9.00 (s, 1H), 8.75 (dd, J=7.8, 3.8 Hz, 1H), 8.57 (d, J=4.9 Hz, 1H), 8.47 (d, J=2.5 Hz, 1H), 8.07-7.94 (m, 4H), 7.90 (d, J=5.0 Hz, 1H), 7.75 (dd, J=8.2, 2.5 Hz, 1H), 7.47 (d, J=8.3 Hz, 1H), 7.38 (dd, J=10.3, 6.4 Hz, 1H), 7.29 (dd, J=11.4, 6.3 Hz, 1H), 4.89 (td, J=8.2, 4.9 Hz, 1H), 3.61 (s, 3H), 3.42-2.99 (m, 8H), 2.20-2.12 (m, 2H), 2.05-1.92 (m, 2H); MS (ESI) m/z 798.26 (M+H)$^+$

Example 27

Synthesis of A-2 and B-2

(Step 1) (2S)-2-[[2,5-Difluoro-4-[[4-(2-tetrahydropyran-4-ylpyrimidin-5-yl)phenyl]sulfonylamino]benzoyl]amino]-3-[5-(1-methyl-2,4-dioxo-pyrido[3,4-d]pyrimidin-3-yl)-2-pyridyl]propionic acid (A-2)

Methyl 3-[5-(1-methyl-2,4-dioxo-1,4-dihydropyrido[3,4-d]pyrimidin-3(2H)-yl)pyridin-2-yl]-L-alaninate (a methyl ester of M-9) <synthesized by a method similar to Example 9> (67.0 mg, 0.190 mmol) and 2,5-difluoro-4-[[4-(2-tetrahydropyran-4-ylpyrimidin-5-yl)phenyl]sulfonylamino]benzoic acid (M-11) <see Example 11 (step 4)> (75.0 mg, 0.160 mmol) were suspended in methylene chloride (2.0 HATU (91.0 mg, 0.240 mmol) and diisopropylethylamine (0.167 ml, 0.960 mmol) were added thereto, and the resulting mixture was stirred at room temperature for 12 hours. The reaction liquid was concentrated under reduced pressure, then a 4 N solution of hydrochloric acid/dioxane (3.0 ml) and water (1.0 ml) were added thereto, and the resulting mixture was stirred at 60° C. for 2 hours. The reaction liquid was concentrated under reduced pressure and then purified by reverse phase HPLC (an H$_2$O/CH$_3$CN system including 0.1% TFA) to obtain a TFA salt of the title compound (30.7 mg, 21%).

$^1$H NMR (400 MHz, DMSO-d$_6$) δ 10.98 (s, 1H), 9.13 (s, 2H), 9.00 (s, 1H), 8.73 (dd, J=7.9, 3.8 Hz, 1H), 8.57 (d, J=5.0 Hz, 1H), 8.46 (d, J=2.4 Hz, 1H), 8.05-7.99 (m, 2H), 7.98-7.93 (m, 2H), 7.90 (d, J=4.9 Hz, 1H), 7.73 (dd, J=8.2, 2.5 Hz, 1H), 7.45 (d, J=8.2 Hz, 1H), 7.38 (dd, J=10.4, 6.4 Hz, 1H), 7.28 (dd, J=11.4, 6.3 Hz, 1H), 4.88 (td, J=8.2, 5.0 Hz, 1H), 3.95 (ddd, J=11.3, 4.4, 2.1 Hz, 2H), 3.61 (s, 3H), 3.48 (td, J=11.6, 2.5 Hz, 2H), 3.42-3.23 (m, 2H), 3.13 (tt, J=11.2, 4.2 Hz, 1H), 1.97-1.75 (m, 4H); MS (ESI) m/z 799.51 (M+H)$^+$

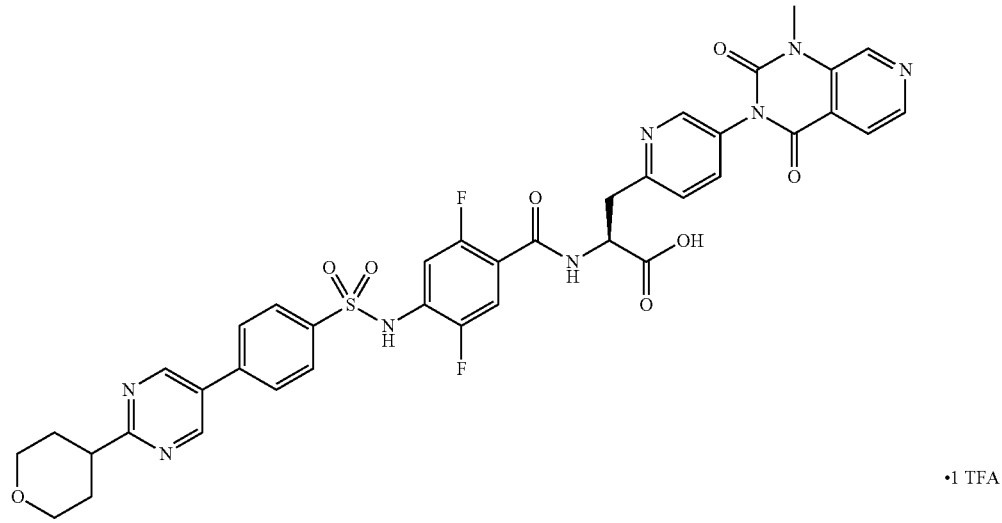 [SMILES: Cn1c(=O)n(-c2ccc(C[C@H](NC(=O)c3cc(F)c(NS(=O)(=O)c4ccc(-c5cnc(C6CCOCC6)nc5)cc4)cc3F)C(=O)O)nc2)c(=O)c2ccncc21]

·1 TFA (Step 2) Cyclohexyl (2S)-2-[[2,5-difluoro-4-[[4-(2-tetrahydropyran-4-ylpyrimidin-5-yl)phenyl]sulfonylamino]benzoyl]amino]-3-[5-(1-methyl-2,4-dioxo-pyrido[3,4-d]pyrimidin-3-yl)-2-pyridyl]propanoate (B-2)

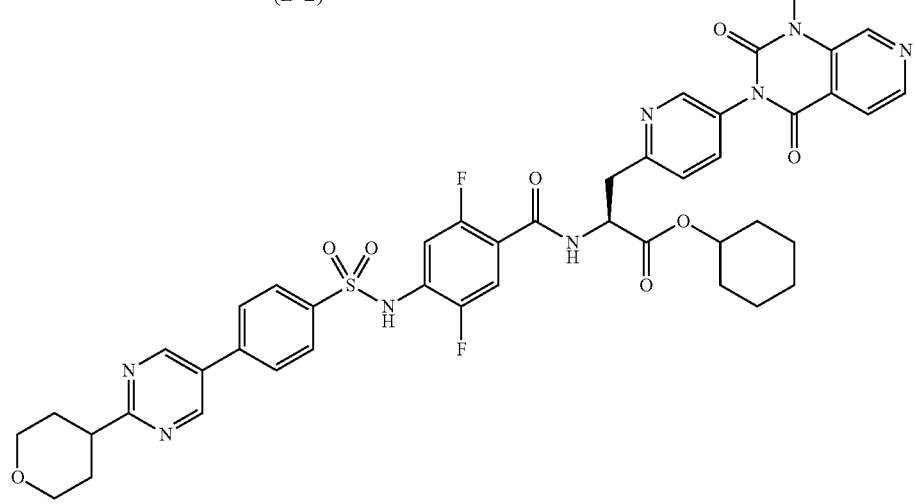

·2 TFA

Cyclohexyl 3-[5-(1-methyl-2,4-dioxo-1,4-dihydropyrido[3,4-d]pyrimidin-3(2H)-yl)pyridin-2-yl]-L-alaninate (M-9) <see Example 9 (step 4)> (107 mg, 0.250 mmol) and 2,5-difluoro-4-[[4-(2-tetrahydropyran-4-ylpyrimidin-5-yl)phenyl]sulfonylamino]benzoic acid (M-11) <see Example 11 (step 4)> (100 mg, 0.210 mmol) were suspended in methylene chloride (3.0 ml), HATU (120 mg, 0.320 mmol) and diisopropylethylamine (0.219 ml, 1.26 mmol) were added thereto, and the resulting mixture was stirred at room temperature for 12 hours. The reaction liquid was concentrated under reduced pressure and then purified by reverse phase HPLC (an H$_2$O/CH$_3$CN system including 0.1% TFA) to obtain a TFA salt of the title compound (48.7 mg, 21%).

$^1$H NMR (400 MHz, DMSO-d$_6$) δ 10.99 (s, 1H), 9.14 (s, 2H), 9.00 (s, 1H), 8.85 (dd, J=7.6, 3.4 Hz, 1H), 8.57 (d, J=4.9 Hz, 1H), 8.45 (d, J=2.4 Hz, 1H), 8.05-8.00 (m, 2H), 7.99-7.94 (m, 2H), 7.90 (d, J=4.9 Hz, 1H), 7.73 (dd, J=8.2, 2.5 Hz, 1H), 7.46 (d, J=8.2 Hz, 1H), 7.38 (dd, J=10.3, 6.3 Hz, 1H), 7.29 (dd, J=11.3, 6.3 Hz, 1H), 4.91 (td, J=7.6, 5.9 Hz, 1H), 4.68 (tt, J=8.2, 3.7 Hz, 1H), 4.01-3.90 (m, 2H), 3.61 (s, 3H), 3.38-3.25 (m, 2H), 3.19-3.07 (m, 1H), 1.97-1.77 (m, 4H), 1.75-1.52 (m, 4H), 1.50-1.17 (m, 7H).; MS (ESI) m/z 881.56 (M+H)$^+$

Example 28

Synthesis of A-3 and B-3

(Step 1) (2S)-2-[[2,5-Difluoro-4-[[4-[2-(methoxymethyl)pyrimidin-5-yl]phenyl]sulfonylamino]benzoyl]amino]-3-[5-(1-methyl-2,4-dioxo-pyrido[3,4-d]pyrimidin-3-yl)-2-pyridyl]propanoic acid (A-3)

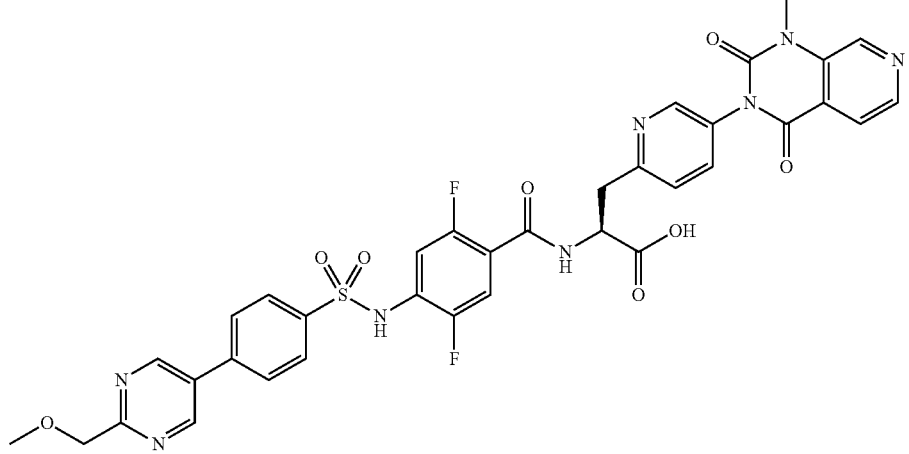

·1 TFA

¹H NMR (400 MHz, DMSO-d₆) δ 10.99 (s, 1H), 9.18 (s, 2H), 9.00 (s, 1H), 8.73 (dd, J=7.8, 3.8 Hz, 1H), 8.57 (d, J=4.9 Hz, 1H), 8.46 (d, J=2.4 Hz, 1H), 8.07-8.02 (m, 2H), 7.99-7.95 (m, 2H), 7.90 (d, J=4.9 Hz, 1H), 7.73 (dd, J=8.2, 2.5 Hz, 1H), 7.46 (d, J=8.2 Hz, 1H), 7.38 (dd, J=10.4, 6.4 Hz, 1H), 7.28 (dd, J=11.3, 6.2 Hz, 1H), 4.93-4.84 (m, 1H), 4.63 (s, 2H), 3.61 (s, 3H), 3.40 (s, 3H), 3.38-3.23 (m, 2H); MS (ESI) m/z 759.46 (M+H)⁺

(Step 2) Cyclohexyl (2S)-2-[[2,5-difluoro-4-[[4-[2-(methoxymethyl)pyrimidin-5-yl]phenyl]sulfonyl amino]benzoyl]amino]-3-[5-(1-methyl-2,4-dioxo-pyrido[3,4-d]pyrimidin-3-yl)-2-pyridyl]propanoate (B-3)

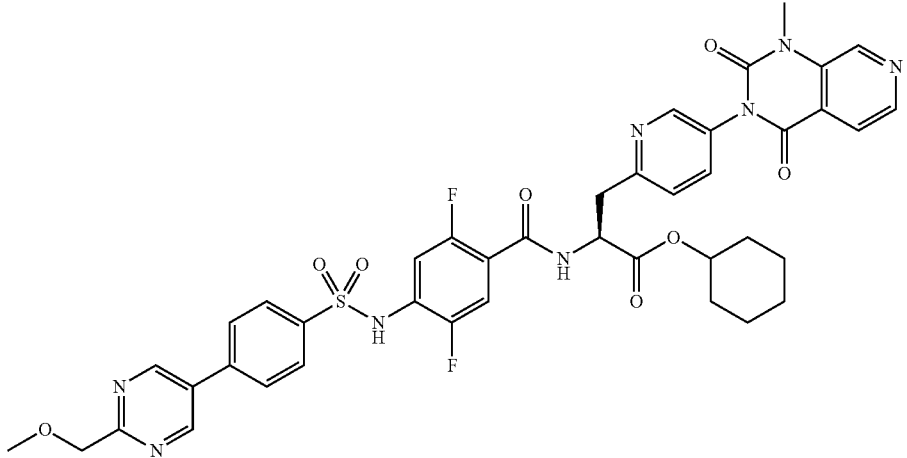

•2 TFA

¹H NMR (400 MHz, DMSO-d₆) δ 11.00 (s, 1H), 9.18 (s, 2H), 9.00 (s, 1H), 8.85 (dd, J=7.6, 3.4 Hz, 1H), 8.57 (d, J=5.0 Hz, 1H), 8.45 (d, J=2.4 Hz, 1H), 8.08-8.02 (m, 2H), 8.01-7.95 (m, 2H), 7.90 (d, J=4.9 Hz, 1H), 7.73 (dd, J=8.2, 2.5 Hz, 1H), 7.46 (d, J=8.2 Hz, 1H), 7.38 (dd, J=10.3, 6.3 Hz, 1H), 7.29 (dd, J=11.3, 6.3 Hz, 1H), 4.97-4.87 (m, 1H), 4.63 (s, 3H), 3.61 (s, 3H), 3.40 (s, 3H), 3.38-3.25 (m, 2H), 1.77-1.51 (m, 4H), 1.46-1.18 (m, 6H); MS (ESI) m/z 841.55 (M+H)⁺

Example 29

Synthesis of A-4 and B-4

(Step 1) (2S)-2-[[2,5-Difluoro-4-[[4-[4-(methoxymethyl)triazol-1-yl]phenyl]sulfonylamino]benzoyl]amino]-3-[5-(1-methyl-2,4-dioxo-pyrido[3,4-d]pyrimidin-3-yl)-2-pyridyl]propanoic acid (A-4)

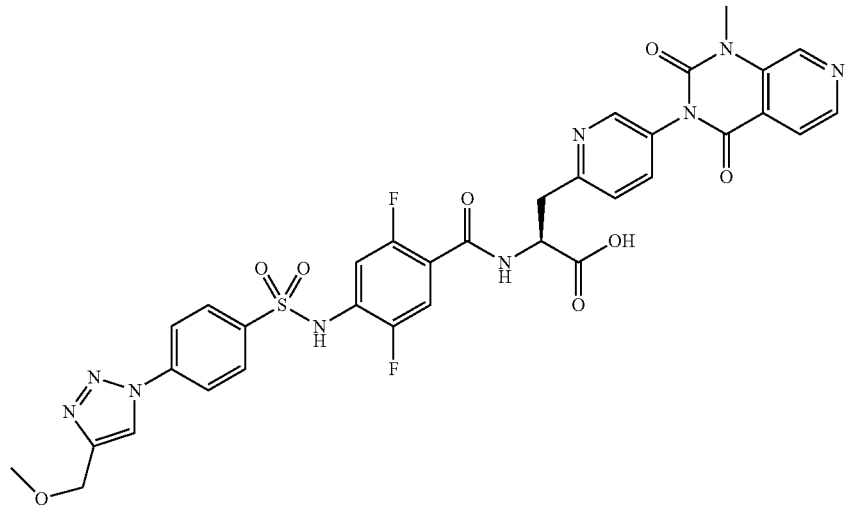

•1 TFA

¹H NMR (400 MHz, DMSO-d₆) δ 10.97 (s, 1H), 9.00 (d, J=0.8 Hz, 1H), 8.93 (s, 1H), 8.74 (dd, J=7.9, 3.7 Hz, 1H), 8.58 (d, J=5.0 Hz, 1H), 8.49-8.47 (m, 1H), 8.20-8.11 (m, 2H), 8.05-8.00 (m, 2H), 7.90 (dd, J=4.9, 0.7 Hz, 1H), 7.76 (dd, J=8.2, 2.0 Hz, 1H), 7.48 (d, J=8.2 Hz, 1H), 7.37 (dd, J=10.3, 6.4 Hz, 1H), 7.27 (dd, J=11.2, 6.2 Hz, 1H), 4.94-4.85 (m, 1H), 4.54 (s, 2H), 3.61 (s, 3H), 3.43-3.23 (m, 5H).; MS (ESI) m/z 748.46 (M+H)⁺

(Step 2) Cyclohexyl (2S)-2-[[2,5-difluoro-4-[[4-[4-(methoxymethyl)triazol-1-yl]phenyl]sulfonylamino]benzoyl]amino]-3-[5-(1-methyl-2-pyrido[3,4-d]pyrimidin-3-yl)-2-pyridyl]propanoate (B-4)

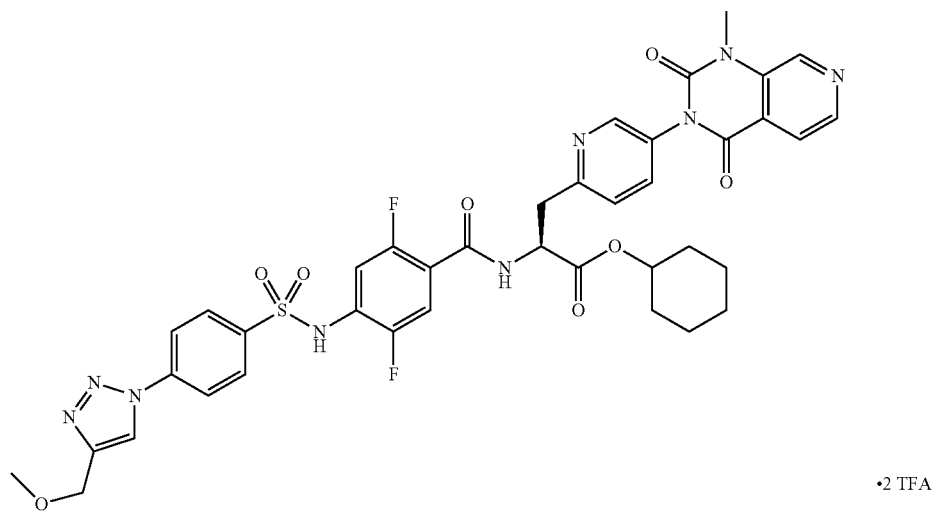 [SMILES: COCc1cn(-c2ccc(S(=O)(=O)Nc3cc(F)c(C(=O)N[C@@H](Cc4ccc(-n5c(=O)c6ccncc6n(C)c5=O)cn4)C(=O)OC4CCCCC4)cc3F)cc2)nn1]

•2 TFA

¹H NMR (400 MHz, DMSO-d₆) δ 10.98 (s, 1H), 9.00 (s, 1H), 8.93 (s, 1H), 8.86 (dd, J=7.7, 3.3 Hz, 1H), 8.57 (d, J=5.0 Hz, 1H), 8.46 (d, J=2.4 Hz, 1H), 8.21-8.12 (m, 2H), 8.07-7.99 (m, 2H), 7.90 (d, J=4.9 Hz, 1H), 7.74 (dd, J=8.2, 2.5 Hz, 1H), 7.47 (d, J=8.2 Hz, 1H), 7.37 (dd, J=10.3, 6.3 Hz, 1H), 7.28 (dd, J=11.1, 6.2 Hz, 1H), 4.97-4.87 (m, 1H), 4.74-4.63 (m, 1H), 4.55 (s, 2H), 3.61 (s, 3H), 3.38-3.28 (m, 5H), 1.79-1.52 (m, 4H), 1.50-1.08 (m, 6H); MS (ESI) m/z 830.63 (M+H)⁺

Example 30

Synthesis of A-5 and B-5

(Step 1) (2S)-2-[[4-[[4-(1-Allyl-2-oxo-pyrimidin-5-yl)phenyl]sulfonylamino]-2,5-difluoro-benzoyl]amino]-3-[5-(1-methyl-2,4-dioxo-pyrido[3,4-d]pyrimidin-3-yl)-2-pyridyl]propanoic acid (A-5)

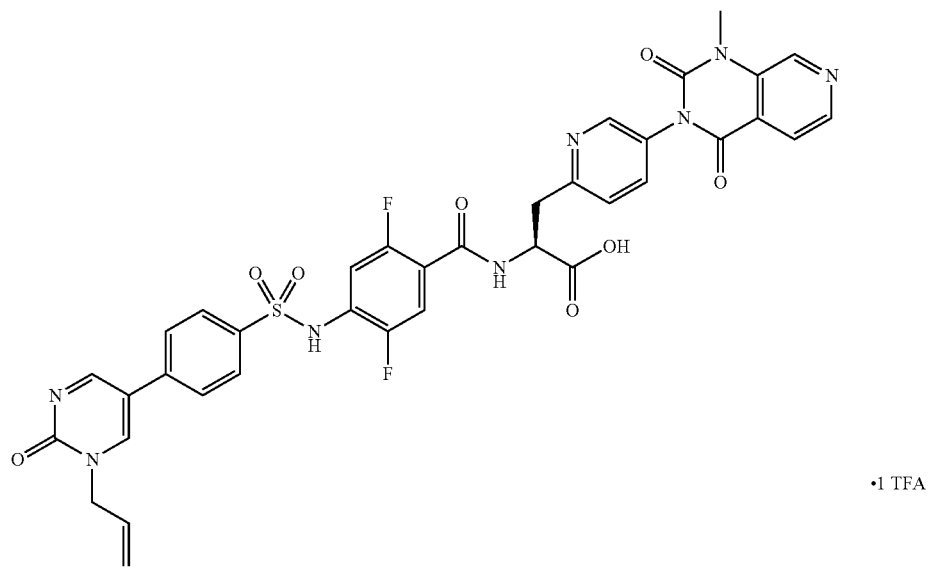 [SMILES: C=CCn1cc(-c2ccc(S(=O)(=O)Nc3cc(F)c(C(=O)N[C@@H](Cc4ccc(-n5c(=O)c6ccncc6n(C)c5=O)cn4)C(=O)O)cc3F)cc2)cnc1=O]

•1 TFA

¹H NMR (400 MHz, DMSO-d₆) δ10.91-10.88 (m, 1H), 9.05 (d, J=3.3 Hz, 1H), 9.00 (d, J=0.7 Hz, 1H), 8.78-8.72 (m, 2H), 8.58 (d, J=4.9 Hz, 1H), 8.51-8.47 (m, 1H), 7.93-7.84 (m, 5H), 7.79-7.74 (m, 1H), 7.49 (d, J=8.3 Hz, 1H), 7.37 (dd, J=10.3, 6.4 Hz, 1H), 7.26 (dd, J=11.4, 6.3 Hz, 1H), 6.07-5.95 (m, 1H), 5.27-5.19 (m, 2H), 4.93-4.86 (m, 1H), 4.58-4.53 (m, 2H), 3.62 (s, 3H), 3.42-3.26 (m, 2H).; MS (ESI) m/z 771.58 (M+H)⁺

(Step 2) Cyclohexyl (2S)-2-[[4-[[4-(1-allyl-2-oxo-pyrimidin-5-yl)phenyl]sulfonylamino]-2,5-difluoro-benzoyl]amino]-3-[5-(1-methyl-2,4-dioxo-pyrido[3,4-d]pyrimidin-3-yl)-2-pyridyl]propanoate (B-5)

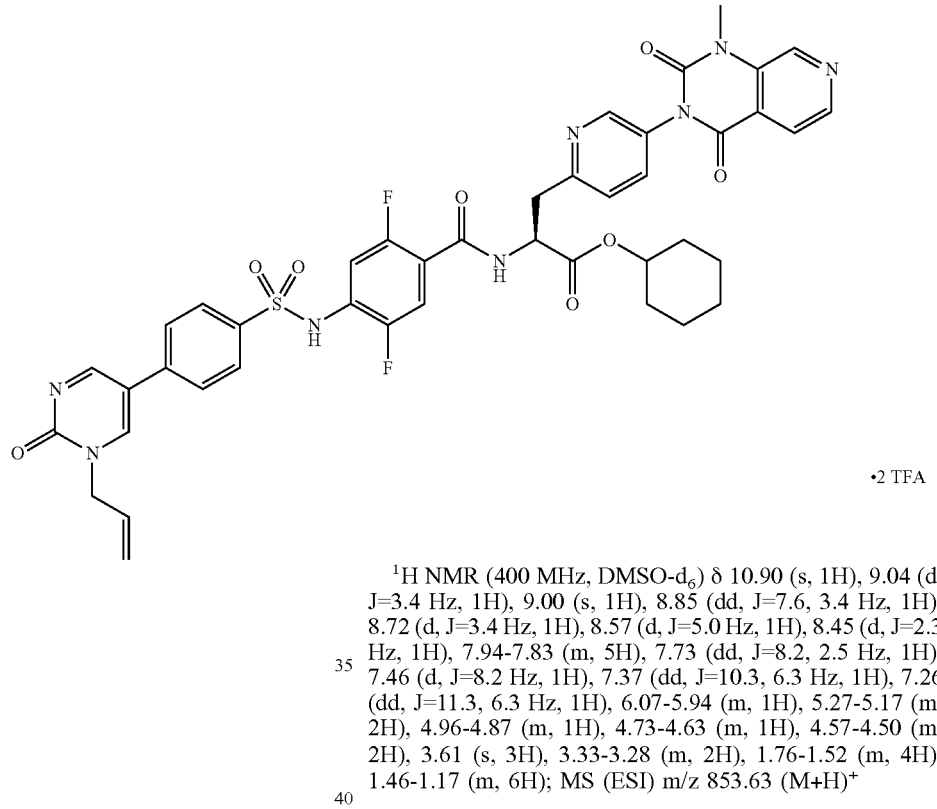

•2 TFA

¹H NMR (400 MHz, DMSO-d₆) δ 10.90 (s, 1H), 9.04 (d, J=3.4 Hz, 1H), 9.00 (s, 1H), 8.85 (dd, J=7.6, 3.4 Hz, 1H), 8.72 (d, J=3.4 Hz, 1H), 8.57 (d, J=5.0 Hz, 1H), 8.45 (d, J=2.3 Hz, 1H), 7.94-7.83 (m, 5H), 7.73 (dd, J=8.2, 2.5 Hz, 1H), 7.46 (d, J=8.2 Hz, 1H), 7.37 (dd, J=10.3, 6.3 Hz, 1H), 7.26 (dd, J=11.3, 6.3 Hz, 1H), 6.07-5.94 (m, 1H), 5.27-5.17 (m, 2H), 4.96-4.87 (m, 1H), 4.73-4.63 (m, 1H), 4.57-4.50 (m, 2H), 3.61 (s, 3H), 3.33-3.28 (m, 2H), 1.76-1.52 (m, 4H), 1.46-1.17 (m, 6H); MS (ESI) m/z 853.63 (M+H)⁺

Example 31

Synthesis of A-6 and B-6

(Step 1) (2S)-2-[[4-[[4-[2-(Ethoxymethyl)pyrimidin-5-yl]phenyl]sulfonylamino]-2,5-difluoro-benzoyl]amino]-3-[5-(1-methyl-2,4-dioxo-pyrido[3,4-d]pyrimidin-3-yl)-2-pyridyl]propanoic acid (A-6)

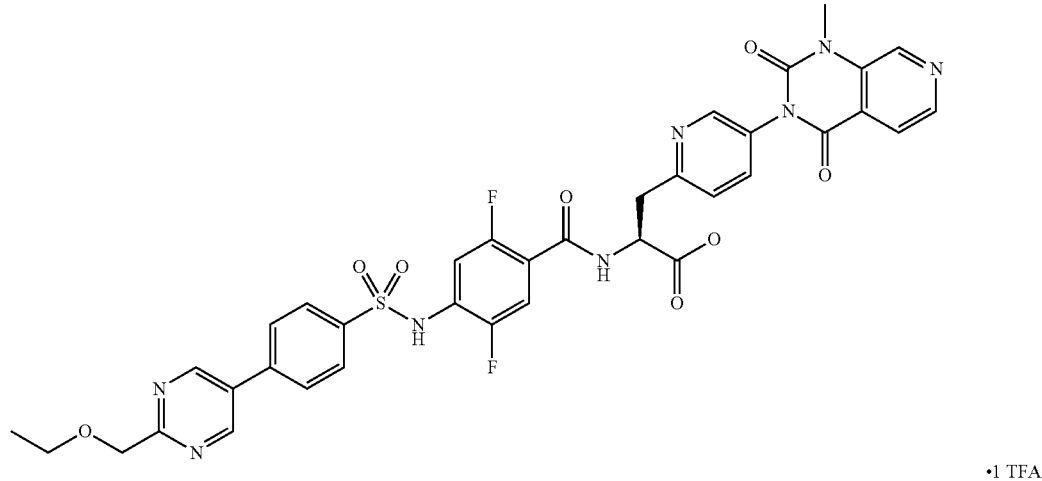 [SMILES: CCOCc1ncc(-c2ccc(S(=O)(=O)Nc3cc(F)c(C(=O)N[C@@H](Cc4ccc(-n5c(=O)c6ccncc6n(C)c5=O)cn4)C(=O)O)cc3F)cc2)cn1]

•1 TFA $^1$H NMR (400 MHz, DMSO-d$_6$) δ 10.99 (s, 1H), 9.17 (s, 2H), 9.00 (s, 1H), 8.74 (dd, J=7.9, 3.8 Hz, 1H), 8.58 (d, J=5.0 Hz, 1H), 8.48 (dd, J=2.6, 1.1 Hz, 1H), 8.08-8.02 (m, 2H), 8.00-7.95 (m, 2H), 7.90 (dd, J=5.0, 0.7 Hz, 1H), 7.76 (ddd, J=9.0, 3.3, 1.9 Hz, 1H), 7.48 (d, J=8.2 Hz, 1H), 7.38 (dd, J=10.4, 6.4 Hz, 1H), 7.29 (dd, J=11.3, 6.2 Hz, 1H), 4.89 (td, J=8.2, 4.9 Hz, 1H), 4.66 (s, 2H), 3.66-3.55 (m, 5H), 3.43-3.25 (m, 2H), 1.17 (t, J=7.0 Hz, 3H).; MS (ESI) m/z 773.58 (M+H)$^+$ (Step 2) Cyclohexyl (2S)-2-[[4-[[4-[2-(ethoxymethyl)pyrimidin-5-yl]phenyl]sulfonylamino]-2,5-difluoro-benzoyl]amino]-3-[5-(1-methyl-2,4-dioxo-pyrido[3,4-d]pyrimidin-3-yl)-2-pyridyl]propanoate (B-6)

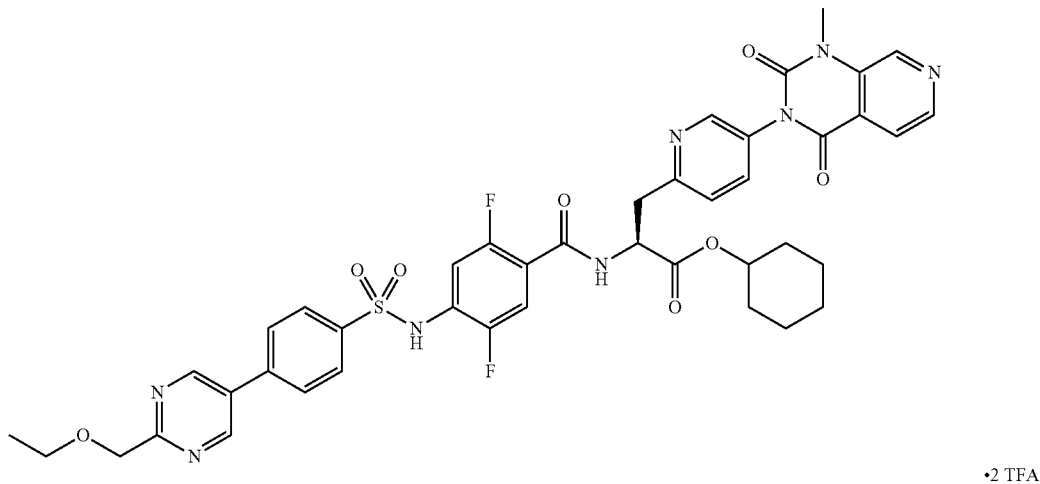 [SMILES: CCOCc1ncc(-c2ccc(S(=O)(=O)Nc3cc(F)c(C(=O)N[C@@H](Cc4ccc(-n5c(=O)c6ccncc6n(C)c5=O)cn4)C(=O)OC4CCCCC4)cc3F)cc2)cn1]

·2 TFA $^1$H NMR (400 MHz, DMSO-d$_6$) δ 11.00 (s, 1H), 9.18 (s, 2H), 9.00 (s, 1H), 8.86 (dd, J=7.6, 3.4 Hz, 1H), 8.57 (d, J=5.0 Hz, 1H), 8.46 (d, J=2.4 Hz, 1H), 8.09-8.02 (m, 2H), 8.00-7.96 (m, 2H), 7.91 (dd, J=5.0, 0.7 Hz, 1H), 7.79-7.71 (m, 1H), 7.47 (d, J=8.3 Hz, 1H), 7.38 (dd, J=10.3, 6.3 Hz, 1H), 7.29 (dd, J=11.3, 6.3 Hz, 1H), 4.98-4.87 (m, 1H), 4.66 (s, 3H), 3.65-3.57 (m, 5H), 3.39-3.24 (m, 2H), 1.80-1.52 (m, 4H), 1.50-1.21 (m, 6H), 1.17 (t, J=7.0 Hz, 3H); MS (ESI) m/z 855.67 (M+H)$^+$

Example 32

Synthesis of A-7 and B-7

(Step 1) (2S)-2-[[2,5-Difluoro-4-[[4-[2-[(isopropylamino)methyl]pyrimidin-5-yl]phenyl]sulfonylamino]benzoyl]amino]-3-[5-(1-methyl-2,4-dioxo-pyrido[3,4-d]pyrimidin-3-yl)-2-pyridyl]propanoic acid (A-7)

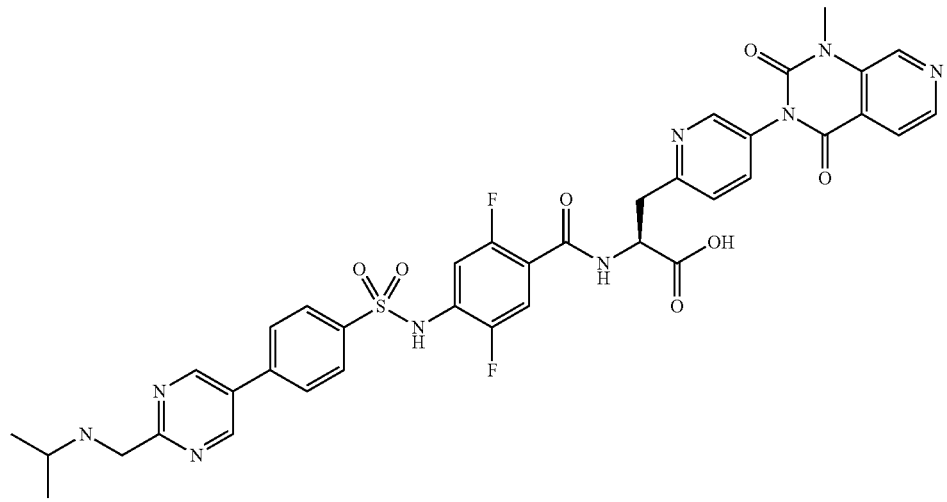

·2 TFA $^1$H NMR (400 MHz, DMSO-d$_6$) δ 11.03 (s, 1H), 9.32 (s, 2H), 9.14 (s, 2H), 9.00 (s, 1H), 8.75 (dd, J=7.8, 4.0 Hz, 1H), 8.58 (d, J=5.0 Hz, 1H), 8.46 (d, J=2.5 Hz, 1H), 8.13-8.08 (m, 2H), 8.02-7.99 (m, 2H), 7.90 (d, J=5.0 Hz, 1H), 7.73 (dd, J=8.2, 2.5 Hz, 1H), 7.45 (d, J=8.2 Hz, 1H), 7.39 (dd, J=10.3, 6.4 Hz, 1H), 7.31 (dd, J=11.4, 6.3 Hz, 1H), 4.89 (td, J=8.1, 5.1 Hz, 1H), 4.54 (t, J=6.2 Hz, 2H), 3.61 (s, 3H), 3.47 (dq, J=11.6, 5.8, 5.4 Hz, 1H), 3.40-3.24 (m, 2H), 1.32 (d, J=6.5 Hz, 6H); MS (ESI) m/z 786.74 (M+H)$^+$ (Step 2) Cyclohexyl (2S)-2-[[2,5-difluoro-4-[[4-[2-[(isopropylamino)methyl]pyrimidin-5-yl]phenyl]sulfonylamino]benzoyl]amino]-3-[5-(1-methyl-2,4-dioxo-pyrido[3,4-d]pyrimidin-3-yl)-2-pyridyl]propanoate (B-7)

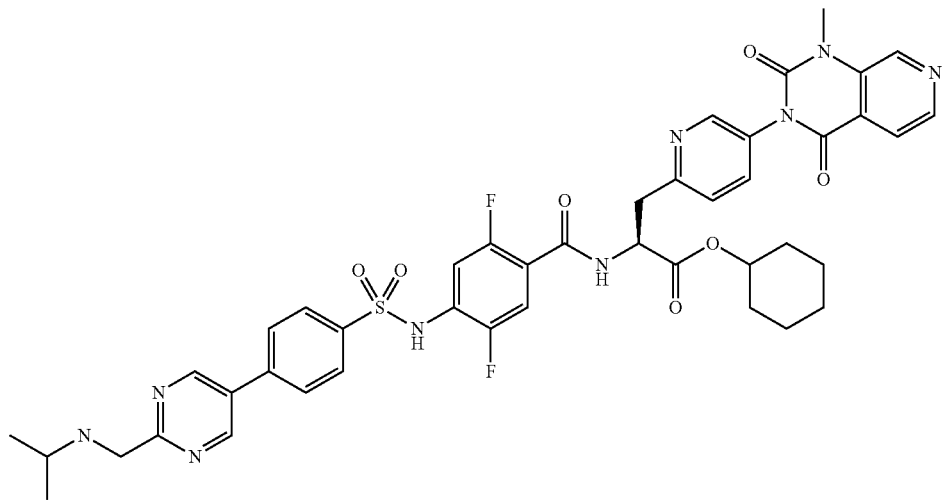

·3 TFA

¹H NMR (400 MHz, DMSO-d₆) δ 11.04 (s, 1H), 9.32 (s, 2H), 9.12 (d, J=6.9 Hz, 2H), 9.00 (d, J=0.7 Hz, 1H), 8.87 (dd, J=7.6, 3.5 Hz, 1H), 8.58 (d, J=5.0 Hz, 1H), 8.45 (dd, J=2.4, 0.7 Hz, 1H), 8.14-8.07 (m, 2H), 8.03-7.99 (m, 2H), 7.91 (dd, J=5.0, 0.7 Hz, 1H), 7.73 (dd, J=8.2, 2.5 Hz, 1H), 7.49-7.44 (m, 1H), 7.40 (dd, J=10.3, 6.4 Hz, 1H), 7.32 (dd, J=11.3, 6.3 Hz, 1H), 4.96-4.88 (m, 1H), 4.72-4.63 (m, 1H), 4.57-4.51 (m, 2H), 3.61 (s, 3H), 3.53-3.42 (m, 1H), 3.38-3.24 (m, 2H), 1.75-1.52 (m, 4H), 1.46-1.21 (m, 12H); MS (ESI) m/z 868.71 (M+H)⁺

Example 33

Synthesis of A-8 and B-8

(Step 1) (2S)-2-[[4-[[4-[2-(2-Dimethylaminoethyl)pyrimidin-5-yl]phenyl]sulfonylamino]-2,5-difluoro-benzoyl]amino]-3-[5-(1-methyl-2,4-dioxo-pyrido[3,4-d]pyrimidin-3-yl)-2-pyridyl]propanoic acid (A-8)

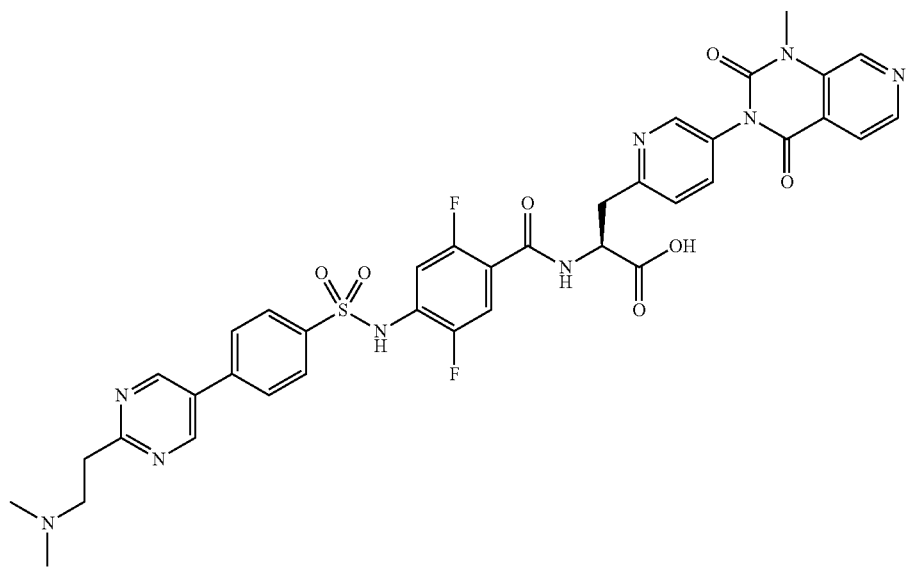

·2 TFA

¹H NMR (400 MHz, DMSO-d₆) δ 11.00 (s, 1H), 9.44 (s, 1H), 9.18 (s, 2H), 9.00 (s, 1H), 8.74 (dd, J=7.8, 3.9 Hz, 1H), 8.58 (d, J=5.0 Hz, 1H), 8.45 (dd, J=2.4, 0.7 Hz, 1H), 8.07-8.02 (m, 2H), 8.00-7.95 (m, 2H), 7.90 (dd, J=4.9, 0.8 Hz, 1H), 7.72 (dd, J=8.2, 2.5 Hz, 1H), 7.45 (d, J=8.2 Hz, 1H), 7.39 (dd, J=10.4, 6.4 Hz, 1H), 7.29 (dd, J=11.4, 6.3 Hz, 1H), 4.92-4.86 (m, 1H), 3.61 (s, 5H), 3.40 (dd, J=8.2, 6.9 Hz, 2H), 3.38-3.24 (m, 2H), 2.88 (d, J=4.4 Hz, 6H); MS (ESI) m/z 786.75 (M+H)⁺

(Step 2) Cyclohexyl (2S)-2-[[4-[[4-[2-(2-dimethyl-aminoethyl)pyrimidin-5-yl]phenyl]sulfonylamino]-2,5-difluoro-benzoyl]amino]-3-[5-(1-methyl-2,4-dioxo-pyrido[3,4-d]pyrimidin-3-yl)-2-pyridyl]propanoate (B-8)

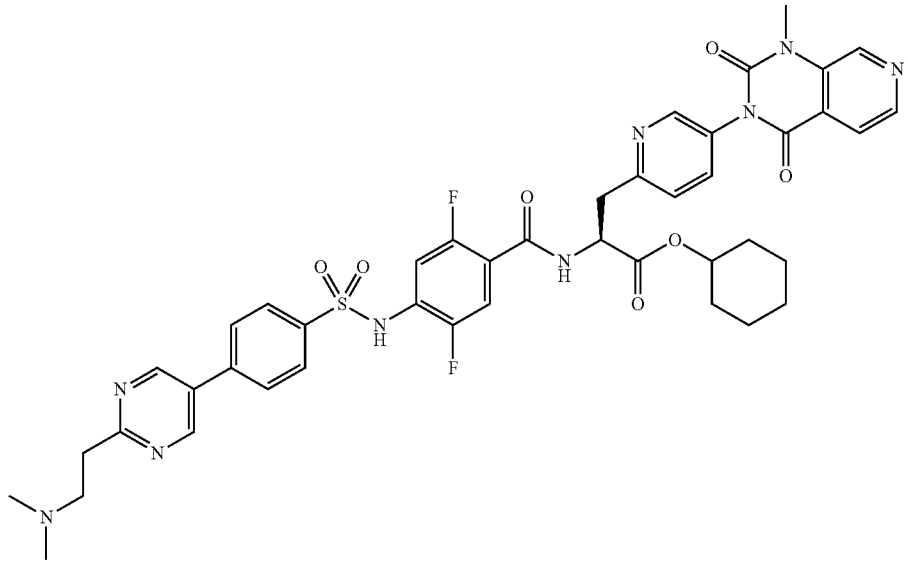

·3 TFA $^1$H NMR (400 MHz, DMSO-d$_6$) δ 11.01 (s, 1H), 9.31 (s, 1H), 9.18 (s, 2H), 9.00 (s, 1H), 8.87 (dd, J=7.6, 3.4 Hz, 1H), 8.58 (d, J=4.9 Hz, 1H), 8.47 (d, J=2.4 Hz, 1H), 8.08-8.02 (m, 2H), 8.01-7.96 (m, 2H), 7.91 (dd, J=5.0, 0.8 Hz, 1H), 7.76 (dd, J=8.2, 2.5 Hz, 1H), 7.48 (d, J=8.2 Hz, 1H), 7.39 (dd, J=10.3, 6.4 Hz, 1H), 7.30 (dd, J=11.3, 6.3 Hz, 1H), 4.98-4.86 (m, 1H), 4.73-4.64 (m, 1H), 3.65-3.57 (m, 5H), 3.47-3.25 (m, 4H), 2.88 (d, J=4.9 Hz, 6H), 1.76-1.52 (m, 4H), 1.48-1.16 (m, 6H); MS (ESI) m/z 868.71 (M+H)$^+$

Example 34

Synthesis of A-9 and B-9

(Step 1) (2S)-2-[[2,5-Difluoro-4-[[5-(2-tetrahydropyran-4-yl-4-pyridyl)-2-pyridyl]sulfonylamino]benzoyl]amino]-3-[5-(1-methyl-2,4-dioxo-pyrido[3,4-d]pyrimidin-3-yl)-2-pyridyl]propanoic acid (A-9)

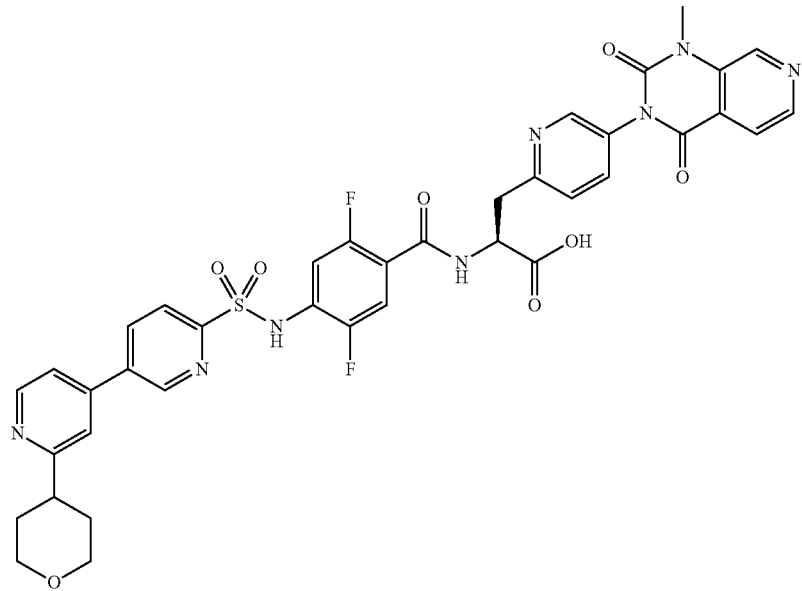

·2 TFA

¹H NMR (400 MHz, DMSO-d₆) δ 11.15 (s, 1H), 9.25 (d, J=2.2 Hz, 1H), 9.00 (s, 1H), 8.75 (dd, J=7.2, 3.9 Hz, 2H), 8.63-8.55 (m, 2H), 8.48 (d, J=2.4 Hz, 1H), 8.18 (d, J=8.3 Hz, 1H), 8.07-7.87 (m, 3H), 7.78-7.74 (m, 1H), 7.52-7.37 (m, 3H), 4.95-4.86 (m, 1H), 4.02-3.95 (m, 2H), 3.61 (s, 3H), 3.51-3.42 (m, 2H), 3.42-3.26 (m, 2H), 3.17-3.08 (m, 1H), 1.95-1.80 (m, 4H); MS (ESI) m/z 799.70 (M+H)⁺

(Step 2) Cyclohexyl (2S)-2-[[2,5-difluoro-4-[[5-(2-tetrahydropyran-4-yl-4-pyridyl)-2-pyridyl]sulfonylamino]benzoyl]amino]-3-[5-(1-methyl-2,4-dioxo-pyrido[3,4-d]pyrimidin-3-yl)-2-pyridyl]propanoate (B-9)

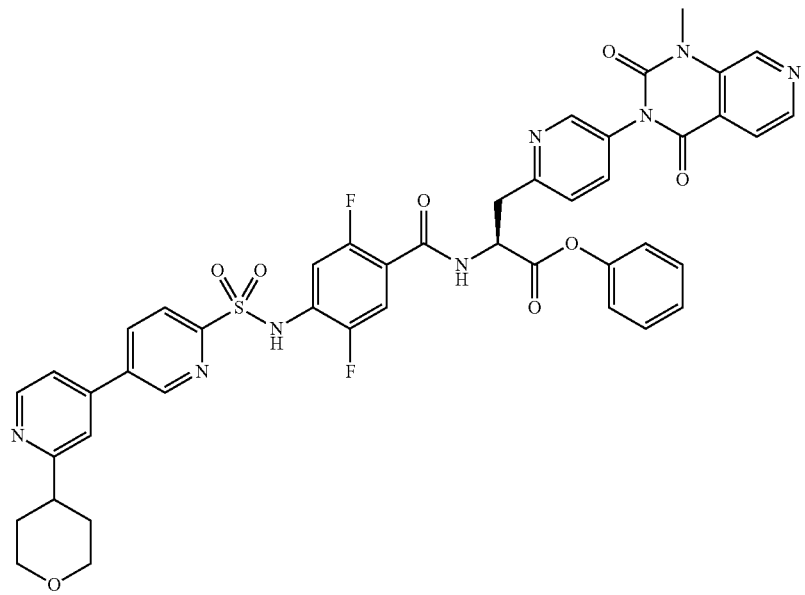

·3 TFA

¹H NMR (400 MHz, DMSO-d₆) δ 11.15 (s, 1H), 9.24 (dd, J=2.4, 0.8 Hz, 1H), 9.00 (s, 1H), 8.87 (dd, J=7.6, 3.5 Hz, 1H), 8.74 (d, J=5.4 Hz, 1H), 8.63-8.55 (m, 2H), 8.47 (dd, J=2.4, 0.7 Hz, 1H), 8.17 (dd, J=8.3, 0.8 Hz, 1H), 7.97 (s, 1H), 7.89 (ddd, J=7.1, 5.2, 1.2 Hz, 2H), 7.75 (dd, J=8.2, 2.5 Hz, 1H), 7.51-7.37 (m, 3H), 4.93 (td, J=7.6, 5.9 Hz, 1H), 4.68 (td, J=8.2, 3.9 Hz, 1H), 3.98 (ddd, J=11.4, 4.2, 2.0 Hz, 2H), 3.61 (s, 3H), 3.46 (td, J=11.4, 2.8 Hz, 2H), 3.40-3.26 (m, 2H), 3.16-3.05 (m, 1H), 1.97-1.78 (m, 4H), 1.76-1.53 (m, 4H), 1.33 (dddt, J=34.0, 24.1, 17.5, 9.8 Hz, 6H): MS (ESI) m/z 881.71 (M+H)⁺

Example 35

Synthesis of A-10 and B-10

(Step 1) (2S)-2-[[2,5-Difluoro-4-[[4-[2-(isopropoxymethyl)pyrimidin-5-yl]phenyl]sulfonylamino]benzoyl]amino]-3-[5-(1-methyl-2,4-dioxopyrido[3,4-d]pyrimidin-3-yl)-2-pyridyl]propanoic acid (A-10)

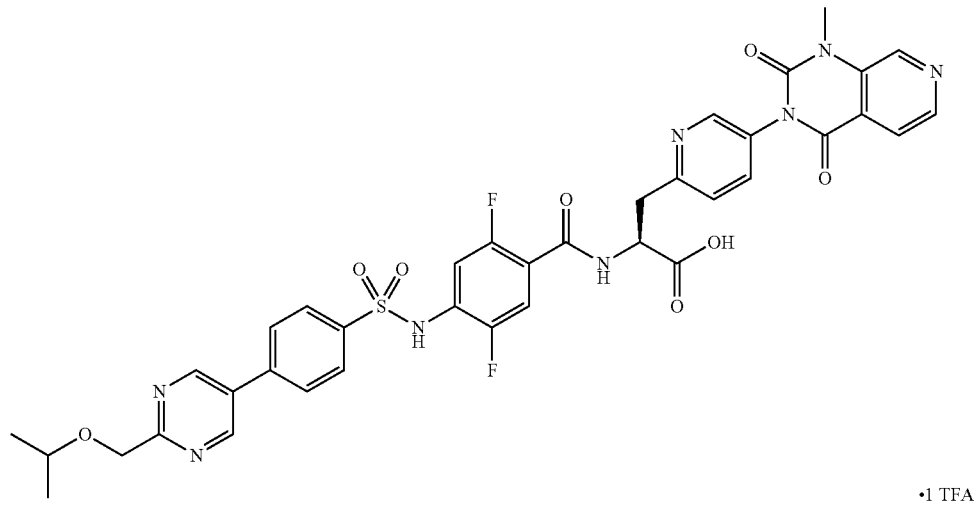 [SMILES: CC(C)OCc1ncc(-c2ccc(S(=O)(=O)Nc3cc(F)c(C(=O)N[C@@H](Cc4ccc(-n5c(=O)c6ccncc6n(C)c5=O)cn4)C(=O)O)cc3F)cc2)cn1]

·1 TFA $^1$H NMR (400 MHz, DMSO-d$_6$) δ 11.00 (s, 1H), 9.17 (s, 2H), 9.00 (d, J=0.8 Hz, 1H), 8.74 (dd, J=7.8, 3.8 Hz, 1H), 8.58 (d, J=4.9 Hz, 1H), 8.49 (dd, J=2.4, 0.7 Hz, 1H), 8.07-8.03 (m, 2H), 8.00-7.96 (m, 2H), 7.91 (dd, J=4.9, 0.7 Hz, 1H), 7.78 (dd, J=8.2, 2.5 Hz, 1H), 7.49 (d, J=8.2 Hz, 1H), 7.39 (dd, J=10.4, 6.4 Hz, 1H), 7.29 (dd, J=11.4, 6.3 Hz, 1H), 4.90 (td, J=8.3, 4.9 Hz, 1H), 4.65 (s, 2H), 3.83-3.72 (m, 1H), 3.61 (s, 3H), 3.43-3.25 (m, 2H), 1.16 (d, J=6.1 Hz, 6H); MS (ESI) m/z 787.62 (M+M$^+$ (Step 2) Cyclohexyl (2S)-2-[[2,5-difluoro-4-[[4-[2-(isopropoxymethyl)pyrimidin-5-yl]phenyl]sulfonylamino]benzoyl]amino]-3-[5-(1-methyl-2,4-dioxopyrido[3,4-d]pyrimidin-3-yl)-2-pyridyl]propanoate (B-10)

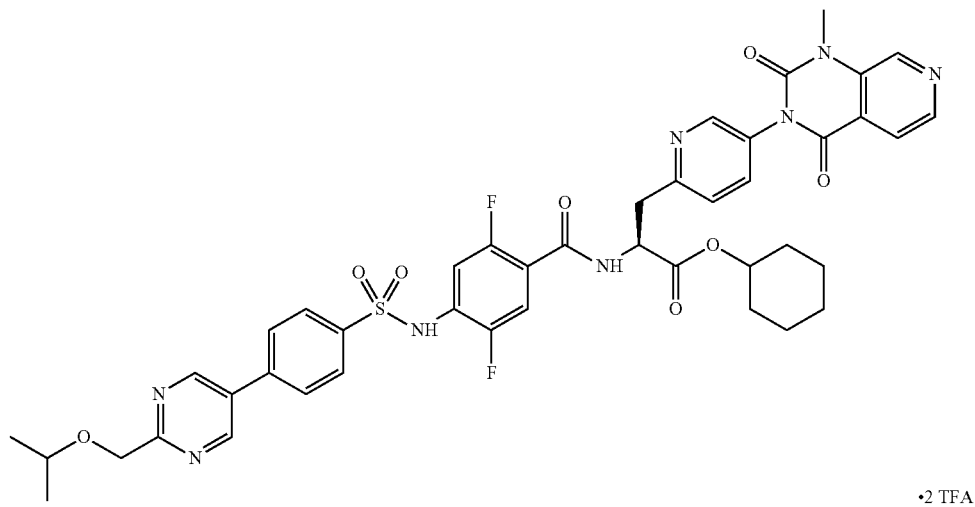 [SMILES: CC(C)OCc1ncc(-c2ccc(S(=O)(=O)Nc3cc(F)c(C(=O)N[C@@H](Cc4ccc(-n5c(=O)c6ccncc6n(C)c5=O)cn4)C(=O)OC4CCCCC4)cc3F)cc2)cn1]

·2 TFA

¹H NMR (400 MHz, DMSO-d₆) δ 11.00 (s, 1H), 9.17 (s, 2H), 9.00 (s, 1H), 8.86 (dd, J=7.6, 3.4 Hz, 1H), 8.57 (d, J=4.9 Hz, 1H), 8.47 (dd, J=2.5, 0.7 Hz, 1H), 8.08-8.02 (m, 2H), 8.01-7.94 (m, 2H), 7.91 (dd, J=5.0, 0.8 Hz, 1H), 7.75 (dd, J=8.2, 2.5 Hz, 1H), 7.47 (d, J=8.3 Hz, 1H), 7.38 (dd, J=10.3, 6.3 Hz, 1H), 7.29 (dd, J=11.3, 6.3 Hz, 1H), 4.97-4.88 (m, 1H), 4.72-4.62 (m, 3H), 3.77 (hept, J=6.1 Hz, 1H), 3.61 (s, 3H), 3.39-3.25 (m, 2H), 1.76-1.53 (m, 4H), 1.48-1.19 (m, 6H), 1.16 (d, J=6.1 Hz, 6H); MS (ESI) m/z 869.67 (M+H)⁺

Example 36

Synthesis of A-11

(Step 1) (2S)-2-[[4-[[4-[2-(Azetidin-1-yl)pyrimidin-5-yl]phenyl]sulfonylamino]-2,5-difluoro-benzoyl]amino]-3-[4-(1,3,4-trimethyl-2,6-dioxo-pyrimidin-5-yl)phenyl]propanoic acid (A-11)

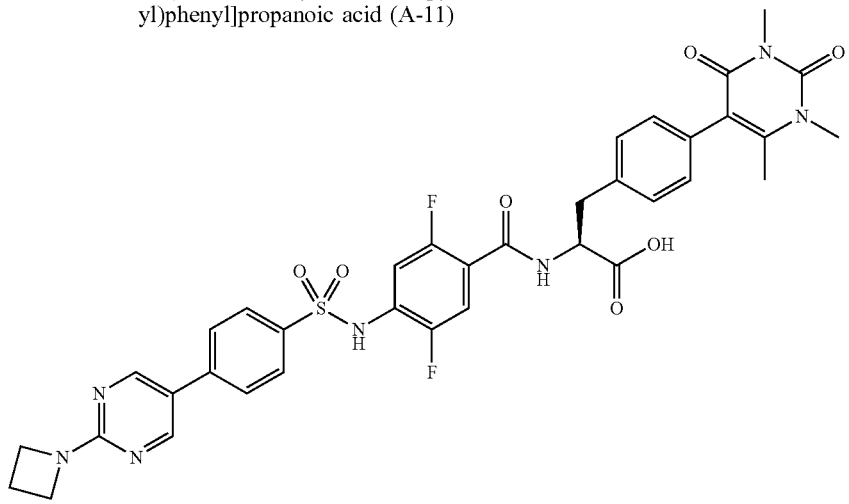

¹H NMR (400 MHz, DMSO-d₆) δ 10.86 (s, 1H), 8.75 (s, 2H), 8.52 (dd, J=8.0, 2.7 Hz, 1H), 7.87 (s, 4H), 7.30-7.20 (m, 4H), 7.10-7.05 (m, 2H), 4.60 (ddd, J=9.9, 7.9, 4.7 Hz, 1H), 4.14-4.06 (m, 4H), 3.38 (s, 3H), 3.20 (s, 4H), 3.00 (dd, J=13.9, 9.9 Hz, 1H), 2.40-2.29 (m, 2H), 2.04 (s, 3H); MS (ESI) m/z 746.66 (M+H)⁺

Example 37

Synthesis of A-12

(Step 1) (2S)-2-[[2,5-Difluoro-4-[[5-(4-methyltriazol-1-yl)-2-pyridyl]sulfonylamino]benzoyl]amino]-3-[4-(1,3,4-trimethyl-2,6-dioxo-pyrimidin-5-yl)phenyl]propanoic acid (A-12)

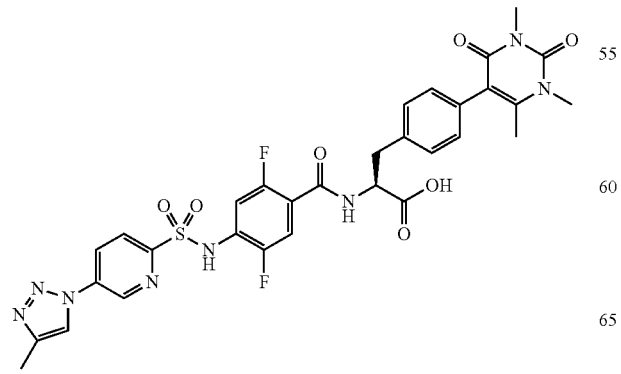

¹H NMR (400 MHz, DMSO-d₆) δ 11.10 (s, 1H), 9.28 (dd, J=2.5, 0.7 Hz, 1H), 8.75 (d, J=0.9 Hz, 1H), 8.59 (dd, J=8.6, 2.5 Hz, 1H), 8.55 (dd, J=8.0, 2.6 Hz, 1H), 8.22 (dd, J=8.6, 0.7 Hz, 1H), 7.36 (dd, J=11.1, 6.3 Hz, 1H), 7.31-7.23 (m, 3H), 7.11-7.05 (m, 2H), 4.62 (ddd, J=9.9, 7.9, 4.7 Hz, 1H), 3.39 (s, 3H), 3.20 (s, 4H), 3.01 (dd, J=13.9, 9.8 Hz, 1H), 2.36 (d, J=0.9 Hz, 3H), 2.06 (s, 3H); MS (ESI) m/z 695.56 (M+H)⁺

Example 38

Synthesis of A-13

Step 1) (2S)-2-[[2,5-Difluoro-4-(2-furylsulfonylamino)benzoyl]amino]-3-[4-(1,3,4-trimethyl-2,6-dioxo-pyrimidin-5-yl)phenyl]propanoic acid (A-13)

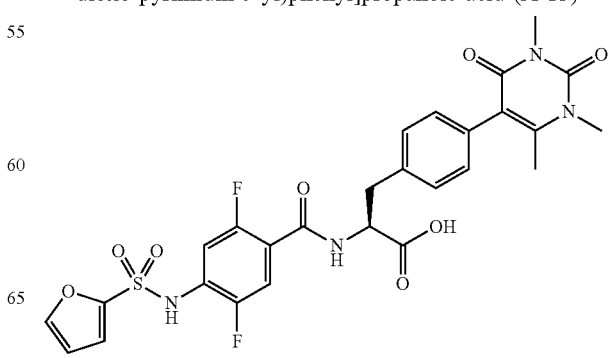

$^1$H NMR (400 MHz, DMSO-d$_6$) δ 11.10 (s, 1H), 8.61 (dd, J=8.0, 2.4 Hz, 1H), 8.02 (dd, J=1.8, 0.9 Hz, 1H), 7.31-7.25 (m, 3H), 7.24-7.16 (m, 2H), 7.11-7.07 (m, 2H), 6.68 (dd, J=3.6, 1.8 Hz, 1H), 4.62 (ddd, J=9.9, 7.9, 4.7 Hz, 1H), 3.40 (s, 3H), 3.21 (s, 4H), 3.02 (dd, J=13.9, 9.9 Hz, 1H), 2.07 (s, 3H); MS (ESI) m/z 603.49 (M+H)$^+$ Example 39

Synthesis of A-14

(Step 1) (2S)-2-[[2,5-Difluoro-4-[[4-[2-(methoxymethyl)pyrimidin-5-yl]phenyl]sulfonylamino]benzoyl]amino]-3-[4-[1-methyl-6-(methylaminomethyl)-2,4-dioxo-quinazolin-3-yl]phenyl]propanoic acid (A-14)

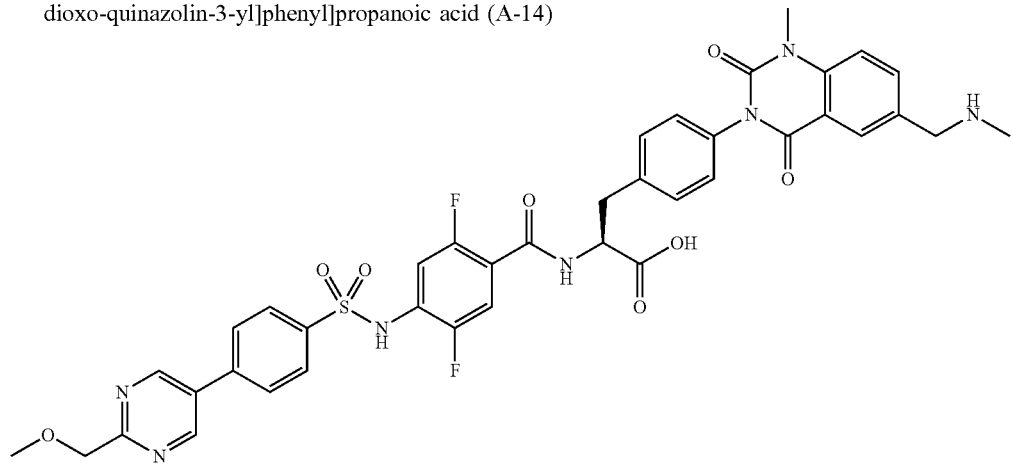

•1 TFA

MS (ESI) m/z 800.99 (M+H)$^+$

Example 40

Synthesis of A-15

(Step 1) (2S)-2-[[2,5-Difluoro-4-[[4-[2-(isopropoxymethyl)pyrimidin-5-yl]phenyl]sulfonylamino]benzoyl]amino]-3-[4-(1,3,4-trimethyl-2,6-dioxo-pyrimidin-5-yl)phenyl]propanoic acid (A-15)

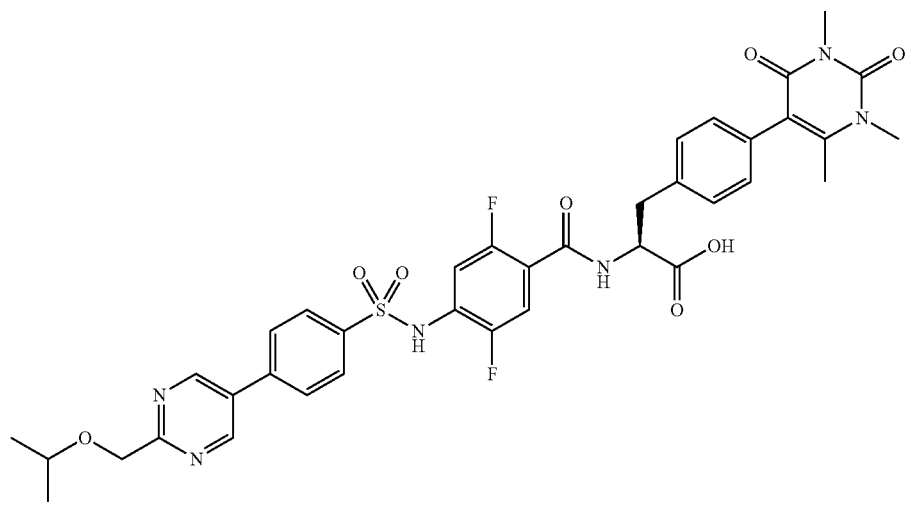 [SMILES: Cc1c(-c2ccc(C[C@H](NC(=O)c3cc(F)c(NS(=O)(=O)c4ccc(-c5cnc(COC(C)C)nc5)cc4)cc3F)C(=O)O)cc2)c(=O)n(C)c(=O)n1C]

$^1$H NMR (400 MHz, DMSO-d$_6$) δ 10.96 (s, 1H), 9.17 (s, 2H), 8.54 (dd, J=7.9, 2.6 Hz, 1H), 8.07-8.03 (m, 2H), 7.98-7.94 (m, 2H), 7.30-7.22 (m, 4H), 7.09-7.05 (m, 2H), 4.68-4.57 (m, 3H), 3.78 (hept, J=6.1 Hz, 1H), 3.38 (s, 3H), 3.20 (s, 4H), 3.00 (dd, J=13.9, 9.9 Hz, 1H), 2.05 (s, 3H), 1.16 (d, J=6.1 Hz, 6H); MS (ESI) m/z 763.58 (M+H)$^+$ Example 41

Synthesis of A-16

(Step 1) (2S)-2-[[2,5-Difluoro-4-[[4-[2-(iso-propoxymethyl)pyrimidin-5-yl]phenyl]sulfo-nylamino]benzoyl]amino]-3-[5-(6-methoxy-1-methyl-2,4-dioxo-pyrido[3,4-d]pyrimidin-3-yl)-2-pyridyl]propanoic acid (A-16)

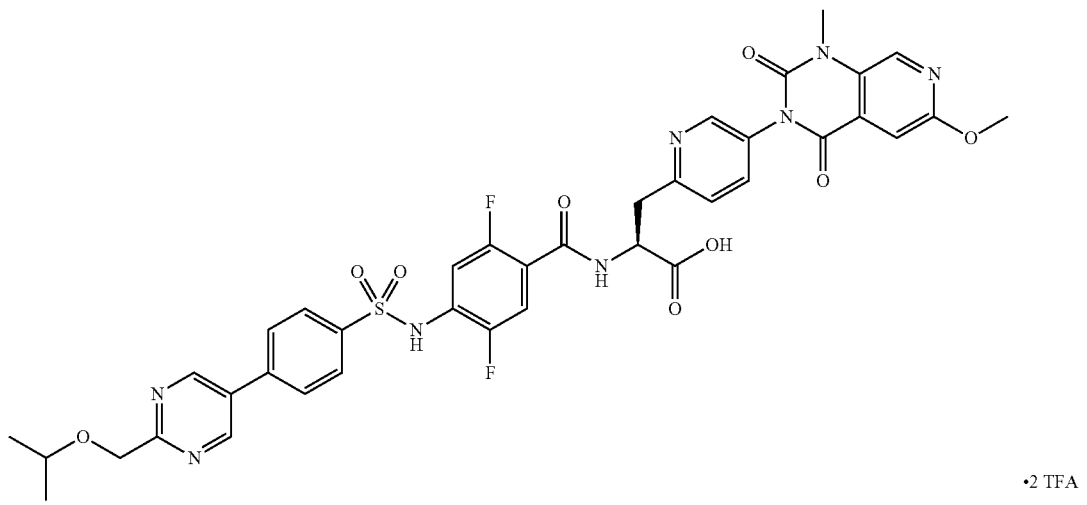 [SMILES: COc1cc2c(=O)n(-c3ccc(C[C@H](NC(=O)c4cc(F)c(NS(=O)(=O)c5ccc(-c6cnc(COC(C)C)nc6)cc5)cc4F)C(=O)O)nc3)c(=O)n(C)c2cn1]

·2 TFA $^1$H NMR (400 MHz, DMSO-d$_6$) δ 10.98 (s, 1H), 9.16 (s, 2H), 8.73 (dd, J=7.9, 3.8 Hz, 1H), 8.56 (d, J=0.8 Hz, 1H), 8.46 (dd, J=2.4, 0.7 Hz, 1H), 8.06-8.01 (m, 2H), 7.99-7.95 (m, 2H), 7.73 (dd, J=8.2, 2.5 Hz, 1H), 7.45 (d, J=8.3 Hz, 1H), 7.38 (dd, J=10.4, 6.4 Hz, 1H), 7.32-7.25 (m, 2H), 4.88 (td, J=8.2, 5.0 Hz, 1H), 4.65 (s, 2H), 3.93 (s, 3H), 3.76 (dq, J=12.1, 6.1 Hz, 1H), 3.55 (s, 3H), 3.40-3.24 (m, 2H), 1.15 (d, J=6.1 Hz, 6H); MS (ESI) m/z 817.59 (M+H)$^+$

Example 42

Synthesis of A-17

(Step 1) (2S)-2-[[2,5-Difluoro-4-[[4-[2-(isopropoxymethyl)pyrimidin-5-yl]phenyl]sulfonylamino]benzoyl]amino]-3-[4-(3-methyl-2,6-dioxopyrimidin-1-yl)phenyl]propanoic acid (A-17)

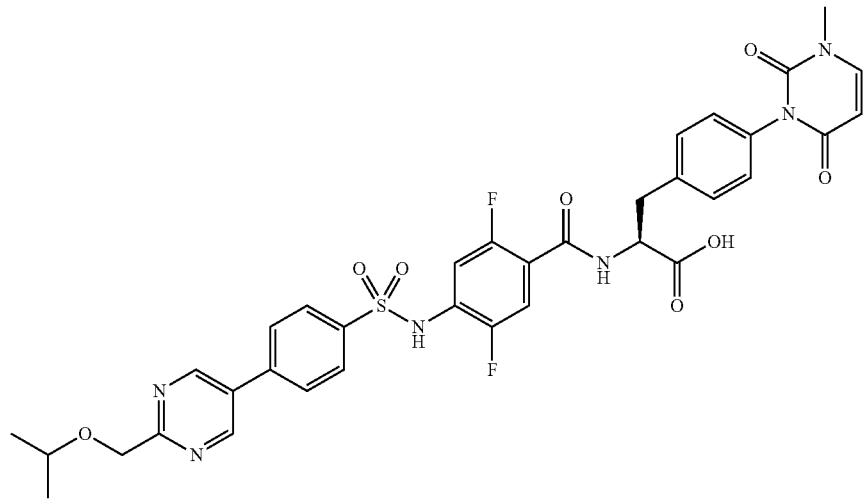 [SMILES: CC(C)OCc1ncc(-c2ccc(S(=O)(=O)Nc3cc(F)c(C(=O)N[C@@H](Cc4ccc(-n5c(=O)ccn(C)c5=O)cc4)C(=O)O)cc3F)cc2)cn1]

$^1$H NMR (400 MHz, DMSO-d$_6$) δ 10.96 (s, 1H), 9.17 (s, 2H), 8.59 (dd, J=7.8, 2.6 Hz, 1H), 8.07-8.02 (m, 2H), 7.99-7.95 (m, 2H), 7.74 (d, J=7.9 Hz, 1H), 7.35-7.23 (m, 4H), 7.12-7.06 (m, 2H), 5.73 (dd, J=7.9, 2.2 Hz, 1H), 4.66 (s, 2H), 4.63-4.55 (m, 1H), 3.83-3.72 (m, 1H), 3.29 (s, 3H), 3.19 (dd, J=14.1, 4.6 Hz, 1H), 3.04 (dd, J=14.1, 9.8 Hz, 1H), 1.16 (d, J=6.1 Hz, 6H); MS (ESI) m/z 735.50 (M+H)$^+$

Example 43

Synthesis of A-18

(Step 1) (2S)-2-[[2,5-Difluoro-4-[[4-[2-(isopropoxymethyl)pyrimidin-5-yl]phenyl]sulfonylamino]benzoyl]amino]-3-[5-(1-methyl-2,4-dioxopyrimido[4,5-d]pyrimidin-3-yl)-2-pyridyl]propanoic acid (A-18)

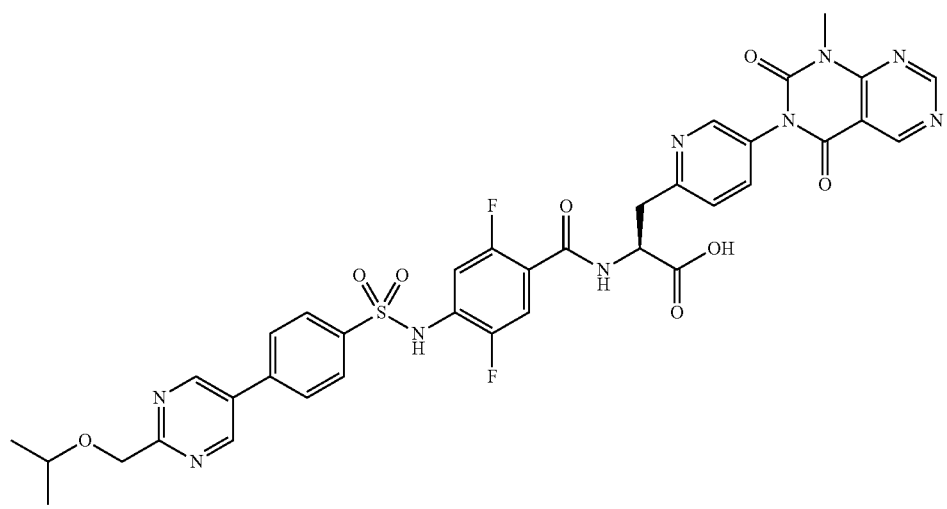

·2 TFA

¹H NMR (400 MHz, DMSO-d₆) δ 10.99 (s, 1H), 9.28 (s, 1H), 9.19 (s, 1H), 9.16 (s, 2H), 8.73 (dd, J=7.9, 3.7 Hz, 1H), 8.46 (d, J=2.5 Hz, 1H), 8.07-8.02 (m, 2H), 7.99-7.95 (m, 2H), 7.73 (dd, J=8.2, 2.5 Hz, 1H), 7.47 (d, J=8.2 Hz, 1H), 7.37 (dd, J=10.4, 6.4 Hz, 1H), 7.28 (dd, J=11.4, 6.3 Hz, 1H), 4.93-4.85 (m, 1H), 4.65 (s, 2H), 3.77 (hept, J=6.1 Hz, 1H), 3.55 (s, 3H), 3.41-3.23 (m, 2H), 1.15 (d, J=6.1 Hz, 6H); MS (ESI) m/z 788.63 (M+H)⁺

Example 44

Synthesis of A-19

(Step 1) (2S)-2-[[2,5-Difluoro-4-[[4-[2-(iso-propoxymethyl)pyrimidin-5-yl]phenyl]sulfonylamino]benzoyl]amino]-3-[4-[3-methyl-2,6-dioxo-4-(trifluoromethyl)pyrimidin-1-yl]phenyl]propanoic acid (A-19)

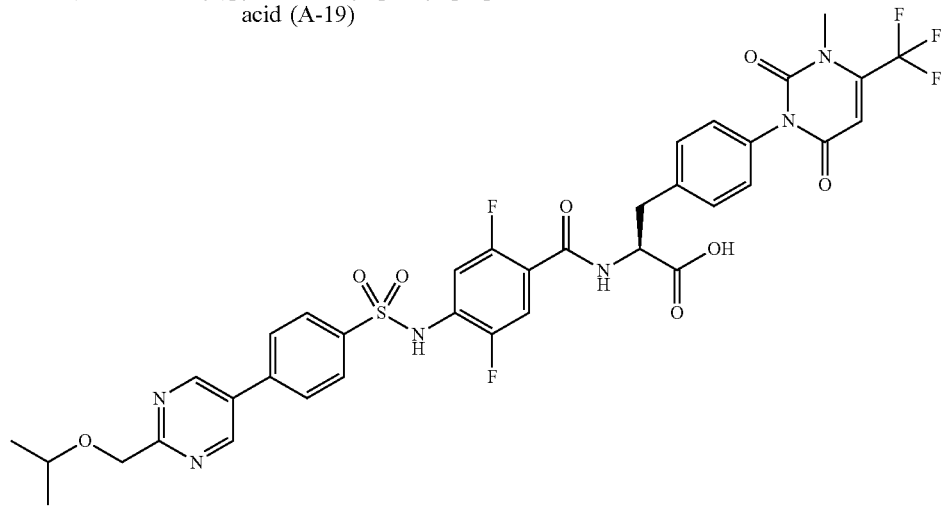 [SMILES: CC(C)OCc1ncc(-c2ccc(S(=O)(=O)Nc3cc(F)c(C(=O)N[C@@H](Cc4ccc(-n5c(=O)cc(C(F)(F)F)n(C)c5=O)cc4)C(=O)O)cc3F)cc2)cn1]

¹H NMR (400 MHz, DMSO-d₆) δ 10.96 (s, 1H), 9.17 (s, 2H), 8.59 (dd, J=7.9, 2.5 Hz, 1H), 8.07-8.02 (m, 2H), 7.99-7.94 (m, 2H), 7.37-7.32 (m, 2H), 7.32-7.23 (m, 2H), 7.18-7.12 (m, 2H), 6.48 (s, 1H), 4.68-4.56 (m, 3H), 3.78 (hept, J=6.1 Hz, 1H), 3.38-3.35 (m, 3H), 3.21 (dd, J=14.0, 4.6 Hz, 1H), 3.04 (dd, J=14.1, 9.9 Hz, 1H), 1.16 (d, J=6.1 Hz, 6H); MS (ESI) m/z 803.62 (M+H)⁺

Example 45

Synthesis of A-20

(Step 1) (2S)-2-[[4-[[4-(2-Ethylpyrimidin-5-yl)phenyl]sulfonylamino]-2,3,5,6-tetrafluoro-benzoyl]amino]-3-[4-(1,3,4-trimethyl-2,6-dioxo-pyrimidin-5-yl)phenyl]propanoic acid (A-20)

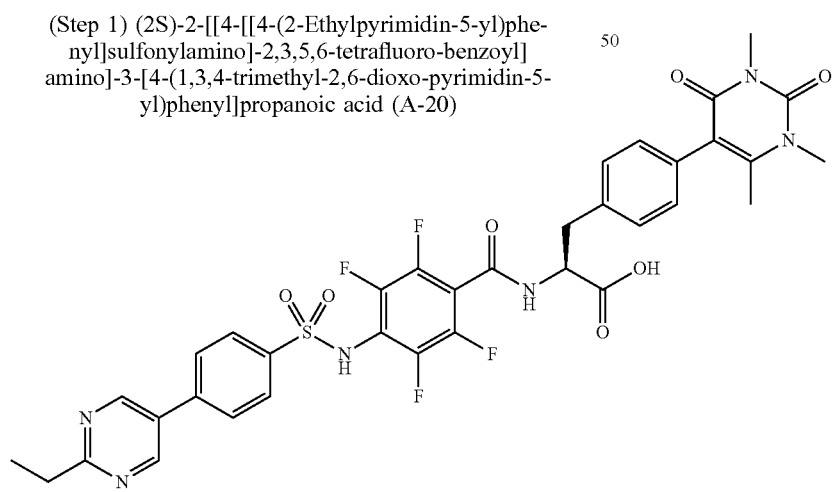

¹H NMR (400 MHz, DMSO-d₆) δ 10.83 (s, 1H), 9.33 (d, J=8.1 Hz, 1H), 9.14 (s, 2H), 8.08-8.02 (m, 2H), 7.93-7.87 (m, 2H), 7.27 (d, J=7.8 Hz, 2H), 7.11-7.06 (m, 2H), 4.73-4.65 (m, 1H), 3.38 (s, 3H), 3.25-3.18 (m, 4H), 3.00-2.91 (m, 3H), 2.06 (s, 3H), 1.32 (t, J=7.6 Hz, 3H); MS (ESI) m/z 755.50 (M+H)⁺

Example 46

Synthesis of A-21

(Step 1) (2S)-2-[[2-Fluoro-4-[[2-methyl-4-(2-pyridyl)phenyl]sulfonylamino]benzoyl]amino]-3-[4-(1,3,4-trimethyl-2,6-dioxo-pyrimidin-5-yl)phenyl]propanoic acid (A-21)

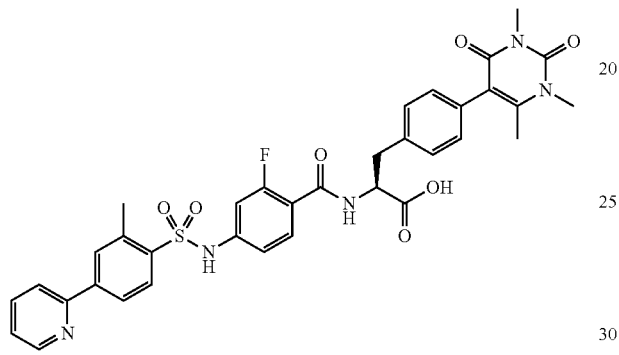

¹H NMR (400 MHz, DMSO-d₆) δ 11.12 (s, 1H), 8.72-8.68 (m, 1H), 8.28 (dd, J=7.9, 3.1 Hz, 1H), 8.12-8.03 (m, 4H), 7.95 (td, J=7.8, 1.8 Hz, 1H), 7.47-7.36 (m, 2H), 7.26-7.21 (m, 2H), 7.07-7.02 (m, 2H), 6.96 (dd, J=8.5, 2.1 Hz, 1H), 6.89 (dd, J=12.4, 2.1 Hz, 1H), 4.62-4.53 (m, 1H), 3.38 (s, 3H), 3.22-3.12 (m, 4H), 2.98 (dd, J=13.9, 9.8 Hz, 1H), 2.68 (s, 3H), 2.04 (s, 3H); MS (ESI) m/z 686.62 (M+H)⁺

Example 47

Synthesis of A-22

(Step 1) (2S)-2[[4-[[4-(Cyclopropylcarbamoyl))phenyl]sulfonylamino]-2,6-difluoro-benzoyl]amino]-3-[4-(1,3,4-trimethyl-2,6-dioxo-pyrimidin-5-yl)phenyl]propanoic acid (A-22)

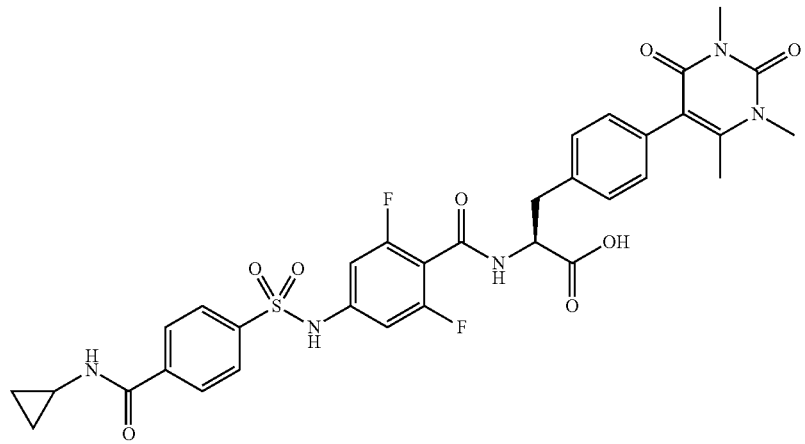 [SMILES: Cc1c(-c2ccc(C[C@H](NC(=O)c3c(F)cc(NS(=O)(=O)c4ccc(C(=O)NC5CC5)cc4)cc3F)C(=O)O)cc2)c(=O)n(C)c(=O)n1C]

$^1$H NMR (400 MHz, DMSO-d$_6$) δ 11.13 (s, 1H), 8.97 (d, J=8.0 Hz, 1H), 8.63 (d, J=4.3 Hz, 1H), 7.97-7.89 (m, 4H), 7.27-7.23 (m, 2H), 7.09-7.04 (m, 2H), 6.76 (d, J=9.0 Hz, 2H), 4.57 (ddd, J=10.1, 8.0, 4.6 Hz, 1H), 3.41 (s, 3H), 3.21 (s, 3H), 3.14 (dd, J=14.0, 4.6 Hz, 1H), 2.97-2.79 (m, 2H), 2.08 (s, 3H), 0.72-0.66 (m, 2H), 0.58-0.52 (m, 2H); MS (ESI) m/z 696.58 (M+H)$^+$ The following compounds (Examples 48 to 79) were synthesized by using methods similar to Example 51 (step 1), (step 2) and Example 52 (step 1) performed to intermediates corresponding to M-1 to M-25 and compounds similar thereto.

Example 48

Synthesis of C-1

(Step 1) Tetrahydropyran-4-yl (2S)-2-[[2,5-difluoro-4-[[4-(2-tetrahydropyran-4-ylpyrimidin-5-yl)phenyl]sulfonylamino]benzoyl]amino]-3-[4-(1-methyl-2,4-dioxo-pyrido[3,4-d]pyrimidin-3-yl)phenyl] propanoate (C-1)

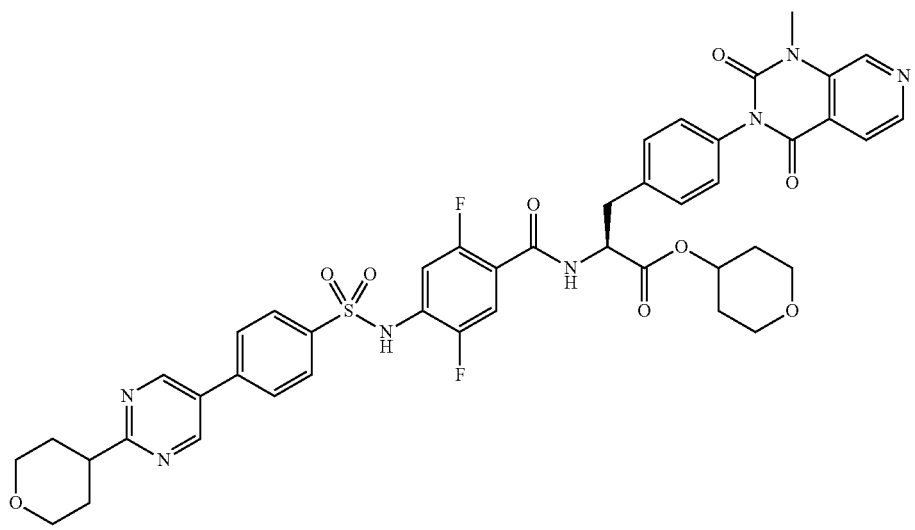

•2 TFA $^1$H NMR (400 MHz, DMSO-d$_6$) δ 10.98 (s, 1H), 9.14 (s, 2H), 8.97 (s, 1H), 8.81 (dd, J=7.3, 1.9 Hz, 1H), 8.54 (d, J=5.0 Hz, 1H), 8.07-8.01 (m, 2H), 8.01-7.94 (m, 2H), 7.88 (d, J=5.0 Hz, 1H), 7.40-7.25 (m, 4H), 7.24-7.19 (m, 2H), 4.94-4.84 (m, 1H), 4.68-4.61 (m, 1H), 4.00-3.91 (m, 2H), 3.79-3.66 (m, 2H), 3.59 (s, 3H), 3.53-3.44 (m, 4H), 3.22-3.07 (m, 3H), 1.95-1.71 (m, 6H), 1.57-1.39 (m, 2H); MS (ESI) m/z 882.68 (M+H)$^+$

Example 49

Synthesis of C-2

(Step 1) Tetrahydropyran-4-ylmethyl (2S)-2-[[2,5-difluoro-4-[[4-(2-tetrahydropyran-4-ylpyrimidin-5-yl)phenyl]sulfonylamino]benzoyl]amino]-3-[4-(1-methyl-2,4-dioxo-pyrido[3,4-d]pyrimidin-3-yl)phenyl]propanoate (C-2)

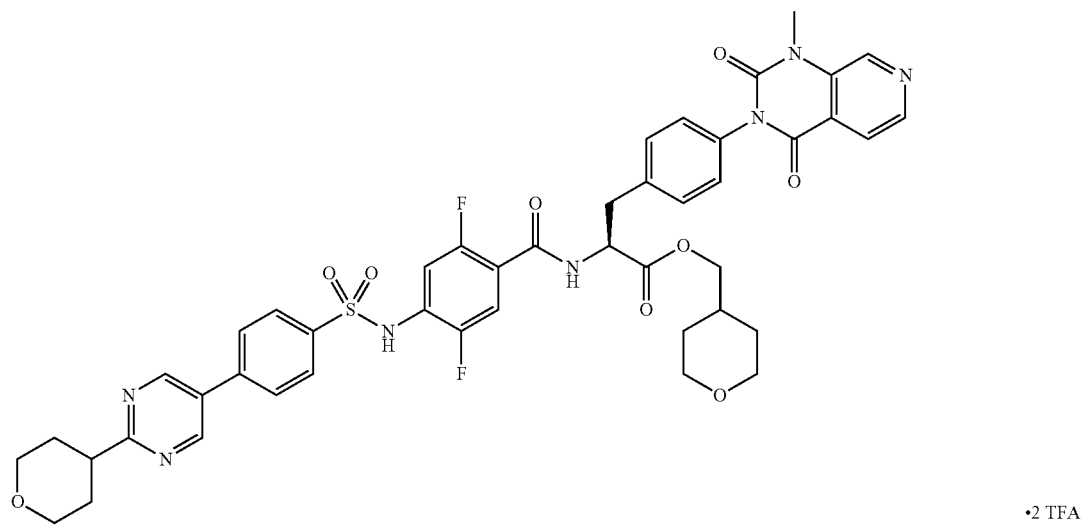

·2 TFA $^1$H NMR (400 MHz, DMSO-d$_6$) δ 11.01-10.91 (m, 1H), 9.14 (s, 2H), 8.97 (s, 1H), 8.80 (dd, J=7.5, 2.0 Hz, 1H), 8.55 (d, J=5.0 Hz, 1H), 8.07-7.94 (m, 4H), 7.88 (d, J=5.0 Hz, 1H), 7.39-7.34 (m, 2H), 7.34-7.25 (m, 2H), 7.24-7.16 (m, 2H), 4.74-4.57 (m, 1H), 4.00-3.89 (m, 4H), 3.83-3.75 (m, 2H), 3.59 (s, 3H), 3.54-3.39 (m, 2H), 3.33-3.05 (m, 5H), 2.01-1.72 (m, 5H), 1.56-1.44 (m, 2H), 1.30-1.10 (m, 2H); MS (ESI) m/z 896.68 (M+H)$^+$

Example 50

Synthesis of C-3

(Step 1) Tetrahydropyran-4-yl (2S)-2-[[2,5-difluoro-4-[[4-(2-tetrahydropyran-4-ylpyrimidin-5-yl)phenyl]sulfonylamino]benzoyl]amino]-3-[6-(1-methyl-2,4-dioxo-pyrido[3,4-d]pyrimidin-3-yl)-3-pyridyl]propanoate (C-3)

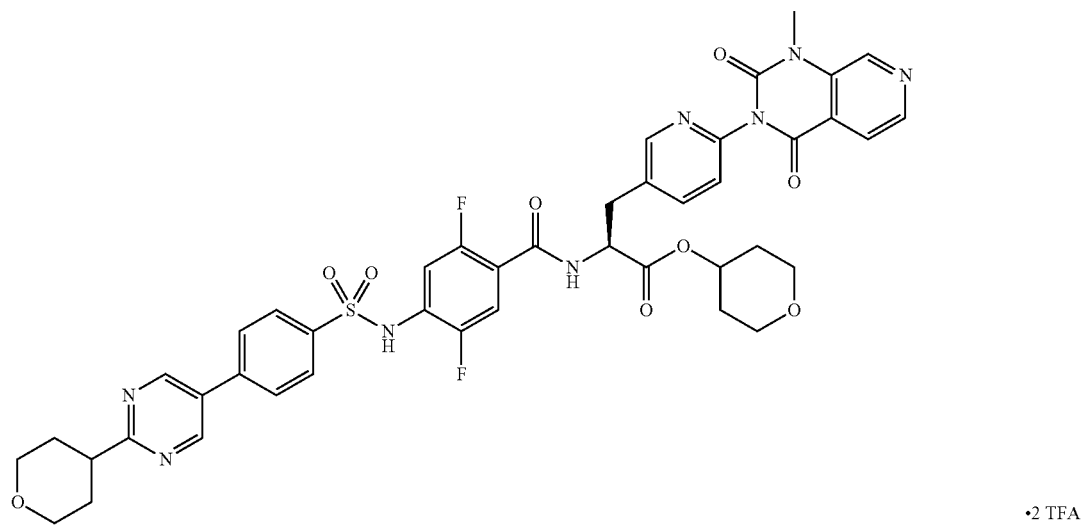 [SMILES: Cn1c(=O)n(-c2ccc(C[C@H](NC(=O)c3cc(F)c(NS(=O)(=O)c4ccc(-c5cnc(C6CCOCC6)nc5)cc4)cc3F)C(=O)OC3CCOCC3)cn2)c(=O)c2ccncc21]

·2 TFA $^1$H NMR (400 MHz, DMSO-d$_6$) δ 10.98 (s, 1H), 9.14 (s, 2H), 8.99 (s, 1H), 8.88 (dd, J=7.6, 1.7 Hz, 1H), 8.56 (d, J=4.9 Hz, 1H), 8.47 (d, J=2.3 Hz, 1H), 8.05-8.01 (m, 2H), 7.99-7.95 (m, 2H), 7.93 (dd, J=8.2, 2.4 Hz, 1H), 7.89 (d, J=4.9 Hz, 1H), 7.41 (d, J=8.0 Hz, 1H), 7.29 (ddd, J=10.8, 6.3, 3.9 Hz, 2H), 4.97-4.84 (m, 1H), 4.76-4.66 (m, 1H), 3.99-3.90 (m, 2H), 3.79-3.66 (m, 2H), 3.59 (s, 3H), 3.54-3.42 (m, 4H), 3.26 (dd, J=14.1, 5.8 Hz, 1H), 3.19-3.07 (m, 2H), 1.96-1.72 (m, 6H), 1.58-1.39 (m, 2H); MS (ESI) m/z 883.72 (M+H)$^+$

Example 51

Synthesis of A-23

(Step 1) Cyclohexyl (2S)-2-[[2,5-difluoro-4-[[4-[2-(methoxymethyl)pyrimidin-5-yl]phenyl]sulfonylamino]benzoyl]amino]-3-[6-(1-methyl-2,4-dioxo-pyrido[3,4-d]pyrimidin-3-yl)-3-pyridyl]propanoate

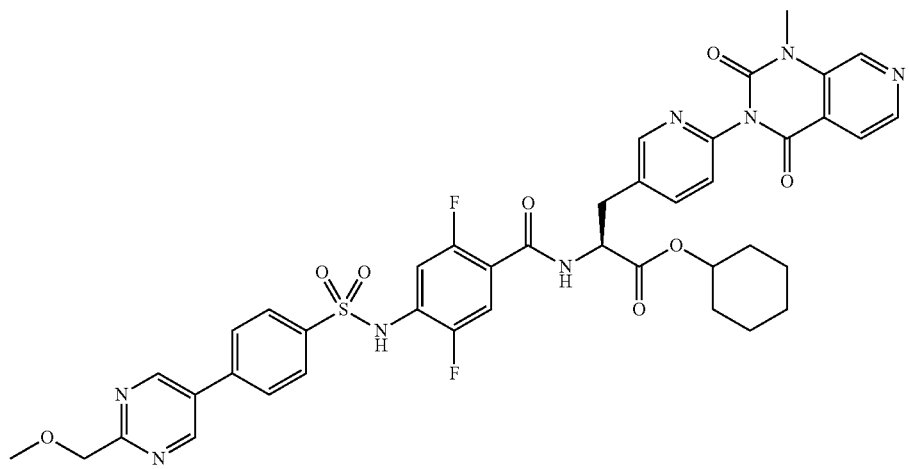

·2 TFA

Cyclohexyl 3-[6-(1-methyl-2,4-dioxo-1,4-dihydropyrido[3,4-d]pyrimidin-3 (2H)-yl)pyridin-3-yl]-L-alaninate (M-1) <see Example 1> (127 mg, 0.280 mmol) and 2,5-difluoro-4-[[4-[2-(methoxymethyl)pyrimidin-5-yl]phenyl]sulfonylamino]benzoic acid (M-11) <see Example 11> (100 mg, 0.230 mmol) were suspended in methylene chloride (4.0 ml), HATU (131 mg, 0.350 mmol) and diisopropylethylamine (0.160 ml, 0.920 mmol) were added thereto, and the resulting mixture was stirred at room temperature for 12 hours. The reaction liquid was concentrated under reduced pressure and then purified by reverse phase HPLC (an $H_2O/CH:CN$ system including 0.1% TFA) to obtain a TFA salt of the title compound (130 mg, 53%) as a white solid.

$^1$H NMR (400 MHz, DMSO-$d_6$): δ 10.97 (s, 1H), 9.18 (s, 2H), 8.99 (s, 1H), 8.84 (dd, J=7.7, 1.7 Hz, 1H), 8.57 (d, J=5.0 Hz, 1H), 8.49-8.43 (m, 1H), 8.10-8.01 (m, 2H), 8.01-7.95 (m, 2H), 7.95-7.85 (m, 2H), 7.40 (dd, J=8.0, 0.8 Hz, 1H), 7.33-7.23 (m, 2H), 4.76-4.64 (m, 2H), 4.63 (s, 2H), 3.59 (s, 3H), 3.40 (s, 3H), 3.24 (dd, J=14.1, 5.6 Hz, 1H), 3.12 (dd, J=14.1, 9.7 Hz, 1H), 1.78-1.58 (m, 4H), 1.50-1.19 (m, 6H); MS(ESI) m/z 841.59 (M+H)$^+$ (Step 2) (2S)-2-[[2,5-Difluoro-4-[[4-[2-(methoxymethyl)pyrimidin-5-yl]phenyl]sulfonylamino]benzoyl]amino]-3-[6-(1-methyl-2,4-dioxo-pyrido[3,4-d]pyrimidin-3-yl)-3-pyridyl]propanoic acid

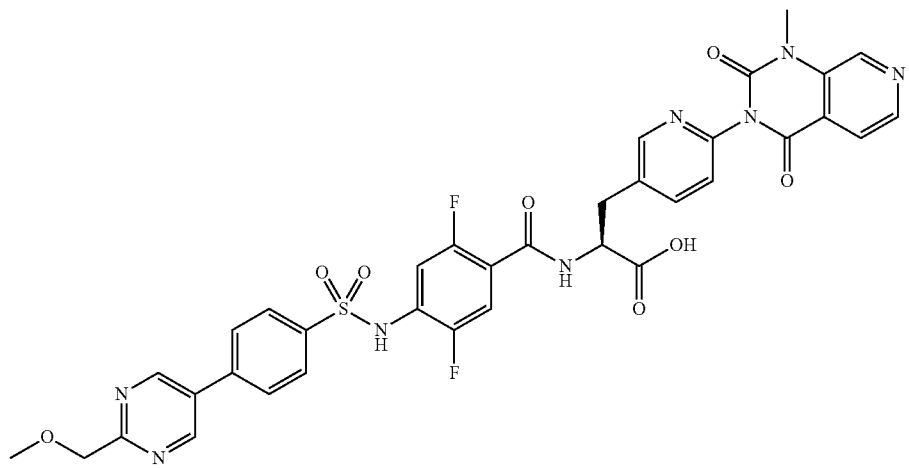

•2 TFA

A 4 N solution of hydrochloric acid/dioxane (3.0 ml) and water (2.0 ml) were added to cyclohexyl (2S)-2-[[2,5-difluoro-4-[[4-[2-(methoxymethyl)pyrimidin-5-yl]phenyl]sulfonylamino]benzoyl]amino]-3-[6-(1-methyl-2,4-dioxo-pyrido[3,4-d]pyrimidin-3-yl)-3-pyridyl]propanoate <see (step 1)> (70.0 mg, 65.0 mmol), and the resulting mixture was stirred at 60° C. for 4 hours. The reaction liquid was concentrated under reduced pressure and then purified by reverse phase HPLC (an $H_2O/CH_3CN$ system including 0.1% TFA) to obtain a TFA salt of the title compound (42.3 mg, 66%) as a white solid.

$^1$H NMR (400 MHz, DMSO-$d_6$): δ 10.96 (s, 1H), 9.18 (s, 2H), 8.99 (s, 1H), 8.69 (dd, J=8.1, 2.2 Hz, 1H), 8.56 (d, J=4.9 Hz, 1H), 8.46 (d, J=2.3 Hz, 1H), 8.09-8.01 (m, 2H), 8.01-7.93 (m, 2H), 7.93-7.85 (m, 2H), 7.40 (d, J=8.0 Hz, 1H), 7.34-7.23 (m, 2H), 4.74-4.64 (m, 1H), 4.62 (s, 2H), 3.59 (s, 3H), 3.40 (s, 3H), 3.29 (dd, J=14.0, 4.6 Hz, 1H), 3.09 (dd, J=14.1, 10.2 Hz, 1H): MS(ESI) m/z 759.5 (M+H)$^+$

Example 52

Synthesis of C-4

(Step 1) Tetrahydropyran-4-yl (2S)-2-[[2,5-difluoro-4-[[4-[2-(methoxymethyl)pyrimidin-5-yl]phenyl]sulfonylamino]benzoyl]amino]-3-[6-(1-methyl-2,4-dioxo-pyrido[3,4-d]pyrimidin-3-yl)-3-pyridyl]propanoate (C-4)

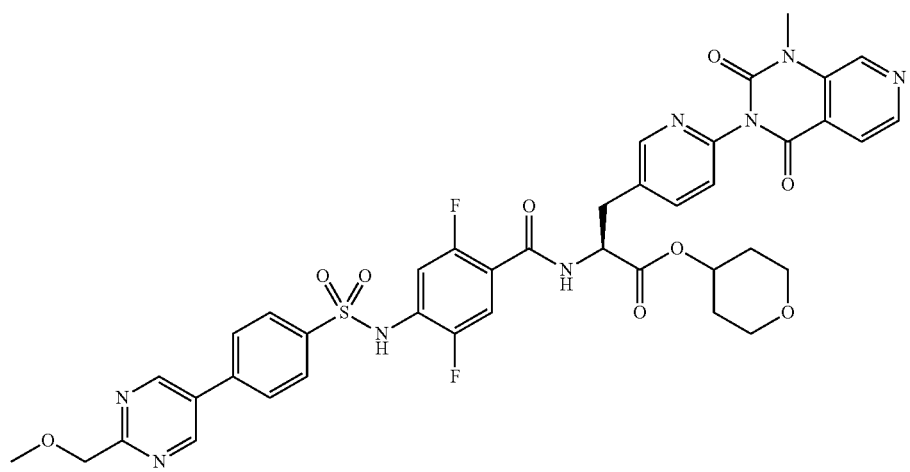

·2 TFA

A 4 N solution of hydrochloric acid dioxane (3.0 ml) and tetrahydro-4-pyranol (1.0 ml) were added to (2S)-2-[[2,5-difluoro-4-[[4-[2-(methoxymethyl)pyrimidin-5-yl]phenyl]sulfonylamino]benzoyl]amino]-3-[6-(1-methyl-2,4-dioxo-pyrido[3,4-d]pyrimidin-3-yl)-3-pyridyl]propanoate <see (step 2)> (100 mg, 101 mmol), and the resulting mixture was stirred at 60° C. for 12 hours. The reaction liquid was concentrated under reduced pressure and then purified by reverse phase HPLC (an $H_2O/CH_3CN$ system including 0.1% TFA) to obtain a TFA salt of the title compound (39.6 mg, 37%) as a white solid.

$^1$H NMR (400 MHz, DMSO-$d_6$) δ 10.98 (s, 1H), 9.18 (s, 2H), 8.99 (s, 1H), 8.91-8.86 (m, 1H), 8.57 (d, J=5.0 Hz, 1H), 8.47 (d, J=2.3 Hz, 1H), 8.07-8.03 (m, 2H), 8.00-7.96 (m, 2H), 7.93 (dd, J=8.2, 2.4 Hz, 1H), 7.89 (d, J=4.9 Hz, 1H), 7.41 (d, J=8.1 Hz, 1H), 7.33-7.24 (m, 2H), 4.96-4.86 (m, 1H), 4.76-4.67 (m, 1H), 4.63 (s, 2H), 3.80-3.67 (m, 2H), 3.59 (s, 3H), 3.49-3.44 (m, 2H), 3.40 (s, 3H), 3.26 (dd, J=14.1, 5.8 Hz, 1H), 3.14 (dd, 1H), 1.88-1.72 (m, 2H), 1.59-1.40 (m, 2H); MS (ESI) m/z 843.59 (M+H)$^+$

Example 53

Synthesis of C-5

(Step 1) Tetrahydropyran-4-ylmethyl (2S)-2-[[2,5-difluoro-4-[[4-[2-(methoxymethyl)pyrimidin-5-yl]phenyl]sulfonylamino]benzoyl]amino]-3-[6-(1-methyl-2,4-dioxo-pyrido[3,4-d]pyrimidin-3-yl)-3-pyridyl]propanoate (C-5)

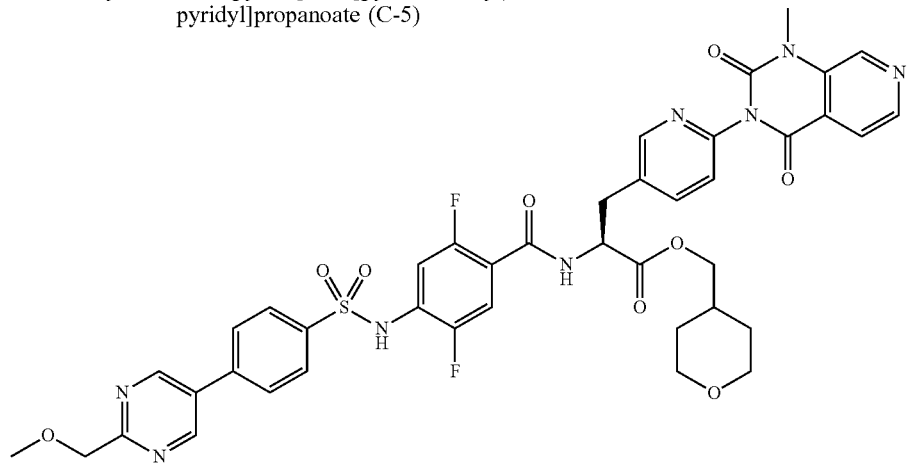

·2 TFA $^1$H NMR (400 MHz, DMSO-d$_6$) δ 10.98 (s, 1H), 9.18 (s, 2H), 8.99 (s, 1H), 8.87 (dd, J=7.7, 1.6 Hz, 1H), 8.57 (d, J=5.0 Hz, 1H), 8.47 (d, J=2.3 Hz, 1H), 8.09-8.02 (m, 2H), 8.00-7.96 (m, 2H), 7.94-7.86 (m, 2H), 7.40 (d, J=8.0 Hz, 1H), 7.32-7.24 (m, 2H), 4.79-4.70 (m, 1H), 4.63 (s, 2H), 3.99-3.89 (m, 2H), 3.84-3.76 (m, 2H), 3.59 (s, 3H), 3.40 (s, 3H), 3.30-3.20 (m, 3H), 3.13 (dd, J=14.1, 9.9 Hz, 1H), 1.89-1.74 (m, 1H), 1.56-1.47 (m, 2H), 1.29-1.12 (m, 2H); MS (ESI) m/z 857.75 (M+H)$^+$

Example 54

Synthesis of C-6

(Step 1) Cyclohexylmethyl (2S)-2-[[2,5-difluoro-4-[[4-[2-(methoxymethyl)pyrimidin-5-yl]phenyl]sulfonyl amino]benzoyl]amino]-3-[6-(1-methyl-2,4-dioxo-pyrido[3,4-d]pyrimidin-3-yl)-3-pyridyl]propanoate (C-6)

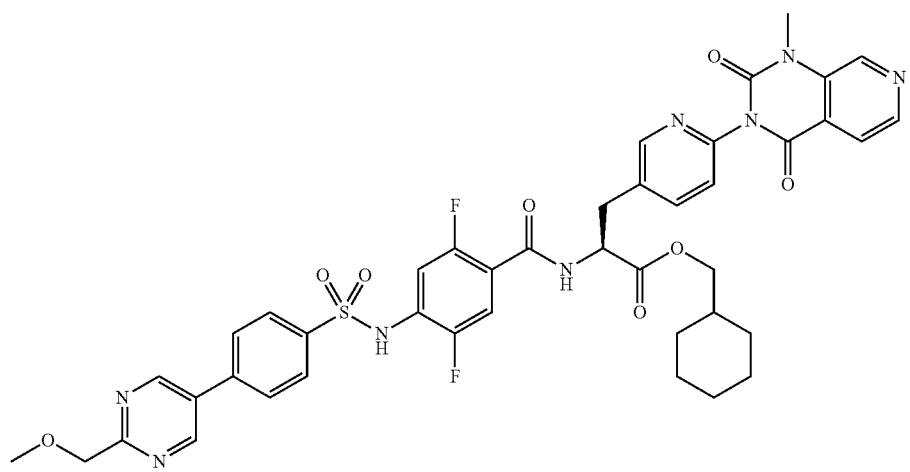

·2 TFA $^1$H NMR (400 MHz, DMSO-d$_6$) δ 10.98 (s, 1H), 9.18 (s, 2H), 8.99 (s, 1H), 8.87-8.83 (m, 1H), 8.57 (d, J=5.0 Hz, 1H), 8.48-8.46 (m, 1H), 8.08-8.02 (m, 2H), 8.00-7.95 (m, 2H), 7.93-7.87 (m, 2H), 7.42-7.38 (m, 1H), 7.31-7.23 (m, 2H), 4.79-4.71 (m, 1H), 4.63 (s, 2H), 3.96-3.84 (m, 2H), 3.59 (s, 3H), 3.40 (s, 3H), 3.28 (dd, J=14.1, 5.0 Hz, 1H), 3.22-3.06 (m, 1H), 1.68-1.54 (m, 5H), 1.22-0.87 (m, 6H); MS (ESI) m/z 855.67 (M+H)$^+$

Example 55

Synthesis of C-7

(Step 1) Isopropyl (2S)-2-[[2,5-difluoro-4-[[4-[2-(methoxymethyl)pyrimidin-5-yl]phenyl]sulfonylamino]benzoyl]amino]-3-[6-(1-methyl-2,4-dioxopyrido[3,4-d]pyrimidin-3-yl)-3-pyridyl]propanoate (C-7)

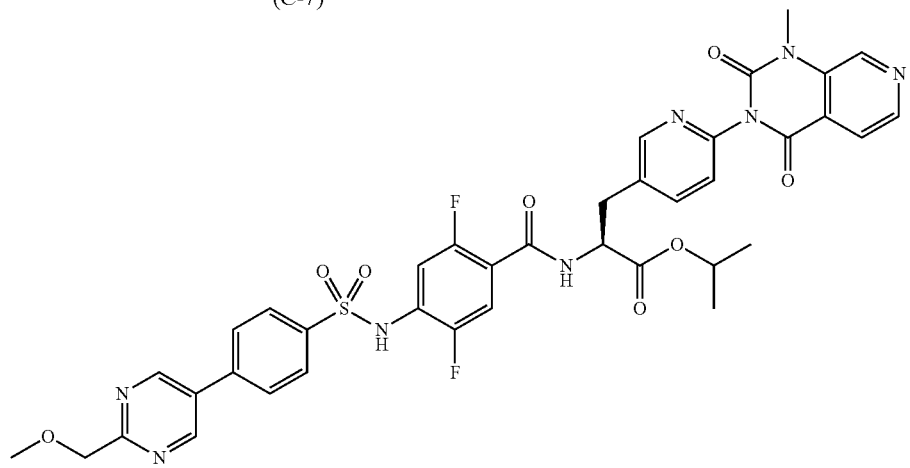

·2 TFA $^1$H NMR (400 MHz, DMSO-d$_6$) δ 10.98 (s, 1H), 9.19 (s, 2H), 8.99 (d, J=0.8 Hz, 1H), 8.83 (dd, J=7.7, 1.8 Hz, 1H), 8.57 (d, J=5.0 Hz, 1H), 8.46 (dd, J=2.5, 0.8 Hz, 1H), 8.08-8.04 (m, 2H), 8.01-7.96 (m, 2H), 7.95-7.87 (m, 2H), 7.40 (dd, J=8.1, 0.7 Hz, 1H), 7.34-7.22 (m, 2H), 4.91 (hept, J=6.3 Hz, 1H), 4.72-4.59 (m, 3H), 3.59 (s, 3H), 3.40 (s, 3H), 3.28-3.06 (m, 2H), 1.16 (dd, J=18.9, 6.2 Hz, 6H); MS (ESI) m/z 801.63 (M+H)$^+$ Example 56

Synthesis of C-8

(Step 1) 2-Ethylbutyl (2S)-2-[[2,5-difluoro-4-[[4-[2-(methoxymethyl)pyrimidin-5-yl]phenyl]sulfonylamino]benzoyl]amino]-3-[6-(1-methyl-2,4-dioxopyrido[3,4-d]pyrimidin-3-yl)-3-pyridyl]propanoate (C-8)

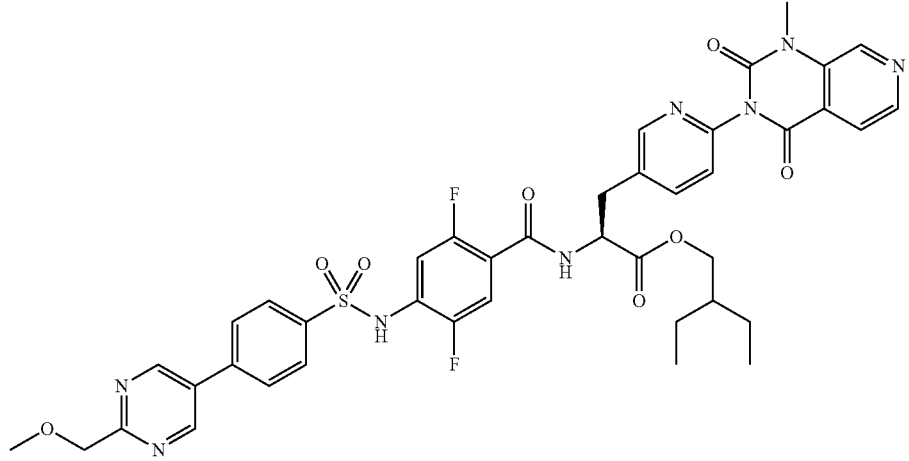

·2 TFA

¹H NMR (400 MHz, DMSO-d₆) δ 10.98 (s, 1H), 9.18 (s, 2H), 8.99 (s, 1H), 8.84 (dd, J=8.0, 1.8 Hz, 1H), 8.57 (d, J=4.9 Hz, 1H), 8.47 (d, J=2.3 Hz, 1H), 8.08-8.03 (m, 2H), 8.00-7.96 (m, 2H), 7.93-7.87 (m, 2H), 7.42-7.38 (m, 1H), 7.31-7.22 (m, 2H), 4.79-4.71 (m, 1H), 4.63 (s, 2H), 4.01 (d, J=5.6 Hz, 2H), 3.59 (s, 3H), 3.40 (s, 3H), 3.28 (dd, J=14.2, 4.9 Hz, 1H), 3.12 (dd, J=14.1, 10.3 Hz, 1H), 1.46 (hept, J=6.2 Hz, 1H), 1.32-1.23 (m, 4H), 0.81 (t, J=7.4 Hz, 6H); MS (ESI) m/z 843.71 (M+H)⁺

Example 57

C-9

(Step 1) 2-Adamantyl (2S)-2-[[2,5-difluoro-4-[[4-[2-(methoxymethyl)pyrimidin-5-yl]phenyl]sulfonylamino]benzoyl]amino]-3-[6-(1-methyl-2,4-dioxopyrido[3,4-d]pyrimidin-3-yl)-3-pyridyl]propanoate (C-9)

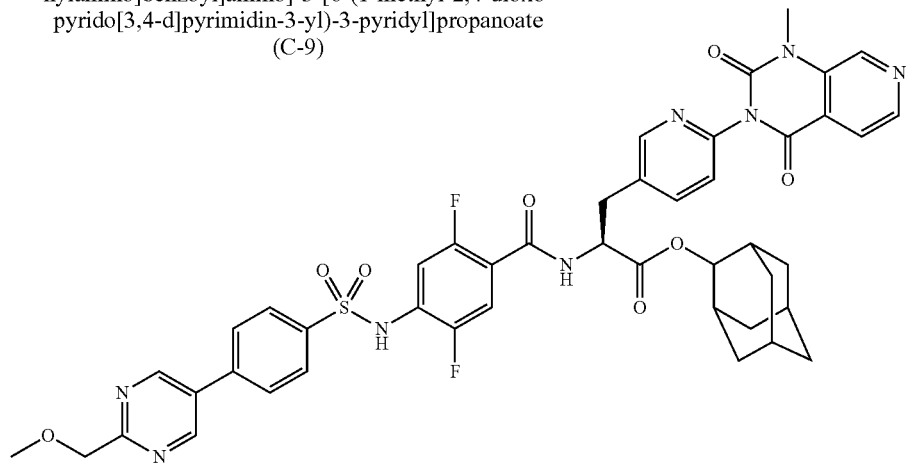

·2 TFA

¹H NMR (400 MHz, DMSO-d₆) δ 10.98 (s, 1H), 9.19 (s, 2H), 8.99 (s, 1H), 8.86 (dd, J=7.8, 1.7 Hz, 1H), 8.57 (d, J=5.0 Hz, 1H), 8.48 (d, J=2.3 Hz, 1H), 8.07-8.03 (m, 2H), 7.99-7.96 (m, 2H), 7.93 (dd, J=8.2, 2.4 Hz, 1H), 7.88 (d, J=4.9 Hz, 1H), 7.40 (d, J=8.0 Hz, 1H), 7.31-7.23 (m, 2H), 4.86 (d, J=3.2 Hz, 1H), 4.82-4.72 (m, 1H), 4.63 (s, 2H), 3.59 (s, 3H), 3.40 (s, 3H), 3.30 (dd, J=14.1, 5.1 Hz, 1H), 3.14 (dd, J=14.1, 10.2 Hz, 1H), 1.99-1.40 (m, 14H); MS (ESI) m/z 893.72 (M+H)⁺

Example 58

C-10

(Step 1) (1-Methyl-4-piperidyl) (2S)-2-[[2,5-difluoro-4-[[4-[2-(methoxymethyl)pyrimidin-5-yl]phenyl]sulfonylamino]benzoylamino]-3-[6-(1-methyl-2,4-dioxo-pyrido[3,4-d]pyrimidin-3-yl)-3-pyridyl]propanoate (C-10)

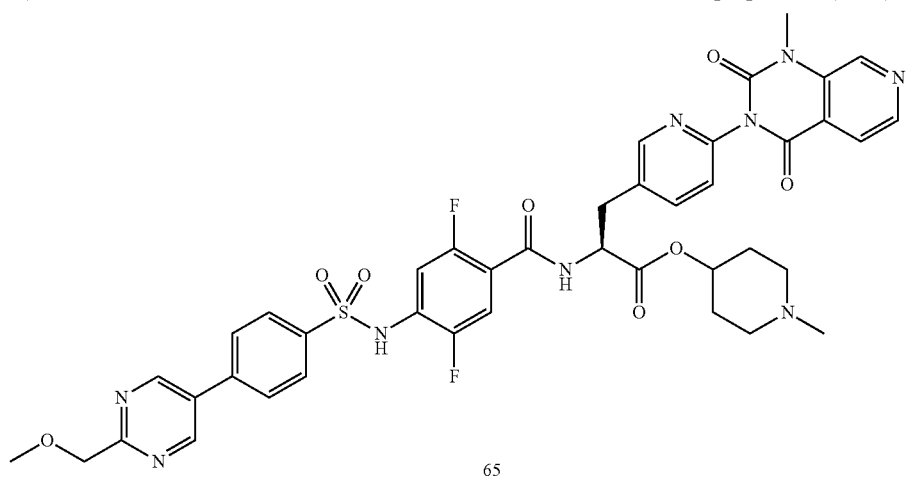

·3 TFA

MS (ESI) m/z 856.67 (M+H)⁺

Example 59

Synthesis of C-11

(Step 1) 1-Ethylpropyl (2S)-2-[[2,5-difluoro-4-[[4-[2-(methoxymethyl)pyrimidin-5-yl]phenyl]sulfonylamino]benzoyl]amino]-3-[6-(1-methyl-2,4-dioxo-pyrido[3,4-d]pyrimidin-3-yl)-3-pyridyl]propanoate (C-11)

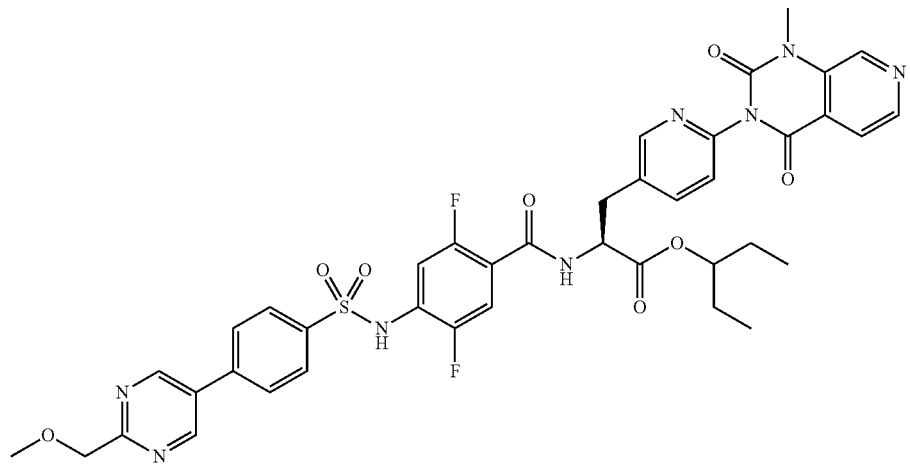

·2 TFA $^1$H NMR (400 MHz, DMSO-d$_6$) δ 10.97 (s, 1H), 9.18 (s, 2H), 8.99 (s, 1H), 8.85 (dd, J=8.0, 1.6 Hz, 1H), 8.56 (d, J=5.0 Hz, 1H), 8.48 (d, J=2.3 Hz, 1H), 8.07-8.04 (m, 2H), 8.00-7.96 (m, 2H), 7.93 (dd, J=8.2, 2.4 Hz, 1H), 7.88 (d, J=4.9 Hz, 1H), 7.40 (d, J=8.1 Hz, 1H), 7.31-7.21 (m, 2H), 4.78-4.66 (m, 2H), 4.63 (s, 2H), 3.59 (s, 3H), 3.40 (s, 3H), 3.27 (dd, J=14.1, 5.3 Hz, 1H), 3.13 (dd, J=14.1, 10.2 Hz, 1H), 1.62-1.41 (m, 4H), 0.86-0.76 (m, 6H); MS (ESI) m/z 829.63 (M+H)$^+$

Example 60

Synthesis of C-12

(Step 1) (4,4-Dimethylcyclohexyl) (2S)-2-[[2,5-difluoro-4-[[4-[2-(methoxymethyl)pyrimidin-5-yl]phenyl]sulfonyl amino]benzoyl]amino]-3-[6-(1-methyl-2,4-dioxo-pyrido[3,4-d]pyrimidin-3-yl)-3-pyridyl]propanoate (C-12)

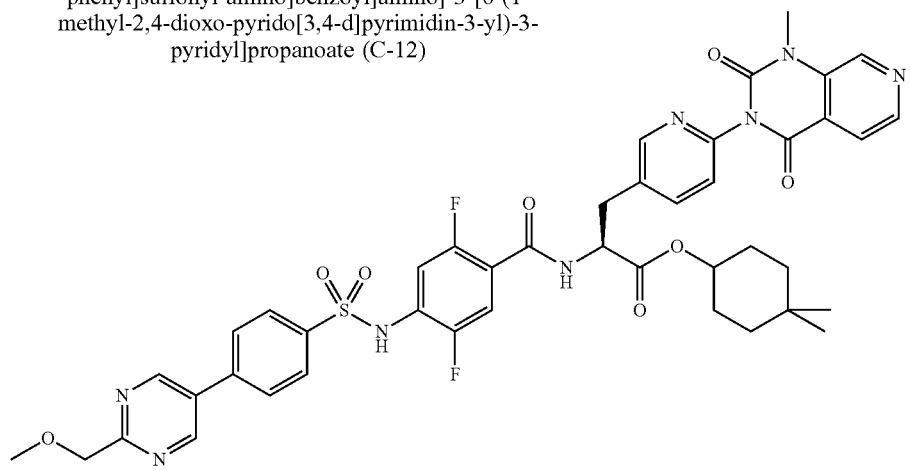

·2 TFA $^1$H NMR (400 MHz, DMSO-d$_6$) δ 10.98 (s, 1H), 9.18 (s, 2H), 8.99 (s, 1H), 8.83 (dd, J=7.6, 1.8 Hz, 1H), 8.57 (d, J=4.9 Hz, 1H), 8.46 (d, J=2.3 Hz, 1H), 8.08-8.02 (m, 2H), 8.00-7.96 (m, 2H), 7.94-7.87 (m, 2H), 7.40 (d, J=8.1 Hz, 1H), 7.32-7.25 (m, 2H), 4.74-4.66 (m, 2H), 4.63 (s, 2H), 3.59 (s, 3H), 3.40 (s, 3H), 3.25 (dd, J=14.1, 5.4 Hz, 1H), 3.13 (dd, J=14.1, 9.8 Hz, 1H), 1.73-1.11 (m, 8H), 0.85 (d, J=15.3 Hz, 6H); MS (ESI) m/z 869.71 (M+H)$^+$

Example 61

Synthesis of C-13

(Step 1) 1-Propylbutyl (2S)-2-[[2,5-difluoro-4-[[4-[2-(methoxymethyl)pyrimidin-5-yl]phenyl]sulfonylamino]benzoyl]amino]-3-[6-(1-methyl-2,4-dioxo-pyrido[3,4-d]pyrimidin-3-yl)-3-pyridyl]propanoate (C-13)

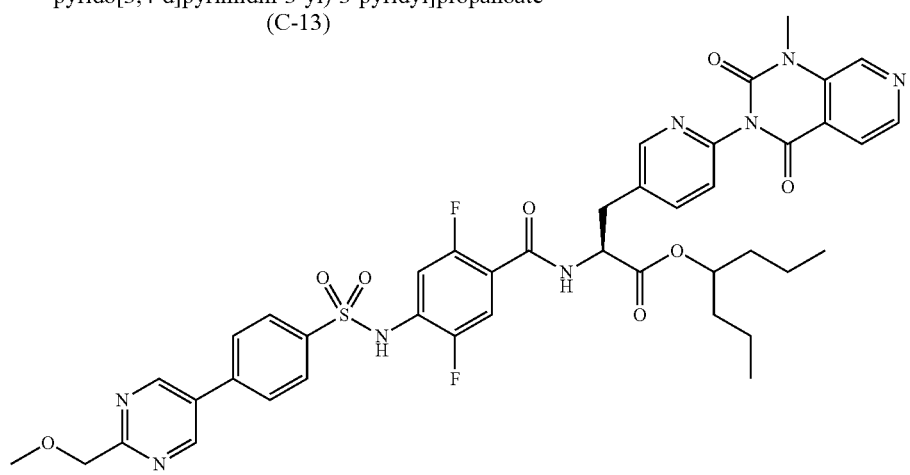

·2 TFA $^1$H NMR (400 MHz, DMSO-d$_6$) δ 10.97 (s, 1H), 9.18 (s, 2H), 8.99 (s, 1H), 8.84 (dd, J=7.8, 1.6 Hz, 1H), 8.57 (d, J=5.0 Hz, 1H), 8.48 (dd, J=2.3, 0.8 Hz, 1H), 8.07-8.03 (m, 2H), 8.00-7.96 (m, 2H), 7.93 (dd, J=8.2, 2.4 Hz, 1H), 7.88 (dd, J=4.9, 0.7 Hz, 1H), 7.40 (dd, J=8.1, 0.7 Hz, 1H), 7.25 (ddd, J=17.9, 10.5, 6.2 Hz, 2H), 4.86 (p, J=6.3 Hz, 1H), 4.77-4.68 (m, 1H), 4.63 (s, 2H), 3.59 (s, 3H), 3.40 (s, 3H), 3.27 (dd, J=14.2, 5.0 Hz, 1H), 3.11 (dd, J=14.1, 10.4 Hz, 1H), 1.52-1.42 (m, 4H), 1.35-1.17 (m, 4H), 0.87-0.81 (m, 6H); MS (ESI) m/z 857.71 (M+H)$^+$ Example 62

Synthesis of C-14

(Step 1) (4,4-Difluorocyclohexyl) (2S)-2-[[2,5-difluoro-4-[[4-[2-(methoxymethyl)pyrimidin-5-yl]phenyl]sulfonyl amino]benzoyl]amino]-3-[6-(1-methyl-2,4-dioxo-pyrido[3,4-d]pyrimidin-3-yl)-3-pyridyl] propanoate (C-14)

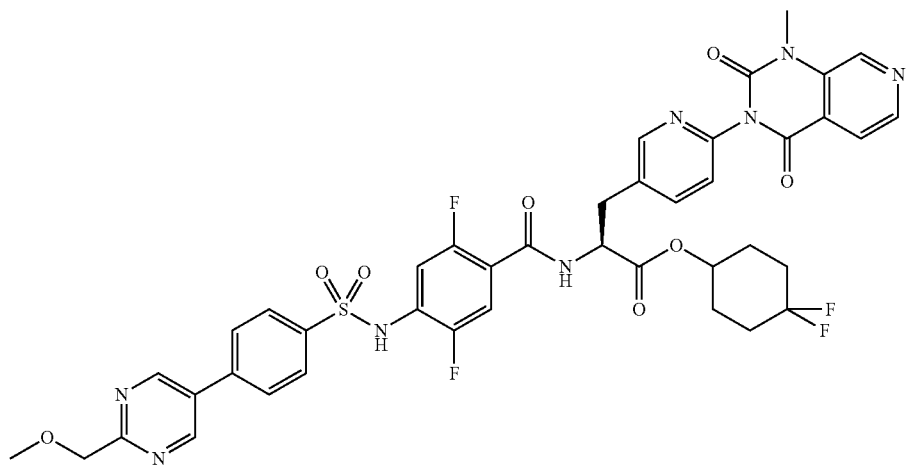

·2 TFA $^1$H NMR (400 MHz, DMSO-d$_6$) δ 10.99 (s, 1H), 9.18 (s, 2H), 8.99 (s, 1H), 8.90 (dd, J=7.5, 1.6 Hz, 1H), 8.57 (d, J=5.0 Hz, 1H), 8.47 (d, J=2.3 Hz, 1H), 8.08-8.03 (m, 2H), 8.00-7.96 (m, 2H), 7.93 (dd, J=8.1, 2.4 Hz, 1H), 7.89 (dd, J=5.0, 0.7 Hz, 1H), 7.43-7.39 (m, 1H), 7.32-7.25 (m, 2H), 4.96-4.88 (m, 1H), 4.77-4.69 (m, 1H), 4.63 (s, 2H), 3.59 (s, 3H), 3.40 (s, 3H), 3.27 (dd, J=14.1, 5.6 Hz, 1H), 3.14 (dd, J=14.1, 9.7 Hz, 1H), 2.05-1.63 (m, 8H); MS (ESI) m/z 877.72 (M+H)$^+$

Example 63

Synthesis of C-15

(Step 1) Ethyl (2S)-2-[[2,5-difluoro-4-[[4-[2-(methoxymethyl)pyrimidin-5-yl]phenyl]sulfonylamino]benzoyl]amino]-3-[6-(1-methyl-2,4-dioxopyrido[3,4-d]pyrimidin-3-yl)-3-pyridyl]propanoate (C-15)

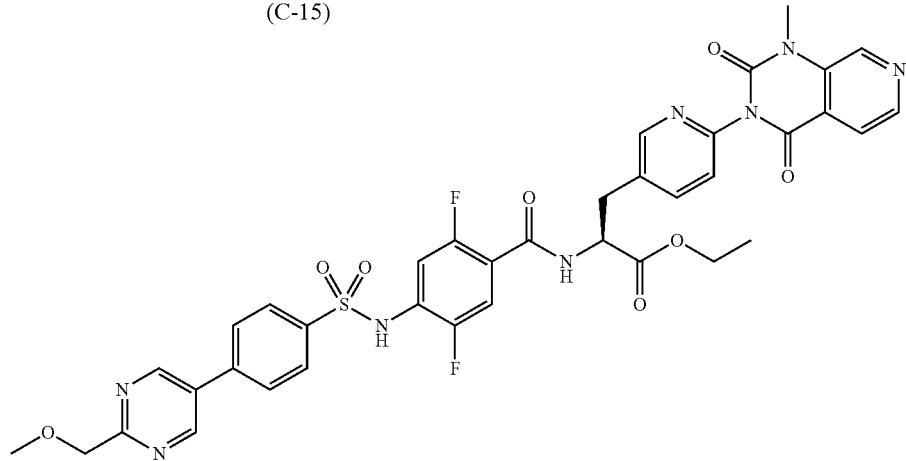

•2 TFA $^1$H NMR (400 MHz, DMSO-d$_6$) δ 10.98 (s, 1H), 9.19 (s, 2H), 8.99 (s, 1H), 8.86 (dd, J=7.8, 1.7 Hz, 1H), 8.57 (d, J=5.0 Hz, 1H), 8.47 (d, J=2.3 Hz, 1H), 8.08-8.03 (m, 2H), 8.00-7.96 (m, 2H), 7.94-7.87 (m, 2H), 7.42-7.39 (m, 1H), 7.33-7.25 (m, 2H), 4.75-4.68 (m, 1H), 4.63 (s, 2H), 4.11 (q, J=7.1 Hz, 2H), 3.59 (s, 3H), 3.40 (s, 3H), 3.25 (dd, J=14.0, 5.6 Hz, 1H), 3.13 (dd, J=14.0, 9.7 Hz, 1H), 1.16 (t, J=7.1 Hz, 3H); MS (ESI) m/z 787.63 (M+H)$^+$

Example 64

Synthesis of C-16

(Step 1) Cyclopentyl (2S)-2-[[2,5-difluoro-4-[[4-[2-(methoxymethyl)pyrimidin-5-yl]phenyl]sulfonylamino]benzoyl]amino]-3-[6-(1-methyl-2,4-dioxopyrido[3,4-d]pyrimidin-3-yl)-3-pyridyl]propanoate (C-16)

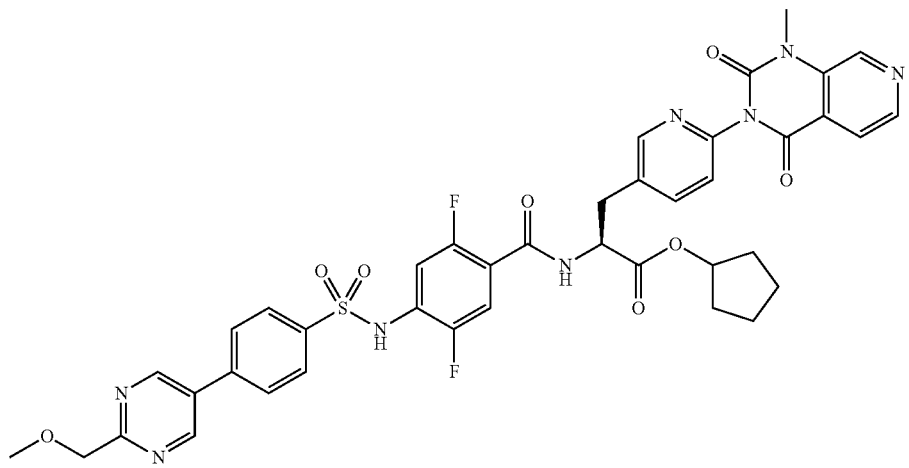

•2 TFA $^1$H NMR (400 MHz, DMSO-d$_6$) δ 10.98 (s, 1H), 9.19 (s, 2H), 8.99 (s, 1H), 8.83 (dd, J=7.7, 1.7 Hz, 1H), 8.57 (d, J=4.9 Hz, 1H), 8.46 (d, J=2.3 Hz, 1H), 8.08-8.03 (m, 2H), 8.01-7.95 (m, 2H), 7.93-7.87 (m, 2H), 7.40 (d, J=8.1 Hz, 1H), 7.32-7.24 (m, 2H), 5.14-5.07 (m, 1H), 4.72-4.59 (m, 3H), 3.59 (s, 3H), 3.40 (s, 3H), 3.24 (dd, J=14.1, 5.5 Hz, 1H), 3.11 (dd, J=14.2, 9.7 Hz, 1H), 1.86-1.46 (m, 8H); MS (ESI) m/z 827.71 (M+H)$^+$

Example 65

Synthesis of C-17

(Step 1) Hexyl (2S)-2-[[2,5-difluoro-4-[[4-[2-(methoxymethyl)pyrimidin-5-yl]phenyl]sulfonylamino]benzoyl]amino]-3-[6-(1-methyl-2,4-dioxopyrido[3,4-d]pyrimidin-3-yl)-3-pyridyl]propanoate (C-17)

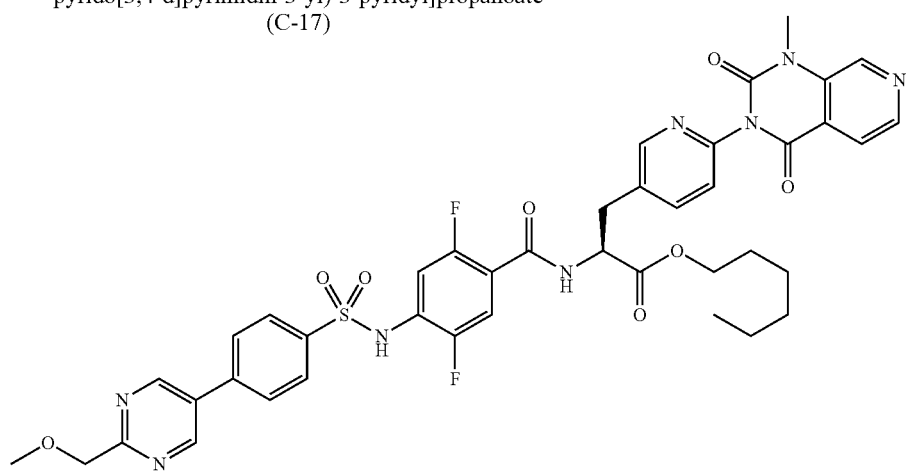

·2 TFA $^1$H NMR (400 MHz, DMSO-d$_6$) δ 10.98 (s, 1H), 9.18 (s, 2H), 8.99 (s, 1H), 8.84 (dd, J=8.0, 1.8 Hz, 1H), 8.57 (d, J=5.0 Hz, 1H), 8.46 (d, J=2.3 Hz, 1H), 8.08-8.03 (m, 2H), 8.00-7.95 (m, 2H), 7.93-7.86 (m, 2H), 7.40 (d, J=8.1 Hz, 1H), 7.31-7.24 (m, 2H), 4.76-4.69 (m, 1H), 4.63 (s, 2H), 4.09-4.02 (m, 2H), 3.59 (s, 3H), 3.40 (s, 3H), 3.27 (dd, J=14.1, 5.2 Hz, 1H), 3.12 (dd, J=14.1, 10.1 Hz, 1H), 1.58-1.48 (m, 2H), 1.32-1.18 (m, 6H), 0.83-0.77 (m, 3H); MS (ESI) m/z 843.71 (M+H)$^+$

Example 66

Synthesis of C-18

(Step 1) Cycloheptyl (2S)-2-[[2,5-difluoro-4-[[4-[2-(methoxymethyl)pyrimidin-5-yl]phenyl]sulfonylamino]benzoyl]amino]-3-[6-(1-methyl-2,4-dioxopyrido[3,4-d]pyrimidin-3-yl)-3-pyridyl]propanoate (C-18)

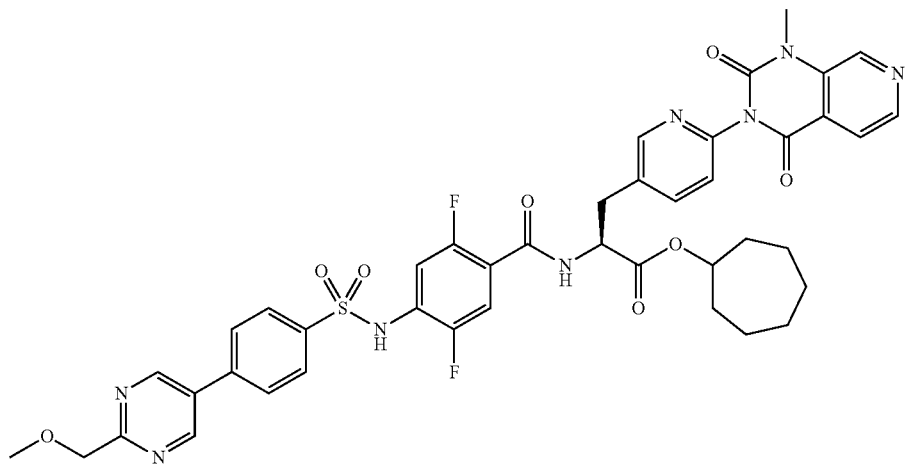

·2 TFA

¹H NMR (400 MHz, DMSO-d₆) δ 10.98 (s, 1H), 9.18 (s, 2H), 8.99 (s, 1H), 8.83 (dd, J=7.5, 1.7 Hz, 1H), 8.57 (d, J=4.9 Hz, 1H), 8.46 (d, J=2.3 Hz, 1H), 8.08-8.03 (m, 2H), 8.00-7.96 (m, 2H), 7.93-7.87 (m, 2H), 7.40 (d, J=8.1 Hz, 1H), 7.28 (dd, J=10.6, 6.2 Hz, 2H), 4.91-4.82 (m, 1H), 4.72-4.64 (m, 1H), 4.63 (s, 2H), 3.59 (s, 3H), 3.40 (s, 3H), 3.24 (dd, J=14.1, 5.5 Hz, 1H), 3.11 (dd, J=14.0, 9.7 Hz, 1H), 1.89-1.30 (m, 12H); MS (ESI) m/z 855.71 (M+H)⁺

Example 67

Synthesis of C-19

(Step 1) Methyl (2S)-2-[[2,5-difluoro-4-[[4-[2-(methoxymethyl)pyrimidin-5-yl]phenyl]sulfonyl amino]benzoyl]amino]-3-[6-(1-methyl-2,4-dioxo-pyrido[3,4-d]pyrimidin-3-yl)-3-pyridyl]propanoate (C-19)

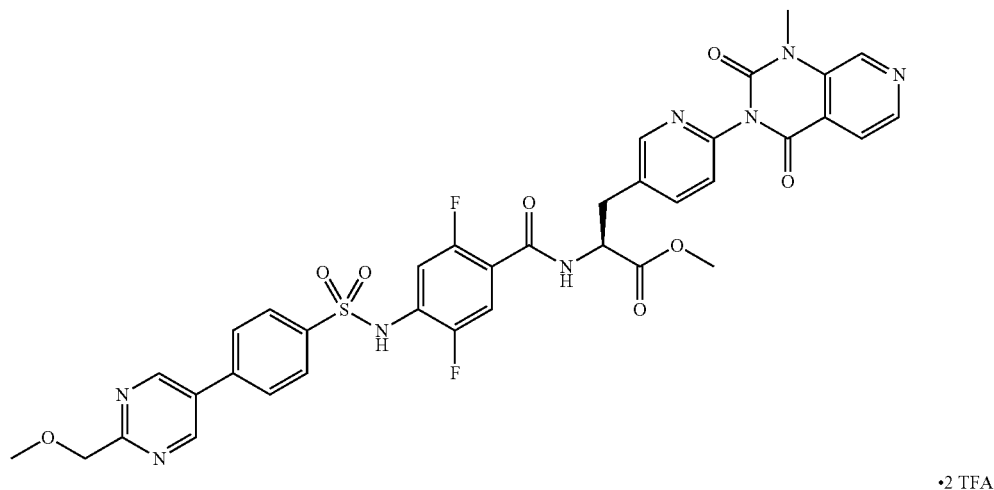 [SMILES: COCc1ncc(-c2ccc(S(=O)(=O)Nc3cc(F)c(C(=O)N[C@@H](Cc4ccc(-n5c(=O)c6ccncc6n(C)c5=O)nc4)C(=O)OC)cc3F)cc2)cn1]

·2 TFA

¹H NMR (400 MHz, DMSO-d₆) δ 11.00 (s, 1H), 9.19 (s, 2H), 8.98 (s, 1H), 8.86 (dd, J=8.1, 2.0 Hz, 1H), 8.56 (d, J=5.0 Hz, 1H), 8.49 (d, J=2.3 Hz, 1H), 8.09-8.03 (m, 2H), 8.02-7.98 (m, 2H), 7.93 (dd, J=8.2, 2.4 Hz, 1H), 7.90-7.87 (m, 1H), 7.43 (d, J=8.1 Hz, 1H), 7.31 (td, J=10.8, 10.4, 6.3 Hz, 2H), 4.82-4.75 (m, 1H), 4.63 (s, 2H), 3.68 (s, 3H), 3.60 (s, 3H), 3.40 (s, 3H), 3.30 (dd, J=14.0, 5.1 Hz, 1H), 3.15 (dd, J=14.1, 10.1 Hz, 1H); MS (ESI) m/z 773.62 (M+H)⁺

Example 68

Synthesis of C-20

(Step 1) 2,2-Dimethylpropyl (2S)-2-[[2,5-difluoro-4-[[4-[2-(methoxymethyl)pyrimidin-5-yl]phenyl]sulfonyl amino]benzoyl]amino]-3-[6-(1-methyl-2,4-dioxo-pyrido[3,4-d]pyrimidin-3-yl)-3-pyridyl]propanoate (C-20)

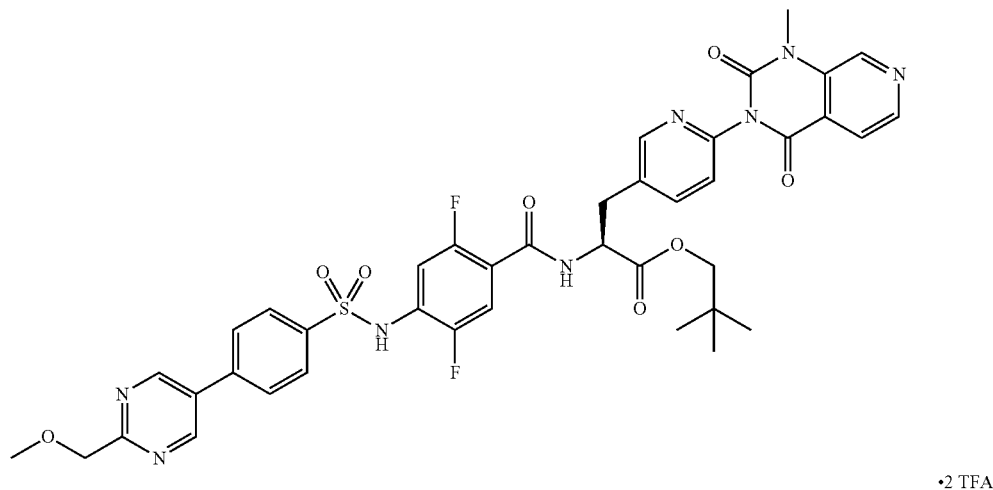 [SMILES: COCc1ncc(-c2ccc(S(=O)(=O)Nc3cc(F)c(C(=O)N[C@@H](Cc4ccc(-n5c(=O)c6ccncc6n(C)c5=O)nc4)C(=O)OCC(C)(C)C)cc3F)cc2)cn1]

·2 TFA $^1$H NMR (400 MHz, DMSO-d$_6$) δ 10.98 (s, 1H), 9.18 (s, 2H), 8.98 (s, 1H), 8.86 (dd, J=7.9, 1.7 Hz, 1H), 8.57 (d, J=5.0 Hz, 1H), 8.47 (d, J=2.3 Hz, 1H), 8.07-8.03 (m, 2H), 7.99-7.96 (m, 2H), 7.92 (dd, J=8.2, 2.4 Hz, 1H), 7.88 (d, J=5.0 Hz, 1H), 7.40 (d, J=8.0 Hz, 1H), 7.30-7.23 (m, 2H), 4.83-4.76 (m, 1H), 4.62 (s, 2H), 3.79 (d, J=1.6 Hz, 2H), 3.59 (s, 3H), 3.40 (s, 3H), 3.31 (dd, J=14.2, 5.0 Hz, 1H), 3.14 (dd, J=14.1, 10.4 Hz, 1H), 0.88 (s, 9H); MS (ESI) m/z 829.67 (M+H)$^+$

Example 69

Synthesis of C-21

(Step 1) Cyclopentylmethyl (2S)-2-[[2,5-difluoro-4-[[4-[2-(methoxymethyl)pyrimidin-5-yl]phenyl]sulfonylamino]benzoyl]amino]-3-[6-(1-methyl-2,4-dioxopyrido[3,4-d]pyrimidin-3-yl)-3-pyridyl]propanoate (C-21)

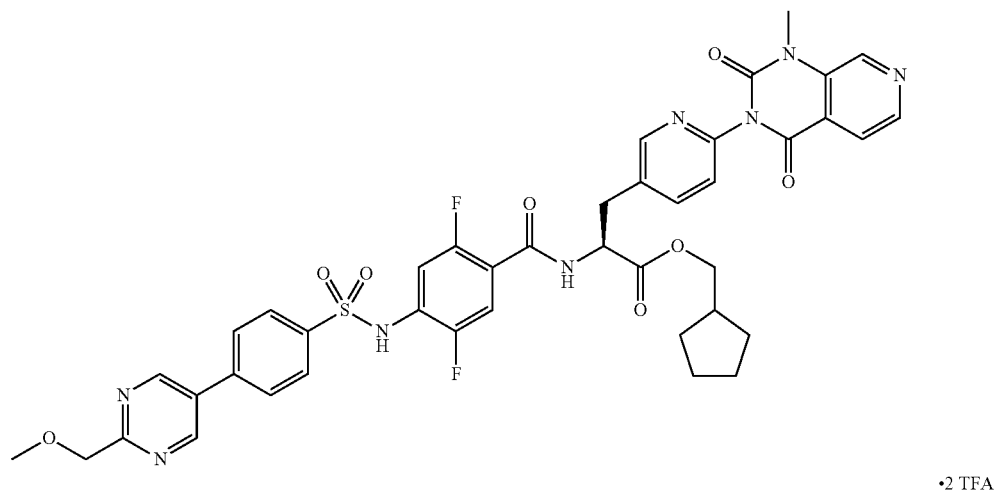 [SMILES: COCc1ncc(-c2ccc(S(=O)(=O)Nc3cc(F)c(C(=O)N[C@@H](Cc4ccc(-n5c(=O)c6ccncc6n(C)c5=O)nc4)C(=O)OCC4CCCC4)cc3F)cc2)cn1]

·2 TFA $^1$H NMR (400 MHz, DMSO-d$_6$) δ 10.99 (s, 1H), 9.18 (s, 2H), 8.99 (s, 1H), 8.85 (dd, J=7.9, 1.8 Hz, 1H), 8.57 (d, J=5.0 Hz, 1H), 8.47 (d, J=2.3 Hz, 1H), 8.08-8.04 (m, 2H), 8.00-7.96 (m, 2H), 7.94-7.87 (m, 2H), 7.43-7.39 (m, 1H), 7.31-7.24 (m, 2H), 4.78-4.70 (m, 1H), 4.63 (s, 2H), 3.97 (d, J=6.9 Hz, 2H), 3.59 (s, 3H), 3.40 (s, 3H), 3.32-3.23 (m, 1H), 3.13 (dd, J=14.1, 10.1 Hz, 1H), 2.13 (hept, J=7.4 Hz, 1H), 1.72-1.40 (m, 6H), 1.25-1.15 (m, 2H); MS (ESI) m/z 841.67 (M+H)$^+$ Example 70

Synthesis of C-22

(Step 1) 1-Adamantylmethyl (2S)-2-[[2,5-difluoro-4-[[4-[2-(methoxymethyl)pyrimidin-5-yl]phenyl]sulfonylamino]benzoyl]amino]-3-[6-(1-methyl-2,4-dioxo-pyrido[3,4-d]pyrimidin-3-yl)-3-pyridyl]propanoate (C-22)

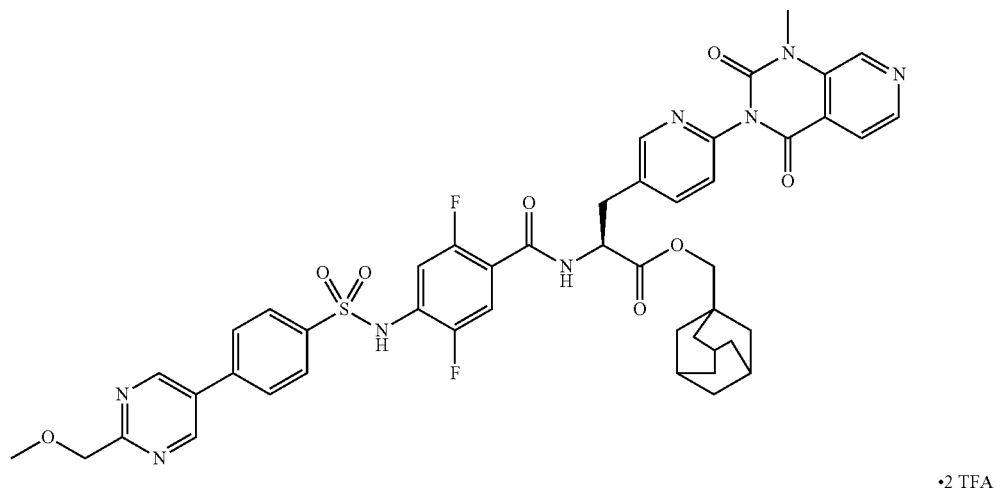 [SMILES: COCc1ncc(-c2ccc(S(=O)(=O)Nc3cc(F)c(C(=O)N[C@@H](Cc4ccc(-n5c(=O)c6ccncc6n(C)c5=O)nc4)C(=O)OCC45CC6CC(CC(C6)C4)C5)cc3F)cc2)cn1]

·2 TFA $^1$H NMR (400 MHz, DMSO-d$_6$) δ 10.98 (s, 1H), 9.19 (s, 2H), 8.99 (s, 1H), 8.84 (dd, J=8.0, 1.8 Hz, 1H), 8.57 (d, J=4.9 Hz, 1H), 8.48 (d, J=2.3 Hz, 1H), 8.08-8.03 (m, 2H), 7.99-7.95 (m, 2H), 7.94-7.86 (m, 2H), 7.43-7.37 (m, 1H), 7.32-7.22 (m, 2H), 4.83-4.74 (m, 1H), 4.63 (s, 2H), 3.67 (d, J=1.8 Hz, 3H), 3.59 (s, 3H), 3.39 (s, 3H), 3.31 (dd, J=14.1, 4.7 Hz, 1H), 3.14 (dd, J=14.1, 10.5 Hz, 1H), 2.00-1.40 (m, 14H); MS (ESI) m/z 907.76 (M+H)$^+$

Example 71

Synthesis of C-23

(Step 1) Cyclobutylmethyl (2S)-2-[[2,5-difluoro-4-[[4-[2-(methoxymethyl)pyrimidin-5-yl]phenyl]sulfonylamino]benzoyl]amino]-3-[6-(1-methyl-2,4-dioxopyrido[3,4-d]pyrimidin-3-yl)-3-pyridyl]propanoate (C-23)

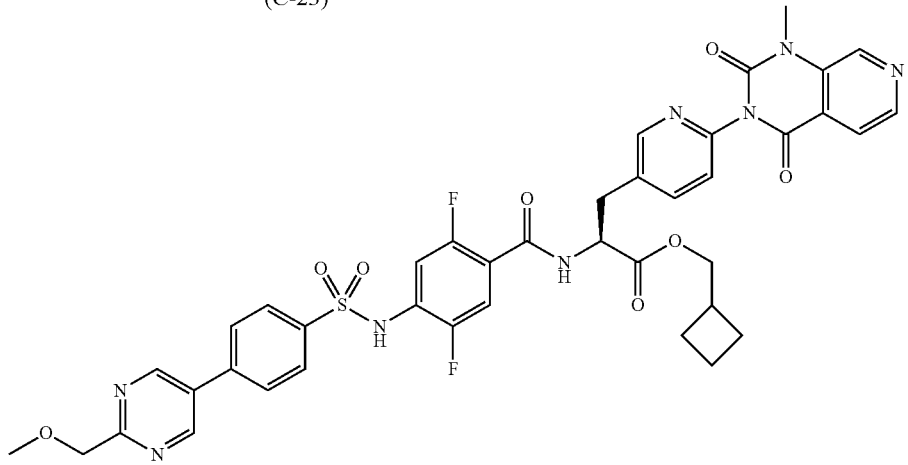

·2 TFA $^1$H NMR (400 MHz, DMSO-d$_6$) δ 10.98 (s, 1H), 9.18 (s, 2H), 8.99 (d, J=0.7 Hz, 1H), 8.86 (dd, J=7.7, 1.7 Hz, 1H), 8.57 (d, J=5.0 Hz, 1H), 8.47 (dd, J=2.4, 0.8 Hz, 1H), 8.09-8.04 (m, 2H), 8.00-7.95 (m, 2H), 7.94-7.87 (m, 2H), 7.40 (dd, J=8.0, 0.8 Hz, 1H), 7.31-7.25 (m, 2H), 4.79-4.70 (m, 1H), 4.63 (s, 2H), 4.05 (d, J=6.5 Hz, 2H), 3.59 (s, 3H), 3.40 (s, 3H), 3.27 (dd, J=14.1, 5.2 Hz, 1H), 3.13 (dd, J=14.1, 10.0 Hz, 1H), 2.61-2.52 (m, 1H), 2.00-1.91 (m, 2H), 1.87-1.66 (m, 4H); MS (ESI) m/z 827.71 (M+H)$^+$

Example 72

Synthesis of C-24

(Step 1) 2-Cyclohexylethyl (2S)-2-[[2,5-difluoro-4-[[4-[2-(methoxymethyl)pyrimidin-5-yl]phenyl]sulfonylamino]benzoyl]amino]-3-[6-(1-methyl-2,4-dioxopyrido[3,4-d]pyrimidin-3-yl)-3-pyridyl]propanoate (C-24)

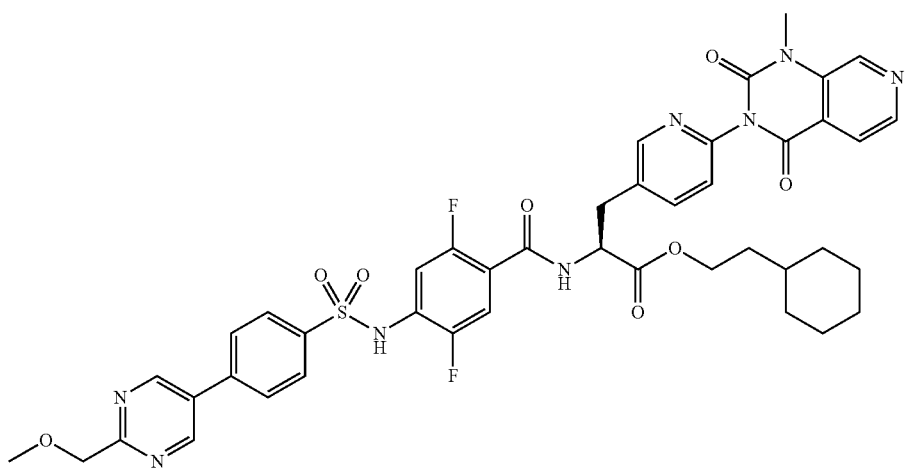

·2 TFA

¹H NMR (400 MHz, DMSO-d₆) δ 10.99 (s, 1H), 9.18 (s, 2H), 8.99 (s, 1H), 8.84 (dd, J=7.8, 1.9 Hz, 1H), 8.57 (d, J=4.9 Hz, 1H), 8.47 (dd, J=2.4, 0.8 Hz, 1H), 8.09-8.03 (m, 2H), 8.01-7.95 (m, 2H), 7.93-7.86 (m, 2H), 7.40 (dd, J=7.9, 0.8 Hz, 1H), 7.34-7.24 (m, 2H), 4.76-4.68 (m, 1H), 4.63 (s, 2H), 4.14-4.08 (m, 2H), 3.59 (s, 3H), 3.40 (s, 3H), 3.31-3.22 (m, 1H), 3.13 (dd, J=14.1, 10.1 Hz, 1H), 1.74-0.74 (m, 13H); MS (ESI) m/z 869.75 (M+H)⁺

Example 73

Synthesis of C-25

(Step 1) (1-Isobutyl-3-methyl-butyl) (2S)-2-[[2,5-difluoro-4-[[4-[2-(methoxymethyl)pyrimidin-5-yl]phenyl]sulfonylamino]benzoyl]amino]-[6-(1-methyl-2,4-dioxo-pyrido[3,4-d]pyrimidin-3-yl)-3-pyridyl]propanoate (C-25)

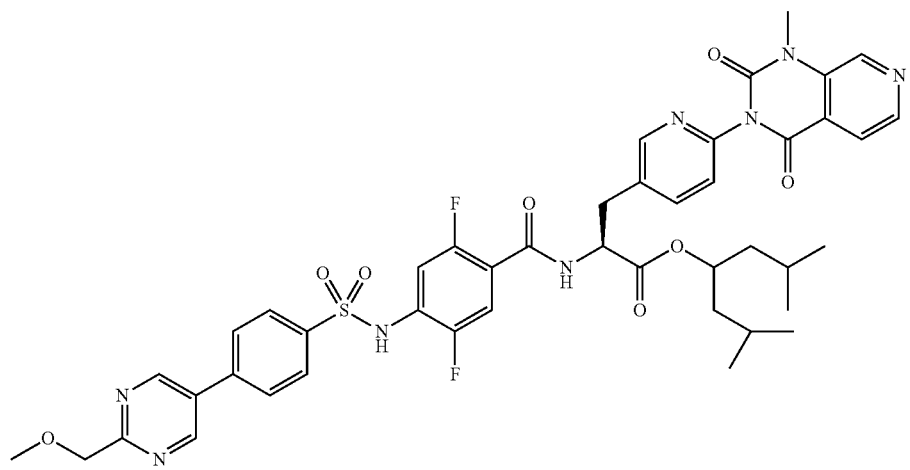

·2 TFA

MS (ESI) m/z 885.80 (M+H)⁺

Example 74

Synthesis of C-26

(Step 1) 4,4,4-Trifluorobutyl (2S)-2-[[2,5-difluoro-4-[[4-[2-(methoxymethyl)pyrimidin-5-yl]phenyl]sulfonylamino]benzoyl]amino]-3-[6-(1-methyl-2,4-dioxo-pyrido[3,4-d]pyrimidin-3-yl)-3-pyridyl]propanoate (C-26)

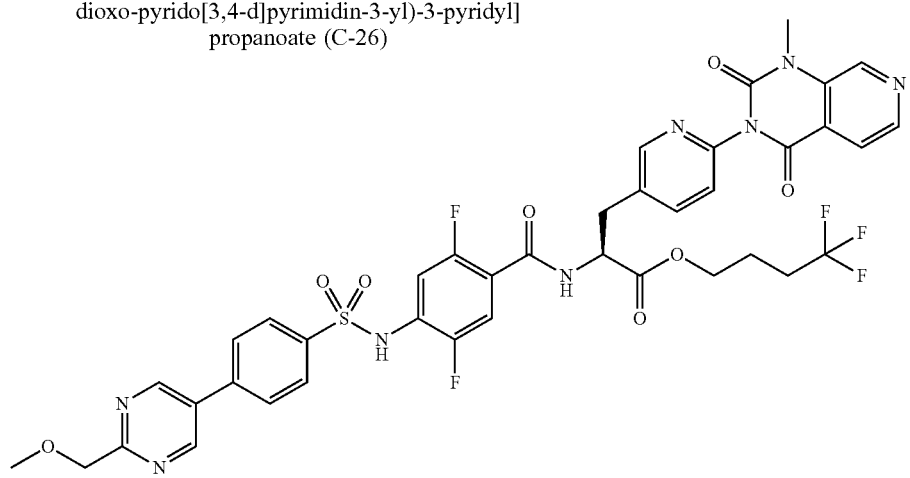

·2 TFA

¹H NMR (400 MHz, DMSO-d₆) δ 10.98 (s, 1H), 9.18 (s, 2H), 8.99 (s, 1H), 8.89 (dd, J=7.5, 1.7 Hz, 1H), 8.57 (d, J=5.0 Hz, 1H), 8.48-8.46 (m, 1H), 8.07-8.03 (m, 2H), 7.99-7.96 (m, 2H), 7.92 (dd, J=8.1, 2.4 Hz, 1H), 7.88 (dd, J=4.9, 0.8 Hz, 1H), 7.41 (dd, J=8.0, 0.7 Hz, 1H), 7.31-7.24 (m, 2H), 4.78-4.70 (m, 1H), 4.63 (s, 2H), 4.21-4.06 (m, 2H), 3.59 (s, 3H), 3.40 (s, 3H), 3.29 (dd, J=14.1, 5.1 Hz, 1H), 3.13 (dd, J=14.1, 10.1 Hz, 1H), 2.39-2.23 (m, 2H), 1.84-1.74 (m, 2H); MS (ESI) m/z 869.63 (M+H)⁺

Example 75

Synthesis of C-27

(Step 1) Cyclobutyl (2S)-2-[[2,5-difluoro-4-[[4-[2-(methoxymethyl)pyrimidin-5-yl]phenyl]sulfonylamino]benzoyl]amino]-3-[6-(1-methyl-2,4-dioxopyrido[3,4-d]pyrimidin-3-yl)-3-pyridyl]propanoate (C-27)

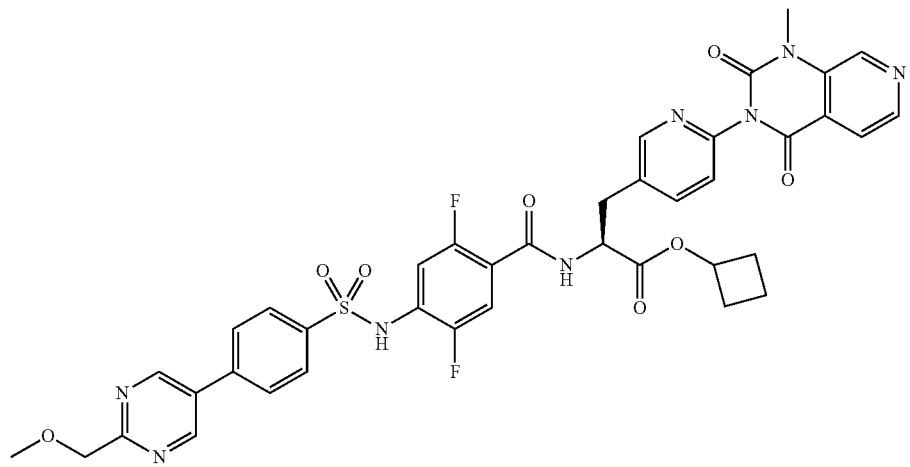

•2 TFA

¹H NMR (400 MHz, DMSO-d₆) δ 10.98 (s, 1H), 9.19 (s, 2H), 8.99 (d, J=0.8 Hz, 1H), 8.85 (dd, J=7.7, 1.7 Hz, 1H), 8.57 (d, J=5.0 Hz, 1H), 8.47 (dd, J=2.3, 0.8 Hz, 1H), 8.08-8.02 (m, 2H), 8.01-7.96 (m, 2H), 7.94-7.87 (m, 2H), 7.41 (dd, J=8.1, 0.7 Hz, 1H), 7.33-7.25 (m, 2H), 4.98-4.87 (m, 1H), 4.74-4.67 (m, 1H), 4.63 (s, 2H), 3.59 (s, 3H), 3.40 (s, 3H), 3.25 (dd, J=14.2, 5.7 Hz, 1H), 3.12 (dd, J=14.0, 9.7 Hz, 1H), 2.31-2.19 (m, 2H), 2.06-1.87 (m, 2H), 1.79-1.68 (m, 1H), 1.65-1.50 (m, 1H); MS (ESI) m/z 813.67 (M+H)⁺

Example 76

Synthesis of C-28

(Step 1) 2,2-Difluoroethyl (2S)-2-[[2,5-difluoro-4-[[4-[2-(methoxymethyl)pyrimidin-5-yl]phenyl]sulfonylamino]benzoyl]amino]-3-[6-(1-methyl-2,4-dioxopyrido[3,4-d]pyrimidin-3-yl)-3-pyridyl]propanoate (C-28)

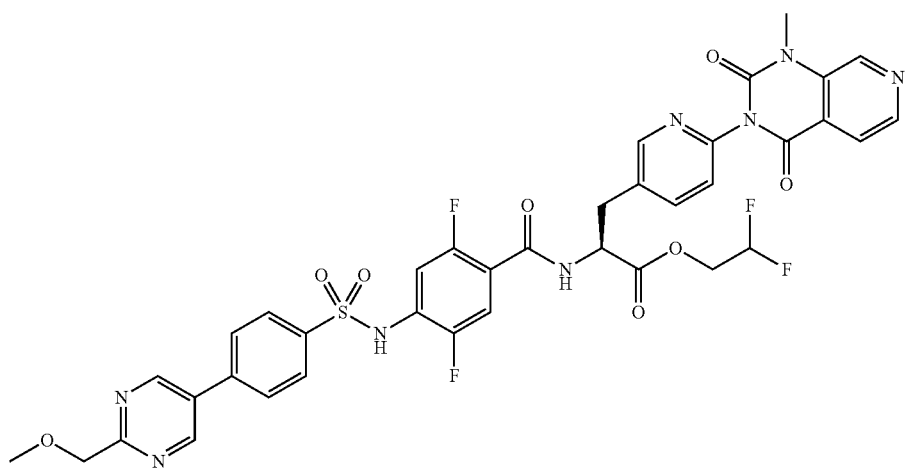

•2 TFA

¹H NMR (400 MHz, DMSO-d₆) δ 10.99 (s, 1H), 9.16 (s, 2H), 9.00 (s, 1H), 8.75 (dd, J=7.8, 3.8 Hz, 1H), 8.57 (d, J=4.9 Hz, 1H), 8.47 (d, J=2.5 Hz, 1H), 8.07-7.94 (m, 4H), 7.90 (d, J=5.0 Hz, 1H), 7.75 (dd, J=8.2, 2.5 Hz, 1H), 7.47 (d, J=8.3 Hz, 1H), 7.38 (dd, J=10.3, 6.4 Hz, 1H), 7.29 (dd, J=11.4, 6.3 Hz, 1H), 4.89 (td, J=8.2, 4.9 Hz, 1H), 3.61 (s, 3H), 3.42-2.99 (m, 8H), 2.20-2.12 (m, 2H), 2.05-1.92 (m, 2H); MS (ESI) m/z 823.63 (M+H)⁺

Example 77

Synthesis of C-29

(Step 1) 3-Cyclohexylpropyl (2S)-2-[[2,5-difluoro-4-[[4-[2-(methoxymethyl)pyrimidin-5-yl]phenyl]sulfonylamino]benzoyl]amino]-3-[6-(1-methyl-2,4-dioxo-pyrido[3,4-d]pyrimidin-3-yl)-3-pyridyl]propanoate (C-29)

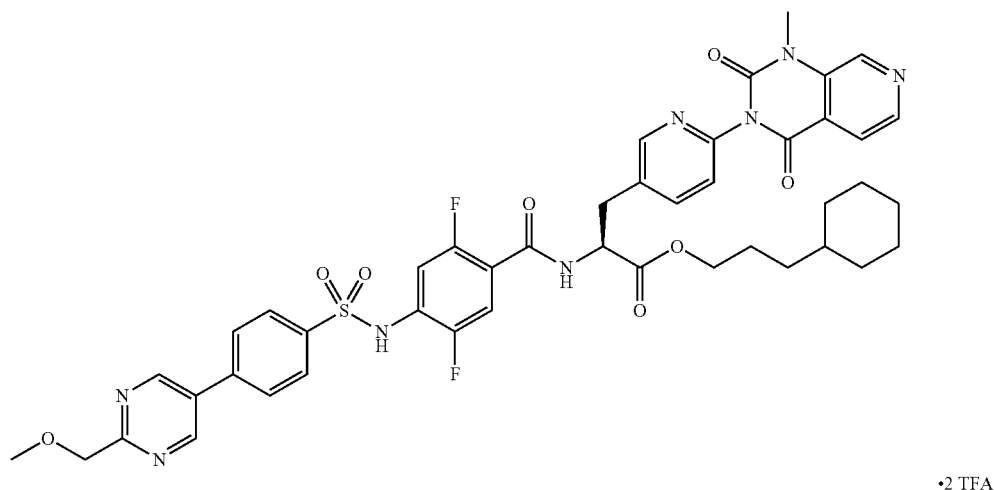 [SMILES: COCc1ncc(-c2ccc(S(=O)(=O)Nc3cc(F)c(C(=O)N[C@@H](Cc4ccc(-n5c(=O)c6ccncc6n(C)c5=O)nc4)C(=O)OCCCC4CCCCC4)cc3F)cc2)cn1]

·2 TFA

¹H NMR (400 MHz, DMSO-d₆) δ 10.99 (s, 1H), 9.18 (s, 2H), 8.99 (s, 1H), 8.84 (dd, J=7.8, 1.8 Hz, 1H), 8.57 (d, J=5.0 Hz, 1H), 8.46 (d, J=2.3 Hz, 1H), 8.09-8.02 (m, 2H), 8.01-7.95 (m, 2H), 7.94-7.86 (m, 2H), 7.40 (d, J=8.1 Hz, 1H), 7.32-7.24 (m, 2H), 4.76-4.67 (m, 1H), 4.63 (s, 2H), 4.08-4.01 (m, 2H), 3.59 (s, 3H), 3.40 (s, 3H), 3.31-3.21 (m, 1H), 3.17-3.07 (m, 1H), 1.68-1.49 (m, 7H), 1.22-0.97 (m, 6H), 0.85-0.70 (m, 2H); MS (ESI) m/z 883.76 (M+H)⁺

Example 78

Synthesis of C-30

(Step 1) Isopentyl (2S)-2-[[2,5-difluoro-4-[[4-[2-(methoxymethyl)pyrimidin-5-yl]phenyl]sulfonylamino]benzoyl]amino]-3-[6-(1-methyl-2,4-dioxopyrido[3,4-d]pyrimidin-3-yl)-3-pyridyl]propanoate (C-30)

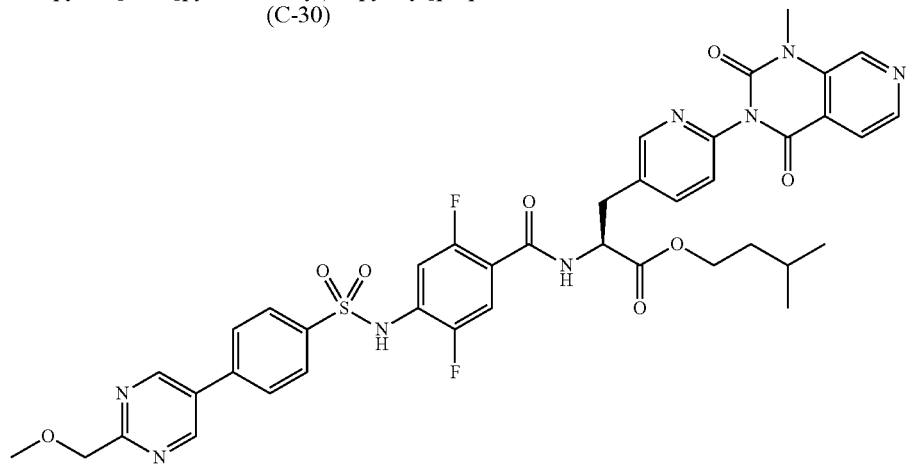

•2 TFA $^1$H NMR (400 MHz, DMSO-d$_6$) δ 10.98 (s, 1H), 9.18 (s, 2H), 8.99 (d, J=0.7 Hz, 1H), 8.86-8.83 (m, 1H), 8.57 (d, J=5.0 Hz, 1H), 8.47-8.45 (m, 1H), 8.07-8.04 (m, 2H), 8.00-7.96 (m, 2H), 7.93-7.86 (m, 2H), 7.40 (dd, J=8.1, 0.7 Hz, 1H), 7.31-7.23 (m, 2H), 4.76-4.68 (m, 1H), 4.63 (s, 2H), 4.10 (t, J=6.7 Hz, 2H), 3.59 (s, 3H), 3.40 (s, 3H), 3.26 (dd, J=14.0, 5.2 Hz, MX 3.12 (dd, J=14.1, 10.0 Hz, 1H), 1.71-1.56 (m, 1H), 1.45 (q, J=6.8 Hz, 2H), 0.85 (d, J=6.6 Hz, 6H); MS (ESI) m/z 829.71 (M+H)$^+$

Example 79

Synthesis of C-31

(Step 1) 2-Cyclopentylethyl (2S)-2-[[2,5-difluoro-4-[[4-[2-(methoxymethyl)pyrimidin-5-yl]phenyl]sulfonylamino]benzoyl]amino]-3-[6-(1-methyl-2,4-dioxopyrido[3,4-d]pyrimidin-3-yl)-3-pyridyl]propanoate (C-31)

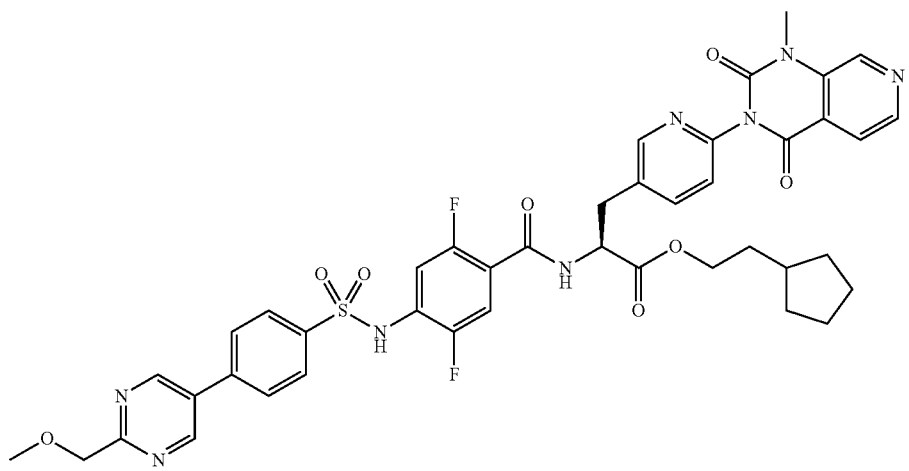

•2 TFA

MS (ESI) m/z 855.99 (M+H)$^+$

Further, by the following methods, intermediate compounds M-26 to M-30, compounds A-24 to A-30 and compounds C-32 to C-46 were synthesized.

Example 80

Synthesis of 4-[[4-(4-ethyltriazol-1-yl)phenyl]sulfonylamino]-2,5-difluorobenzoic acid (M-26)

(Step 1) Methyl 4-[[4-(4-ethyltriazol-1-yl)phenyl]sulfonylamino]-2,5-difluoro-benzoate

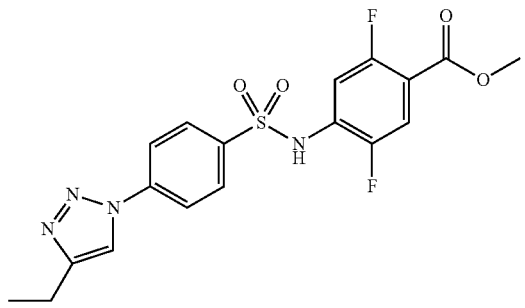 [SMILES: CCc1cn(-c2ccc(S(=O)(=O)Nc3cc(F)c(C(=O)OC)cc3F)cc2)nn1]

L-proline (1.6 g, 20 mol %, 14 mmol), CuSO$_4$.5H$_2$O g, 10 mol %, 6.8 mmol), sodium ascorbate (2.7 g, 20 mol %, 14 mmol), sodium azide (6.50 g, 100 mmol), potassium carbonate (11.4 g, 82.6 mmol), methyl 2-pentynoate (6.76 g, 69 mmol), methyl 2,5-difluoro-4-[(4-iodophenyl)sulfonylamino]benzoate obtained in Example 13 (Step 2) (31.2 g, 69 mmol), DMSO (225 mL), and water (25 mL) were sequentially added in a 1 vial. The resulting mixture was gently stirred at 65° C. overnight, and a mixture of concentrated ammonium water (500 mL), water (1.0 L), and ethyl acetate (400 mL) was added. The aqueous phase was extracted with ethyl acetate (600 mL×10), the organic phase was washed with a saturated saline solution (3.0 L), dried over sodium sulfate and filtered, and the solvent was distilled off under reduced pressure to obtain the title compound (14.2 g, 49%).
$^1$H NMR (CD$_3$OD, 400 MHz): δ 8.37 (s, 1H), 8.13-8.06 (m, 2H), 8.10-7.96 (m, 2H), 7.45-7.04 (m, 2H), 3.27 (s, 3H), 1.72-1.64 (m, 2H), 1.04-1.02 (m, 3H).

Step 2) 4-[[4-(4-Ethyltriazol-1-yl)phenyl]sulfonylamino]-2,5-difluorobenzoic acid (M-26)

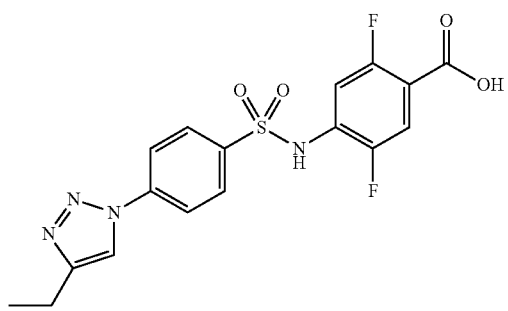 [SMILES: CCc1cn(-c2ccc(S(=O)(=O)Nc3cc(F)c(C(=O)O)cc3F)cc2)nn1]

The compound obtained in step 1 (14.1 g, 33.4 mmol) was dissolved in methanol (60 mL), a 2 N aqueous solution of lithium hydroxide (30 mL) was added, then the resulting mixture was stirred at room temperature for 30 minutes, then completion of the reaction was verified, and 4 N hydrochloric acid was added for adjustment of the pH to 4 to 5. The precipitated white solid was filtered and the obtained solid was dried to obtain the title compound as a white solid.
$^1$H NMR (DMSO-d$_6$, 400 MHz): δ 13.41 (br s, 1H), 11.10 (br s, 1H), 8.70 (s, 1H), 8.13 (d, J=8.8 Hz, 2H), 8.04 (d, J=8.8 Hz, 2H), 7.63-7.59 (m, 1H), 7.30-7.25 (m, 1H), 2.73 (q, J=7.2 Hz, 2H), 1.26 (t, J=7.2 Hz, 3H); MS (ESI) m/z 409 (M+H)$^+$.

Example 81

Synthesis of 2,5-Difluoro-4-[(4-tetrahydropyran-4-ylphenyl)sulfonylamino]benzoic acid (M-27)

(Step 1) Methyl 4-{[4-(3,6-dihydro-2H-pyran-4-yl)phenyl]sulfonylamino}-2,5-difluorobenzoate

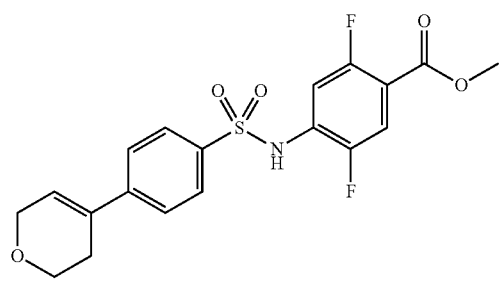 [SMILES: COC(=O)c1cc(F)c(NS(=O)(=O)c2ccc(C3=CCOCC3)cc2)cc1F]

Methyl 2,5-difluoro-4-[(4-iodophenyl)sulfonylamino]benzoate obtained in step 2 of Example 13 (0.2 g, 0.44 mmol) was dissolved in N,N'-dimethylformamide (5 mL) and water (1 mL), 3,6-dihydro-2H-pyran-4-boronic acid pinacol ester (0.11 g, 0.53 mmol), [1,1'-bis(diphenylphosphino)ferrocene]dichloropalladium(II) (18 m g, 0.022 mmol), and potassium acetate (0.15 g, 1.1 mmol) were added thereto, and the resulting mixture was stirred at 100° C. for 4 hours. The reaction solution was cooled to room temperature and filtered through Celite, and the filtrate was concentrated under reduced pressure. The obtained residue was purified by silica gel column chromatography (hexane/ethyl acetate). MS (ESI) m/z 410 (M+H)$^+$.

Step 2) 2,5-Difluoro-4-[(4-tetrahydropyran-4-ylphenyl)sulfonylamino]benzoic acid (M-27)

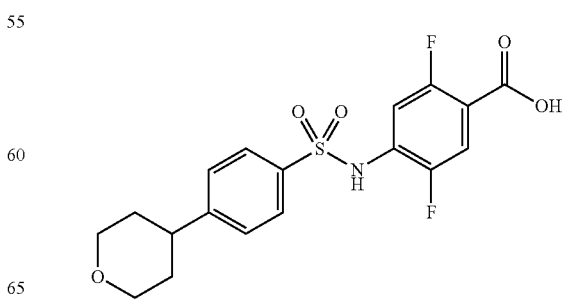

The compound obtained in step 1 was dissolved in methanol (20 mL), 10% palladium/carbon of a catalyst amount was added thereto, and the resulting mixture was stirred in the presence of hydrogen gas at room temperature overnight. The reaction solution was filtered, and the filtrate was concentrated. A 2 N solution of sodium hydroxide (4 mL) and methanol were added to the obtained residue, and the resulting mixture was stirred at room temperature for 3 hours. The reaction liquid was neutralized with 2 N hydrochloric acid, purified by reverse phase HPLC (an H₂O/CH₃CN system including 0.1% TFA), and freeze-dried to obtain the title compound.

¹H NMR (400 MHz, DMSO-d₆) δ 10.97 (s, 1H) 7.84-7.77 (m, 2H), 7.60 (dd, J=10.7, 6.6 Hz, 1H), 7.53-7.47 (m, 2H), 7.24 (dd, J=11.8, 6.4 Hz, 1H), 3.98-3.88 (m, 2H), 3.46-3.38 (m, 2H), 2.93-2.80 (m, 1H), 1.77-1.54 (m, 4H); MS (ESI) m/z 398 (M+H)⁺.

Example 82

Synthesis of 2,5-difluoro-4-{[4-(2-isopropylpyrimidin-5-yl)phenyl]sulfonylamino}Benzoic acid (M-28)

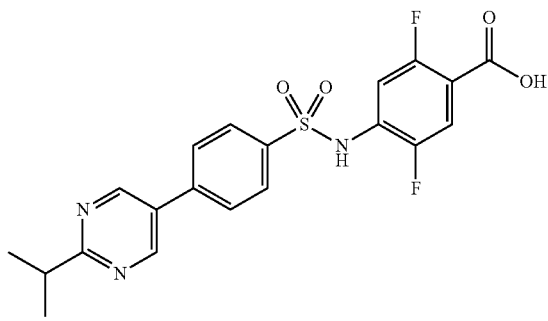 [SMILES: CC(C)c1ncc(-c2ccc(S(=O)(=O)Nc3cc(F)c(C(=O)O)cc3F)cc2)cn1]

2-Isopropylpyrimidin-5-ylboronic acid was used instead of 3,6-dihydro-2H-pyran-4-boronic acid pinacol ester obtained in step 1 of Example 81, and the title compound was synthesized by a similar method. MS (ESI) m/z 434 (M+H)⁺.

Example 83

Synthesis of methyl (2S)-2-amino-3-[5-(1,3,4-trimethyl-2,6-dioxopyrimidin-5-5-yl)-2-pyridyl]propanoate (M-29)

(Step 1) Methyl (2S)-2-(tert-butoxycarbonylamino)-3-[(5-(4,4,5,5-tetramethyl-1,3,2-dioxaboran-2-yl)-2-pyridyl]-propanoate

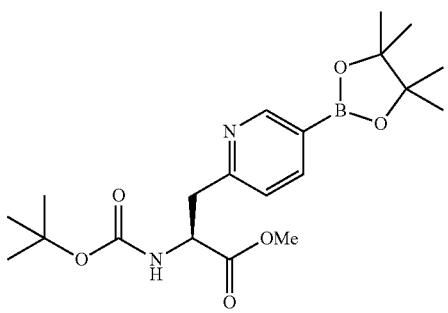 [SMILES: COC(=O)[C@H](Cc1ccc(B2OC(C)(C)C(C)(C)O2)cn1)NC(=O)OC(C)(C)C]

Methyl (2S)-3-(5-bromo-2-pyridyl)-2-(tert-butoxycarbonylamino)propanoate (556 mg, 1.55 mmol) was dissolved in N,N'-dimethylformamide (10 mL), bis(pinacolato)diborane (588 mg, 2.32 mmol), [1,1'-bis(diphenylphosphino)ferrocene]dichloropalladium (II) (57 m g, 0.078 mmol), and potassium acetate (456 mg, 4.64 mmol) were added thereto, and the resulting mixture was stirred at 80° C. overnight. The reaction solution was cooled to room temperature and filtered through Celite, and the filtrate was concentrated under reduced pressure. Ethyl acetate was added to the obtained residue, and the mixture was sequentially washed with water and a saturated saline solution. The solvent was distilled off under reduced pressure, and the obtained residue was purified by silica gel column chromatography (hexane/ethyl acetate) to obtain the title compound. MS (ESI) m/z 407 (M+H)⁺.

(Step 2) (2S)-2-Amino-3-[5-(1,3,4-trimethyl-2,6-dioxopyrimidin-5-5-yl)-2-pyridyl]propanoate (M-29)

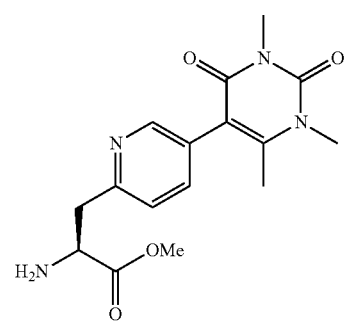 [SMILES: COC(=O)[C@@H](N)Cc1ccc(-c2c(C)n(C)c(=O)n(C)c2=O)cn1]

The compound obtained in step 1 was used instead of N-(tert-butoxycarbonyl)-4-(4,4,5,5-tetramethyl-1,3,2-dioxaborolan-2-yl)-L-phenylalaninate obtained in step 5 of Example 2, and the title compound was synthesized by a similar method.

MS (ESI) m/z 333 (M+H)⁺.

Example 84

Synthesis of Methyl 3-[6-(1-methyl-2,4-dioxo-1,4-dihydropyrido[3,4-d]pyrimidin-3(2H)-yl)pyridin-3-yl]-L-alaninate (M-30)

(Step 1) Methyl 3-({[(5-bromopyridin-2-yl)amino]carbonyl}amino)isonicotinate

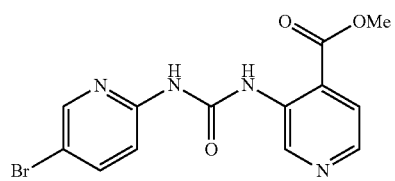 [SMILES: COC(=O)c1ccncc1NC(=O)Nc1ccc(Br)cn1]

Methyl 3-aminoisonicotinate (4.80 g, 32.0 mmol) and diisopropylethylamine (8.20 g, 64.0 mmol) were dissolved in methylene chloride (100 mL), a solution of triphosgene (3.10 g, 10.4 mmol) in methylene chloride (20 mL) was added thereto, and the resulting mixture was stirred at 0° C. for 3 hours. 5-Bromopyridin-2-amine (4.60 g, 26.6 mmol) was added to this solution, and the resulting mixture was further stirred at room temperature for 12 hours. The reaction solution was concentrated under reduced pressure, then ethyl acetate was added thereto, the resulting mixture was washed with a saturated aqueous solution of sodium hydrogen carbonate, water, and a saturated saline solution, and dried over anhydrous sodium sulfate. The solvent was removed under reduced pressure, and the obtained residue was purified by silica gel column chromatography (petroleum ether/ethyl acetate=1:1 to 1:2) to obtain the title compound (6.2 g, 67%).

$^1$H NMR (400 MHz, DMSO-$d_6$): δ 11.0 (s, 1H), 10.3 (s, 1H), 9.4 (s, 1H), 8.39 (d, J=5.2 Hz, 2H), 8.0 (d, J=8.8 Hz, 1H), 7.54 (d, J=4.8 Hz, 1H), 7.48 (d, J=8.8 Hz, 1H), 3.92 (s, 3H).

(Step 2) 3-(5-Bromopyridin-2-yl)-1-methylpyrido[3,4-d]pyrimidine-2,4(1H,3H)-dione

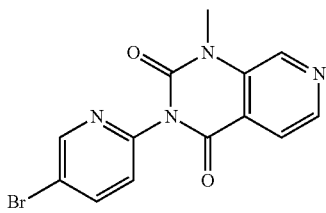 [SMILES: Cn1c(=O)n(-c2ccc(Br)cn2)c(=O)c2ccncc21]

Methyl 3-({[(5-bromopyridin-2-yl)amino]carbonyl}amino)isonicotinate (6.20 g, 17.7 mmol) was dissolved in N,N'-dimethylformamide (60 mL), an aqueous solution (4.0 mL) of potassium carbonate (600 mg, 4.34 mmol) was added thereto, and the resulting mixture was stirred at room temperature for 3 hours. p-Toluenesulfonic acid methyl ester (4.40 g, 23.6 mmol) and potassium carbonate (3.00 g, 21.7 mmol) were added to the reaction solution, and the resulting mixture was stirred at room temperature for 12 hours. The reaction solution was diluted with water (100 mL) and extracted with ethyl acetate (100 mL×3). The extracts were combined, washed with a saturated saline solution, and dried over anhydrous sodium sulfate, and then the solvent was removed under reduced pressure. The obtained residue was purified by silica gel column chromatography (petroleum ether/ethyl acetate=1:1) to obtain the title compound (5.2 g, 88%).

$^1$H NMR (400 MHz, DMSO-$d_6$): δ 9.00 (s, 1H), 8.77 (d, J=2.4 Hz, 1H), 8.58 (d, J=4.8 Hz, 1H), 8.32-8.30 (m, 1H), 7.91 (d, J=4.8 Hz, 1H), 7.52 (d, J=8.8 Hz, 1H), 3.61 (s, 3H).

(Step 3) Methyl N-(tert-butoxycarbonyl)-3-[6-(1-methyl-2,4-dioxo-1,4-dihydropyrido[3,4-d]pyrimidin-3(2H)-yl)pyridin-3-yl]-L-alaninate Zinc (2.40 g, 36.7 mmol) was heated at 200° C. for 30 minutes and cooled to room temperature, this operation was repeated 3 times, then a solution of dibromoethane (0.340 g, 1.82 mmol) in N,N'-dimethylformamide (5.0 mL) was added. An operation of heating the obtained reaction mixture to 90° C. and cooling the reaction mixture to room temperature was repeated twice, then chlorotrimethylsilane (40.0 mg, 0.364 mmol) was added, and the resulting mixture was stirred at room temperature for 30 minutes. A solution of methyl N-(tert-butoxycarbonyl)-3-iodin-L-alaninate (2.00 g, 6.08 mmol) in N,N'-dimethylformamide (5.0 mL) was added dropwise, the resulting mixture was stirred at 35° C. for 2.5 hours, then 3-(5-bromopyridin-2-yl)-1-methylpyrido[3,4-d]pyrimidine-2,4(1H, 3H)-dione (2.60 g, 7.80 mmol) and bis(triphenylphosphine)palladium(II) chloride (230 mg, 0.328 mmol) were further added to the reaction solution, and the resulting mixture was stirred at 70° C. for 2 hours. The reaction solution was cooled to room temperature, diluted with water, and extracted with ethyl acetate (20 mL×3). The extracts were combined, washed with a saturated saline solution, dried over anhydrous sodium sulfate, and then the solvent was removed. The obtained residue was purified by silica gel column chromatography (petroleum ether/ethyl acetate=1:1 to 1:2) to obtain the title compound (300 mg, 11%).

$^1$H NMR (400 MHz, CDCl$_3$): δ 8.83 (s, 1H), 8.62 (d, J=3.6 Hz, 1H), 8.46 (s, 1H), 8.05 (d, J=3.2 Hz, 1H), 7.75 (d, J=4.4 Hz, 1H), 7.29-7.27 (m, 1H), 5.16-5.12 (m, 1H), 4.69-4.67 (m, 1H), 3.76 (s, 3H), 3.72 (s, 3H), 3.23-3.20 (m, 2H), 1.45 (s, 9H).

(Step 4) Methyl 3-[6-(1-methyl-2,4-dioxo-1,4-dihydropyrido[3,4-d]pyrimidin-3(2H)-yl)pyridin-3-yl]-L-alaninate (M-30)

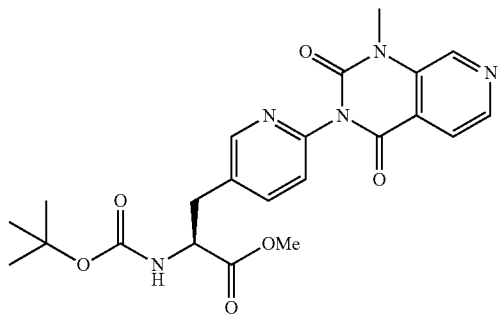 [SMILES: COC(=O)[C@H](Cc1ccc(-n2c(=O)c3ccncc3n(C)c2=O)nc1)NC(=O)OC(C)(C)C]

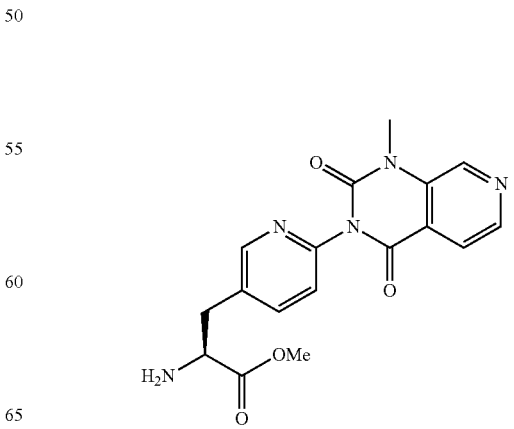

4 N Hydrochloric acid/ethyl acetate (5.0 mL) was added to methyl N-(tert-butoxycarbonyl)-3-[6-(1-methyl-2,4-dioxo-1,4-dihydropyrido[3,4-d]pyrimidin-3(2H)-yl)pyridin-3-yl]-L-alaninate (300 mg, 0.659 mmol), and the resulting mixture was stirred at room temperature for 1 hour. The obtained white solid was filtered and dried under reduced pressure to obtain a hydrochloride of the title compound (M-30) (253 mg, 98%).

$^{1}$H NMR (400 MHz, CD$_{3}$OD): δ 9.29 (s, 1H), 8.77 (d, J=6.0 Hz, 1H), 8.62 (d, J=2.0 Hz, 1H), 8.57 (d, J=5.6 Hz, 1H), 8.09 (dd, J=8.0, 2.0 Hz, 1H), 7.64 (dd, J=15.6, 8.0 Hz, 1H), 4.55-4.51 (m, 1H), 3.88 (s, 3H), 3.76 (s, 3H), 3.52-3.48 (m, 1H), 3.46-3.41 (m, 1H); MS (ESI) m/z 356 (M+H)$^{+}$.

Example 85

(2S)-2-[[2,5-difluoro-4-[[4-[2-isopropoxymethyl)pyrimidin-5-yl]phenyl]sulfonylamino]benzoyl]amino]-3-[4-(1-methyl-2,4-dioxo-pyrido[3,4-d]pyrimidin-3-yl)phenyl]propanoic acid (A-24)

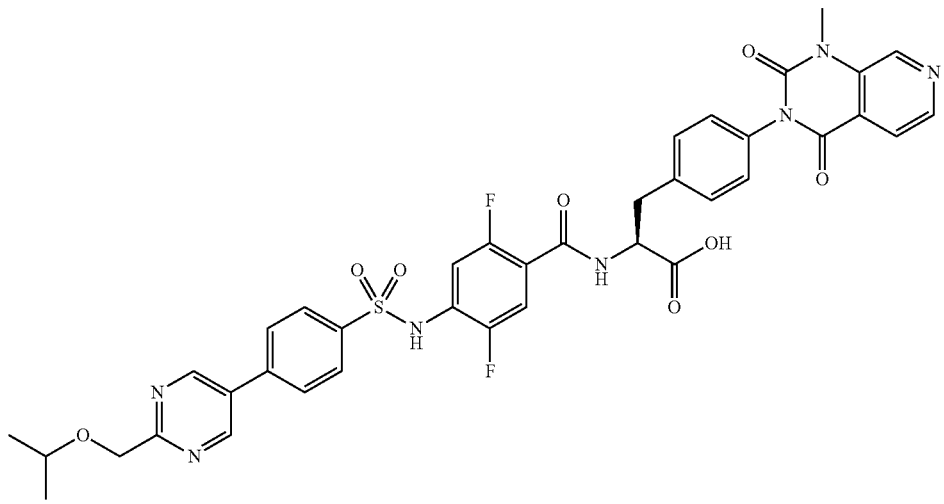 [SMILES: CC(C)OCc1ncc(-c2ccc(S(=O)(=O)Nc3cc(F)c(C(=O)N[C@@H](Cc4ccc(-n5c(=O)c6ccncc6n(C)c5=O)cc4)C(=O)O)cc3F)cc2)cn1]

The title compound was obtained by a method similar to step 1 of Example 27 by using methyl 4-(1-methyl-2,4-dioxo-1,4-dihydropyrido[3,4-d]pyrimidin-3 (2H)-yl)-L-phenylalaninate (M-8) and 2,5-difluoro-4-[[4-[2-(isopropoxymethyl)pyrimidin-5-yl]phenyl]sulfonylamino]benzoic acid (M-19).

$^{1}$H NMR (400 MHz, DMSO-d6) δ 10.97 (s, 1H), 9.16 (s, 2H), 8.96 (s, 1H), 8.60 (dd, J=8.0, 2.6 Hz, 1H), 8.55 (d, J=4.9 Hz, 1H), 8.09-8.01 (m, 2H), 8.00-7.94 (m, 2H), 7.87 (d, J=4.9 Hz, 1H), 7.36 (d, J=8.3 Hz, 2H), 7.34-7.23 (m, 2H), 7.21 (d, J=8.3 Hz, 1H), 4.68-4.58 (m, 4H), 3.77 (sep, J=6.1 Hz, 1H), 3.58 (s, 3H), 3.25-3.18 (m, 1H), 3.12-3.01 (m, 1H), 1.15 (d, J=6.1 Hz, 6H); MS (ESI) m/z 786 (M+H)$^{+}$.

Example 86

(2S)-2-[[2,5-Difluoro-4-[[4-(2-tetrahydropyran-4-ylpyrimidin-5-yl)phenyl]sulfonylamino]benzoyl]amino]-3-[4-(1,3,4-trimethyl-2,6-dioxopyrimidin-5-yl)phenyl]propanoic acid (A-25)

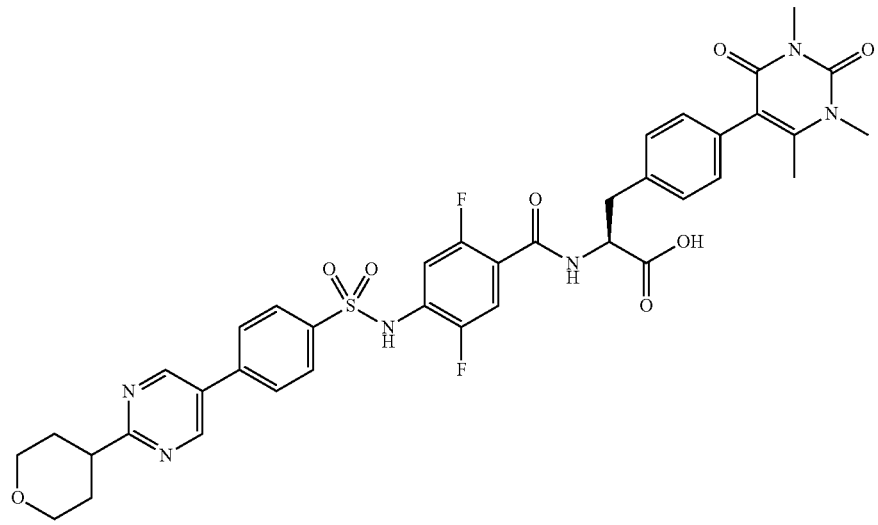 [SMILES: Cc1c(-c2ccc(C[C@H](NC(=O)c3cc(F)c(NS(=O)(=O)c4ccc(-c5cnc(C6CCOCC6)nc5)cc4)cc3F)C(=O)O)cc2)c(=O)n(C)c(=O)n1C]

The title compound was obtained by a method similar to step 1 of Example 27 by using methyl (2S)-2 amino-3-[4-(1,3,4-trimethyl-2,6-dioxo-pyrimidin-5-yl)phenyl]propanoate (M-2) and 2,5-difluoro-4-[[4-(2-tetrahydropyran-4-ylpyrimidin-5-yl)phenyl]sulfonylamino]benzoic acid (M-11).

$^1$H NMR (400 MHz, DMSO-d6) δ 10.95 (s, 1H), 9.14 (s, 2H), 8.54 (dd, J=8.0, 2.6 Hz, 1H), 8.13-7.99 (m, 2H), 7.99-7.81 (m, 2H), 7.40-7.16 (m, 4H), 7.16-6.65 (m, 2H), 4.85-4.47 (m, 1H), 4.22-3.89 (m, 2H), 3.89-3.54 (m, 2H), 3.38 (s, 3H), 3.29-3.08 (m, 5H), 3.00 (dd, J=13.9, 9.9 Hz, 1H), 2.05 (s, 3H), 2.00-1.64 (m, 4H); MS (ESI) m/z 775 (M+H)$^+$.

Example 87

(2S)-2-[[2,5-Difluoro-4-[(4-tetrahydropyran-4-yl-phenyl)sulfonylamino]benzoyl]amino]-3-[4-(1,3,4-trimethyl-2,6-dioxopyrimidin-5-yl)phenyl]propanoic acid (A-26)

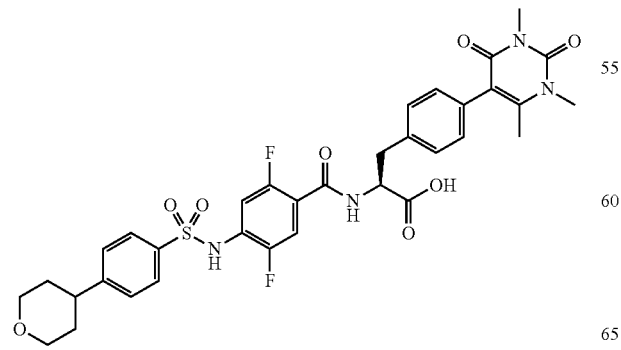

The title compound was obtained by a method similar to step 1 of Example 27 by using methyl (2S)-2 amino-3-[4-(1,3,4-trimethyl-2,6-dioxo-pyrimidin-5-yl)phenyl]propanoate (M-2) and 2,5-difluoro-4-[(4-tetrahydropyran-4-ylphenyl)sulfonylamino]benzoic acid (M-27).

$^1$H NMR (400 MHz, DMSO-d6) δ 10.72 (s, 1H), 8.45 (dd, J=8.0, 2.7 Hz, 1H), 7.70 (d, J=8.4 Hz, 2H), 7.42 (d, J=8.4 Hz, 2H), 7.30-7.17 (m, 4H), 7.17-6.88 (m, 2H), 4.67-4.42 (m, 1H), 3.97-3.76 (m, 2H), 3.68-3.25 (m, 5H), 3.14 (s, 3H), 3.13-3.07 (m, 1H), 3.00-2.86 (m, 1H), 2.86-2.68 (m, 1H), 2.00 (m, 3H), 1.75-1.46 (m, 4H); MS (ESI) m/z 697 (M+H)$^+$.

Example 88

(2S)-2-[[2,5-Difluoro-4-[[(4-(2-isopropylpyrimidin-5-yl)phenyl]sulfonylamino]benzoyl]amino]-3-[4-(1,3,4-trimethyl-2,6-dioxopyrimidin-5-yl)phenyl]propanoic acid (A-27)

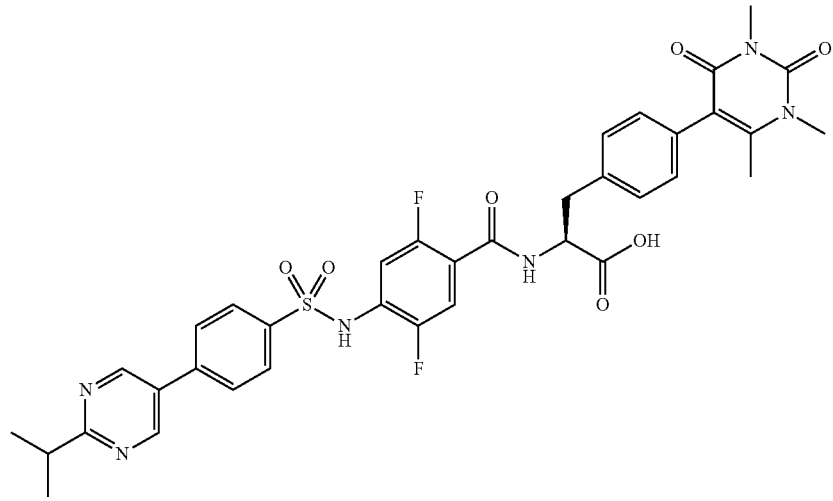 [SMILES: Cc1c(-c2ccc(C[C@H](NC(=O)c3cc(F)c(NS(=O)(=O)c4ccc(-c5cnc(C(C)C)nc5)cc4)cc3F)C(=O)O)cc2)c(=O)n(C)c(=O)n1C]

The title compound was obtained by a method similar to step 1 of Example 27 by using methyl (2S)-2-amino-3-[4-(1,3,4-trimethyl-2,6-dioxo-pyrimidin-5-yl)phenyl]propanoate (M-2) and 2,5-difluoro-4-{[4-(2-isopropylpyrimidin-5-yl)phenyl]sulfonylamino}Benzoic acid (M-28).

$^1$H NMR (400 MHz, DMSO-d6) δ 10.95 (s, 1H), 9.11 (s, 2H), 8.53 (dd, J=8.0, 2.6 Hz, 1H), 8.02 (d, J=8.6 Hz, 2H), 7.99-7.84 (m, 2H), 7.40-7.16 (m, 4H), 7.16-6.94 (m, 2H), 4.76-4.35 (m, 1H), 3.37 (s, 3H), 3.28-3.10 (m, 5H), 3.00 (dd, J=13.9, 9.9 Hz, 1H), 2.05 (s, 3H), 1.31 (d, J=6.9 Hz, 6H); MS (ESI) m/z 733 (M+H)$^+$.

Example 89

(2S)-2-[[2,5-Difluoro-4-[[4-(2-tetrahydropyran-4-ylpyrimidin-5-yl)phenyl]sulfonylamino]benzoyl]amino]-3-[5-(1,3,4-trimethyl-2,6-dioxopyrimidin-5-yl)-2-pyridyl]propanoic acid (A-28)

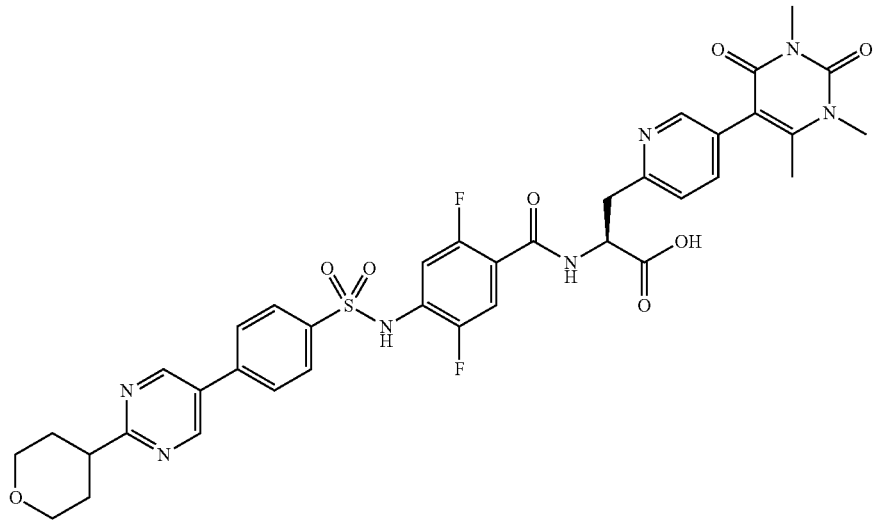 [SMILES: Cc1c(-c2ccc(C[C@H](NC(=O)c3cc(F)c(NS(=O)(=O)c4ccc(-c5cnc(C6CCOCC6)nc5)cc4)cc3F)C(=O)O)nc2)c(=O)n(C)c(=O)n1C]

The title compound was obtained by a method similar to step 1 of Example 27 by using methyl (2S)-2-amino-3-[5-(1,3,4-trimethyl-2,6-dioxopyrimidin-5-pyridyl]propanoate (M-29) and 2,5-difluoro-4-[[4-(2-tetrahydropyran-4-ylpyrimidin-5-yl)phenyl]sulfonylamino]benzoic acid (M-11).

$^1$H NMR (400 MHz, DMSO-d6) δ 10.98 (s, 1H), 9.13 (s, 2H), 8.72 (dd, J=7.9, 3.6 Hz, 1H), 8.41 (d, J=2.2 Hz, 1H), 8.11-8.00 (m, 2H), 8.00-7.89 (m, 2H), 7.73 (d, J=7.9 Hz, 1H), 7.47 (d, J=8.0 Hz, 1H), 7.34 (dd, J=10.3, 6.4 Hz, 1H), 7.27 (dd, J=11.4, 6.3 Hz, 1H), 5.04-4.70 (m, 1H), 4.13-3.89 (m, 2H), 3.46 (s, 2H), 3.41 (s, 3H), 3.35-3.24 (m, 1H), 3.22 (s, 3H), 3.18-3.02 (m, 2H), 2.11 (s, 3H), 1.98-1.60 (m, 4H); MS (ESI) m/z 776 (M+H)$^+$.

Reference Example 1

(2S)-2-[[2,5-Difluoro-4-[[4-(2-tetrahydropyran-4 ylpyrimidin 5-yl)phenyl]sulfonylamino]benzoyl]amino]-3-[6-(1-methyl-2,4-dioxo-pyrido[3,4-d]pyrimidin-3-yl)-3-pyridyl]propanoic acid (A-29)

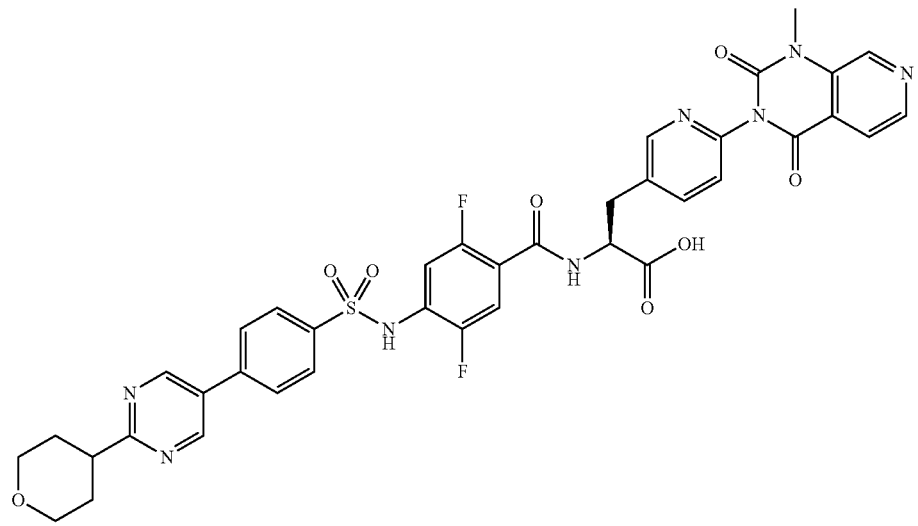

The title compound was obtained by a method similar to step 1 of Example 27 by using methyl 3-[6-(1-methyl-2,4-dioxo-1,4-dihydropyrido[3,4-d]pyrimidin-3(2H)-yl)pyridin-3-yl]-L-alaninate (M-30) and 2,5-difluoro-4-[[4-(2-tetrahydropyran-4-ylpyrimidin-5-yl)phenyl]sulfonylamino]benzoic acid (M-11).

$^1$H NMR (400 MHz, DMSO-$d_6$): δ 10.95 (s, 1H), 9.13 (s, 2H), 8.99 (s, 1H), 8.69 (dd, J=8.2, 2.2 Hz, 1H), 8.56 (d, J=5.0 Hz, 1H), 8.46 (d, J=2.3 Hz, 1H), 8.06-7.99 (m, 2H), 7.99-7.92 (m, 2H), 7.92-7.85 (m, 2H), 7.43-7.36 (m, 1H), 7.33-7.22 (m, 2H), 4.74-4.63 (m, 1H), 4.00-3.90 (m, 2H), 3.59 (s, 3H), 3.54-3.42 (m, 2H), 3.29 (dd, J=14.1, 4.6 Hz, 1H), 3.19-3.03 (m, 2H), 1.95-1.74 (m, 4H); MS(ESI) m/z 799.51 (M+H)$^+$.

Reference Example 2

(2S)-2-[[2,5-Difluoro-4-[[4-[2-(methoxymethyl)pyrimidin-5-yl]phenyl]sulfonylamino]benzoyl]amino]-3-[4-(1-methyl-2,4-dioxo-pyrido[3,4-d]pyrimidin-3-yl)phenyl]propanoic acid (A-30)

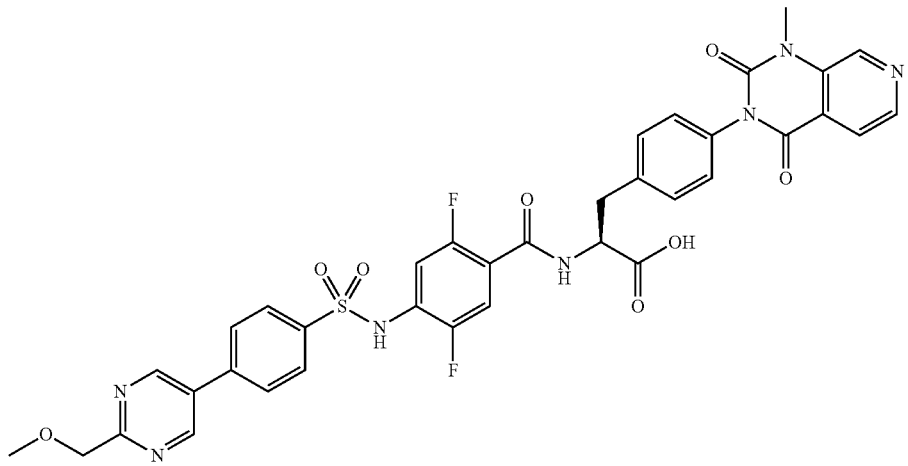 [SMILES: COCc1ncc(-c2ccc(S(=O)(=O)Nc3cc(F)c(C(=O)N[C@@H](Cc4ccc(-n5c(=O)c6ccncc6n(C)c5=O)cc4)C(=O)O)cc3F)cc2)cn1]

The title compound was obtained by a method similar to step 1 of Example 27 by using methyl 4-(1-methyl-2,4-dioxo-1,4-dihydropyrido[3,4-d]pyrimidin-3(2H)-yl)-L-phenylalaninate (M-8) and 2,5-difluoro-4-[[4-[2-(isopropoxymethyl)pyrimidin-5-yl]phenyl]sulfonylamino]benzoic acid (M-19).

$^1$H NMR (400 MHz, DMSO-$d_6$): δ 10.97 (s, 1H), 9.18 (s, 2H), 8.96 (s, 1H), 8.60 (dd, J=8.0, 2.6 Hz, 1H), 8.55 (d, J=5.0 Hz, 1H), 8.10-8.02 (m, 2H), 8.02-7.94 (m, 2H), 7.88 (d, J=5.0 Hz, 1H), 7.40-7.24 (m, 4H), 7.24-7.17 (m, 2H), 4.63 (s, 3H), 3.59 (s, 3H), 3.40 (s, 3H), 3.23 (dd, J=14.0, 4.5 Hz, 1H), 3.06 (dd, J=14.0, 9.9 Hz, 1H); MS(ESI) m/z 758.54 (M+H)$^+$.

Example 90

Isopropyl (2S)-2-[[4-[[4-(1-allyl-2-oxopyrimidin-5-yl)phenyl]sulfonylamino]-2,5-difluoro-benzoyl]amino]-3-[5-(1-methyl-2,4-dioxo-pyrido[3,4-d]pyrimidin-3-yl)-2-pyridyl]propanoate (C-32)

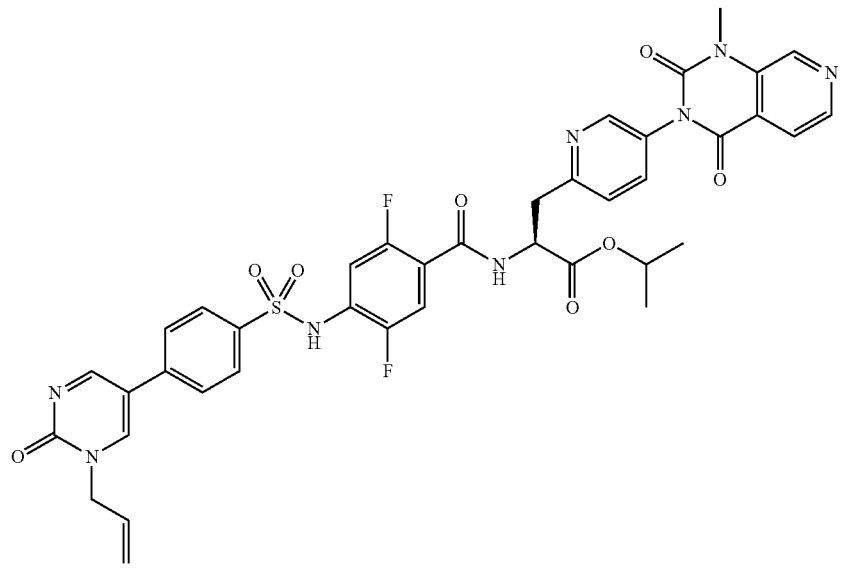 [SMILES: C=CCn1cc(-c2ccc(S(=O)(=O)Nc3cc(F)c(C(=O)N[C@@H](Cc4ccc(-n5c(=O)c6ccncc6n(C)c5=O)cn4)C(=O)OC(C)C)cc3F)cc2)cnc1=O]

Isopropanol alcohol (4 mL) and 4 N hydrochloric acid/dioxane (2 mL) were added to A-5 (80 mg, 0.10 mmol), and the resulting mixture was stirred at 60° C. for 2 hours. The reaction liquid was concentrated under reduced pressure, the obtained residue was purified by reverse phase HPLC (an H₂O/CH₃CN system including 0.1% TFA) to obtain a TFA salt of the title compound (53 mg, 57%).

$^1$H NMR (400 MHz, DMSO-d6) δ 10.90 (s, 1H), 9.04 (d, J=3.4 Hz, 1H), 9.00 (s, 1H), 8.85 (dd, J=7.6, 3.3 Hz, 1H), 8.74 (d, J=3.4 Hz, 1H), 8.58 (d, J=4.9 Hz, 1H), 8.46 (dd, J=2.4, 0.7 Hz, 1H), 7.93-7.84 (m, 5H), 7.74 (dd, J=8.2, 2.5 Hz, 1H), 7.47 (d, J=8.2 Hz, 1H), 7.38 (dd, J=10.3, 6.3 Hz, 1H), 7.26 (dd, J=11.3, 6.3 Hz, 1H), 6.07-5.95 (m, 1H), 5.26-5.17 (m, 2H), 4.94-4.79 (m, 2H), 4.54 (dt, J=5.9, 1.4 Hz, 2H), 3.61 (s, 3H), 3.36-3.23 (m, 2H), 1.15 (d, J=6.2 Hz, 3H), 1.10 (d, J=6.2 Hz, 3H); MS (ESI) m/z 813 (M+H)⁺.

A method similar to Example 90 was performed by using A-5, A-20, A-29, or A-30 as carboxylic acid and methanol, ethanol, isopropyl alcohol, 3-pentanol, 2-methoxyethanol, or N-(2-hydroxy)morpholine as alcohol to synthesize C-33 to C-42.

Example 91

1-Ethylpropyl (2S)-2-[[4-[[4-(1-allyl-2-oxopyrimidin-5-yl)phenyl]sulfonylamino]-2,5-difluoro-benzoyl]amino]-3-[5-(1-methyl-2,4-dioxo-pyrido[3,4-d]pyrimidin-3-yl)-2-pyridyl]propanoate (C-33)

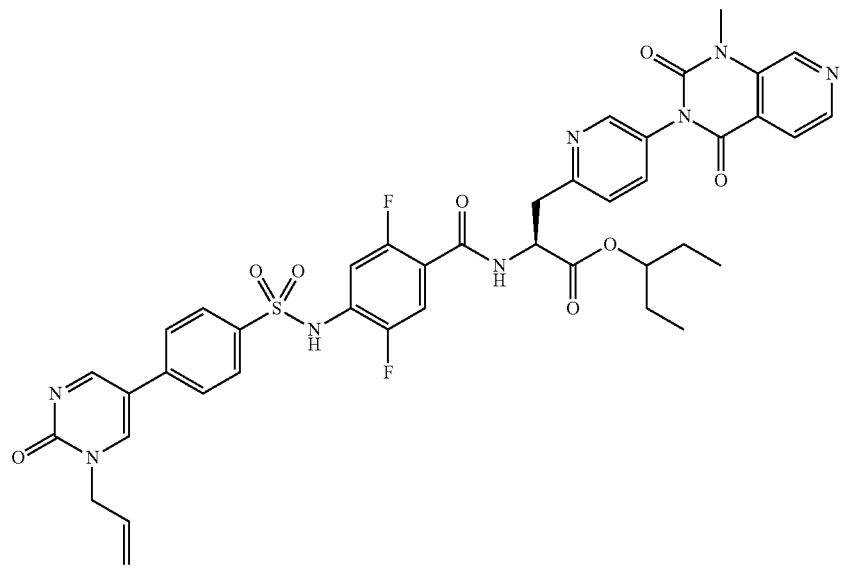 [SMILES: C=CCn1cc(-c2ccc(S(=O)(=O)Nc3cc(F)c(C(=O)N[C@@H](Cc4ccc(-n5c(=O)c6ccncc6n(C)c5=O)cn4)C(=O)OC(CC)CC)cc3F)cc2)cnc1=O]

¹H NMR (400 MHz, DMSO-d6) δ 10.90 (s, 1H), 9.04 (d, J=3.4 Hz, 1H), 9.00 (s, 1H), 8.88 (dd, J=7.6, 3.3 Hz, 1H), 8.73 (d, J=3.4 Hz, 1H), 8.57 (d, J=4.9 Hz, 1H), 8.46 (d, J=2.4 Hz, 1H), 7.94-7.83 (m, 5H), 7.74 (dd, J=8.2, 2.5 Hz, 1H), 7.47 (d, J=8.2 Hz, 1H), 7.35 (dd, J=10.3, 6.3 Hz, 1H), 7.26 (dd, J=11.3, 6.2 Hz, 1H), 6.08-5.93 (m, 1H), 5.27-5.17 (m, 2H), 5.02-4.91 (m, 1H), 4.72-4.61 (m, 1H), 4.57-4.50 (m, 2H), 3.61 (s, 3H), 3.41-3.24 (m, 2H), 1.63-1.32 (m, 4H), 0.86-0.68 (m, 6H); MS (ESI) m/z 841 (M+H)⁺.

Example 92

Methyl (2S)-2-[[2,5-difluoro-4-[[4-(2-tetrahydropyran-4-ylpyrimidin-5-yl)phenyl]sulfonylamino]benzoyl]amino]-3-[6-(1-methyl-2,4-dioxo-pyrido[3,4-d]pyrimidin-3-yl)-3-pyridyl]propanoate (C-34)

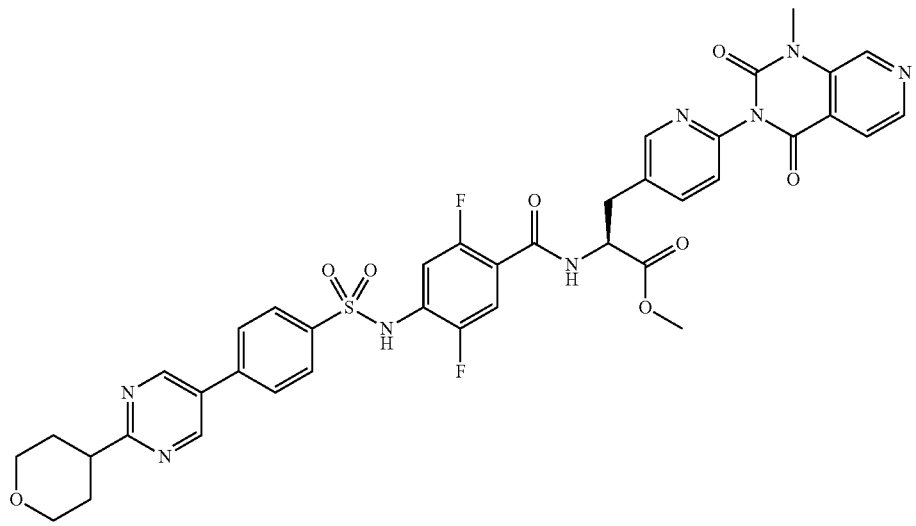 [SMILES: COC(=O)[C@H](Cc1ccc(-n2c(=O)c3ccncc3n(C)c2=O)nc1)NC(=O)c1cc(F)c(NS(=O)(=O)c2ccc(-c3cnc(C4CCOCC4)nc3)cc2)cc1F]

¹H NMR (400 MHz, DMSO-d6) δ 10.99 (s, 1H), 9.14 (s, 2H), 8.99 (s, 1H), 8.86 (dd, J=8.0, 2.0 Hz, 1H), 8.57 (d, J=5.0 Hz, 1H), 8.47 (d, J=2.0 Hz, 1H), 8.07-8.00 (m, 2H), 8.00-7.94 (m, 2H), 7.94-7.85 (m, 2H), 7.41 (d, J=8.0 Hz, 1H), 7.37-7.23 (m, 2H), 4.87-4.67 (m, 1H), 4.05-3.88 (m, 2H), 3.67 (s, 3H), 3.61 (s, 3H), 3.54-3.43 (m, 2H), 3.33-3.22 (m, 1H), 3.22-3.03 (m, 2H), 2.02-1.72 (m, 4H); MS(ESI) m/z 813.47 (M+H)⁺.

Example 93

Ethyl (2S)-2-[[2,5-difluoro-4-[[4-(2-tetrahydropyran-4-ylpyrimidin-5-yl)phenyl]sulfonylamino]benzoyl]amino]-3-[6-(1-methyl-2,4-dioxo-pyrido[3,4-d]pyrimidin-3-yl)-3-pyridyl]propanoate (C-35)

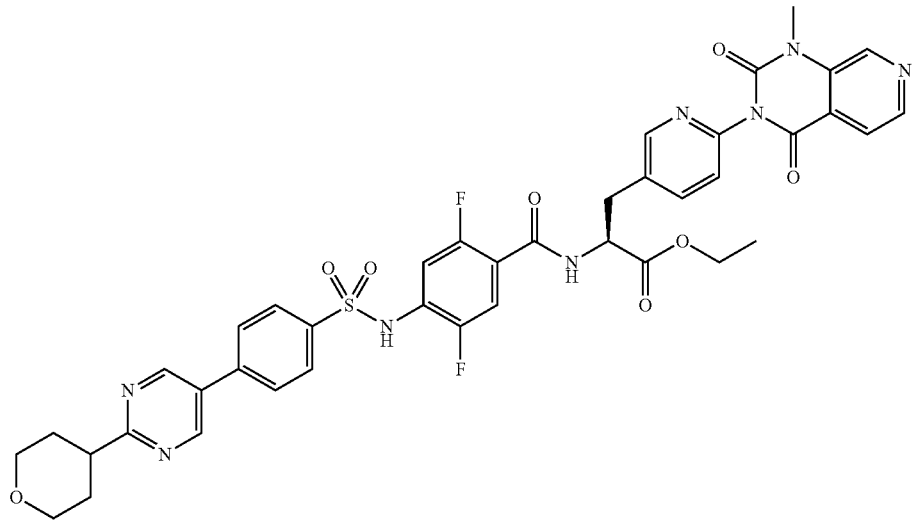 [SMILES: CCOC(=O)[C@H](Cc1ccc(-n2c(=O)c3ccncc3n(C)c2=O)nc1)NC(=O)c1cc(F)c(NS(=O)(=O)c2ccc(-c3cnc(C4CCOCC4)nc3)cc2)cc1F]

¹H NMR (400 MHz, DMSO-d6) δ 10.98 (s, 1H), 9.14 (s, 2H), 8.99 (s, 1H), 8.86 (dd, J=7.7, 1.7 Hz, 1H), 8.57 (d, J=4.9 Hz, 1H), 8.47 (d, J=2.3 Hz, 1H), 8.06-8.00 (m, 2H), 7.99-7.94 (m, 2H), 7.94-7.87 (m, 2H), 7.41 (d, J=8.1 Hz, 1H), 7.34-7.24 (m, 2H), 4.78-4.63 (m, 1H), 4.11 (q, J=7.1 Hz, 2H), 4.00-3.90 (m, 2H), 3.59 (s, 3H), 3.49-3.41 (m, 2H), 3.25 (dd, J=14.1, 5.6 Hz, 1H), 3.18-3.07 (m, 2H), 1.98-1.70 (m, 4H), 1.16 (t, J=7.1 Hz, 3H); MS (ESI) m/z 827 (M+H)⁺.

Example 94

Isopropyl (2S)-2-[[2,5-difluoro-4-[[4-(2-tetrahydropyran-4-ylpyrimidin-5-yl)phenyl]sulfonylamino]benzoyl]amino]-3-[6-(1-methyl-2,4-dioxo-pyrido[3,4-d]pyrimidin-3-yl)-3-pyridyl]propanoate (C-36)

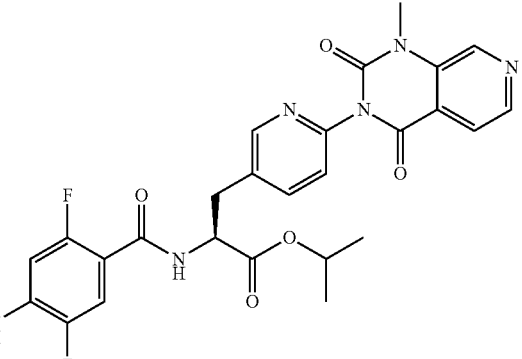

¹H NMR (400 MHz, DMSO-d6) δ 10.97 (s, 1H), 9.14 (s, 2H), 8.99 (s, 1H), 8.87-8.79 (m, 1H), 8.56 (d, J=5.0 Hz, 1H), 8.46 (d, J=2.3 Hz, 1H), 8.03 (d, J=8.6 Hz, 2H), 7.97 (d, J=8.6 Hz, 2H), 7.94-7.85 (m, 2H), 7.40 (d, J=8.1 Hz, 1H), 7.28 (ddd, J=11.1, 6.3, 4.5 Hz, 2H), 4.91 (sep, J=6.2 Hz, 1H), 4.72-4.61 (m, 1H), 4.02-3.90 (m, 2H), 3.59 (s, 3H), 3.52-3.39 (m, 2H), 3.28-3.03 (m, 3H), 1.98-1.71 (m, 4H), 1.18 (d, J=6.2 Hz, 3H), 1.13 (d, J=6.2 Hz, 3H); MS (ESI) m/z 841 (M+H)⁺.

Example 95

1-Ethylpropyl (2S)-2-[[2,5-difluoro-4-[[4-(2-tetrahydropyran-4-ylpyrimidin-5-yl)phenyl]sulfonylamino]benzoyl]amino]-3-[6-(1-methyl-2,4-dioxo-pyrido[3,4-d]pyrimidin-3-yl)-3-pyridyl]propanoate (C-37)

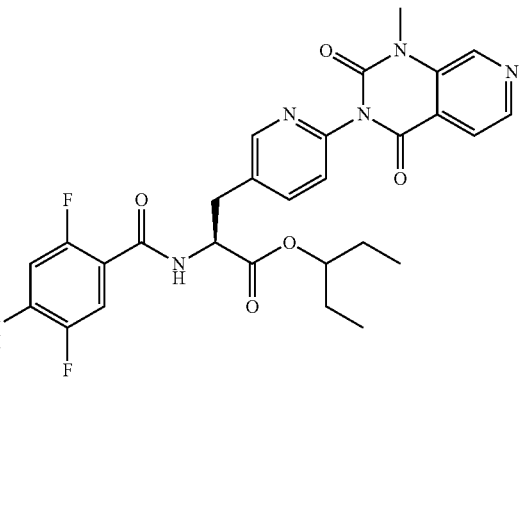

¹H NMR (400 MHz, DMSO-d6) δ 10.97 (s, 1H), 9.14 (s, 2H), 8.99 (s, 1H), 8.86 (d, J=7.8 Hz, 1H), 8.57 (d, J=5.0 Hz, 1H), 8.49 (s, 1H), 8.03 (d, J=8.1 Hz, 2H), 7.99-7.91 (m, 3H), 7.89 (d, J=4.9 Hz, 1H), 7.40 (d, J=8.0 Hz, 1H), 7.32-7.20 (m, 2H), 4.82-4.62 (m, 2H), 4.01-3.89 (m, 2H), 3.60 (s, 3H), 3.53-3.42 (m, 2H), 3.33-3.22 (m, 1H), 3.19-3.02 (m, 2H), 1.98-1.74 (m, 4H), 1.63-1.40 (m, 4H), 0.90-0.73 (m, 6H); MS (ESI) m/z 869 (M+H)⁺.

Example 96

2-Methoxyethyl (2S)-2-[[2,5-difluoro-4-[[4-(2-tetrahydropyran-4-ylpyrimidin-5-yl)phenyl]sulfonylamino]benzoyl]amino]-3-[6-(1-methyl-2,4-dioxopyrido[3,4-d]pyrimidin-3-yl)-3-pyridyl]propanoate
(C-38)

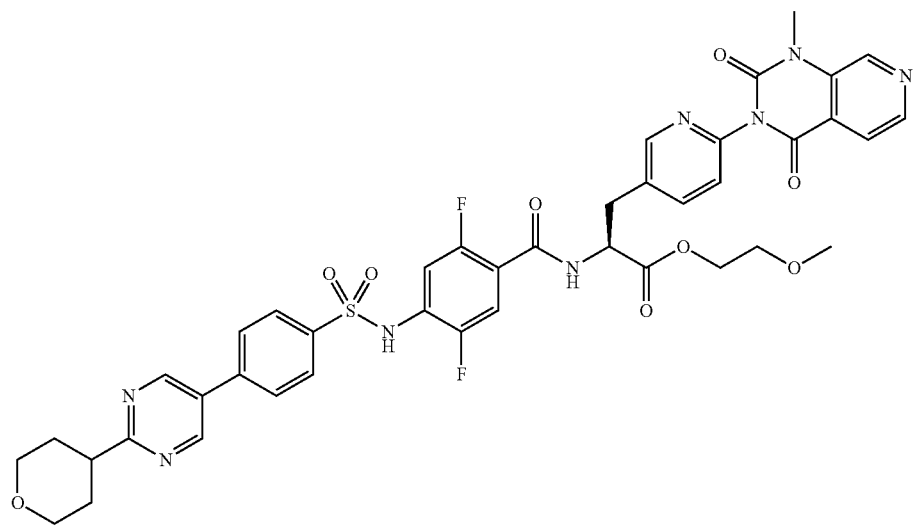 [SMILES: COCCOC(=O)[C@H](Cc1ccc(-n2c(=O)c3ccncc3n(C)c2=O)nc1)NC(=O)c1cc(F)c(NS(=O)(=O)c2ccc(-c3cnc(C4CCOCC4)nc3)cc2)cc1F]

¹H NMR (400 MHz, DMSO-d6) δ 10.97 (s, 1H), 9.14 (s, 2H), 8.99 (s, 1H), 8.87 (dd, J=7.9, 1.7 Hz, 1H), 8.56 (d, J=5.0 Hz, 1H), 8.47 (d, J=2.4 Hz, 1H), 8.06-7.99 (m, 2H), 7.98-7.85 (m, 4H), 7.40 (d, J=8.1 Hz, 1H), 7.33-7.22 (m, 2H), 4.81-4.69 (m, 1H), 4.24-4.15 (m, 2H), 4.00-3.90 (m, 2H), 3.59 (s, 3H), 3.54-3.42 (m, 4H), 3.30-3.25 (m, 1H), 3.24 (s, 3H), 3.19-3.04 (m, 2H), 1.94-1.74 (m, 4H); MS (ESI) m/z 857 (M+H)⁺.

Example 97

2-Morpholinoethyl (2S)-2-[[2,5-difluoro-4-[[4-(2-tetrahydropyran-4-ylpyrimidin-5-yl)phenyl]sulfonylamino]benzoyl]amino]-3-[6-(1-methyl-2,4-dioxo-pyrido[3,4-d]pyrimidin-3-yl)-3-pyridyl]propanoate (C-39)

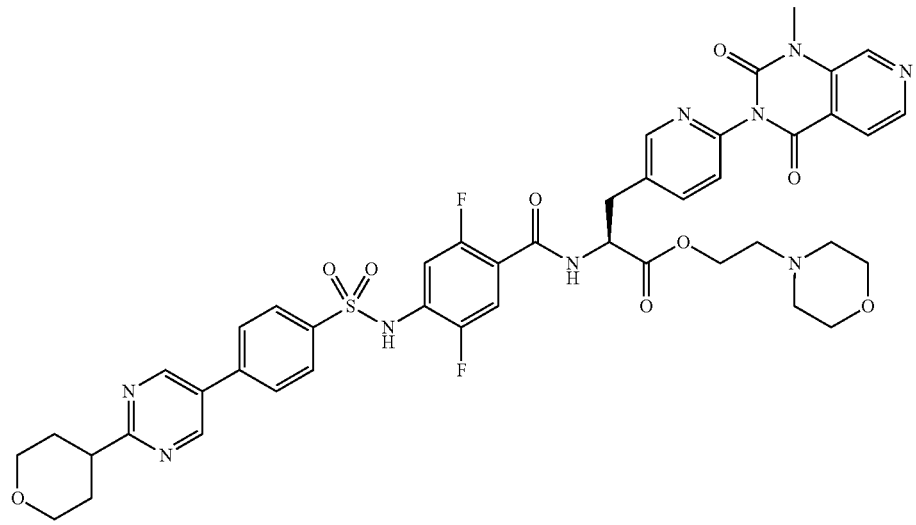 [SMILES: Cn1c(=O)n(-c2ccc(C[C@H](NC(=O)c3cc(F)c(NS(=O)(=O)c4ccc(-c5cnc(C6CCOCC6)nc5)cc4)cc3F)C(=O)OCCN3CCOCC3)cn2)c(=O)c2ccncc21]

$^1$H NMR (400 MHz, DMSO-d6) δ 11.00 (s, 1H), 9.14 (s, 2H), 9.03-8.93 (m, 2H), 8.57 (d, J=4.9 Hz, 1H), 8.49 (d, J=2.3 Hz, 1H), 8.07-7.85 (m, 6H), 7.46-7.40 (m, 1H), 7.39-7.21 (m, 2H), 4.91-4.78 (m, 1H), 4.53-4.35 (m, 2H), 4.00-3.64 (m, 8H), 3.59 (s, 3H), 3.54-3.35 (m, 4H), 3.24-3.02 (m, 5H), 1.96-1.72 (m, 4H); MS (ESI) m/z 912 (M+H)$^+$.

Example 98

Isopropyl (2S)-2-[[2,5-difluoro-4-[[4-[2-(methoxymethyl)pyrimidin-5-yl]phenyl]sulfonylamino]benzoyl]amino]-3-[4-(1-methyl-2,4-dioxo-pyrido[3,4-d]pyrimidin-3-yl)phenyl]propanoate (C-40)

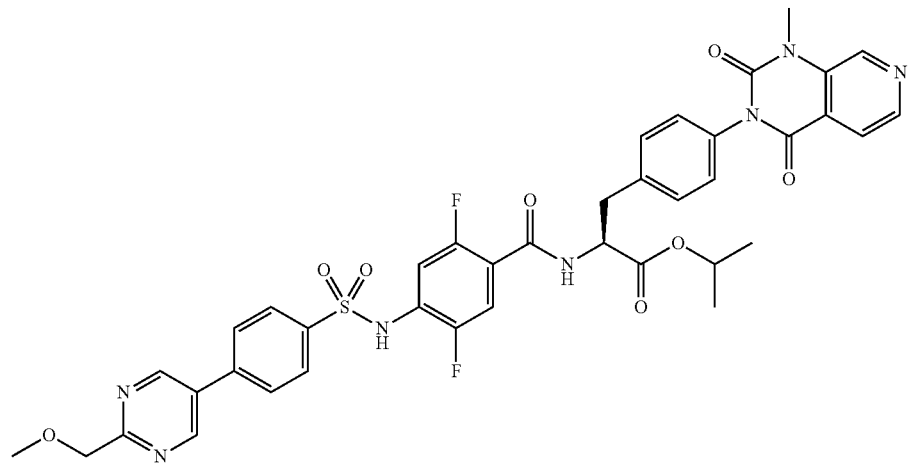 [SMILES: COCc1ncc(-c2ccc(S(=O)(=O)Nc3cc(F)c(C(=O)N[C@@H](Cc4ccc(-n5c(=O)c6ccncc6n(C)c5=O)cc4)C(=O)OC(C)C)cc3F)cc2)cn1]

¹H NMR (400 MHz, DMSO-d6) δ 10.97 (s, 1H), 9.19 (s, 2H), 8.97 (s, 1H), 8.76 (dd, J=7.3, 2.0 Hz, 1H), 8.55 (d, J=5.0 Hz, 1H), 8.16-8.02 (m, 2H), 8.02-7.93 (m, 2H), 7.88 (dd, J=5.0, 0.8 Hz, 1H), 7.42-7.35 (m, 2H), 7.35-7.24 (m, 2H), 7.24-7.12 (m, 2H), 5.02-4.81 (m, 1H), 4.70-4.51 (m, 3H), 3.59 (s, 3H), 3.40 (s, 3H), 3.26-3.00 (m, 2H), 1.18 (d, J=6.2 Hz, 3H), 1.12 (d, J=6.2 Hz, 3H); MS (ESI) m/z 800 (M+H)⁺.

Example 99

1-Ethylpropyl (2S)-2-[[2,5-difluoro-4-[[4-[2-(methoxymethyl)pyrimidin-5-yl]phenyl]sulfonylamino]benzoyl]amino]-3-[4-(1-methyl-2,4-dioxopyrido[3,4-d]pyrimidin-3-yl)phenyl]propanoate (C-41)

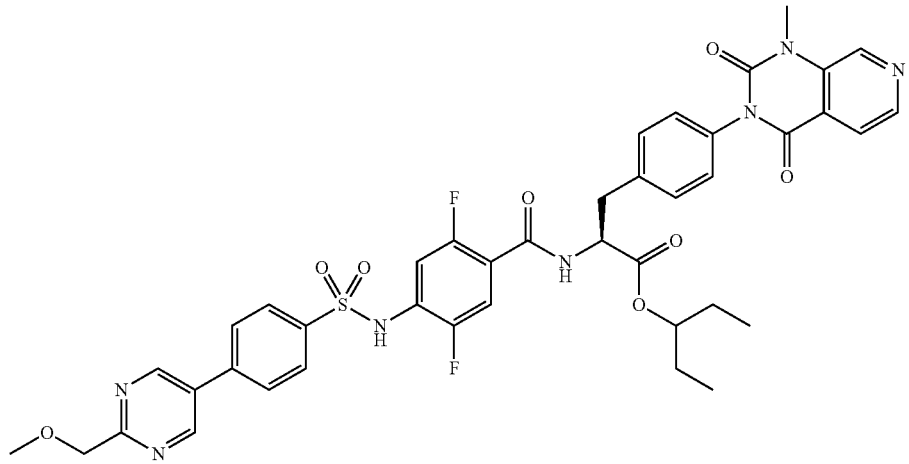 [SMILES: CCC(CC)OC(=O)[C@H](Cc1ccc(-n2c(=O)c3ccncc3n(C)c2=O)cc1)NC(=O)c1cc(F)c(NS(=O)(=O)c2ccc(-c3cnc(COC)nc3)cc2)cc1F]

¹H NMR (400 MHz, DMSO-d6) δ 10.98 (s, 1H), 9.18 (s, 2H), 8.96 (s, 1H), 8.79 (dd, J=7.7, 1.9 Hz, 1H), 8.55 (d, J=5.0 Hz, 1H), 8.13-8.02 (m, 2H), 8.02-7.93 (m, 2H), 7.88 (d, J=5.0 Hz, 1H), 7.48-7.35 (m, 2H), 7.33-7.24 (m, 2H), 7.25-7.16 (m, 2H), 4.77-4.59 (m, 4H), 3.59 (s, 3H), 3.47-3.37 (m, 3H), 3.27-3.16 (m, 1H), 3.16-3.03 (m, 1H), 1.64-1.37 (m, 4H), 0.90-0.73 (m, 6H); MS(ESI) m/z 828.47 (M+H)⁺.

Example 100

Methyl (2S)-2-[[4-[[4-(2-ethylpyrimidin-5-yl)phenyl]sulfonylamino]-2,3,5,6-tetrafluorobenzoyl]amino]-3-[4-(1,3,4-trimethyl-2,6-dioxopyrimidin-5-yl)phenyl]propanoate (C-42)

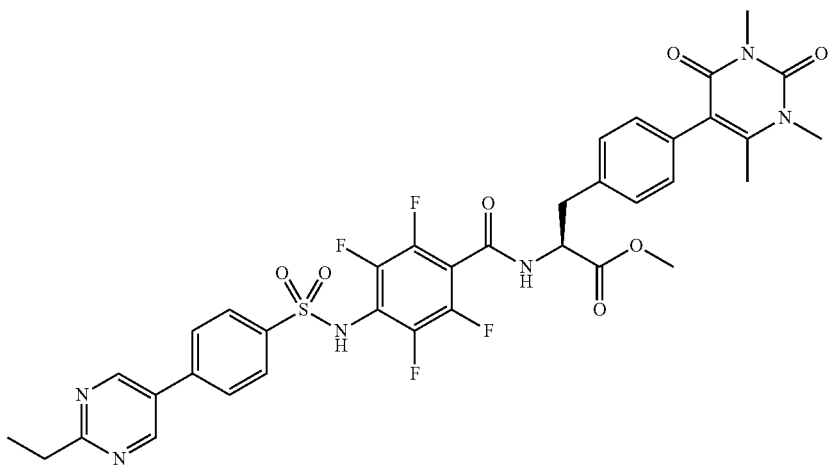 [SMILES: CCc1ncc(-c2ccc(S(=O)(=O)Nc3c(F)c(F)c(C(=O)N[C@@H](Cc4ccc(-c5c(C)n(C)c(=O)n(C)c5=O)cc4)C(=O)OC)c(F)c3F)cc2)cn1]

¹H NMR (400 MHz, DMSO-d6) δ 10.85 (s, 1H), 9.46 (d, J=7.9 Hz, 1H), 9.14 (s, 2H), 8.05 (d, J=8.5 Hz, 2H), 7.90 (d, J=8.4 Hz, 2H), 7.31-7.21 (m, 2H), 7.14-6.91 (m, 2H), 5.03-4.58 (m, 1H), 3.50-3.26 (m, 4H), 3.26-3.11 (m, 6H), 3.11-2.82 (m, 3H), 2.20-1.87 (m, 3H), 1.32 (t, J=7.6 Hz, 3H); MS (ESI) m/z 769 (M+H)⁺.

Example 101

2,5-Difluoro-N-[(1S)-2-(hydroxyamino)-1-[[6-(1-methyl-2,4-dioxo-pyrido[3,4-d]pyrimidin-3-yl)-3-pyridyl]methyl]-2-oxo-ethyl]-4-[[4-[2-(methoxymethyl)pyrimidin-5-yl]phenyl]sulfonylamino]benzamide (C-43)

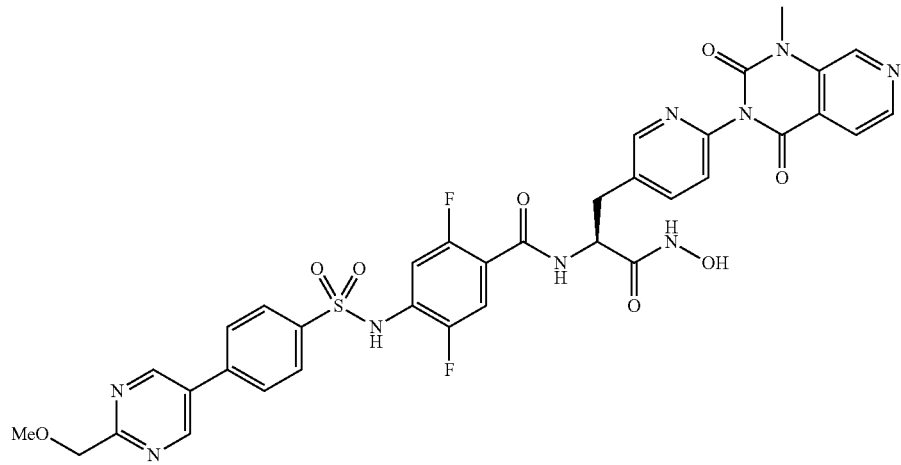 [SMILES: COCc1ncc(-c2ccc(S(=O)(=O)Nc3cc(F)c(C(=O)N[C@@H](Cc4ccc(-n5c(=O)c6ccncc6n(C)c5=O)nc4)C(=O)NO)cc3F)cc2)cn1]

(2S)-2-[[2,5-Difluoro-4-[[4-[2-(methoxymethyl)pyrimidin-5-yl]phenyl]sulfonylamino]benzoyl]amino]-3-[6-(1-methyl-2,4-dioxo-pyrido[3,4-d]pyrimidin-3-yl)-3-pyridyl]propanoic acid (A-23) (50.2 mg, 0.0662 mmol), 1-hydroxy-7-azabenzotriazole (10.8 mg, 0.0794 mmol), and hydroxyamine hydrochloride (13.8 mg, 0.199 mmol) were dissolved in acetonitrile (2 mL), diisopropylethylamine (45.0 μL, 0.265 mmol) and O-(7-azabenzotriazol-1-yl)-N,N,N',N',-tetramethyluronium hexafluorophosphate (30.2 mg, 0.0794 mmol) were added thereto, and the resulting mixture was stirred at room temperature overnight. The reaction liquid was concentrated under reduced pressure, the obtained residue was purified by reverse phase HPLC (an H₂O/CH₃CN system including 0.1% TFA) to obtain a TFA salt of the title compound (26.5 mg, 45%).

¹H NMR (400 MHz, DMSO-d₆) δ 10.94 (s, 1H), 10.86 (s, 1H), 9.18 (s, 2H), 8.99 (s, 1H), 8.70-8.61 (m, 1H), 8.57 (d, J=5.0 Hz, 1H), 8.54-8.41 (m, 1H), 8.09-8.02 (m, 2H), 8.00-7.94 (m, 2H), 7.92-7.83 (m, 2H), 7.40 (d, J=8.1 Hz, 1H), 7.26 (ddd, J=13.0, 10.6, 6.3 Hz, 2H), 4.67-4.58 (m, 3H), 3.59 (s, 3H), 3.40 (s, 3H), 3.11 (dd, J=14.0, 5.0 Hz, 1H), 3.02 (dd, J=14.0, 9.8 Hz, 1H); MS (ESI) m/z 774 (M+H).

A method similar to Example 101 was performed by using A-29 as carboxylic acid and hydroxyamine hydrochloride or methoxyamine hydrochloride as amine to synthesize C-44 and C-45.

Example 102
2,5-Difluoro-N-[(1S)-2-(hydroxyamino)-1-[[6-(1-methyl-2,4-dioxopyrido[3,4-d]pyrimidin-3-yl)-3-pyridyl]methyl]-2-oxoethyl]-4-[[4-(2-tetrahydropyran-4-ylpyrimidin-5-yl)phenyl]sulfonylamino]benzamide (C-44)
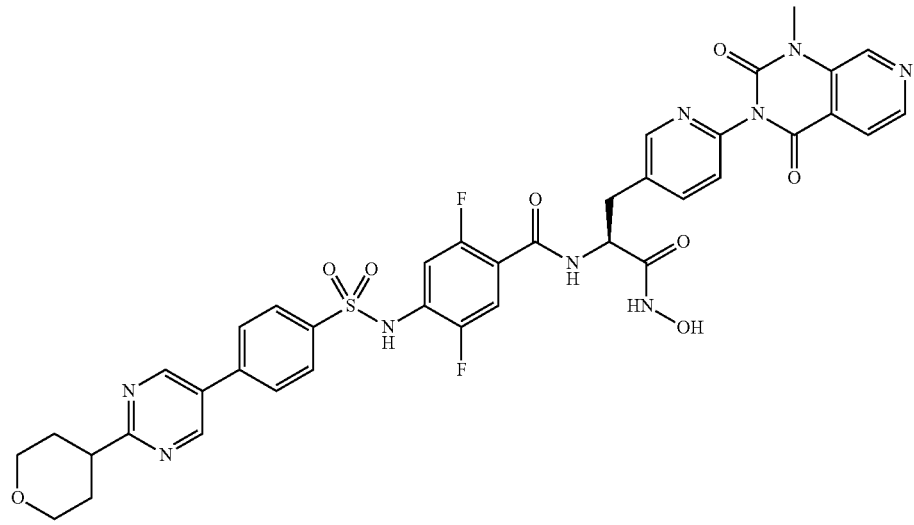 [SMILES: Cn1c(=O)n(-c2ccc(C[C@H](NC(=O)c3cc(F)c(NS(=O)(=O)c4ccc(-c5cnc(C6CCOCC6)nc5)cc4)cc3F)C(=O)NO)cn2)c(=O)c2ccncc21]
MS(ESI) m/z 814.63 (M+H)$^+$.
Example 103
2,5-Difluoro-N-[(1S)-2-(methoxyamino)-1-[[6-(1-methyl-2,4-dioxopyrido[3,4-d]pyrimidin-3-yl)-3-pyridyl]methyl]-2-oxoethyl]-4-[[4-(2-tetrahydropyran-4-yl pyrimidin-5-yl)phenyl]sulfonylamino]benzamide (C-45)
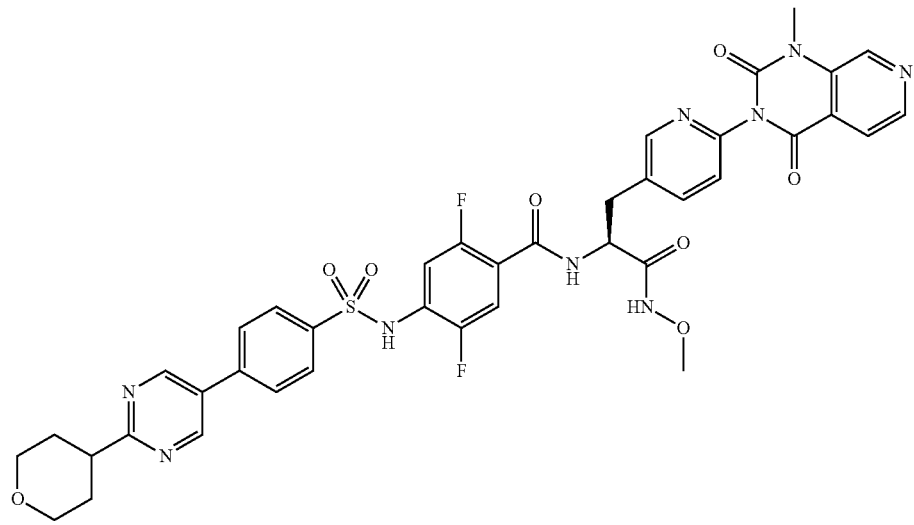 [SMILES: CONC(=O)[C@H](Cc1ccc(-n2c(=O)c3ccncc3n(C)c2=O)nc1)NC(=O)c1cc(F)c(NS(=O)(=O)c2ccc(-c3cnc(C4CCOCC4)nc3)cc2)cc1F]

¹H NMR (400 MHz, DMSO-d₆) δ 11.43 (s, 1H), 10.96 (s, 1H), 9.14 (s, 2H), 8.99 (s, 1H), 8.70 (d, J=8.0 Hz, 1H), 8.57 (d, J=5.0 Hz, 1H), 8.45 (d, J=2.4 Hz, 1H), 8.04 (d, J=8.3 Hz, 2H), 7.97 (d, J=8.3 Hz, 2H), 7.93-7.82 (m, 2H), 7.41 (d, J=8.0 Hz, 1H), 7.38-7.16 (m, 2H), 4.67-4.47 (m, 1H), 4.05-3.87 (m, 2H), 3.60 (s, 3H), 3.51 (s, 3H), 3.50-3.42 (m, 2H), 3.23-2.98 (m, 3H), 2.03-1.69 (m, 4H); MS(ESI) m/z 828.71 (M+H)⁺.

Example 104

Isopropyl (2S)-2-[[4-[[4-(4-ethyltriazol-1-yl)phenyl]sulfonylamino]-2,5-difluorobenzoyl]amino]-3-[4-(1-methyl-2,4-dioxopyrido[3,4-d]pyrimidin-3-yl)phenyl]propanoate (C-46)

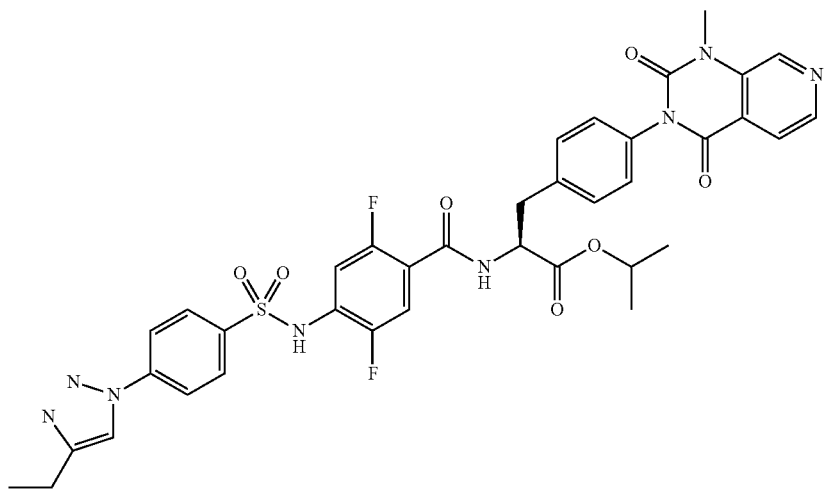 [SMILES: CC/C(N)=C/N(N)c1ccc(S(=O)(=O)Nc2cc(F)c(C(=O)N[C@@H](Cc3ccc(-n4c(=O)c5ccncc5n(C)c4=O)cc3)C(=O)OC(C)C)cc2F)cc1]

A method similar to step 1 of Example 27 was performed by using methyl 4-(1-methyl-2,4-dioxo-1,4-dihydropyrido[3,4-d]pyrimidin-3 (2H)-yl)-L-phenylalaninate (M-8) and 4-[[4-(4-ethyltriazol-1-yl)phenyl]sulfonylamino]-2,5-difluorobenzoic acid (M-26) to obtain carboxylic acid, and then an isopropyl ester of the obtained product was produced by a method similar to Example 90 to obtain the title compound.

¹H NMR (400 MHz, DMSO-d₆) δ 10.93 (s, 1H), 8.97 (s, 1H), 8.76 (dd, J=7.4, 1.8 Hz, 1H), 8.69 (s, 1H), 8.55 (d, J=5.0 Hz, 1H), 8.23-8.09 (m, 2H), 8.09-7.93 (m, 2H), 7.88 (d, J=5.0 Hz, 1H), 7.36 (d, J=8.1 Hz, 2H), 7.34-7.23 (m, 2H), 7.21 (d, J=8.2 Hz, 2H), 5.06-4.72 (m, 1H), 4.72-4.53 (m, 1H), 3.59 (s, 3H), 3.26-3.00 (m, 2H), 2.72 (q, J=7.6 Hz, 2H), 1.25 (t, J=7.5 Hz, 3H), 1.18 (d, J=6.2 Hz, 3H), 1.12 (d, J=6.2 Hz, 3H); MS (ESI) m/z 773 (M+H)⁺.

(1) Evaluation Test for VCAM-1/α4β1 Integrin Binding Inhibitory Activity

The ability of test substances to inhibit the binding of Jurkat cell strain, a human T-cell line known to express α4β1 integrin, to VCAM-1 was examined.

A 96-well microtiter plate was coated overnight at 4° C. with a recombinant human VCAM-1/Fc (R&D systems) solution diluted with a buffer A (carbonate buffer, pH 9.6). After washing once with PBS, 150 μL/well of Block Ace (manufactured by Snow Brand Milk Products Co., Ltd.) was added, and it was incubated at room temperature for 2 hours. After removal, it was washed once with PBS.

100 μL of each of test substances and Jurkat cells diluted with a binding buffer solution (DMEM containing 40 mM HEPES, 0.2% BSA, and 4 mM MnCl₂) to various concentrations was added to the plate coated with the VCAM-1/Fc, and it was incubated at 30° C. for 15 minutes to 60 minutes. After the cells were bound to the wells, unbound cells were removed by washing with PBS. 50 μL/well of a buffer solution C (PBS containing 1.5% Triton X-100) was added to the plate to dissolve the bound Jurkat cells. 30 μL of substrate buffer (Promega, CytoTox 96 Non-Radioactive Cytotoxicity Assay) was added to 30 μL of a cell lysate to allow a reaction for 30 minutes at room temperature in a dark place. 30 μL of stop solution (Promega, CytoTox 96 Non-Radioactive Cytotoxicity Assay) was added thereto to determine the absorbance at 490 nm using a plate reader. The absorbance was obtained herein by detecting the activity of lactate dehydrogenase (LDH) eluted in a supernatant of each well, that is, the absorbance is proportional to the number of Jurkat cells remaining on the plate by being bound to VCAM-1. The test was duplicated, and the cell binding rate at various concentrations with the absorbance of the well containing no test substance being taken as 100% was determined, to calculate the concentration IC₅₀ at which 50% of binding was inhibited. As test compounds, carboxylic acid compounds (compounds A-1 to A-28) among the compounds synthesized in concerned Examples were used. The same applies to the following description.

(2) Evaluation Test for MAdCAM-1/α4β7 Integrin Binding Inhibitory Activity

The ability of test substances to inhibit the binding of RPMI-8866 cell strain, a human B-cell line known to express αc4β7 integrin, to MAdCAM-1 was examined.

A 96-well microtiter plate was coated overnight at 4° C. with a recombinant mouse MAdCAM-1/Fc (R&D systems) solution diluted with the buffer A (carbonate buffer, pH 9.6). After washing once with PBS, 150 μL/well of Block Ace (manufactured by Snow Brand Milk Products Co., Ltd.) was added, and it was incubated at room temperature for 2 hours. After removal, it was washed once with PBS.

100 μL of each of test substances and RPMI-8866 cells diluted with a binding buffer solution (DMEM containing 40 mM HEPES, 0.2% BSA, and 4 mM MnCl₂) to various concentrations was added to the plate coated with MAdCAM-1/Fc, and it was incubated at 30° C. for 15 minutes to 60 minutes. After the cells were bound to the wells, unbound cells were removed by washing with PBS. 50 μL/well of the buffer solution C (PBS containing 1.5% Triton X-100) was added to the plate to dissolve the bound RPMI-8866 cells. 30 μL of substrate buffer (Promega, CytoTox 96 Non-Radioactive Cytotoxicity Assay) was added to 30 μL of a cell lysate to allow a reaction for 30 minutes at room temperature in a dark place. 30 μL of stop solution (Promega, CytoTox 96 Non-Radioactive Cytotoxicity Assay) was added thereto to determine the absorbance at 490 nm using a plate reader. The absorbance was obtained herein by detecting the activity of lactate dehydrogenase (LDH) eluted in a supernatant of each well, that is, the absorbance is proportional to the number of RPMI-8866 cells remaining on the plate by being bound to MAdCAM-1. The test was duplicated, and the cell binding rate at various concentrations with the absorbance of the well containing no test substance being taken as 100% was determined, to calculate the concentration $IC_{50}$ at which 50% of binding was inhibited.

The selectivity was determined by dividing the $IC_{50}$ value in the evaluation test for VCAM-1/α4β1 integrin binding inhibitory activity by the $IC_{50}$ value in the evaluation test for MAdCAM-1/α4β7 integrin binding inhibitory activity.

(3) Evaluation Test (1) for MAdCAM-1/α4β7 Integrin Binding Inhibitory Activity in the Presence of Serum The ability of test substances to inhibit the binding of RPMI-8866 cell line, a human B-cell line known to express α4β7 integrin, to MAdCAM-1 was examined.

A 96-well microtiter plate was coated overnight at 4° C. with a recombinant mouse MAdCAM-1/Fc (R&D systems) solution diluted with the buffer A (carbonate buffer, pH 9.6). After washing once with PBS, 150 μL/well of Block Ace (manufactured by Snow Brand Milk Products Co., Ltd.) was added, and it was incubated at room temperature for 2 hours. After removal, it was washed once with PBS.

100 μL of each of test substances and RPMI-8866 cells diluted with a binding buffer solution (DMEM containing 40 mM HEPES, 0.2% BSA, and 4 mM $MnCl_2$) to various concentrations was added to the plate coated with MAdCAM-1/Fc, so that human serum was contained at a final concentration of 50%, and it was incubated at 30° C. for 15 minutes to 60 minutes. After the cells were bound to the wells, unbound cells were removed by washing with PBS. 50 μL/well of the buffer solution C (PBS containing 1.5% Triton X-100) was added to the plate to dissolve the bound RPMI-8866 cells. 30 μL of substrate buffer (Promega, CytoTox 96 Non-Radioactive Cytotoxicity Assay) was added to 30 μL of a cell lysate to allow a reaction for 30 minutes at room temperature in a dark place. 30 μL of stop solution (Promega, CytoTox 96 Non-Radioactive Cytotoxicity Assay) was added thereto to determine the absorbance at 490 nm using a plate reader. The absorbance was obtained herein by detecting the activity of lactate dehydrogenase (LDH) eluted in a supernatant of each well, that is, the absorbance is proportional to the number of RPMI-8866 cells remaining on the plate by being bound to MAdCAM-1. The test was duplicated, and the cell binding rate at various concentrations with the absorbance of the well containing no test substance being taken as 100% was determined, to calculate the concentration $IC_{50}$ at which 50% of binding was inhibited.

Table 1 and Table 2 show the results. It was confirmed that all the compounds described herein had selectivity, which was determined by dividing the $IC_{50}$ value in the evaluation test for VCAM-1/α4β1 integrin binding inhibitory activity by the $IC_{50}$ value in the evaluation test for MAdCAM-1/α4β7 integrin binding inhibitory activity, of 100 times or more and thus had preferable properties. The evaluation test for VCAM-1/α4β1 integrin binding inhibitory activity and the evaluation test for MAdCAM-1/α4β7 integrin binding inhibitory activity were conducted in accordance with the aforementioned methods described in the tests (1) and (2).

TABLE 1

| Example No. | α4β7 Serum<br>Activity rank when α4β7 serum was added<br>1-10 nM: A,<br>10-50 nM: B,<br>50-200 nM: C,<br>>200 nM: D |
|---|---|
| Example 26 | B |
| Example 27 | C |
| Example 28 | B |
| Example 29 | C |
| Example 30 | B |
| Example 33 | B |
| Example 34 | B |
| Example 36 | C |
| Example 37 | B |
| Example 38 | B |
| Example 39 | B |
| Example 40 | C |
| Example 41 | D |
| Example 42 | C |
| Example 43 | D |
| Example 44 | C |
| Example 45 | B |
| Example 46 | D |
| Example 47 | B |
| Example 51 | B |

TABLE 2

| Example No. | α4β7 Serum<br>Activity rank when α4β7 serum was added<br>1-10 nM: A,<br>10-50 nM: B,<br>50-200 nM: C,<br>>200 nM: D |
|---|---|
| Example 85 | B |
| Example 86 | B |
| Example 87 | D |
| Example 88 | C |
| Example 89 | D |

As is obvious from the results of the selectivity determined by dividing the $IC_{50}$ value in the evaluation test for VCAM-1/α4β1 integrin binding inhibitory activity by the $IC_{50}$ value in the evaluation test for MAdCAM-1/α4β7 integrin binding inhibitory activity, the compounds of the present invention, as compared with the compound of Patent Literature 1, has high selectivity with a low effect on α4β1 and a high effect on α4β7, and it can be seen from the results of Table 1 that, in particular, the MAdCAM-1/α4β7 integrin binding inhibitory activity in the presence of serum is high. The high selectivity with a low effect on α4β1 and a high effect on α4β7 can reduce the action on α4β1 that suppresses infiltration of lymphocytes circulating throughout the whole body, and can significantly suppress the action on α4β7 that specifically acts on the intestinal tract, and thus has an advantage of being capable of treating adaptation disease efficiently.

What is claimed is:

1. A sulfonamide derivative represented by the general formula (1) below or a pharmaceutically acceptable salt thereof:

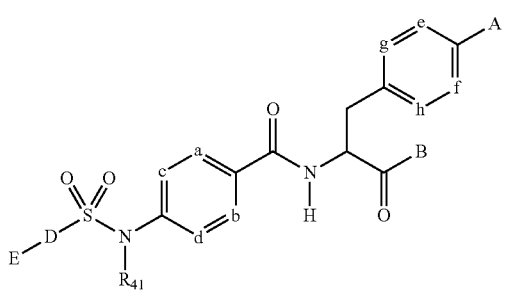

wherein

A represents a group represented by the general formula (2-1), (2-2), (2-3) or (2-4) below:

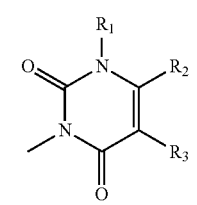

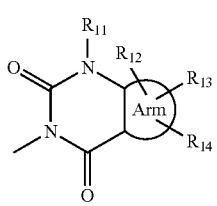

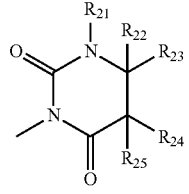

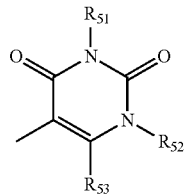

wherein

Arm is a cyclic alkyl group or an aromatic ring containing 0, 1, 2, 3, or 4 heteroatoms selected from oxygen atoms, sulfur atoms and nitrogen atoms, $R_1$, $R_{11}$, $R_{21}$, $R_{51}$, and $R_{52}$ each independently represent any one of a hydrogen atom, a halogen atom, a hydroxyl group, a lower alkyl group, a lower alkenyl group, a lower alkynyl group, a lower alkoxy group, a lower alkylthio group, a hydroxy-lower alkyl group, a hydroxy-lower alkenyl group, a hydroxy-lower alkoxy group, a halogen-lower alkyl group, a halogeno-lower alkoxy group, a halogeno-lower alkylthio group, a halogeno-lower alkenyl group, a nitro group, a cyano group, an amino group, a lower alkylamino group, a lower alkylamino-lower alkyl group, a carboxyl group, a lower alkyloxycarbonyl group, a carbamoyl group, a lower alkanoyl group, an aroyl group, a lower alkylsulfonyl group, a sulfamoyl group, and an ammonium group, $R_{12}$, $R_{13}$, and $R_{14}$ each independently represent any one of a hydrogen atom, a halogen atom, a hydroxyl group, a lower alkyl group, a lower alkenyl group, a lower alkynyl group, a lower alkoxy group, a lower alkylthio group, a hydroxy-lower alkyl group, a hydroxy-lower alkenyl group, a hydroxy-lower alkoxy group, a halogeno-lower alkyl group, a halogeno-lower alkoxy group, a halogeno-lower alkylthio group, a halogeno-lower alkenyl group, a nitro group, a cyano group, an amino group, a lower alkylamino group, a lower alkoxy-lower alkylene group, a lower alkylthio-lower alkylene group, a lower alkylamino-lower alkylene group, a lower alkylamino-lower alkyl group, a carboxyl group, a lower alkyloxycarbonyl group, a carbamoyl group, a lower alkanoyl group, an aroyl group, a lower alkylsulfonyl group, a sulfamoyl group, and an ammonium group, and $R_2$, $R_3$, $R_{22}$, $R_{23}$, $R_{24}$, $R_{25}$, and $R_{53}$ each independently represent any one of a hydrogen atom, a halogen atom, a hydroxyl group, a lower alkyl group, a lower alkenyl group, a lower alkynyl group, a lower alkoxy group, a lower alkylthio group, a hydroxy-lower alkyl group, a hydroxy-lower alkenyl group, a hydroxy-lower alkoxy group, a halogeno-lower alkyl group, a halogeno-lower alkoxy group, a halogeno-lower alkylthio group, a halogeno-lower alkenyl group, a nitro group, a cyano group, an amino group, a lower alkylamino group, a lower alkylamino-lower alkyl group, a carboxyl group, a lower alkyloxycarbonyl group, a carbamoyl group, a lower alkanoyl group, an aroyl group, a lower alkylsulfonyl group, a sulfamoyl group, and an ammonium group, B represents any one of an alkoxy group having 1 to 10 carbon atoms, a hydroxyl group, or a hydroxyamino group, these groups being optionally substituted with a substituent selected from the group consisting of an aryl group, a hydroxyl group, an alkyl group having 1 to 10 carbon atoms, a lower alkoxy group, a lower alkylamino group, a halogen atom, and a heterocyclic group, $R_{41}$ represents a hydrogen atom or a lower alkyl group, a, b, c, and d independently represent C—$R_{31}$, C—$R_{32}$, C—$R_{33}$, or C—$R_{34}$, respectively, wherein one or two of a, b, c, and d may represent a nitrogen atom, $R_{31}$, $R_{32}$, $R_{33}$, and $R_{34}$ each independently represent any one of a hydrogen atom, a halogen atom, a lower alkyl group, a lower alkoxy group, and a nitro group, wherein any one of $R_{31}$, $R_{32}$, $R_{33}$, and $R_{34}$ is a halogen atom or a lower alkyl group, e, f, g, and h independently represent C—$R_{35}$, C—$R_{36}$, C—$R_{37}$, or C—$R_{38}$, respectively, wherein one or two of e, f, g, and h may represent a nitrogen atom, $R_{35}$, $R_{36}$, $R_{37}$, and $R_{38}$ each independently represent any one of a hydrogen atom, a halogen atom, a lower alkyl group, a lower alkoxy group, and a nitro group, D represents a phenyl group or a heterocyclic group, optionally having a substituent selected from the group consisting of a halogen atom, a hydroxyl group, a lower alkyl group, a lower alkenyl group, a lower alkynyl group, a lower alkoxy group, a lower alkylthio group, a hydroxy-lower alkyl group, a hydroxy-lower alkenyl group, a hydroxy-lower alkoxy group, a halogeno-lower alkyl group, a halogeno-lower alkoxy group, a halogeno-lower alkylthio group, a halogeno-lower alkenyl group, a nitro group, a cyano group, an amino group, a carboxyl group, a lower alkyloxycarbonyl group, a carbamoyl group, a lower alkanoyl group, an aroyl group, a lower alkylsulfonyl group, a sulfamoyl group, a lower alkoxy-lower alkylene group, a lower alkylthio-lower alkylene group, a lower alkylamino-lower alkylene group, and an ammonium group, when A represents a group represented by the general formula (2-1), (2-2), or (2-3), E represents: a 5- or 6-membered heterocyclic group substituted with a substituent selected from the group consisting of a 3- to 8-membered saturated ring group containing a nitrogen atom connected by a carbon atom, a 3- to 8-membered saturated or unsaturated ring group containing a heteroatom selected from an oxygen atom and a sulfur atom, a lower alkoxy-lower alkylene group, a lower alkylthio-lower alkylene group, a lower alkylamino-lower alkylene group, a lower alkylamino group, and a lower alkenylamino group; or a 5- or 6-membered cyclic ketone group containing 1 to 4 nitrogen atoms as atoms constituting the ring, the cyclic ketone group being substituted with a lower alkyl group or a lower alkenyl group, and when A represents a group represented by the general formula (2-4), E represents: a phenyl group or a 5- or 6-membered heterocyclic group optionally having a substituent selected from the group consisting of a halogen atom, a hydroxyl group, a lower alkyl group, a lower alkenyl group, a lower alkynyl group, a lower alkoxy group, a lower alkylthio group, a hydroxy-lower alkyl group, a hydroxy-lower alkenyl group, a hydroxy-lower alkoxy group, a halogeno-lower alkyl group, a halogeno-lower alkoxy group, a halogeno-lower alkylthio group, a halogeno-lower alkenyl group, a 3- to 8-membered saturated ring group containing a nitrogen atom connected by a carbon atom, a 3- to 8-membered saturated or unsaturated ring group containing a heteroatom selected from an oxygen atom and a sulfur atom, a lower alkoxy-lower alkylene group, a lower alkylthio-lower alkylene group, a lower alkylamino-lower alkylene group, a lower alkylamino group, a lower alkenylamino group, a nitro group, a cyano group, an amino group, a 4- to 6-membered cyclic amino group, a carboxyl group, a lower alkyloxycarbonyl group, a carbamoyl group, a lower alkanoyl group, an aroyl group, a lower alkylsulfonyl group, a sulfamoyl group, and an ammonium group; an aminocarbonyl group optionally having a substituent selected from the group consisting of a hydroxyl group, a lower alkyl group, a lower alkenyl group, a lower alkynyl group, a lower alkoxy group, a hydroxy-lower alkyl group, a hydroxy-lower alkenyl group, a hydroxy-lower alkoxy group, a halogeno-lower alkyl group, a halogeno-lower alkoxy group, a halogeno-lower alkenyl group, an amino group, a lower alkylamino group, an aryl group, a heterocyclic group, a heterocyclic lower alkyl group, a lower alkylsulfonyl group, and a sulfamoyl group; a hydrogen atom; a halogen atom; a hydroxyl group; a lower alkyl group; a lower alkenyl group; a lower alkynyl group; a lower alkoxy group; a lower alkylthio group; a hydroxy-lower alkyl group; a hydroxy-lower alkenyl group; a hydroxy-lower alkoxy group; a halogeno-lower alkyl group; a halogeno-lower alkoxy group; a halogeno-lower alkylthio group; a halogeno-lower alkenyl group; a nitro group; a cyano group; an amino group; a carboxyl group; a dihydroxyboryl group; a lower alkylcarbonyl group; a lower alkyloxycarbonyl group; a carbamoyl group; a lower alkanoyl group; an aroyl group; a lower alkylsulfonyl group; a sulfamoyl group; an ammonium group; a lower alkylaminoalkylene group; or a 5- or 6-membered cyclic ketone group containing 1 to 4 nitrogen atoms as atoms constituting the ring, the cyclic ketone group being substituted with a lower alkyl group or a lower alkenyl group, wherein the lower alkylcarbonyl group and the lower alkyloxycarbonyl group may form a fused ring by being bonded to the phenyl group of D, provided that the sulfonamide derivative excludes sulfonamide derivatives selected from the group consisting of (a) to (h) below:

(a) (2S)-2-[[2,5-difluoro-4-[[4-(2-tetrahydropyran-4-ylpyrimidin-5-yl)phenyl]sulfonylamino]benzoyl]amino]-3-[4-(1-methyl-2,4-dioxo-pyrido[3,4-d]pyrimidin-3-yl)phenyl]propanoic acid

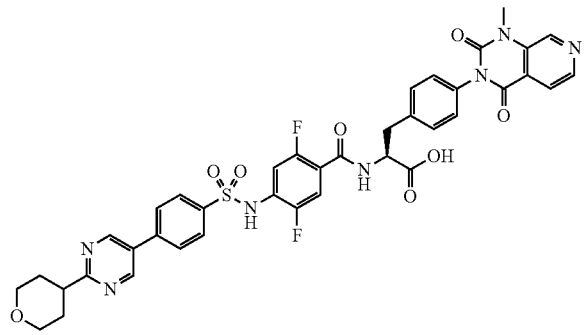 [SMILES: Cn1c(=O)n(-c2ccc(C[C@H](NC(=O)c3cc(F)c(NS(=O)(=O)c4ccc(-c5cnc(C6CCOCC6)nc5)cc4)cc3F)C(=O)O)cc2)c(=O)c2ccncc21]

(b) cyclohexyl (2S)-2-[[2,5-difluoro-4-[[4-(2-tetrahydropyran-4-ylpyrimidin-5-yl)phenyl]sulfonylamino]benzoyl]amino]-3-[4-(1-methyl-2,4-dioxo-pyrido[3,4-d]pyrimidin-3-yl)phenyl]propionate

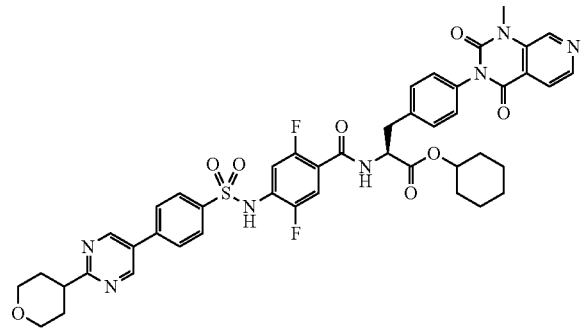 [SMILES: Cn1c(=O)n(-c2ccc(C[C@H](NC(=O)c3cc(F)c(NS(=O)(=O)c4ccc(-c5cnc(C6CCOCC6)nc5)cc4)cc3F)C(=O)OC3CCCCC3)cc2)c(=O)c2ccncc21]

(c) (2S)-2-[[2,5-difluoro-4-[[4-(2-tetrahydropyran-4-ylpyrimidin-5-yl)phenyl]sulfonylamino]benzoyl]amino]-3-[6-(1-methyl-2,4-dioxo-pyrido[3,4-d]pyrimidin-3-yl)-3-pyridyl]propanoic acid

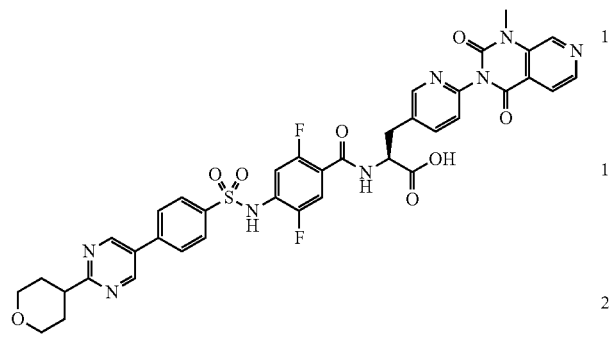

(d) cyclohexyl (2S)-2-[[2,5-difluoro-4-[[4-(2-tetrahydropyran-4-ylpyrimidin-5-yl)phenyl]sulfonylamino]benzoyl]amino]-3-[6-(1-methyl-2,4-dioxo-pyrido[3,4-d]pyrimidin-3-yl)-3-pyridyl]propanoate

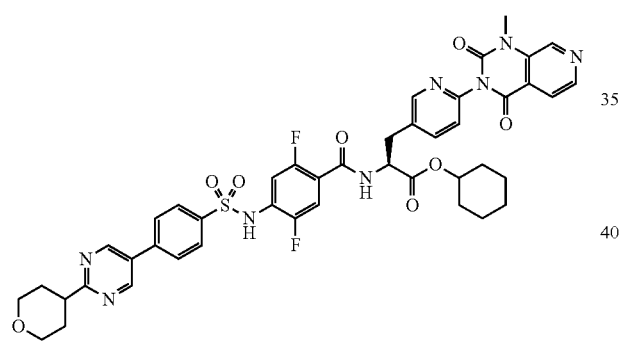

(e) (2S)-2-[[2,5-difluoro-4-[[4-[2-(methoxymethyl)pyrimidin-5-yl]phenyl]sulfonylamino]benzoyl]amino]-3-[4-(1-methyl-2,4-dioxo-pyrido[3,4-d]pyrimidin-3-yl)phenyl]propanoic acid

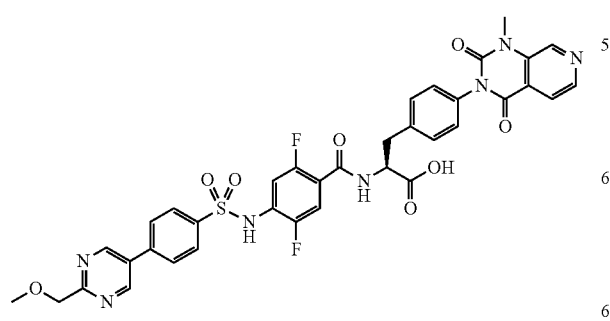

(f) cyclohexyl (2S)-2-[[2,5-difluoro-4-[[4-[2-(methoxymethyl)pyrimidin-5-yl]phenyl]sulfonylamino]benzoyl]amino]-3-[4-(1-methyl-2,4-dioxo-pyrido[3,4-d]pyrimidin-3-yl)phenyl]propanoate

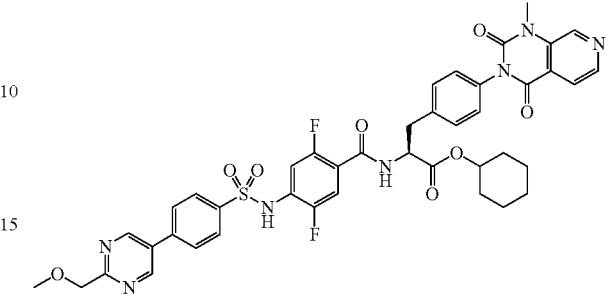

(g) (2S)-2-[[2,5-difluoro-4-[[4-[2-(methoxymethyl)pyrimidin-5-yl]phenyl]sulfonylamino]benzoyl]amino]-3-[6-(1-methyl-2,4-dioxo-pyrido[3,4-d]pyrimidin-3-yl)-3-pyridyl]propanoic acid

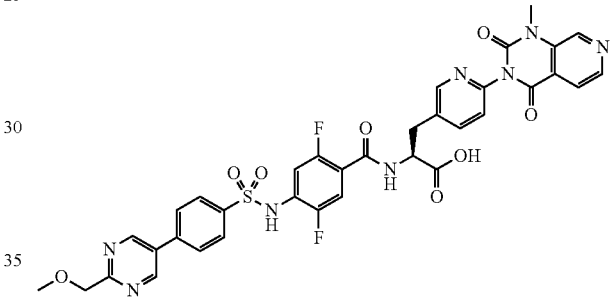

and
(h) cyclohexyl (2S)-2-[[2,5-difluoro-4-[[4-[2-(methoxymethyl)pyrimidin-5-yl]phenyl]sulfonylamino]benzoyl]amino]-3-[6-(1-methyl-2,4-dioxo-pyrido[3,4-d]pyrimidin-3-yl)-3-pyridyl]propanoate

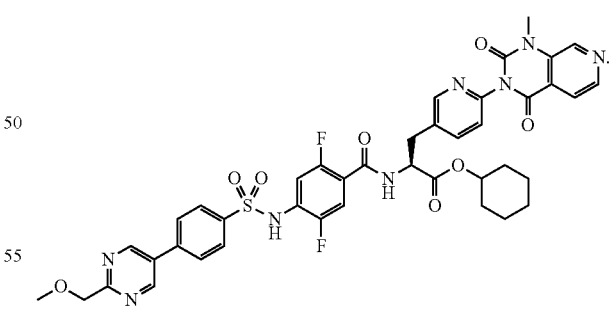

2. The sulfonamide derivative or a phau laceutically acceptable salt thereof according to claim 1, wherein D is a phenyl group optionally having a substituent selected from the group consisting of a lower alkyl group, a halogen atom, a hydroxyl group, and a lower alkoxy group.

3. The sulfonamide derivative or a pharmaceutically acceptable salt thereof according to claim 1, wherein D is a 6-membered aromatic heterocyclic group optionally having a substituent selected from the group consisting of a lower alkyl group, a halogen atom, and a lower alkoxy group, and having a nitrogen atom as an atom constituting the ring.

4. The sulfonamide derivative or a pharmaceutically acceptable salt thereof according to claim 3, wherein the heterocyclic group of D is a pyridyl group optionally having a substituent selected from the group consisting of a lower alkyl group, a halogen atom, and a lower alkoxy group.

5. The sulfonamide derivative or a pharmaceutically acceptable salt thereof according to claim 1, wherein the 5- or 6-membered heterocyclic group of E is selected from the group consisting of a pyridyl group, a pyridazyl group, a pyrimidyl group, a pyrazinyl group, a pyrrolyl group, a triazolyl group, and a tetrazole group, and the cyclic ketone group of E is a 5- or 6-membered cyclic ketone group containing 2 or 3 nitrogen atoms as atoms constituting the ring.

6. The sulfonamide derivative or a pharmaceutically acceptable salt thereof according to claim 1, wherein A represents a group represented by the general formula (2-4), and E is a 5- or 6-membered aromatic heterocyclic group containing 1, 2, 3 or 4 heteroatoms selected from oxygen atoms, sulfur atoms and nitrogen atoms and optionally having a substituent selected from the group consisting of a lower alkyl group, a lower alkoxy group, a lower alkoxy-lower alkylene group, and a halogen atom.

7. The sulfonamide derivative or a pharmaceutically acceptable salt thereof according to claim 6, wherein the aromatic heterocyclic group is selected from the group consisting of a pyridyl group, a pyridazyl group, a pyrimidyl group, a pyrazinyl group, a pyrrolyl group, a furanyl group, a thiophenyl group, a thiazolyl group, an oxazolyl group, a triazolyl group, and a tetrazole group.

8. The sulfonamide derivative or a pharmaceutically acceptable salt thereof according to claim 1, wherein
A represents a group represented by the general formula (2-4), and
E is an aminocarbonyl group optionally substituted with a lower alkyl group, a heterocyclic group, or a heterocyclic lower alkyl group, or a lower alkylaminoalkylene group.

9. The sulfonamide derivative or a pharmaceutically acceptable salt thereof according to claim 1, wherein the heterocyclic group of E is a pyridyl group, a pyrimidyl group, a triazolyl group, and a tetrazole group optionally having a substituent selected from the group consisting of a 3- to 8-membered saturated or unsaturated ring group containing a heteroatom selected from an oxygen atom and a sulfur atom, a lower alkoxy-lower alkylene group, and a lower alkylamino-lower alkylene group.

10. The sulfonamide derivative or a pharmaceutically acceptable salt thereof according to claim 1, wherein A represents a group represented by the general formula (2-2), and $R_{12}$, $R_{13}$, and $R_{14}$ are selected from the group consisting of a lower alkyl group, a lower alkoxy group, a lower alkoxy-lower alkylene group, a lower alkylamino-lower alkylene group, and a halogen atom.

11. The sulfonamide derivative or a pharmaceutically acceptable salt thereof according to claim 1, wherein B is a lower alkoxy group or hydroxyl group, optionally substituted with a substituent selected from the group consisting of a lower alkyl group, a lower alkoxy group, a lower alkylamino group, a halogen atom, and a heterocyclic group.

12. The sulfonamide derivative or a pharmaceutically acceptable salt thereof according to claim 1, wherein the lower alkyl group is a straight-chain, branched-chain, or cyclic alkyl group.

13. The sulfonamide derivative or a pharmaceutically acceptable salt thereof according to claim 1, wherein $R_1$, $R_{11}$, $R_{21}$, $R_{51}$, and $R_{52}$ are lower alkyl groups.

14. The sulfonamide derivative or a pharmaceutically acceptable salt thereof according to claim 1, wherein Arm is selected from the group consisting of a phenyl group, a pyridyl group, a pyrimidyl group, and an imidazolyl group.

15. The sulfonamide derivative or a pharmaceutically acceptable salt thereof according to claim 1, wherein
A represents a group represented by the general formula (2-2), and
E represents a 5- or 6-membered heterocyclic group containing 1 to 4 nitrogen atoms, the 5- or 6-membered heterocyclic group being substituted with a substituent selected from the group consisting of a lower alkyl group, a lower alkoxy-lower alkylene group, and a 5- or 6-membered heterocyclic group containing an oxygen atom; or a cyclic ketone group containing 1 to 4 nitrogen atoms, the cyclic ketone group being substituted with a lower alkyl group or a lower alkenyl group.

16. The sulfonamide derivative or a pharmaceutically acceptable salt thereof according to claim 15, wherein
B is optionally substituted with a substituent selected from the group consisting of an alkyl group having 1 to 10 carbon atoms, a lower alkoxy group, and a heterocyclic group containing 1 to 4 heteroatoms selected from oxygen atoms and nitrogen atoms, and
Arm is a pyridyl group.

17. The sulfonamide derivative or a pharmaceutically acceptable salt thereof according to claim 1, wherein
A represents a group represented by the general formula (2-4),
E is a 5- or 6-membered heterocyclic group containing an oxygen atom, or a 5- or 6-membered heterocyclic group containing 1 to 4 nitrogen atoms, and
E optionally has a substituent selected from a lower alkyl group, a lower alkoxy-lower alkylene group, and a 5- or 6-membered heterocyclic group containing an oxygen atom.

18. The sulfonamide derivative or a pharmaceutically acceptable salt thereof according to claim 1, wherein
E represents: a 5- or 6-membered heterocyclic group substituted with a 3- to 8-membered saturated or unsaturated ring group containing a heteroatom selected from an oxygen atom and a sulfur atom; or a 5- or 6-membered cyclic ketone group containing 1 to 4 nitrogen atoms as atoms constituting the ring, the cyclic ketone group being substituted with a lower alkyl group or a lower alkenyl group.

19. The sulfonamide derivative or a pharmaceutically acceptable salt thereof according to claim 18, wherein D is a phenyl group.

20. The sulfonamide derivative or a pharmaceutically acceptable salt thereof according to claim 19, wherein two of $R_{31}$, $R_{32}$, $R_{33}$, and $R_{34}$ are halogen atoms and the others are hydrogen atoms.

21. The sulfonamide derivative or a pharmaceutically acceptable salt thereof according to claim 20, which is a compound represented by any one of the following formulae or a pharmaceutically acceptable salt thereof:

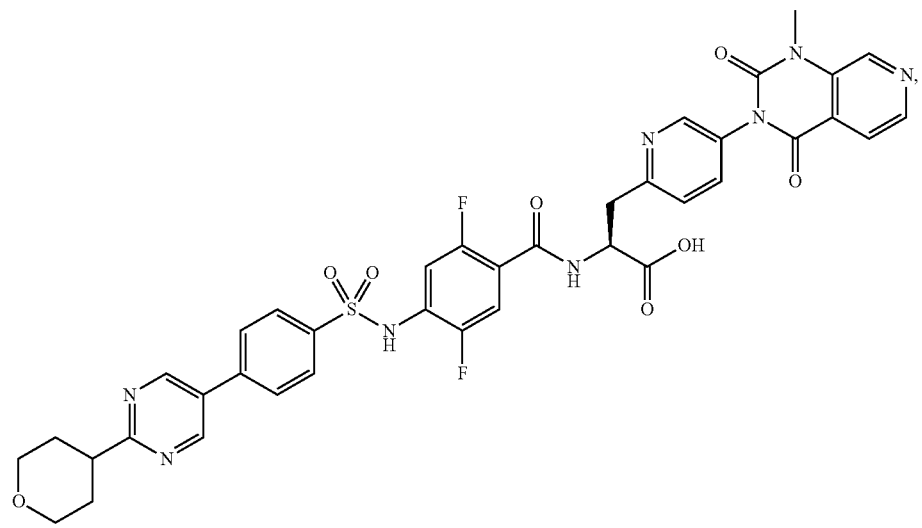
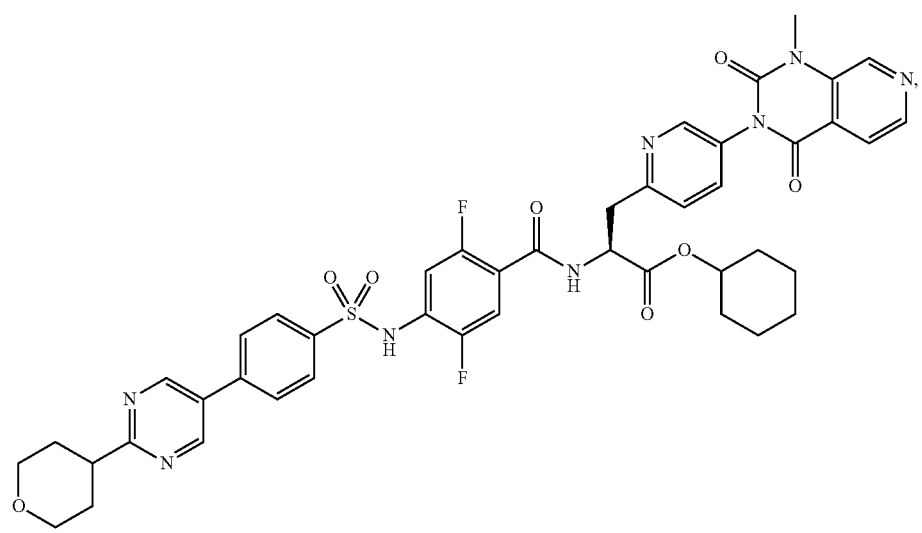
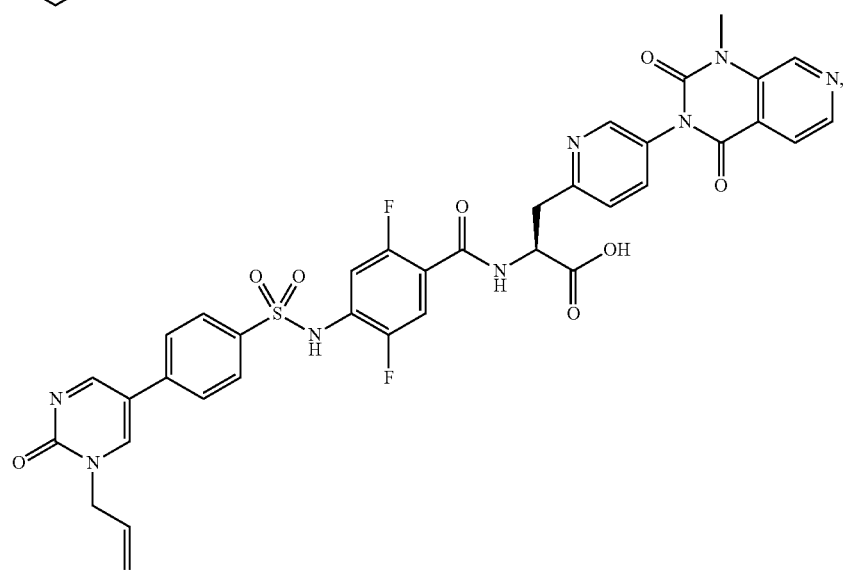

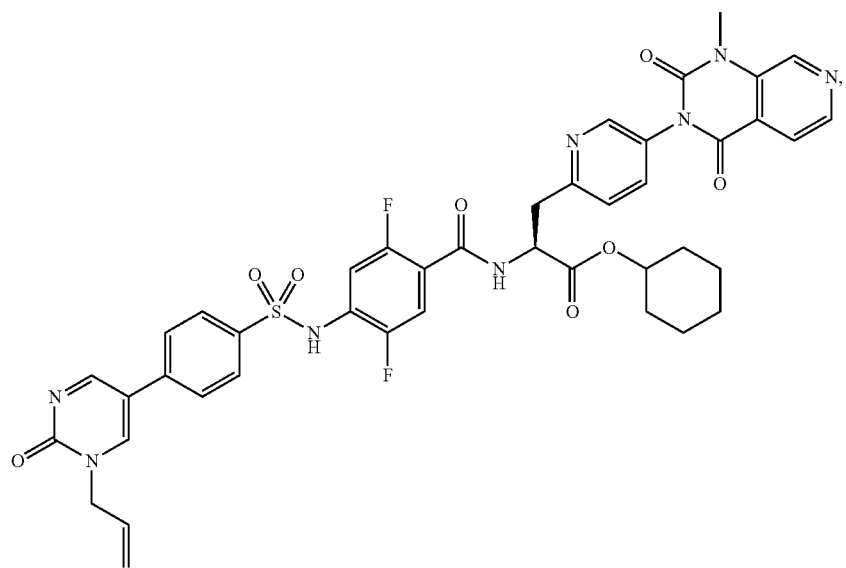
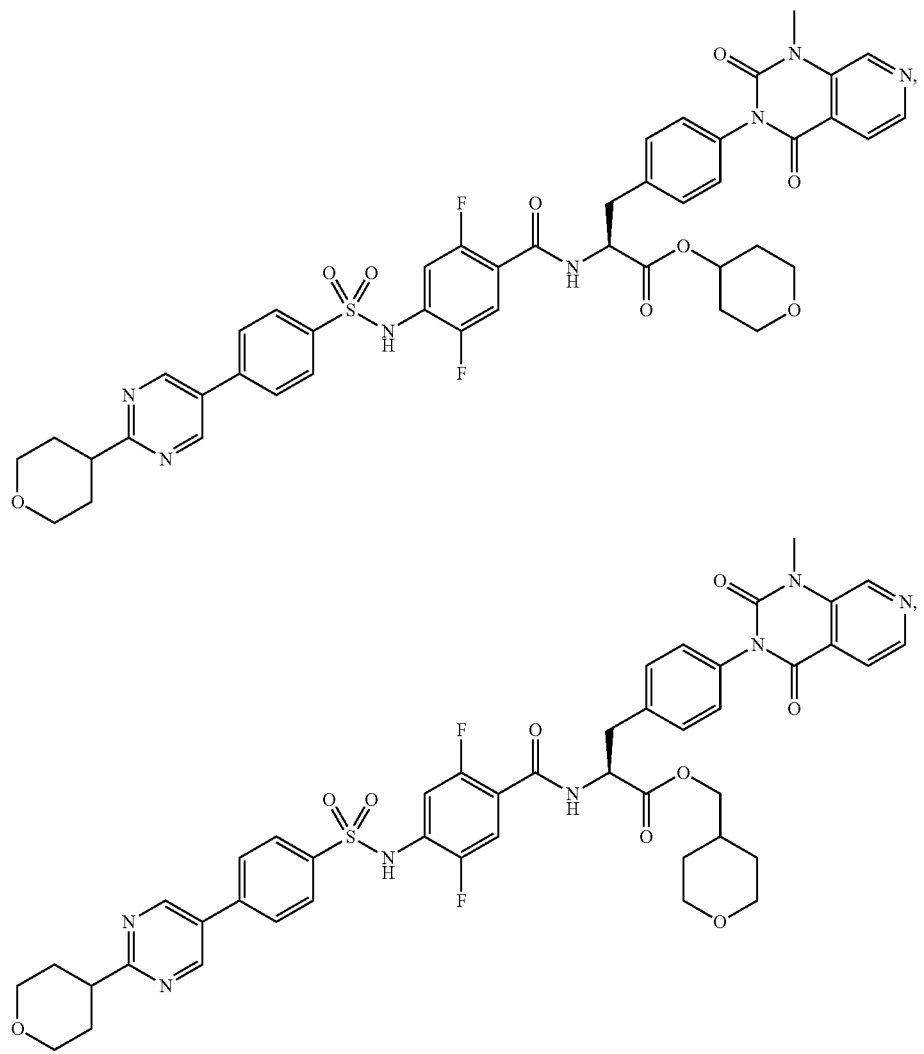

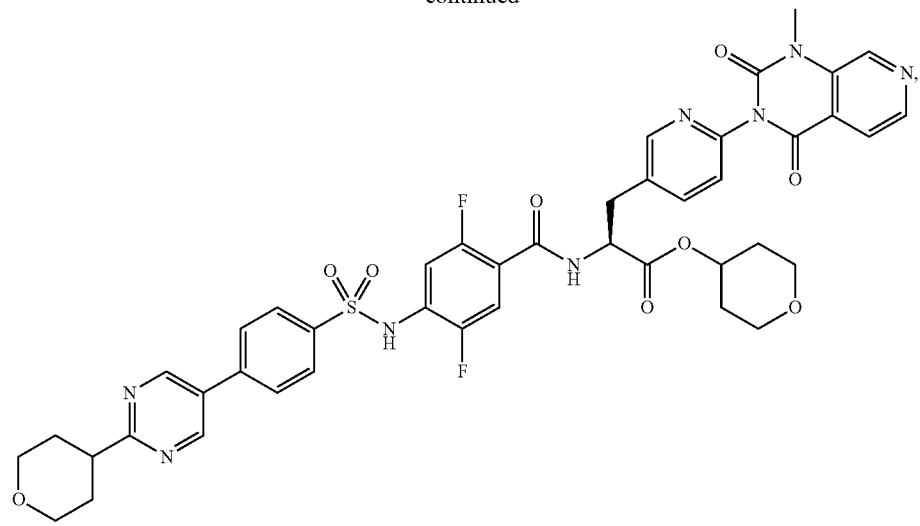
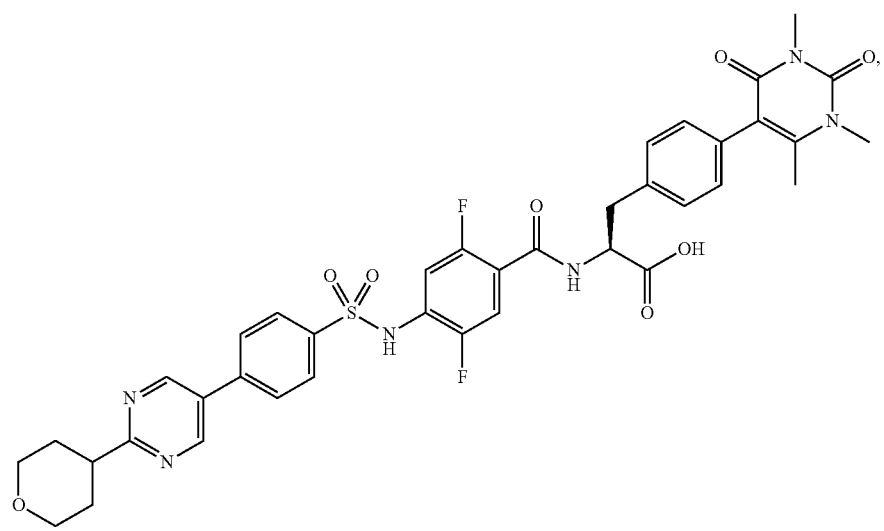
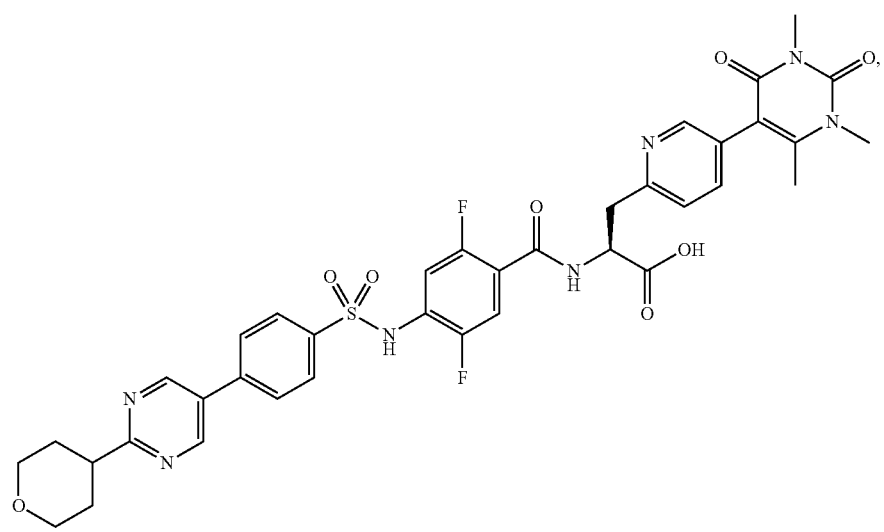

-continued
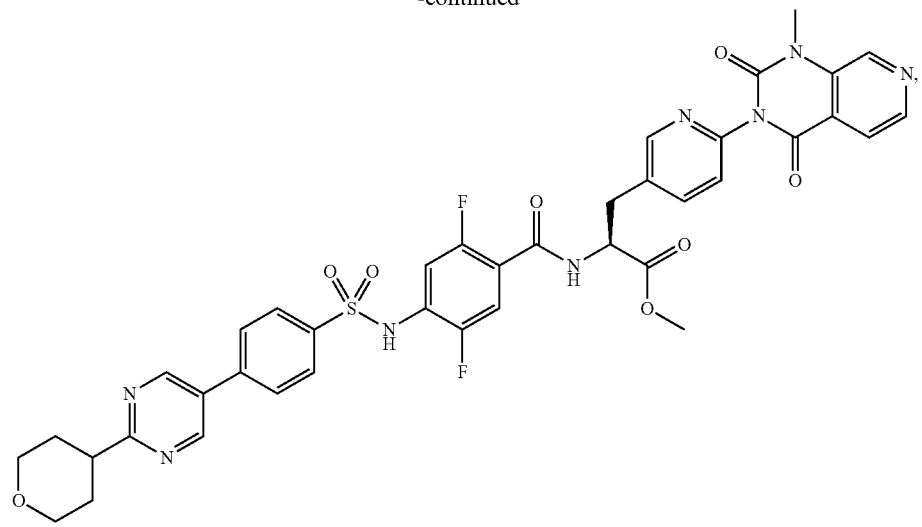
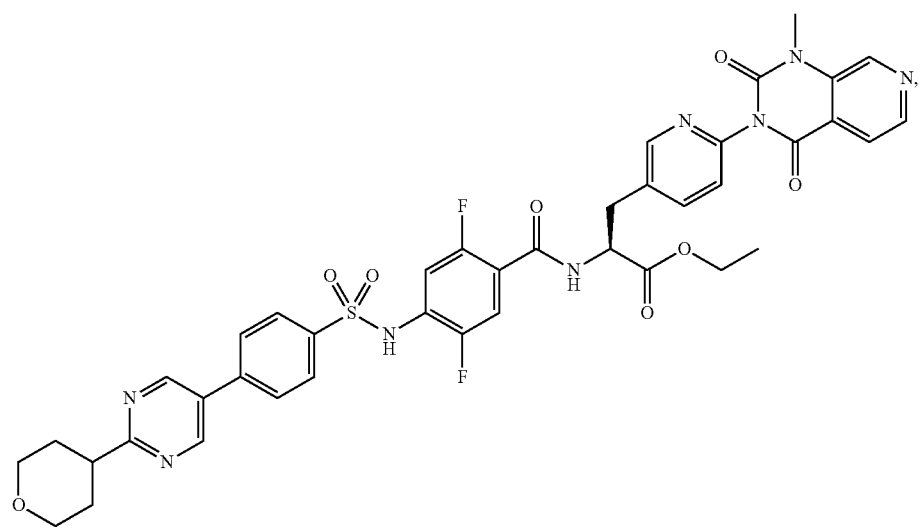
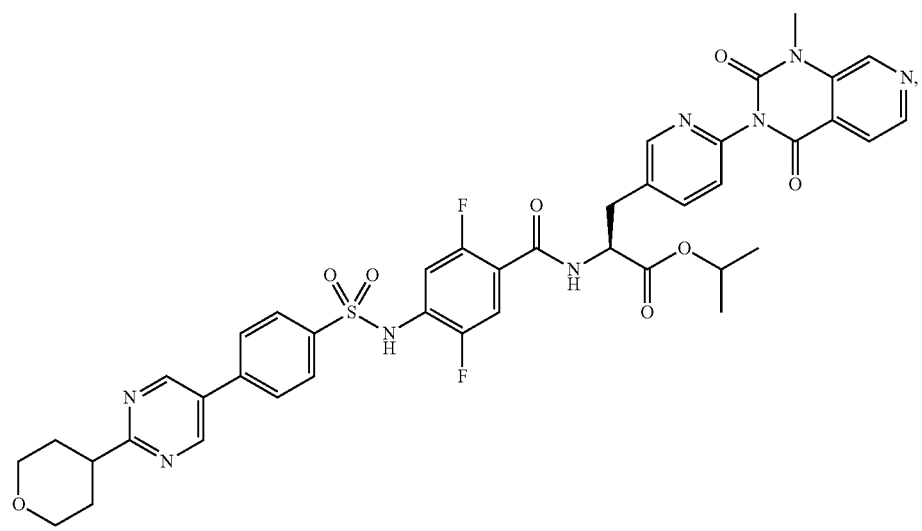

-continued
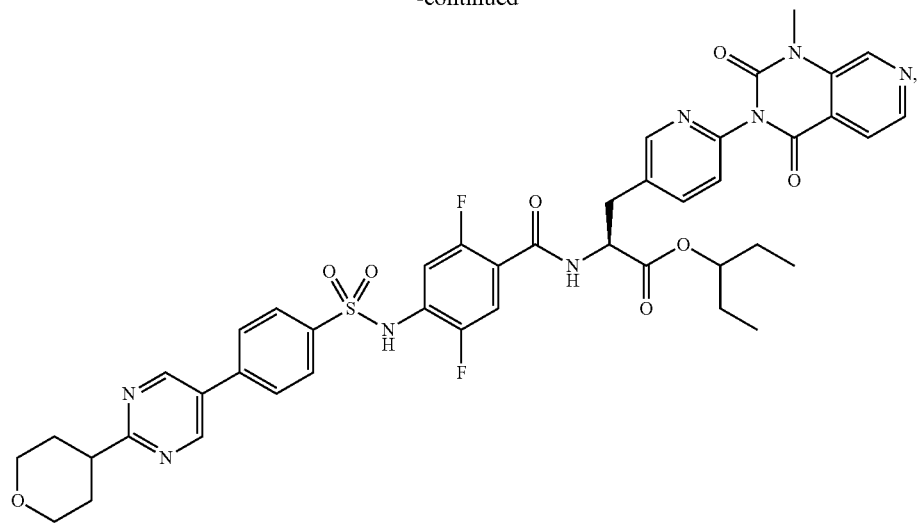
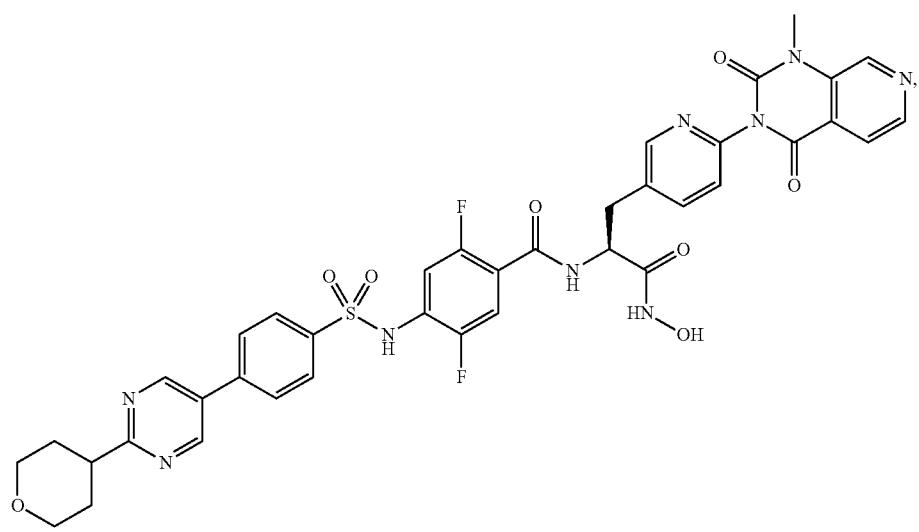
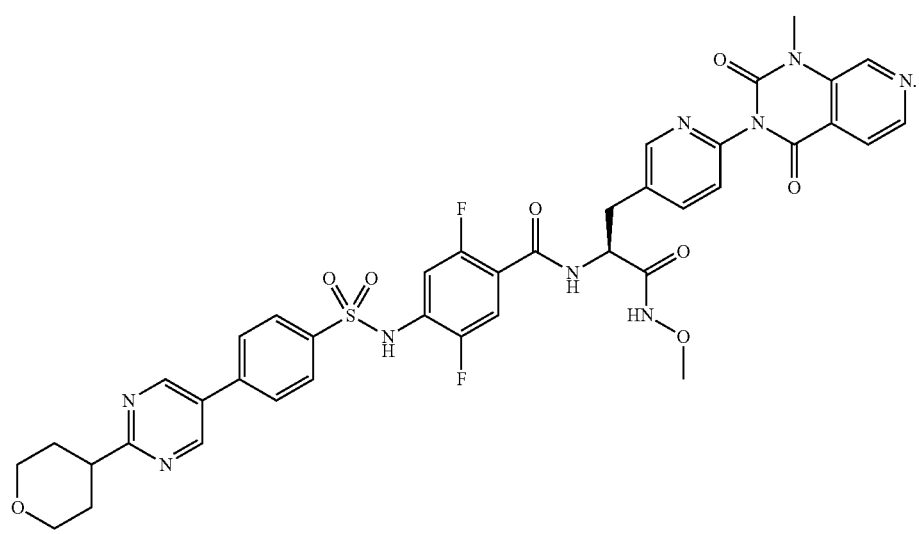

22. A pharmaceutical composition comprising the sulfonamide derivative or a pharmaceutically acceptable salt thereof according to claim 1.

23. A pharmaceutical composition comprising the sulfonamide derivative or a pharmaceutically acceptable salt thereof according to claim 21.

24. A therapeutic agent or a preventive agent for inflammatory disease in which an α4β7integrin-dependent adhesion process is involved in pathological conditions, the agent comprising the sulfonamide derivative or a pharmaceutically acceptable salt thereof according to claim 1,
wherein said inflammatory disease in which an α4β7integrin-dependent adhesion process is involved is rheumatoid arthritis, inflammatory bowel disease, systemic lupus erythematosus, multiple sclerosis, Sjogren's syndrome, asthma, psoriasis, arteriosclerosis, restenosis, or transplant rejection, in a human subject.

25. A therapeutic agent or a preventive agent for inflammatory disease in which an α4β7integrin-dependent adhesion process is involved in pathological conditions, the agent comprising the sulfonamide derivative or a pharmaceutically acceptable salt thereof according to claim 21,
wherein said inflammatory disease in which an α4β7integrin-dependent adhesion process is involved is rheumatoid arthritis, inflammatory bowel disease, systemic lupus erythematosus, multiple sclerosis, Sjogren's syndrome, asthma, psoriasis, arteriosclerosis, restenosis, or transplant rejection, in a human subject.

26. An α4β7integrin inhibitor comprising the sulfonamide derivative or a pharmaceutically acceptable salt thereof according to claim 1.

27. An α4β7integrin inhibitor comprising the sulfonamide derivative or a pharmaceutically acceptable salt thereof according to claim 21.

* * * * *